US012774280B2

(12) United States Patent
Zhang et al.

(10) Patent No.: US 12,774,280 B2
(45) Date of Patent: Oct. 27, 2026

(54) SUBSTITUTED TRICYCLIC AZA-HETEROCYCLES AS SOS1 INHIBITORS

(71) Applicant: Viva Star Biosciences (Suzhou) Co., Ltd., Suzhou (CN)

(72) Inventors: Hongjian Zhang, Plainsboro, NJ (US); Jingjing Ji, Shanghai (CN); Peihua Sun, Shanghai (CN)

(73) Assignee: Viva Star Biosciences (Suzhou) Co., Ltd., Suzhou (CN)

( * ) Notice: Subject to any disclaimer, the term of this patent is extended or adjusted under 35 U.S.C. 154(b) by 382 days.

(21) Appl. No.: 18/280,175

(22) PCT Filed: Mar. 1, 2022

(86) PCT No.: PCT/US2022/018328

§ 371 (c)(1),
(2) Date: Sep. 1, 2023

(87) PCT Pub. No.: WO2022/187236

PCT Pub. Date: Sep. 9, 2022

(65) Prior Publication Data

US 2024/0109891 A1 Apr. 4, 2024

(30) Foreign Application Priority Data

Mar. 2, 2021 (WO) ................ PCT/CN2021/078597

(51) Int. Cl.
*C07D 471/14* (2006.01)
*C07D 487/04* (2006.01)

(52) U.S. Cl.
CPC ......... *C07D 471/14* (2013.01); *C07D 487/04* (2013.01)

(58) Field of Classification Search
CPC ... C07D 471/14; C07D 487/04; C07D 487/14
See application file for complete search history.

(56) References Cited

FOREIGN PATENT DOCUMENTS

| | | | |
|---|---|---|---|
| CN | 113354651 | A | 9/2021 |
| WO | WO-97/42192 | A1 | 11/1997 |
| WO | WO-2018/172250 | A1 | 9/2018 |
| WO | WO-2021/105960 | A1 | 6/2021 |

OTHER PUBLICATIONS

Guerrini, “Pyrazolo[1,5-a]quinazoline scaffold as 5-deaza analogue of pyrazolo[5,1-c][1,2,4]benzotriazine system: synthesis of new derivatives, biological activity on GABAA receptor subtype and molecular dynamic study”, J Enzyme Inhib Med Chem, 2016; 31(2): 195-204.*
Hillig et al., “Discovery of potent SOS1 inhibitors that block RAS activation via disruption of the RAS-SOS1 interaction”, PNAS, vol. 116, No. 7, Feb. 12, 2019, pp. 2551-2560.
International Search Report and Written Opinion issued for PCT PCT/US2022/018328 dated May 6, 2022 (9 pages).
RN No. 2419351-31-6 etc.

* cited by examiner

*Primary Examiner* — Sahar Javanmard
(74) *Attorney, Agent, or Firm* — Foley & Lardner LLP

(57) ABSTRACT

This application relates to novel heterotricyclic compounds and analogues, their manufacture, pharmaceutical compositions comprising them, and their use as medicaments for treating a disease associated with mammalian RAS (Rat sarcoma virus) family proteins.

55 Claims, 2 Drawing Sheets

SUBSTITUTED TRICYCLIC AZA-HETEROCYCLES AS SOS1 INHIBITORS

CROSS-REFERENCE TO RELATED APPLICATIONS

This application is a U.S. National Phase Application under 35 U.S.C. § 371 of PCT International Application No. PCT/US2022/018328, filed on Mar. 1, 2022, which claims priority to PCT International Application No. PCT/CN2021/078597, filed Mar. 2, 2021, the entire contents of which are incorporated herein by reference.

FIELD

This application relates to novel substituted tricyclic aza-heterocycles and analogues, their manufacture, pharmaceutical compositions comprising them, and their use as medicaments for treating a disease associated with mammalian RAS (Rat sarcoma virus) family proteins.

BACKGROUND

RAS (Rat sarcoma virus) proteins belong to a superfamily of small GTPases and act as a "binary switch" in cellular signal transduction. As depicted in the diagram in FIG. 1 [Biomark Cancer, 2016; 8(Suppl 1): 27-35.], RAS proteins exert their effects via the GDP/GTP cycle (the nucleotide exchange cycle). GEFs (Guanine nucleotide exchange factors) stimulate GDP/GTP exchange, leading to the formation of RAS-GTP complex, which interacts with and turns on the downstream effector pathways. Because cellular concentrations of GTP are much higher than GDP (up to 10-fold higher), the active RAS-GTP is thus in the RAS-On state as a net result. In contrast, GAPs (GTPase activating proteins) enhance the hydrolysis of GTP, leading to the formation of RAS-GDP complex which is unable to engage downstream effectors, thus resulting in a RAS-Off or inactive state. Mutations in RAS genes promote the formation of the RAS-GTP complex and an overtly "active state" drives tumor cell proliferation and survival, leading to poor prognosis of several cancer types due to altered tumor metabolism and drug resistance.

RAS genes encode four highly homologous RAS proteins (83 to 85% amino acid sequence identity): HRAS (Harvey rat sarcoma viral oncogene homolog), NRAS (Neuroblastoma RAS viral oncogene homolog), and KRAS4A (Kirsten rat sarcoma viral oncogene homologue 4A) and KRAS4B [Cell. 2017 Jun. 29; 170(1):17-33; Sci. Signal. 2020, 13, eaay 6013]. Since the discovery of mutationally activated human RAS genes as important oncogenes, mutations in KRAS, HRAS and NRAS have been linked to poor prognosis of different forms of human cancers [Ras history, Small GTPases, 2010, 1:1, 2-27, DOI: 10.4161/sgtp.1.1.12178]. To date, activating mutations in RAS proteins are found in approximately 24% of all cancers, among which KRAS mutation is a major driver in 90% of pancreatic ductal adenocarcinoma (PDAC), 43% of colorectal cancer (CRC), and 26% of nonsmall-cell lung cancer (NSCLC), affecting pathways involved in cell proliferation, differentiation, and apoptosis [Cell. 2017 Jun. 29; 170(1): 17-33; Oncogene. 2018 May; 37(18):2444-2455.]. Because of high cellular concentrations of GTP and a small/shallow binding pocket in the RAS-GTP complex, direct targeting of the GTP binding site via competitive inhibition has not been fruitful in the discovery and development of RAS inhibitors (particularly KRAS inhibitors) as antitumor agents.

The RAS signaling pathway is associated with multiple upstream initiators (such as RTKs, receptor tyrosine kinases), downstream effectors, and binding partners (chaperon proteins), etc. As illustrated in the diagram shown in FIG. 2 [Oncotarget. 2014 Sep. 15; 5 (17):7285-302; Sci. Signal. 2020, 13, eaay6013]. SOS (Son of sevenless, a GEF) plays a critical role in converting RAS-GDP (Off) to RAS-GTP (On), thus activating downstream effector RAF/MEK/ERK and/or PI3K/AKT/mTOR pathways and promoting tumor cell proliferation and survival [Oncotarget. 2014 Sep. 15; 5 (17):7285-302; Cell. 2017 Jun. 29; 170(1):17-33]. As such, the RAS:SOS interaction and/or various stages of RAS signaling have been explored to identify tumor vulnerabilities for therapeutic intervention of various RAS mutation driven cancers [Biochemical Journal (2019) 476 365-374; Sci Signal. 2020 Mar. 24; 13(624): eaay 6013].

SOS1 (Son of sevenless homolog 1) is the most studied GEF that is involved in RAS signaling. The RAS:SOS1 interaction, particularly KRAS:SOS1 interaction, has been explored as a key vulnerability in KRAS mutation driven cancers. It has been shown that SOS1-mediated cross-activation of oncogenic RAS is essential for tumorigenesis and the depletion of SOS1 reduced the proliferation rate and survival of tumor cells harboring KRAS mutations [Nat Commun. 2012; 3:1168. doi: 10.1038/ncomms 2173.]. Studies have also demonstrated that the disruption (or inhibition) of RAS:SOS1 interaction could be achieved by small molecules, as exemplified by BAY-293 and BI-2852 [Proc Natl Acad Sci USA. 2019 Feb. 12; 116(7):2551-2560; Proc Natl Acad Sci USA. 2019 Aug. 6; 116(32):15823-15829]. BAY-293, a selective inhibitor of the KRAS:SOS1 interaction, prevents the formation of the KRAS:SOS1 complex and blocks the reloading of KRAS with GTP, leading to anti-proliferative activity [Proc Natl Acad Sci USA. 2019 Feb. 12; 116(7):2551-2560]. In comparison, BI-2852, a KRAS inhibitor that binds with nanomolar affinity to a pocket between switch I and II on RAS, blocks all GEF, GAP, and effector interactions with KRAS, leading to inhibition of downstream signaling and antiproliferative effect, suggesting the switch I/II pocket of RAS is druggable by small molecules [Proc Natl Acad Sci USA. 2019 Aug. 6; 116(32): 15823-15829]. The above findings clearly demonstrate the essential role of SOS1 as a GEF in KRAS mutant cancers and that the KRAS:SOS1 interaction in RAS signaling can be targeted for therapeutic intervention.

In addition to cancers, aberrant activities of RAS proteins are associated with various diseases, generally termed RASopathies [J Hum Genet. 2016 January; 61(1):33-9.]. In contrast to RAS mutation driven cancers, RASopathies are a group of clinical syndromes caused by hyperactivation of the RAS/MAPK pathway [Cell. 2017 Jun. 29; 170(1):17-33]. Evidence has implied that somatic mutations in RAS and SOS genes play an important role in the pathogenesis of these developmental disorders including neurofibromatosis type 1, Noonan syndrome, Noonan syndrome with multiple lentigines, Costello syndrome, cardiofaciocutaneous syndrome, and capillary malformation-arteriovenous syndrome [Ann Oncol. 2020 Mar. 30; S0923-7534(20)36378-X.]. Therefore, a RAS:SOS inhibitor may be used to treat not only RAS mutation driven cancers but also RASopathies caused by aberrant RAS signaling activities. Furthermore, a recent study demonstrates that knocking down the expression of KRAS using antisense oligonucleotides reduces fibrosis by 50% and prevents the loss of renal function in a mouse model of chronic folic acid nephropathy [Sci Rep.

2019 Sep. 30; 9(1):14010], suggesting that targeting KRAS expression and activity represents an utility in the treatment of renal dysfunction associated with fibrosis.

SUMMARY

The present technology describes novel RAS:SOS (e.g., KRAS:SOS1) small molecules inhibitors which disrupt the interaction between RAS and SOS and prevent the activation of RAS proteins particularly KRAS. The inhibition of the RAS:SOS (e.g., KRAS:SOS1) complex formation results in significant inhibitory effects on downstream effector pathways, leading to profound reduction in proliferation and survival of RAS or KRAS mutation driven cancers. The described RAS:SOS (e.g., KRAS:SOS1) inhibitors may be used to treat various RAS mutation driven cancers such as PDAC, NSCLC, CRC, as well as RASopathies. In addition, small molecule compounds disclosed herein show good pharmaceutical properties including solubility, ADME (absorption, distribution, metabolism, and excretion), pharmacokinetics, CYP inhibition and other safety profiles. Finally, RAS:SOS (e.g., KRAS:SOS1) inhibitors may be used for in-pathway combinations, with inhibitors of upstream RTKs or SHP2 and downstream RAF, MEK, ERK, PI3K, AKT, or mTOR, to achieve better antitumor efficacy.

In one aspect, the present technology relates to a compound of Formula I, a compound of Formula II,

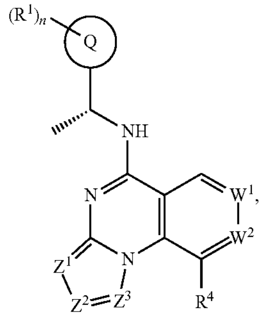

(I)

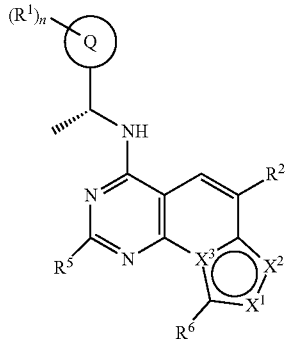

(II)

or a pharmaceutically acceptable salt thereof, and/or a tautomer thereof, and/or a stereoisomer thereof, wherein:

Q at each occurrence is independently a ring selected from phenyl or a 5- or 6-membered heteroaryl group, wherein the heteroaryl group comprises at least one carbon atom and 1-4 additional heteroatoms independently selected from nitrogen, oxygen or sulfur;

$Z^1$ is N or $CR^5$;

$Z^2$ is N or $CR^6$;

$Z^3$ is N or $CR^7$;

$W^1$ is $CR^2$ or $NR^2$;

$W^2$ is $CR^3$ when $W^1$ is $CR^2$, and $W^2$ is C(O) when $W^1$ is $NR^2$;

$X^1$ is N, $NR^7$, or $CR^9$;

$X^2$ is N, $NR^7$, or $CR^7$;

$X^3$ is N or C;

$R^1$ at each occurrence is independently hydrogen, halogen, $C_{1-6}$alkyl, halo$C_{1-6}$alkyl, $C_{1-6}$alkenyl, $C_{1-6}$alkynyl, OH, $C_{1-6}$alkyl-OH, halo$C_{1-6}$alkyl-OH, $C_{1-6}$alkoxy, halo$C_{1-6}$alkoxy, CN, —$NR^aR^b$, $C_{3-7}$cycloalkyl, $C_{3-7}$cycloalkyl-OH, $C_{3-7}$cycloalkoxy, —$S(O)_t$—$C_{1-6}$alkyl, —$S(O)_t$—$NR^aR^b$, phenyl, or 3-7-membered heterocyclyl, wherein the phenyl and 3-7-membered heterocyclyl are optionally substituted with 1-4 substituents independently selected from $C_{1-4}$alkyl, halo$C_{1-4}$alkyl, $C_{1-4}$alkoxy, halo$C_{1-4}$alkoxy, $C_{1-4}$alkyl-OH, halo$C_{1-4}$alkyl-OH, OH, halogen, CN, —$S(O)_t$—$C_{1-6}$alkyl, —$S(O)_t$—$NR^aR^b$, —$NR^aR^b$, or $C_{1-4}$alkyl-$NR^aR^b$; or two adjacent $R^1$ groups, together with the carbon atoms to which they are attached, form a 5-7-membered carbocyclic or heterocyclic ring optionally substituted with 1-3 substituents independently selected from $C_{1-4}$alkyl, halo$C_{1-4}$alkyl, $C_{1-4}$alkoxy, halo$C_{1-4}$alkoxy, $C_{1-4}$alkyl-OH, halo$C_{1-4}$alkyl-OH, OH, halogen, CN, —$NR^aR^b$, $C_{1-4}$alkyl-$NR^aR^b$, or oxo group (═O);

$R^2$ at each occurrence is independently hydrogen, halogen, CN, —$OR^a$, —$NR^aR^b$, $C_{1-6}$alkyl, halo$C_{1-6}$alkyl, $C_{2-6}$alkenyl, $C_{2-6}$alkynyl, $C_{3-7}$cycloalkyl, 3-7-membered heterocyclyl, phenyl, or 5-6-membered heteroaryl, wherein each of the $C_{1-6}$alkyl, halo$C_{1-6}$alkyl, $C_{2-6}$alkenyl, $C_{2-6}$alkynyl, $C_{3-7}$cycloalkyl, 3-7-membered heterocyclyl, phenyl, and 5-6-membered heteroaryl is optionally substituted with 1-5 $R^8$;

$R^3$ at each occurrence is independently hydrogen, halogen, $C_{1-6}$alkyl, halo$C_{1-6}$alkyl, $C_{1-6}$alkoxy, halo$C_{1-6}$ alkoxy, $C_{1-6}$alkyl-OH, CN, $C_{3-7}$cycloalkyl, $C_{3-7}$cycloalkyl-OH, $C_{3-7}$cycloalkoxy, —$NH_2$, —$NHC_{1-4}$alkyl, —$N(C_{1-4}alkyl)_2$, or 3-7-membered cyclic amine;

$R^4$ at each occurrence is independently hydrogen, halogen, $C_{1-6}$alkyl, halo$C_{1-6}$alkyl, $C_{1-6}$alkoxy, halo$C_{1-6}$ alkoxy, CN, $NH_2$, $C_{3-7}$cycloalkyl or $C_{3-7}$cycloalkoxy;

$R^5$ at each occurrence is independently hydrogen, halogen, $C_{1-4}$alkyl, or halo$C_{1-4}$alkyl;

$R^6$ at each occurrence is independently hydrogen or $C_{1-4}$alkyl;

$R^7$ at each occurrence is independently hydrogen, $C_{1-4}$alkyl or halo$C_{1-4}$alkyl;

$R^8$ at each occurrence is independently hydrogen, halogen, $C_{1-4}$alkyl, halo$C_{1-4}$alkyl, $C_{1-4}$alkoxy, $C_{2-4}$alkenyl, $C_{2-4}$alkynyl, $C_{3-7}$cycloalkyl, $C_{3-7}$cycloalkoxy, 3-7-membered heterocyclyl, phenyl, 5-6-membered heteroaryl, —$OR^a$, —$SR^a$, $S(O)_tR^a$, —$S(O)_t$—$NR^aR^b$, —OC(O)—$R^a$, —$NR^aR^b$, —$C(O)R^a$, —$C(O)OR^a$, —$OC(O)NR^aR^b_2$, —$C(O)NR^aR^b$, —$N(R^a)C(O)OR^a$, —$N(R^a)C(O)R^a$, —$N(R^a)C(O)NR^aR^b$, —$N(R^a)C(NR^a)NR^aR^b$, —$N(R^a)S(O)_tNR^aR^b$, —$P({=}O)(R^a)(R^b)$, —O—$P({=}O)(OR^a)(OR)$, or oxo group (═O);

$R^9$ at each occurrence is independently hydrogen or $C_{1-4}$alkyl;

$R^a$ and $R^b$ at each occurrence are independently hydrogen, $C_{1-6}$alkyl, halo$C_{1-6}$alkyl, $C_{1-6}$alkyl-OH, $C_{1-6}$alkoxy, $C_{3-7}$cycloalkyl, 3-7-membered heterocyclyl, $C_{1-6}$alkyl-$NH_2$, $C_{1-6}$alkyl-$NHC_{1-4}$alkyl, $C_{1-6}$alkyl-$N(C_{1-4}alkyl)_2$, or $C_{1-6}$alkyl-(3-7-membered cyclic amine), wherein each of the foregoing groups may be optionally substituted by one to three substituents independently selected from the group consisting of $C_{1-4}$alkyl, halo$C_{1-4}$alkyl, halogen, OH, $NH_2$, $C_{1-4}$alkoxy, halo$C_{1-4}$alkoxy, CN, and —C(O)$C_{1-4}$alkyl; or $R^a$ and $R^b$, together with the nitrogen atom to which they are attached, form a saturated or unsaturated heterocyclic ring containing from three to seven ring atoms, which ring may optionally contain an additional one or two heteroatoms independently selected from the group consisting of nitrogen, oxygen and sulfur, and which ring may be optionally substituted by one to three substituents independently selected from the group consisting of $C_{1-4}$alkyl, —C(O)$C_{1-4}$alkyl, phenyl and benzyl;

n at each occurrence is independently 1, 2 or 3, and t at each occurrence is independently 1 or 2.

In some embodiments, the compounds of Formula I and Formula II are selected from compounds of Formulae (IA), (IB), (IIA), (IIB) and (IIC):

(IA)

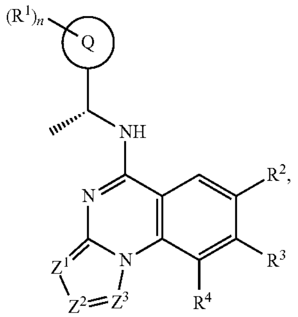

(IB)

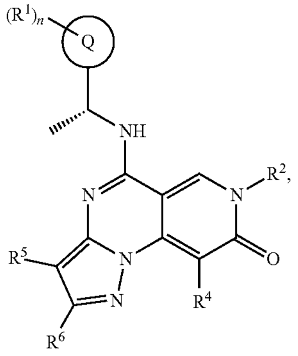

(IIA)

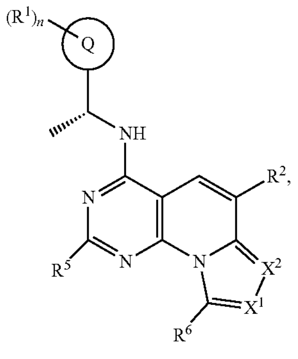

-continued (IIB)

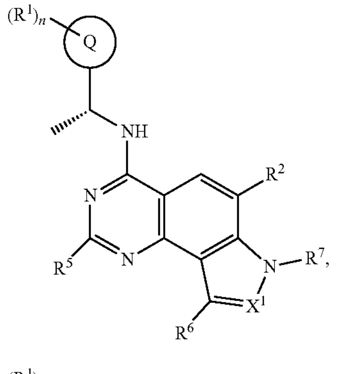

(IIC)

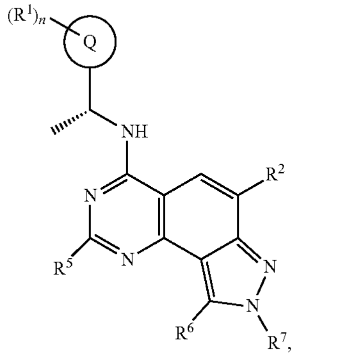

pharmaceutically acceptable salts, tautomers and/or stereoisomers thereof, wherein each variable is defined as for compounds of Formula I or Formula II, or may have any value disclosed herein.

The technology also relates to a pharmaceutical composition comprising a compound of Formulae (I)-(II) (including but not limited to those of Formula IA, IB, IIA, IIB, IIC), its manufacture and use as medicaments for treating or preventing a disease or condition mediated by mammalian Ras family proteins. Accordingly, the compounds of Formulae (I)-(II) (including but not limited to those of Formula IA, IB, IIA, IIB, IIC) are useful for treating or preventing cancer, including breast cancer, leukemia, prostate cancer, ovarian cancer, pancreatic cancer, colon cancer, lung cancer, endometrial cancer, thyroid cancer, cholangiocarcinoma, multiple myeloma, melanoma, uterine cancer, head and neck squamous cell carcinoma, diffuse large B cell lymphoma, esophageal cancer, hepatocellular cancer, glioblastoma, renal cancer, sarcoma, bladder cancer, urothelial cancer, gastric cancer, or cervical cancer. Additionally, the compounds of Formulae (I)-(II) (including but not limited to those of Formula IA, IB, IIA, IIB, IIC) are useful for treating or preventing RASopathies.

DETAILED DESCRIPTION

Figure 1:
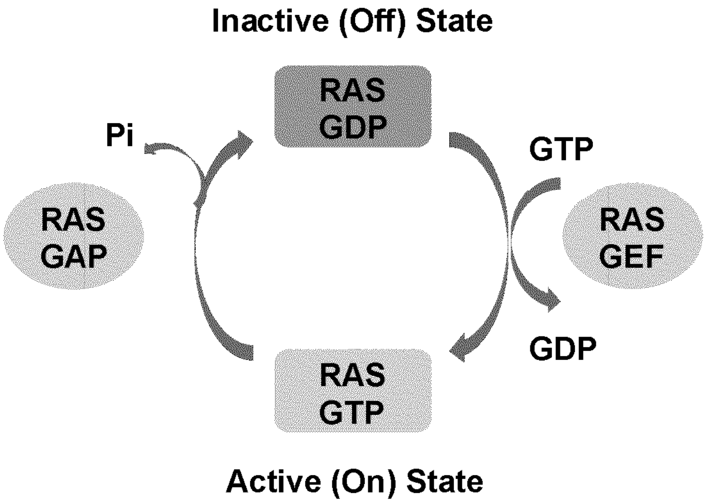
FIG. 1 schematically illustrates how RAS proteins exert their effects via the GDP/GTP cycle (the nucleotide exchange cycle), and lead to RAS-GDP (off) and RAS-GTP (on) states. Mutations in RAS genes that promote formation of the latter can drive tumor cell proliferation and survival FIG. 2 schematically illustrates how SOS (Son of sevenless, a GEF) plays a critical role in converting RAS-GDP (Off) to RAS-GTP (On), thus activating downstream effector RAF/MEK/ERK and/or PI3K/AKT/mTOR pathways and promoting tumor cell proliferation and survival.
Figure 2:
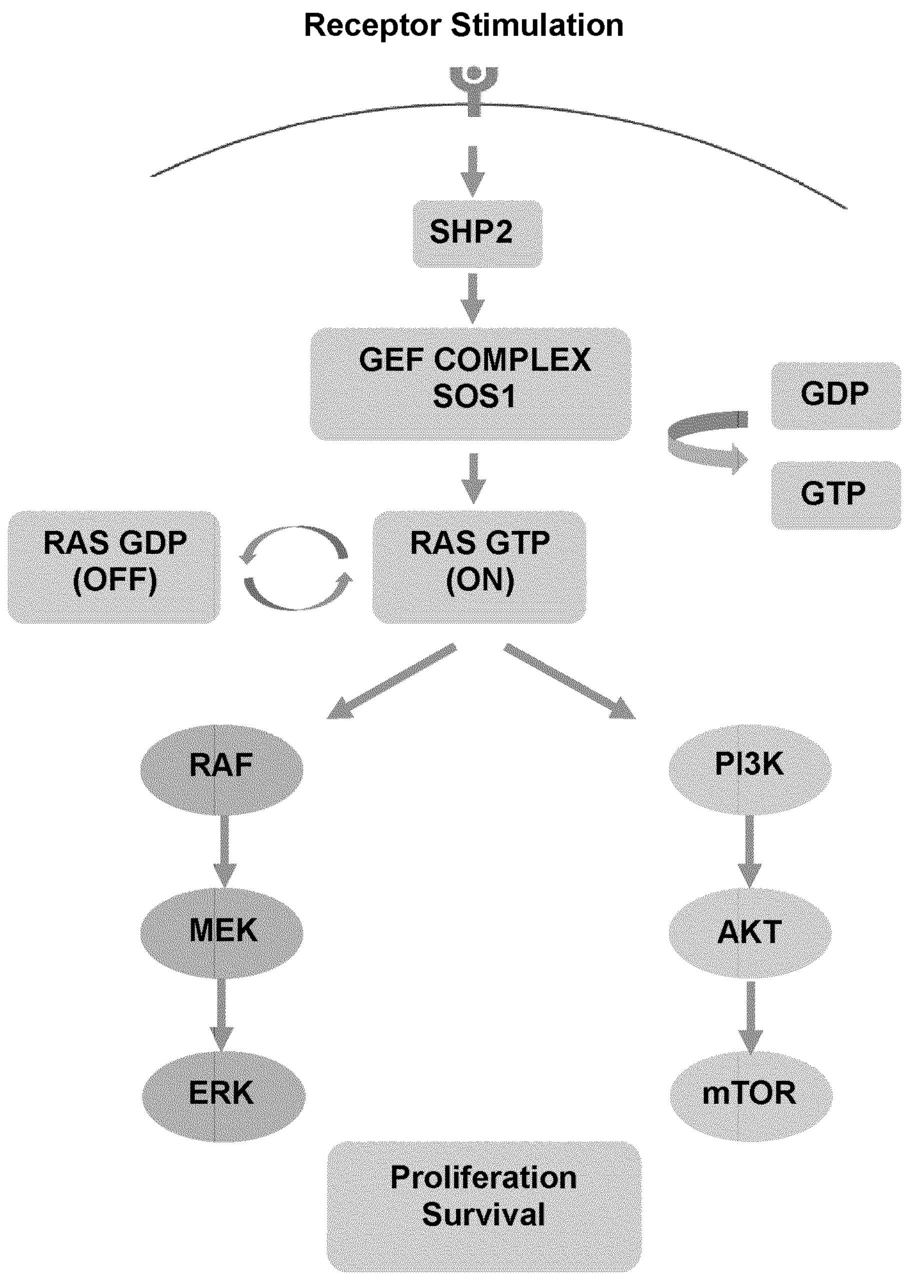

In one aspect, the present technology provides compounds, and their pharmaceutically acceptable forms, including, but not limited to, salts, hydrates, solvates, isomers, stereoisomers, enantiomers, prodrugs, and isotopically labeled derivatives thereof.

In another aspect, the present technology provides methods of treating and/or managing various diseases and disorders, which comprises administering to a patient a therapeutically effective amount of a compound provided herein, or a pharmaceutically acceptable form (e.g., salts, hydrates, solvates, isomers, stereoisomers, enantiomers, prodrugs, and isotopically labeled derivatives) thereof. Non-limiting examples of diseases and disorders are described herein.

In another aspect, the present technology provides methods of preventing various diseases and disorders, which comprises administering to a patient in need of such prevention a prophylactically effective amount of a compound provided herein, or a pharmaceutically acceptable form (e.g., salts, hydrates, solvates, isomers, stereoisomers, prodrugs, and isotopically labeled derivatives) thereof. Non-limiting examples of diseases and disorders are described herein.

In another aspect, a compound provided herein, or a pharmaceutically acceptable form (e.g., salts, hydrates, solvates, isomers, stereoisomers, prodrugs, and isotopically labeled derivatives) thereof, can be administered in combination with another drug ("second active agent") or treatment. Second active agents include small molecules and large molecules (e.g., proteins and antibodies).

Also provided herein are pharmaceutical compositions (e.g., single unit dosage forms) that can be used in the methods provided herein. In one embodiment, pharmaceutical compositions comprise a compound provided herein, or a pharmaceutically acceptable form (e.g., salts, hydrates, solvates, isomers, stereoisomers, prodrugs, and isotopically labeled derivatives) thereof, and optionally one or more second active agents.

While specific embodiments have been discussed, the specification is illustrative only and not restrictive. Many variations of this disclosure will become apparent to those skilled in the art upon review of this specification.

Unless defined otherwise, all technical and scientific terms used herein have the same meaning as is commonly understood by one of ordinary skill in the art to which this specification pertains.

DEFINITIONS

As used in the specification and claims, the singular form "a", "an" and "the" includes plural references unless the context clearly dictates otherwise.

As used herein, "agent" or "biologically active agent" or "second active agent" refers to a biological, pharmaceutical, or chemical compound or another moiety. Non-limiting examples include simple or complex organic or inorganic molecules, a peptide, a protein, an oligonucleotide, an antibody, an antibody derivative, an antibody fragment, a vitamin, a vitamin derivative, a carbohydrate, a toxin, or a chemotherapeutic compound, and metabolites thereof. Various compounds can be synthesized, for example, small molecules and oligomers (e.g., oligopeptides and oligonucleotides), and synthetic organic compounds based on various core structures. In addition, various natural sources can provide active compounds, such as plant or animal extracts, and the like. A skilled artisan can readily recognize that there is no limit as to the structural nature of the agents of this disclosure.

"Administration" of a disclosed compound encompasses the delivery to a subject of a compound as described herein, or a prodrug or other pharmaceutically acceptable derivative thereof, using any suitable formulation or route of administration, as discussed herein.

The term "co-administration," "administered in combination with," and their grammatical equivalents, as used herein, encompasses administration of two or more agents to the subject so that both agents and/or their metabolites are present in the subject at the same time. Co-administration includes simultaneous administration in separate compositions, administration at separate times in separate compositions, or administration in a composition in which both agents are present.

The term "effective amount" or "therapeutically effective amount" refers to that amount of a compound or pharmaceutical composition described herein that is sufficient to affect the intended application including, but not limited to, disease treatment, as illustrated below. In some embodiments, the amount is that effective for detectable inhibition of SOS1, which, for example, can be determined in a KRAS:SOS1 binding assay. The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a response in target cells, e.g., reduction of cell migration. The specific dose will vary depending on, for example, the compounds chosen, the species of subject and their age/existing health conditions or risk for health conditions, the dosing regimen to be followed, the severity of the disease, whether it is administered in combination with other agents, timing of administration, the tissue to which it is administered, and the physical delivery system in which it is carried.

All methods described herein can be performed in any suitable order unless otherwise indicated herein or otherwise clearly contradicted by context.

As used herein, the terms "treatment", "treating", "palliating" "managing" and "ameliorating" are used interchangeably herein. These terms refer to an approach for obtaining beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compounds and/or compositions can be administered to a patient at risk of developing a disease, or to a patient reporting one or more of the physiological symptoms of a disease, even though a diagnosis of this disease may not have been made.

The terms "preventing" and "prophylaxis" as used herein refer to administering a pharmaceutical compound or medicament or a composition including the pharmaceutical compound or medicament to a subject before a disease, disorder, or condition fully manifests itself, to forestall the appearance and/or reduce the severity of one or more symptoms of the disease, disorder or condition. The person of ordinary skill in the art recognizes that the term "prevent" is not an absolute term. In the medical art it is understood to refer to the prophylactic administration of a drug to diminish the likelihood or seriousness of a disease, disorder or condition, or a symptom thereof, and this is the sense that such terms are used in this disclosure.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

The term "in vivo" refers to an event that takes place in a subject's body. In vivo also includes events occurring in rodents, such as rats, mice, guinea pigs, and the like.

The term "in vitro" refers to an event that takes places outside of a subject's body. For example, an in vitro assay encompasses any assay conducted outside of a subject. In vitro assays encompass cell-based assays in which cells, alive or dead, are employed. In vitro assays also encompass a cell-free assay in which no intact cells are employed.

As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J. Pharmaceutical Sciences* (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. For example, pharmaceutically acceptable salts include adipate, alginate, ascorbate, aspartate, benzenesulfonate, besylate, benzoate, bisulfate, borate, butyrate, camphorate, camphor sulfonate, citrate, cyclopentane propionate, digluconate, dodecyl sulfate, ethane sulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, lactic acid, trifluoracetic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The salts can be prepared in situ during the isolation and purification of the disclosed compounds, or separately, such as by reacting the free base or free acid of a parent compound with a suitable base or acid, respectively. Pharmaceutically acceptable salts derived from appropriate bases include alkali metal, alkaline earth metal, ammonium and $N^+(C_{1-4}alkyl)^4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines, including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt can be chosen from ammonium, potassium, sodium, calcium, and magnesium salts.

As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or 1 to about 2, about 3 or about 4, solvent or water molecules. It will be understood that the term "compound" as used herein encompasses the compound and solvates of the compound, as well as mixtures thereof.

In some embodiments, the pharmaceutically acceptable form is a prodrug. As used herein, the term "prodrug" refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs can increase the bioavailability of the compound when administered to a subject (e.g., by permitting enhanced absorption into the blood following oral administration) or which enhance delivery to a biological compartment of interest (e.g., the brain or lymphatic system) relative to the parent compound. Exemplary prodrugs include derivatives of a disclosed compound with enhanced aqueous solubility or active transport through the gut membrane, relative to the parent compound.

The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," *A.C.S. Symposium Series*, Vol. 14, and in *Bioreversible Carriers in Drug Design*, ed. Edward B. Roche, American Pharmaceutical Association and Pergamon Press, 1987, both of which are incorporated in full by reference herein. Exemplary advantages of a prodrug can include, but are not limited to, its physical properties, such as enhanced water solubility for parenteral administration at physiological pH compared to the parent compound, or it can enhance absorption from the digestive tract, or it can enhance drug stability for long-term storage.

The term "prodrug" is also meant to include any covalently bonded carriers, which release the active compound in vivo when such prodrug is administered to a subject. Prodrugs of an active compound, as described herein, can be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. Other examples of prodrugs include compounds that comprise —NO, —$NO_2$, —ONO, or —$ONO_2$ moieties. Prodrugs can typically be prepared using well known methods, such as those described in *Burger's Medicinal Chemistry and Drug Discovery,* 172-178, 949-982 (Manfred E. Wolff ed., 5th ed., 1995), and *Design of Prodrugs* (H. Bundgaard ed., Elselvier, New York, 1985).

For example, if a disclosed compound or a pharmaceutically acceptable form of the compound contains a carboxylic acid functional group, a prodrug can comprise a pharmaceutically acceptable ester formed by the replacement of the hydrogen atom of the acid group with a group such as $(C_{1-8})$alkyl, $(C_{1-12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 10 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—$(C_{1-2})$alkylamino$(C_{2-3})$alkyl (such as [3-dimethylaminoethyl), carbamoyl-$(C_{1-2})$alkyl, N,N-di$(C_{1-2})$alkylcarbamoyl-$(C_{1-2})$ alkyl and piperidino-, pyrrolidino- or morpholino$(C_{2-3})$alkyl.

Similarly, if a disclosed compound contains an alcohol functional group, a prodrug can be formed by the replacement of the hydrogen atom of the alcohol group with a group such as $(C_{1-6})$alkanoyloxymethyl, 1-(($(C_{1-6})$alkanoyloxy) ethyl, 1-methyl-1-(($(C_{1-6})$alkanoyloxy)ethyl, $(C_{1-6})$alkoxycarbonyloxymethyl, N—$(C_{1-6})$alkoxycarbonylaminomethyl, succinoyl, $(C_{1-6})$alkanoyl, α-amino$(C_{1-4})$alkanoyl, arylacyl, and α-aminoacyl, or α-aminoacyl-α-aminoacyl, where each α-aminoacyl group is independently selected from the naturally occurring L-amino acids, —$P(O)(OH)_2$, —$P(O)(O(C_{1-6})alkyl)_2$ or glycosyl (the radical resulting from the removal of a hydroxyl group of the hemiacetal form of a carbohydrate).

If a disclosed compound incorporates an amine functional group, a prodrug can be formed by the replacement of a hydrogen atom in the amine group with a group such as R-carbonyl, RO-carbonyl, NRR'-carbonyl where R and R' are each independently selected from $(C_{1-10})$alkyl, $(C_{3-7})$ cycloalkyl, benzyl, a natural α-aminoacyl or natural α-aminoacyl-natural-α-aminoacyl, —C(OH)C(O)O$Y^1$ wherein $Y^1$ is H, $(C_{1-6})$alkyl or benzyl; —C(O$Y^2$)$Y^3$ wherein $Y^2$ is $(C_{1-4})$alkyl and $Y^3$ is $(C_{1-6})$alkyl, carboxy$(C_{1-6})$alkyl, amino $(C_{1-4})$alkyl or mono-N— or di-N,N—$(C_{1-6})$alkylaminoalkyl; and —C($Y^4$)$Y^5$ wherein $Y^4$ is H or methyl and $Y^5$ is mono-N— or di-N—$(C_{1-6})$alkylamino, morpholino, piperidin-1-yl or pyrrolidin-1-yl.

In some embodiments, the disclosed compounds may encompass an isomer. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof, and other mixtures thereof, as falling within the scope of this disclosure.

Geometric isomers can be represented by the symbol ----- which denotes a bond that can be a single, double or triple bond as described herein. Provided herein are various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or"trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of plane of the ring are designated "cis/trans."

"Enantiomers" are a pair of stereoisomers that are non-superimposable mirror images of each other. A mixture of a pair of enantiomers in any proportion can be known as a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, optically substantially pure forms and intermediate mixtures. Optically active (R)- and (S)-isomers can be prepared, for example, using chiral synthons or chiral reagents, or resolved using conventional techniques.

In some embodiments, an enantiomer is provided partly or substantially free of the corresponding enantiomer, and may be referred to as "optically enriched," "enantiomerically enriched," "enantiomerically pure," and "non-racemic," as used interchangeably herein. The "enantiomeric excess" or "% enantiomeric excess" of a composition can be calculated using the equation shown below. In the example shown below, a composition contains 90% of one enantiomer, e.g., the S enantiomer, and 10% of the other enantiomer, e.g., the R enantiomer.

$$ee=(90-10)/100=80\%.$$

Thus, a composition containing 90% of one enantiomer and 10% of the other enantiomer is said to have an enantiomeric excess of 80%. In some embodiments, compositions described herein contain an enantiomeric excess of at least about 50%, at least about 60%, at least about 70%, at least about 80%, at least about 90%, at least about 95%, at least about 98%, at least about 99%, or at least about 99.5% of the S enantiomer, or a range between and including any two of the foregoing values (e.g., 50-99.5% ee). In other words, the compositions contain an enantiomeric excess of the S enantiomer over the R enantiomer. In other embodiments, some compositions described herein contain an enantiomeric excess of at least about 50%, at least about 60%, at least about 70%, at least about 80%, at least about 90%, at least about 95%, at least about 98%, at least about 99%, or at least about 99.5% of the R enantiomer or a range between any two of the foregoing values (e.g., 50-99.5% ee). In other words, the compositions contain an enantiomeric excess of the R enantiomer over the S enantiomer. Where the enrichment of one enantiomer is much greater than about 80% by weight, the compositions are referred to as "substantially enantiomerically enriched," "substantially enantiomerically pure" or a "substantially non-racemic" preparation.

Thus, a composition containing 90% of one enantiomer and 10% of the other enantiomer is said to have an enantiomeric excess of 80%. In some embodiments, compositions described herein contain an enantiomeric excess of at least about 50%, at least about 60%, at least about 70%, at least about 80%, at least about 90%, at least about 95%, at least about 98%, at least about 99%, or at least about 99.5% of the S enantiomer, or a range between and including any two of the foregoing values (e.g., 50-99.5% ee). In other words, the compositions contain an enantiomeric excess of the S enantiomer over the R enantiomer. In other embodiments, some compositions described herein contain an enantiomeric excess of at least about 50%, at least about 60%, at least about 70%, at least about 80%, at least about 90%, at least about 95%, at least about 98%, at least about 99%, or at least about 99.5% of the R enantiomer or a range between any two of the foregoing values (e.g., 50-99.5% ee). In other words, the compositions contain an enantiomeric excess of the R enantiomer over the S enantiomer. Where the enrichment of one enantiomer is much greater than about 80% by weight, the compositions are referred to as "substantially enantiomerically enriched," "substantially enantiomerically pure" or a "substantially non-racemic" preparation.

Optical isomers can be obtained by resolution of the racemic mixtures according to conventional processes, e.g., by formation of diastereoisomeric salts, by treatment with an optically active acid or base. Examples of appropriate acids include, but are not limited to, tartaric, diacetyltartaric, dibenzoyltartaric, ditoluoyltartaric, and camphorsulfonic acid. The separation of the mixture of diastereoisomers by crystallization followed by liberation of the optically active bases from these salts affords separation of the isomers. Another method involves synthesis of covalent diastereoisomeric molecules by reacting disclosed compounds with an optically pure acid in an activated form or an optically pure isocyanate. The synthesized diastereoisomers can be separated by conventional means such as chromatography, distillation, crystallization or sublimation, and then hydrolyzed to deliver the enantiomerically enriched compound. Optically active compounds can also be obtained by using active starting materials. In some embodiments, these isomers can be in the form of a free acid, a free base, an ester or a salt.

In any embodiments, the pharmaceutically acceptable form is a tautomer. As used herein, the term "tautomer" is a type of isomer that includes two or more interconvertible compounds resulting from at least one formal migration of a hydrogen atom and at least one change in valency (e.g., a single bond to a double bond, a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. Exemplary tautomerizations include, but are not limited to, keto-to-enol; amide-to-imide; lactam-to-lactim; enamine-to-imine; and enamine-to-(a different) enamine tautomerizations. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The disclosure also embraces pharmaceutically acceptable forms that are "isotopically labeled derivatives" which are compounds that are identical to those recited herein, except that one or more atoms are replaced by an atom having an atomic mass or mass number different from the atomic mass or mass number usually found in nature. Examples of isotopes that can be incorporated into disclosed compounds include isotopes of hydrogen, carbon, nitrogen, oxygen, phosphorus, fluorine and chlorine, such as $^2H$, $^3H$, $^{13}C$ $^{14}C$, $^{15}N$, $^{18}O$, $^{17}O$, $^{31}P$, $^{32}P$, $^{35}S$, $^{18}F$, and $^{36}Cl$, respectively. Certain isotopically-labeled disclosed compounds (e.g., those labeled with $^3H$ and $^{14}C$) are useful in compound and/or substrate tissue distribution assays. Tritiated (i.e., $^3H$) and carbon-14 (i.e., $^{14}C$) isotopes can allow for ease of preparation and detectability. Further, substitution with heavier isotopes such as deuterium (i.e., $^2H$) can afford certain therapeutic advantages resulting from greater metabolic stability (e.g., increased in vivo half-life or reduced dosage requirements). Isotopically labeled disclosed compounds can generally be prepared by substituting an isotopically labeled reagent for a non-isotopically labeled reagent. In some embodiments, provided herein are compounds that can also contain unnatural proportions of atomic isotopes at one or more of atoms that constitute such compounds. All isotopic variations of the compounds as disclosed herein, whether radioactive or not, are encompassed within the scope of the present disclosure. In some embodiments, radiolabeled compounds are useful for studying metabolism and/or tissue distribution of the compounds or to alter the rate or path of metabolism or other aspects of biological functioning.

"Pharmaceutically acceptable carrier" or "pharmaceutically acceptable excipient" includes any and all solvents, dispersion media, coatings, antibacterial and antifungal agents, isotonic and absorption delaying agents and the like. The pharmaceutically acceptable carrier or excipient does not destroy the pharmacological activity of the disclosed compound and is nontoxic when administered in doses sufficient to deliver a therapeutic amount of the compound. The use of such media and agents for pharmaceutically active substances is well known in the art. Except insofar as any conventional media or agent is incompatible with the active ingredient, its use in the therapeutic compositions as disclosed herein is contemplated. Non-limiting examples of pharmaceutically acceptable carriers and excipients include sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols, such as polyethylene glycol and propylene glycol; esters such as ethyl oleate and ethyl laurate; agar; buffering agents such as magnesium hydroxide and aluminum hydroxide; alginic acid; isotonic saline; Ringer's solution; ethyl alcohol; phosphate buffer solutions; non-toxic compatible lubricants such as sodium lauryl sulfate and magnesium stearate; coloring agents; releasing agents; coating agents; sweetening, flavoring and perfuming agents; preservatives; antioxidants; ion exchangers; alumina; aluminum stearate; lecithin; self emulsifying drug delivery systems (SEDDS) such as d-atocopherol polyethyleneglycol 1000 succinate; surfactants used in pharmaceutical dosage forms such as Tweens or other similar polymeric delivery matrices; serum proteins such as human serum albumin; glycine; sorbic acid; potassium sorbate; partial glyceride mixtures of saturated vegetable fatty acids; water, salts or electrolytes such as protamine sulfate, disodium hydrogen phosphate, potassium hydrogen phosphate, sodium chloride, and zinc salts; colloidal silica; magnesium trisilicate; polyvinyl pyrrolidone; cellulose-based substances; polyacrylates; waxes; and polyethylene-polyoxypropylene-block polymers. Cyclodextrins such as α-, β-, and γ-cyclodextrin, or chemically modified derivatives such as hydroxyalkylcyclodextrins, including 2- and 3-hydroxypropyl-cyclodextrins, or other solubilized derivatives can also be used to enhance delivery of compounds described herein.

Definitions of specific functional groups and chemical terms are described in more detail below. The chemical elements are identified in accordance with the Periodic Table of the Elements, CAS version, Handbook of Chemistry and Physics, 75th ed., inside cover, and specific functional groups are generally defined as described therein. Additionally, general principles of organic chemistry, as well as specific functional moieties and reactivity, are described in *Organic Chemistry*, Thomas Sorrell, University Science Books, Sansalito, 1999; Smith and March *March's Advanced Organic Chemistry,* 5th ed., John Wiley & Sons, Inc., New York, 2001; Larock, *Comprehensive Organic Transformations*, VCH Publishers, Inc., New York, 1989; and Carruthers, *Some Modern Methods of Organic Synthesis,* 3rd ed., Cambridge University Press, Cambridge, 1987.

Recitation of ranges of values herein merely serve as a shorthand method of referring individually to each separate value and sub-range falling within the range, unless otherwise indicated herein, and each separate value and sub-range is incorporated into the specification as if it were individually recited herein. For example, "$C_{1-6}$ alkyl" will be understood to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl. Likewise, 1-4 substituents will be understood to encompass 1, 2, 3, 4, 1-2, 1-3, 1-4, 2-3, 2-4 or 3-4 substituents. Hence, it will be understood that recitation of a range of values herein supports each individual value and subrange encompassed by the range and that the inventors contemplated and were in possession of each such individual value and subrange.

"Alkyl" refers to a straight or branched hydrocarbon chain radical consisting solely of carbon and hydrogen atoms, containing no unsaturation, having from one to ten carbon atoms (e.g., $C_{1-10}$ alkyl). Whenever it appears herein, a numerical range such as "1 to 10" refers to each integer in the given range; e.g., "1 to 10 carbon atoms" means that the alkyl group can consist of 1, 2, 3, 4, 5, 6, 7, 8, 9, or 10 carbon atoms, although the present definition also covers the occurrence of the term "alkyl" where no numerical range is designated. In some embodiments, alkyl groups have 1 to 10, 1 to 8, 1 to 6, or 1 to 3 carbon atoms. Representative saturated straight chain alkyls include, but are not limited to, methyl, ethyl, n-propyl, n-butyl, n-pentyl, and n-hexyl groups; while saturated branched alkyls include, but are not limited to, isopropyl, sec-butyl, isobutyl, tert-butyl, isopentyl, 2-methylbutyl, 3-methylbutyl, 2-methylpentyl, 3-methylpentyl, 4-methylpentyl, 2methylhexyl, 3-methylhexyl, 4-methylhexyl, 5-methylhexyl, 2,3-dimethylbutyl, and the like. The alkyl is attached to the parent molecule by a single bond. Unless stated otherwise in the specification, an alkyl group may be optionally substituted by one or more of substituents disclosed herein. In a non-limiting embodiment, a substituted alkyl can be selected from fluoromethyl, difluoromethyl, trifluoromethyl, 2-fluoroethyl, 3-fluoropropyl, hydroxymethyl, 2-hydroxyethyl, 3hydroxypropyl, benzyl, and phenethyl.

"Alkenyl" refers to a straight or branched hydrocarbon chain radical group consisting solely of carbon and hydrogen atoms, containing at least one double bond, and having from two to ten carbon atoms (i.e., $C_{2-10}$ alkenyl). Whenever it appears herein, a numerical range such as "2 to 10" refers to each integer in the given range; e.g., "2 to 10 carbon atoms" means that the alkenyl group can consist of 2 carbon atoms, 3 carbon atoms, etc., up to and including 10 carbon atoms. In any embodiments, an alkenyl comprises two to eight carbon atoms. In other embodiments, an alkenyl comprises two to six carbon atoms (e.g., $C_{2-6}$ alkenyl). The alkenyl is attached to the parent molecular structure by a single bond, for example, ethenyl (i.e., vinyl), prop-1-enyl (i.e., allyl), but-1-enyl, pent-1-enyl, penta-1,4-dienyl, and the like. The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), 2-methylprop-2-enyl ($C_4$), butadienyl ($C_4$) and the like. Examples of $C_{2-6}$ alkenyl groups include the aforementioned $C_{2-4}$ alkenyl groups as well as pentenyl ($C_5$), pentadienyl ($C_5$), hexenyl ($C_6$), 2,3-dimethyl-2-butenyl ($C_6$) and the like. Additional examples of alkenyl include heptenyl ($C_7$), octenyl ($C_8$), octatrienyl ($C_8$) and the like. Unless stated otherwise in the specification, an alkenyl group may be optionally substituted by one or more of substituents disclosed herein.

"Alkynyl" refers to a straight or branched hydrocarbon chain radical group consisting solely of carbon and hydrogen atoms, containing at least one triple bond, having from two to ten carbon atoms (i.e., $C_{2-10}$ alkynyl). Whenever it appears herein, a numerical range such as "2 to 10" refers to each integer in the given range; e.g., "2 to 10 carbon atoms" means that the alkynyl group can consist of 2 carbon atoms, 3 carbon atoms, etc., up to and including 10 carbon atoms. In any embodiments, an alkynyl comprises two to eight carbon atoms. In other embodiments, an alkynyl has two to six carbon atoms (e.g., $C_{2-6}$ alkynyl). The alkynyl is attached to the parent molecular structure by a single bond, for example, ethynyl, propynyl, butynyl, pentynyl, 3-methyl-4-pentynyl, hexynyl, and the like. Unless stated otherwise in the specification, an alkynyl group may be optionally substituted by one or more of substituents disclosed herein.

"Alkoxy" refers to the group —O-alkyl, including from 1 to 10 carbon atoms of a straight, branched, saturated cyclic configuration and combinations thereof, attached to the parent molecular structure through an oxygen. Examples include methoxy, ethoxy, propoxy, isopropoxy, butoxy, tbutoxy, pentoxy, cyclopropyloxy, cyclohexyloxy and the like. "Lower alkoxy" refers to alkoxy groups containing one to six carbons. In some embodiments, $C_{1-4}$alkoxy is an alkoxy group which encompasses both straight and branched chain alkyls of from 1 to 4 carbon atoms. Unless stated otherwise in the specification, an alkoxy group may be optionally substituted by one or more of substituents disclosed herein. The terms "alkenoxy" and "alkynoxy" mirror the above description of "alkoxy" wherein the prefix "alk" is replaced with "alken" or "alkyn" respectively, and the parent "alkenyl" or "alkynyl" terms are as described herein.

"Aromatic" or "aryl" refers to a radical with 6 to 14 ring atoms (e.g., $C_{6-14}$ aromatic or $C_6$14 aryl) which has at least one ring having a conjugated pi electron system which is carbocyclic (e.g., phenyl, fluorenyl, and naphthyl). In some embodiments, the aryl is a $C_{6-10}$ aryl group. For example, bivalent radicals formed from substituted benzene derivatives and having the free valences at ring atoms are named as substituted phenylene radicals. In other embodiments, bivalent radicals derived from univalent polycyclic hydrocarbon radicals whose names end in "-yl" by removal of one hydrogen atom from the carbon atom with the free valence are named by adding "idene" to the name of the corresponding univalent radical, e.g., a naphthyl group with two points of attachment is termed naphthylidene. Whenever it appears herein, a numerical range such as "6 to 14 aryl" refers to each integer in the given range; e.g., "6 to 14 ring atoms" means that the aryl group can consist of 6 ring atoms, 7 ring atoms, etc., up to and including 14 ring atoms. The term includes monocyclic or fused-ring polycyclic (i.e., rings which share adjacent pairs of ring atoms) groups. Polycyclic aryl groups include bicycles, tricycles, tetracycles, and the like. In a multi-ring group, only one ring is required to be aromatic, so groups such as indanyl are encompassed by the aryl definition. Non-limiting examples of aryl groups include phenyl, phenalenyl, naphthalenyl, tetrahydronaphthyl, phenanthrenyl, anthracenyl, fluorenyl, indolyl, indanyl, and the like. Unless stated otherwise in the specification, an aryl group may be optionally substituted by one or more of substituents disclosed herein.

"Cycloalkyl" and "carbocyclyl" each refer to a monocyclic or polycyclic radical that contains only carbon and hydrogen, and can be saturated or partially unsaturated. Partially unsaturated cycloalkyl groups can be termed "cycloalkenyl" if the carbocycle contains at least one double bond, or "cycloalkynyl" if the carbocycle contains at least one triple bond. Cycloalkyl groups include groups having from 3 to 13 ring atoms (i.e., $C_{3-13}$ cycloalkyl). Whenever it appears herein, a numerical range such as "3 to 10" refers to each integer in the given range; e.g., "3 to 13 carbon atoms" means that the cycloalkyl group can consist of 3 carbon atoms, 4 carbon atoms, 5 carbon atoms, etc., up to and including 13 carbon atoms. The term "cycloalkyl" also includes bridged and spiro-fused cyclic structures containing no heteroatoms. The term also includes monocyclic or fused-ring polycyclic (i.e., rings which share adjacent pairs of ring atoms) groups. Polycyclic aryl groups include bicycles, tricycles, tetracycles, and the like. In some embodiments, "cycloalkyl" can be a $C_{3-8}$ cycloalkyl radical. In some embodiments, "cycloalkyl" can be a $C_{3-5}$ cycloalkyl radical. Illustrative examples of cycloalkyl groups include, but are not limited to the following moieties: $C_{3-6}$ carbocyclyl groups include, without limitation, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$) and the like. Examples of $C_{3-7}$ carbocyclyl groups include norbornyl ($C_7$). Examples of $C_{3-8}$ carbocyclyl groups include the aforementioned $C_{3-7}$ carbocyclyl groups as well as cycloheptyl($C_7$), cycloheptadienyl ($C_7$), cycloheptatrienyl ($C_7$), cyclooctyl ($C_8$), bicyclo[2.2.1]heptanyl, bicyclo [2.2.2]octanyl, and the like. Examples of $C_{3-13}$ carbocyclyl groups include the aforementioned $C_{3-8}$ carbocyclyl groups as well as octahydro-1H indenyl, decahydronaphthalenyl, spiro[4.5]decanyl and the like. Unless stated otherwise in the specification, a cycloalkyl group may be optionally substituted by one or more of substituents disclosed herein. The terms "cycloalkenyl" and "cycloalkynyl" mirror the above description of "cycloalkyl" wherein the prefix "alk" is replaced with "alken" or "alkyn" respectively, and the parent "alkenyl" or "alkynyl" terms are as described herein. For example, a cycloalkenyl group can have 3 to 13 ring atoms, such as 5 to 8 ring atoms. In some embodiments, a cycloalkynyl group can have 5 to 13 ring atoms.

"Halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof, preferably substituted with one, two, or three halo groups. For example, the terms "fluoroalkyl" and "fluoroalkoxy" include haloalkyl and haloalkoxy groups, respectively, in which the halo is fluorine, such as, but not limited to, trifluoromethyl, difluoromethyl, 2,2,2trifluoroethyl, 1-fluoromethyl-2-fluoroethyl, —O—$CHF_2$, and the like. Each of the alkyl, alkenyl, alkynyl and alkoxy groups are as defined herein and can be optionally further substituted as defined herein.

"Heteroaryl" or, alternatively, "heteroaromatic" refers to a refers to a radical of a 5-18 membered monocyclic or polycyclic (e.g., bicyclic, tricyclic, tetracyclic and the like) aromatic ring system (e.g., having 6, 10 or 14 $\pi$ electrons shared in a cyclic array) having one or more ring carbon atoms and 1-6 ring heteroatoms provided in the aromatic ring system, wherein each heteroatom is independently selected from nitrogen, oxygen, phosphorous and sulfur ("5-18 membered heteroaryl"). Heteroaryl polycyclic ring systems can include one or more heteroatoms in one or both rings. Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms. In some instances, a heteroaryl can have 5 to 14 ring atoms. In some embodiments, the heteroaryl has, for example, bivalent radicals derived from univalent heteroaryl radicals whose names end in "-yl" by removal of one hydrogen atom from the atom with the free valence are named by adding "-ene" to the name of the corresponding univalent radical, e.g., a pyridyl group with two points of attachment is a pyridylene.

For example, an N-containing "heteroaromatic" or "heteroaryl" moiety refers to an aromatic group in which at least one of the skeletal atoms of the ring is a nitrogen atom. One or more heteroatom(s) in the heteroaryl radical can be optionally oxidized. One or more nitrogen atoms, if present, can also be optionally quaternized. Heteroaryl also includes ring systems substituted with one or more nitrogen oxide (—O—) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocyclyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having one or more ring carbon atoms and 1-4 ring heteroatoms provided in the aromatic ring system, wherein each heteroatom is independently selected from nitrogen, oxygen, phosphorous, and sulfur ("5-10 membered heteroaryl"). In some embodiments, a heteroaryl group is a 5-8 membered aromatic ring system having one or more ring carbon atoms and 1-4 ring heteroatoms provided in the aromatic ring system, wherein each heteroatom is independently selected from nitrogen, oxygen, phosphorous, and sulfur ("5-8 membered heteroaryl"). In some embodiments, a heteroaryl group is a 5-6 membered aromatic ring system having one or more ring carbon atoms and 1-4 ring heteroatoms provided in the aromatic ring system, wherein each heteroatom is independently selected from nitrogen, oxygen, phosphorous, and sulfur ("5-6 membered heteroaryl"). In some embodiments, the 5-6 membered heteroaryl has 1-3 ring heteroatoms independently selected from nitrogen, oxygen, phosphorous, and sulfur. In some embodiments, the 5-6 membered heteroaryl has 1-2 ring heteroatoms independently selected from nitrogen, oxygen, phosphorous, and sulfur. In some embodiments, the 5-6 membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4] oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzopyranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno [2,3-d]pyrimidinyl, 5,6-dihydrobenzo[h]quinazolinyl, 5,6-dihydrobenzo[h]cinnolinyl, 6,7-dihydro-5H benzo[6,7]cyclohepta[1,2-c]pyridazinyl, dibenzofuranyl, dibenzothiophenyl, furanyl, furazanyl, furanonyl, furo [3,2-c]pyridinyl, 5,6,7,8,9,10-hexahydrocyclocta[d] pyrimidinyl, 5,6,7,8,9,10-hexahydrocycloocta[d] pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d] pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo [4,5] thieno [2,3-d]pyrimidinyl, 6,7,8,9-tetrahydro-5H-cyclohepta[4,5]thieno [2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e., thienyl). Unless stated otherwise in the specification, a heteroaryl group may be optionally substituted by one or more of substituents disclosed herein.

"Heterocyclyl", "heterocycloalkyl" or "heterocarbocyclyl" each refer to any 3 to 18-membered non-aromatic radical monocyclic or polycyclic moiety comprising at least one carbon atom and at least one heteroatom selected from nitrogen, oxygen, phosphorous and sulfur. A heterocyclyl group can be a monocyclic, bicyclic, tricyclic or tetracyclic ring system, wherein the polycyclic ring systems can be a fused, bridged or spiro ring system. Heterocyclyl polycyclic ring systems can include one or more heteroatoms in one or both rings. A heterocyclyl group can be saturated or partially unsaturated. Partially unsaturated heterocycloalkyl groups can be termed "heterocycloalkenyl" if the heterocyclyl contains at least one double bond, or "heterocycloalkynyl" if the heterocyclyl contains at least one triple bond. Whenever it appears herein, a numerical range such as "5 to 18" refers to each integer in the given range; e.g., "5 to 18 ring atoms" means that the heterocyclyl group can consist of 5 ring atoms, 6 ring atoms, etc., up to and including 18 ring atoms. For example, bivalent radicals derived from univalent heterocyclyl radicals whose names end in "-yl" by removal of one hydrogen atom from the atom with the free valence are named by adding "-ene" to the name of the corresponding univalent radical, e.g., a piperidine group with two points of attachment is a piperidylene.

An N-containing heterocyclyl moiety refers to a non-aromatic group in which at least one of the ring atoms is a nitrogen atom. The heteroatom(s) in the heterocyclyl radical can be optionally oxidized. One or more nitrogen atoms, if present, can be optionally quaternized. Heterocyclyl also includes ring systems substituted with one or more nitrogen oxide (—O—) substituents, such as piperidinyl N-oxides. The heterocyclyl is attached to the parent molecular structure through any atom of any of the ring(s).

"Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment to the parent molecular structure is on the heterocyclyl ring. In some embodiments, a heterocyclyl group is a 5-14 membered non-aromatic ring system having one or more ring carbon atoms and 1-4 ring heteroatoms, wherein each heteroatom is independently selected from nitrogen, oxygen, phosphorous and sulfur ("5-14 membered heterocyclyl"). In some embodiments, a heterocyclyl group is a 3-10 membered non-aromatic ring system having one or more ring carbon atoms and 1-4 ring heteroatoms, wherein each heteroatom is independently selected from nitrogen, oxygen, phosphorous and sulfur ("3-10 membered heterocyclyl"). In some embodiments, a heterocyclyl group is a 5-8 membered non-aromatic ring system having one or more ring carbon atoms and 1-4 ring heteroatoms, wherein each heteroatom is independently selected from nitrogen, oxygen, phosphorous and sulfur ("5-8 membered heterocyclyl"). In some embodiments, a heterocyclyl group is a 5-6 membered non-aromatic ring system having one or more ring carbon atoms and 1-4 ring heteroatoms, wherein each heteroatom is independently selected from nitrogen, oxygen, phosphorous and sulfur ("5-6 membered heterocyclyl"). In some embodiments, the 5-6 membered heterocyclyl has 1-3 ring heteroatoms independently selected from nitrogen, oxygen phosphorous and sulfur. In some embodiments, the 5-6 membered heterocyclyl has 1-2 ring heteroatoms independently selected from nitrogen, oxygen, phosphorous and sulfur. In some embodiments, the 5-6 membered heterocyclyl has 1 ring heteroatom selected from nitrogen, oxygen, phosphorous and sulfur.

"Heterocyclyl" may include one or more ketone group (—C(═O)—) as part of the ring. Examples of a ketone-containing heterocycle include, without limitation, pyridin-2(1H)-one, pyrazin-2(1H)-one, pyrimidin-2(1H)-one, pyrimidin-4(3H)-one, pyridazin-3(2H)-one, pyridin-4(1H)-one, imidazolidin-2-one, 1,3-dihydro-2H-imidazol-2-one, 2,4-dihydro-3H-1,2,4-triazol-3-one, oxazol-2(3H)-one, and oxazolidin-2-one. A ketone-containing heterocyclyl is obtainable by removing a hydrogen atom from its corresponding ketone-containing heterocycle at any available N—H or C—H position.

Exemplary 3-membered heterocyclyls containing 1 heteroatom include, without limitation, azirdinyl, oxiranyl, and thiorenyl. Exemplary 4-membered heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2, 5-dione. Exemplary 5-membered heterocyclyls containing 2 heteroatoms include, without limitation, dioxolanyl, oxathiolanyl, thiazolidinyl, and dithiolanyl. Exemplary 5-membered heterocyclyls containing 3 heteroatoms include, without limitation, triazolinyl, diazolonyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6 membered heterocyclyl groups containing 2 heteroatoms include, without limitation, piperazinyl, morpholinyl, thiomorpholinyl, dithianyl, dioxanyl, and triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, benzoxanyl, benzopyrrolidinyl, benzopiperidinyl, benzoxolanyl, benzothiolanyl, benzothianyl, tetrahydroindolyl, tetrahydroquinolinyl, tetrahydroisoquinolinyl, decahydroquinolinyl, decahydroisoquinolinyl, 3-1H-benzimidazol-2-one, (1-substituted)-2-oxo-benzimidazol-3-yl, octahydrochromenyl, octahydroisochromenyl, decahydronaphthyridinyl, decahydro-1,8-naphthyridinyl, octahydropyrrolo[3,2-b]pyrrole, phenanthridinyl, indolinyl, phthalimidyl, naphthalimidyl, chromanyl, chromenyl, 1H-benzo[e] [1,4]diazepinyl, 1,4,5,7-tetrahydropyrano[3,4-b]pyrrolyl, 5,6-dihydro-4H-furo[3,2-b]pyrrolyl, 6,7-dihydro-5H-furo [3,2-b]pyranyl, 5,7-dihydro-4H-thieno [2,3-c]pyranyl, 2,3-dihydro-1H-pyrrolo[2,3-b]pyridinyl, hydrofuro[2,3-b]pyridinyl, 4,5,6,7 tetrahydro-1H-pyrrolo[2,3-b]pyridinyl, 4,5,6,7-tetrahydrofuro [3,2-c]pyridinyl, 4,5,6,7-tetrahydrothieno[3,2-b]pyridinyl, 1,2,3,4-tetrahydro-1,6-naphthyridinyl, and the like.

Unless stated otherwise in the specification, a heterocyclyl group may be optionally substituted by one or more of substituents disclosed herein.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

A "leaving group or atom" is any group or atom that will, under the reaction conditions, cleave from the starting material, thus promoting reaction at a specified site. Suitable non-limiting examples of such groups unless otherwise specified include halogen atoms, mesyloxy, p-nitrobenzensulphonyloxy, trifluoromethyloxy, and tosyloxy groups.

"Protecting group" has the meaning conventionally associated with it in organic synthesis, i.e., a group that selectively blocks one or more reactive sites in a multifunctional compound such that a chemical reaction can be carried out selectively on another unprotected reactive site and such that the group can readily be removed after the selective reaction is complete. Non-limiting embodiments of functional groups that can be masked with a protecting group include an amine, hydroxy, thiol, carboxylic acid, and aldehyde. For example, a hydroxy protected form is where at least one of the hydroxy groups present in a compound is protected with a hydroxy protecting group. A variety of protecting groups are disclosed, for example, Greene's Protective Groups in Organic Synthesis, Fifth Edition, Wiley (2014), incorporated herein by reference in its entirety. For additional background information on protecting group methodologies (materials, methods and strategies for protection and deprotection) and other synthetic chemistry transformations useful in producing the compounds described herein, see in R. Larock, Comprehensive organic Transformations, VCH Publishers (1989); Greene's Protective Groups in Organic Synthesis, Fifth Edition, Wiley (2014); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995). These references are incorporated herein by reference in their entirety.

The terms "substituted" or "substitution" mean that at least one hydrogen present on a group atom (e.g., a carbon or nitrogen atom) is replaced with a permissible substituent, e.g., a substituent which upon substitution for the hydrogen results in a stable compound, e.g., a compound which does not spontaneously undergo transformation such as by rearrangement, cyclization, elimination, or other reaction. Unless otherwise indicated, a "substituted" group can have a substituent at one or more substitutable positions of the group, and when more than one position in any given structure is substituted, the substituent is either the same or different at each position. Substituents include one or more group(s) individually and independently selected from acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —$Si(R^a)_3$, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, —$N(R^a)C(NR^a)N(R^a)_2$, —$N(R^a)S(O)_tN(R^a)_2$ (where t is 1 or 2), —$P(=O)(R^a)(R^a)$, or —O—$P(=O)(OR^a)_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties (other than hydrogen) can be optionally substituted with one or more substituents (up to six, valence permitting) independently selected from OH, $NH_2$, oxo, halo, nitro, COOH, $C(O)NH_2$ or cyano. For example, a cycloalkyl substituent can have a halide substituted at one or more ring carbons, and the like. The protecting groups that can form the protective derivatives of the above substituents are known to those of skill in the art and can be found in references such as Greene and Wuts, above.

Suitable substituents include, but are not limited to, haloalkyl and trihaloalkyl, alkoxyalkyl, halophenyl, -M-heteroaryl, -M-heterocycle, -M-aryl, -M-$OR^a$, -M-$SR^a$, -M-$N(R^a)_2$, -M-$OC(O)N(R^a)_2$, -M-$C(=NR^a)N(R^a)_2$, -M-$C(=NR^a)OR^a$, -M-$P(O)(R^a)_2$, $Si(R^a)_3$, -M-$NR^aC(O)R^a$, -M-$NR^aC(O)OR^a$, -M-$C(O)R^a$, -M-$C(=S)R^a$, -M-$C(=S)NR^aR^a$, -M-$C(O)N(R^a)_2$, -M-$C(O)NR^a$-M-$N(R^a)_2$, -M-$NR^aC(NR^a)N(R^a)_2$, -M-$NR^aC(S)N(R^a)_2$, -M-$S(O)_2R^a$, -M $C(O)R^a$, -M-$OC(O)R^a$, -$MC(O)SR^a$, -M-$S(O)_2N(R^a)_2$, —C(O)-M-$C(O)R^a$, -$MCO_2R^a$, -$MC(=O)N(R^a)_2$, -M-$C(=NH)N(R^a)_2$, and -M-$OC(=NH)N(R^a)_2$ (wherein M is a $C_{1-6}$ alkyl group).

When a ring system (e.g., cycloalkyl, heterocyclyl, aryl, or heteroaryl) is substituted with several substituents varying within an expressly defined range, it is understood that the total number of substituents does not exceed the normal available valencies under the existing conditions. Thus, for example, a phenyl ring substituted with "p" substituents (where "p" ranges from 0 to 5) can have 0 to 5 substituents, whereas it is understood that a pyridinyl ring substituted with "p" substituents has several substituents ranging from 0 to 4. The maximum number of substituents that a group in the disclosed compounds can have can be easily determined. The substituted group encompasses only those combinations of substituents and variables that result in a stable or chemically feasible compound. A stable compound or chemically feasible compound is one that, among other factors, has stability sufficient to permit its preparation and detection. In some embodiments, disclosed compounds are sufficiently stable that they are not substantially altered when kept at a temperature of 40° C. or less, in the absence of moisture (e.g., less than about 10%, less than about 5%, less than about 2%, less than about 1%, or less than about 0.5%) or other chemically reactive conditions, for e.g., at least about 3 days, at least about a week, at least about 2 weeks, at least about 4 weeks, or at least about 6 weeks.

The terms "combine, combining, to combine, combination" refer to the action of adding at least one chemical substance to another chemical substance(s) either sequentially or simultaneously. In some embodiments, bringing these chemical substances together can result in transformation of the initial chemical substances into one or more different chemical substances. This transformation can occur through one or more chemical reactions, e.g., where covalent bonds are formed, broken, rearranged and the like. A non-limiting example can include hydrolysis of an ester into an alcohol and carboxylic acid which can result from the combination of the ester with a suitable base. In another non-limiting example, an aryl fluoride can be combined with an amine to provide an aryl amine through a substitution process. These terms also include changes in association of charged chemical substances and creation of charged chemical substances, such as, but not limited to, N-oxide formation, acid addition salt formation, basic addition salt formation, and the like. These terms include the creation and/or transformation of radical chemical substances and isotopically labeled chemical substances.

The terms "convert, converting, to convert, conversion" refer to a subset of "combination" and its grammatical equivalents, where the action of one or more reagents transforms one or more functional groups on a chemical substance to another functional group(s). For example, a conversion includes, but is not limited to, transforming a nitro functional group on a chemical substance to an amine with a reducing agent. Conversions also include changes in charged chemical substances, radical chemical substances and isotopically labeled chemical substances. However, the term "convert" does not include alteration of conserved bonds in disclosed genuses and compounds.

Compounds

In one aspect, the present technology relates to a compound of Formula I or Formula II:

(I)

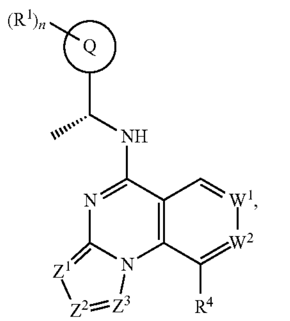

(II)

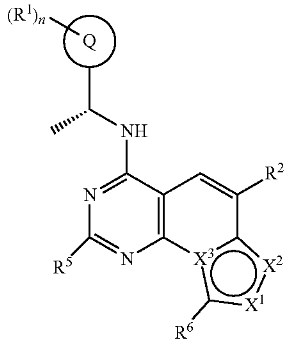

or a pharmaceutically acceptable salt thereof, and/or a tautomer thereof, and/or a stereoisomer thereof, wherein:

Q at each occurrence is independently a ring selected from phenyl or a 5- or 6-membered heteroaryl group, wherein the heteroaryl group comprises at least one carbon atom and 1-4 additional heteroatoms independently selected from nitrogen, oxygen or sulfur;

$Z^1$ is N or $CR^5$;

$Z^2$ is N or $CR^6$;

$Z^3$ is N or $CR^7$;

$W^1$ is $CR^2$ or $NR^2$;

$W^2$ is $CR^3$ when $W^1$ is $CR^2$, and $W^2$ is C(O) when $W^1$ is $NR^2$;

$X^1$ is N, $NR^7$, or $CR^9$;

$X^2$ is N, $NR^7$ or $CR^7$;

$X^3$ is N or C;

$R^1$ at each occurrence is independently hydrogen, halogen, $C_{1-6}$alkyl, halo$C_{1-6}$alkyl, $C_{1-6}$alkenyl, $C_{1-6}$alkynyl, OH, $C_{1-6}$alkyl-OH, halo$C_{1-6}$alkyl-OH, $C_{1-6}$alkoxy, halo$C_{1-6}$alkoxy, CN, —$NR^aR^b$, $C_{3-7}$cycloalkyl, $C_{3-7}$cycloalkyl-OH, $C_{3-7}$cycloalkoxy, —$S(O)_t$—$C_{1-6}$alkyl, —$S(O)_t$—$NR^aR^b$, phenyl, or 3-7-membered heterocyclyl, wherein the phenyl and 3-7-membered heterocyclyl are optionally substituted with 1-4 substituents independently selected from $C_{1-4}$alkyl, halo$C_{1-4}$alkyl, $C_{1-4}$alkoxy, halo$C_{1-4}$alkoxy, $C_{1-4}$alkyl-OH, halo$C_{1-4}$alkyl-OH, OH, halogen, CN, —$S(O)_t$—$C_{1-6}$alkyl, —$S(O)_t$—$NR^aR^b$, —$NR^aR^b$, and $C_{1-4}$alkyl-$NR^aR^b$, or two adjacent $R^1$ groups, together with the carbon atoms to which they are attached, form a 5-7-membered carbocyclic or heterocyclic ring optionally substituted with 1-3 substituents independently selected from $C_{1-4}$alkyl, halo$C_{1-4}$alkyl, $C_{1-4}$alkoxy, halo$C_{1-4}$alkoxy, $C_{1-4}$alkyl-OH, halo$C_{1-4}$alkyl-OH, OH, halogen, CN, —$NR^aR^b$, $C_{1-4}$alkyl-$NR^aR^b$, and oxo group (═O);

$R^2$ at each occurrence is independently hydrogen, halogen, CN, —$OR^a$, —$NR^aR^b$, $C_{1-6}$alkyl, halo$C_{1-6}$alkyl, $C_{2-6}$alkenyl, $C_{2-6}$alkynyl, $C_{3-7}$cycloalkyl, 3-7-membered heterocyclyl, phenyl, or 5-6-membered heteroaryl, wherein each of the $C_{1-6}$alkyl, halo$C_{1-6}$alkyl, $C_{2-6}$alkenyl, $C_{2-6}$alkynyl, $C_{3-7}$cycloalkyl, 3-7-membered heterocyclyl, phenyl, and 5-6-membered heteroaryl is optionally substituted with 1-5 $R^8$;

$R^3$ at each occurrence is independently hydrogen, halogen, $C_{1-6}$alkyl, halo$C_{1-6}$alkyl, $C_{1-6}$alkoxy, halo$C_{1-6}$ alkoxy, $C_{1-6}$alkyl-OH, CN, $C_{3-7}$cycloalkyl, $C_{3-7}$cycloalkyl-OH, $C_{3-7}$cycloalkoxy, —$NH_2$, —NH$C_{1-4}$alkyl, —N($C_{1-4}$alkyl)$_2$, or 3-7-membered cyclic amine;

$R^4$ at each occurrence is independently hydrogen, halogen, $C_{1-6}$alkyl, halo$C_{1-6}$alkyl, $C_{1-6}$alkoxy, halo$C_{1-6}$ alkoxy, CN, $NH_2$, $C_{3-7}$cycloalkyl or $C_{3-7}$cycloalkoxy;

$R^5$ at each occurrence is independently hydrogen, halogen, $C_{1-4}$alkyl, or halo$C_{1-4}$alkyl;

$R^6$ at each occurrence is independently hydrogen or $C_{1-4}$alkyl;

$R^7$ at each occurrence is independently hydrogen, $C_{1-4}$alkyl or halo$C_{1-4}$alkyl;

$R^8$ at each occurrence is independently hydrogen, halogen, $C_{1-4}$alkyl, halo$C_{1-4}$alkyl, $C_{1-4}$alkoxy, $C_{2-4}$alkenyl, $C_{2-4}$alkynyl, $C_{3-7}$cycloalkyl, $C_{3-7}$cycloalkoxy, 3-7-membered heterocyclyl, phenyl, 5-6-membered heteroaryl, —$OR^a$, —$SR^a$, $S(O)_tR^a$, —$S(O)_t$—$NR^aR^b$, —OC(O)—$R^a$, —$NR^aR^b$, —C(O)$R^a$, —C(O)$OR^a$, —OC(O)$NR^aR^b{}_2$, —C(O)$NR^aR^b$, —N($R^a$)C(O)$OR^a$, —N($R^a$)C(O)$R^a$, —N($R^a$)C(O)$NR^aR^b$, —N($R^a$)C($NR^a$)$NR^aR^b$, —N($R^a$)$S(O)_tNR^aR^b$, —P(═O)($R^a$)($R^b$), —O—P(═O)($OR^a$)($OR^b$), or oxo group (═O);

$R^9$ at each occurrence is independently hydrogen or $C_{1-4}$alkyl;

$R^a$ and $R^b$ at each occurrence are independently hydrogen, $C_{1-6}$alkyl, halo$C_{1-6}$alkyl, $C_{1-6}$alkyl-OH, $C_{1-6}$alkoxy, $C_{3-7}$cycloalkyl, 3-7-membered heterocyclyl, $C_{1-6}$alkyl-$NH_2$, $C_{1-6}$alkyl-NH$C_{1-4}$alkyl, $C_{1-6}$alkyl-N($C_{1-4}$alkyl)$_2$, or $C_{1-6}$alkyl-(3-7-membered cyclic amine), wherein each of the foregoing groups may be optionally substituted by one to three substituents independently selected from the group consisting of $C_{1-4}$alkyl, halo$C_{1-4}$ alkyl, halogen, OH, $NH_2$, $C_{1-4}$alkoxy, halo$C_{1-4}$alkoxy, CN, and —C(O)$C_{1-4}$alkyl; or $R^a$ and $R^b$, together with the nitrogen atom to which they are attached, form a saturated or unsaturated heterocyclic ring containing from three to seven ring atoms, which ring may optionally contain an additional one or two heteroatoms independently selected from the group consisting of nitrogen, oxygen and sulfur, and which ring may be optionally substituted by one to three substituents independently selected from the group consisting of $C_{1-4}$alkyl, —C(O)$C_{1-4}$alkyl, phenyl and benzyl;

n at each occurrence is independently 1, 2 or 3, and t at each occurrence is independently 1 or 2.

It will be understood by those of skill in the art that the circle in the depiction of the 5-membered ring of Formula II indicates the ring is aromatic.

In any embodiments, $Z^1$ may be N. In some embodiments, $Z^1$ is $CR^5$.

In any embodiments, $Z^2$ may be N. In some embodiments, $Z^2$ is $CR^6$.

In any embodiments, $Z^3$ may be N. In some embodiments, $Z^3$ is $CR^7$. In any embodiments, one of $Z^1$, $Z^2$ and $Z^3$ is N.

In some embodiments, the present technology relates to a compound of Formula IA:

(IA)

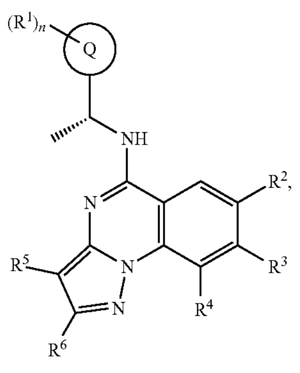

or a pharmaceutically acceptable salt thereof, and/or a tautomer thereof, and/or a stereoisomer thereof, wherein Q, $R^1$, $R^2$, $R^3$, $R^4$, $R^5$, $R^6$, $R^8$, $R^a$, $R^b$, n and t are each as defined above, or may have any of the values disclosed herein.

In some embodiments, the present technology relates to a compound of Formula IB:

(IB)

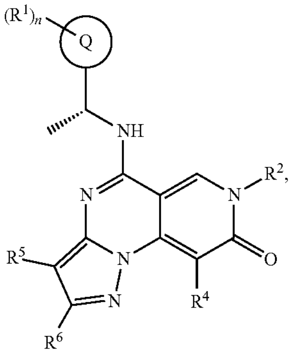

or a pharmaceutically acceptable salt thereof, and/or a tautomer thereof, and/or a stereoisomer thereof, wherein Q, $R^1$, $R^2$, $R^4$, $R^5$, $R^6$, $R^8$, $R^a$, $R^b$, n and t are each as defined above, or may have any of the values disclosed herein.

In some embodiments, the present technology relates to a compound of Formula IIA:

(IIA)

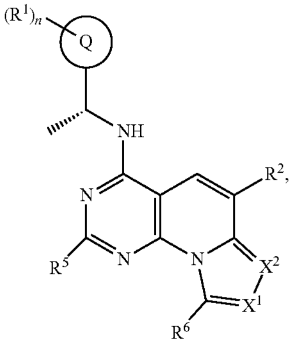

or a pharmaceutically acceptable salt thereof, and/or a tautomer thereof, and/or a stereoisomer thereof, wherein Q, $X^1$, $X^2$, $R^1$, $R^2$, $R^5$, $R^6$, $R^7$, $R^8$, $R^9$, $R^a$, $R^b$, n and t are each as defined above, or may have any of the values disclosed herein.

In some embodiments, the present technology relates to a compound of Formula IIB:

(IIB)

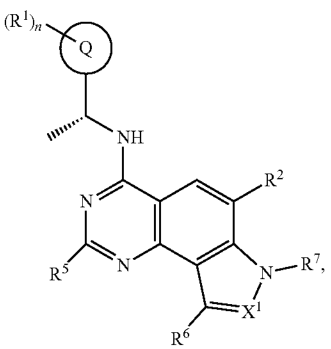

or a pharmaceutically acceptable salt thereof, and/or a tautomer thereof, and/or a stereoisomer thereof, wherein Q, $X^1$, $R^1$, $R^2$, $R^5$, $R^6$, $R^7$, $R^8$, $R^9$, $R^a$, $R^b$, n and t are each as defined above, or may have any of the values disclosed herein.

In some embodiments, the present technology relates to a compound of Formula IIC:

(IIC)

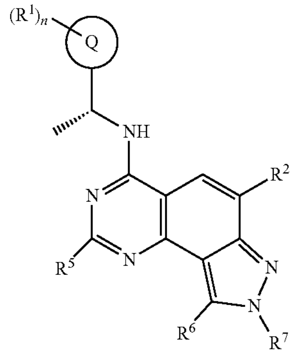

or a pharmaceutically acceptable salt thereof, and/or a tautomer thereof, and/or a stereoisomer thereof, wherein Q, $R^1$, $R^2$, $R^5$, $R^6$, $R^7$, $R^8$, n, and t are defined as above or may have any value disclosed herein.

In any embodiments of the compounds herein (including but not limited to compounds of Formulas I, IA, IB, II, IIA, IIB, or IIC), Q at each occurrence may be phenyl. In certain other embodiments, Q at each occurrence is independently a 5-membered heteroaryl group. In yet other embodiments, Q at each occurrence is independently a 6-membered heteroaryl group. In yet other embodiments, Q at each occurrence is thiophenyl. In yet other embodiments, Q at each occurrence is pyridinyl.

In some embodiments, $R^1$ at each occurrence is independently hydrogen, halogen, $C_{1-6}$alkyl, halo$C_{1-6}$alkyl, —$NR^aR^b$, OH, $C_{1-6}$alkyl-OH, halo$C_{1-6}$alkyl-OH, $C_{1-6}$alkoxy, halo$C_{1-6}$alkoxy, CN, $C_{3-7}$cycloalkyl, $C_{3-7}$cycloalkyl-OH, $C_{3-7}$cycloalkoxy or —$S(O)_t$—$C_{1-6}$alkyl. In certain other embodiments, at least one $R^1$ is independently phenyl or 3-7-membered heterocyclyl, wherein the phenyl and 3-7-membered heterocyclyl are optionally substituted with 1-4 substituents independently selected from $C_{1-4}$alkyl, halo$C_{1-4}$alkyl, $C_{1-4}$alkoxy, halo$C_{1-4}$alkoxy, $C_{1-4}$alkyl-OH, halo$C_{1-4}$alkyl-OH, OH, halogen, CN, —$S(O)_t$—$C_{1-6}$alkyl, —$S(O)_t$—$NR^aR^b$, —$NR^aR^b$ and $C_{1-4}$alkyl-$NR^aR^b$. In yet other embodiments, two adjacent $R^1$ groups, together with the carbon atoms to which they are attached, form a 5-7-membered carbocyclic or heterocyclic ring optionally substituted with 1-3 substituents independently selected from $C_{1-4}$alkyl, halo$C_{1-4}$alkyl, $C_{1-4}$alkoxy, halo$C_{1-4}$alkoxy, $C_{1-4}$alkyl-OH, halo$C_{1-4}$alkyl-OH, OH, halogen, CN, —$NR^aR^b$, $C_{1-4}$alkyl-$NR^aR^b$, and oxo group (=O). In yet other embodiments, two adjacent $R^1$ groups, together with the carbon atoms to which they are attached, form a 5-6-membered carbocyclic ring optionally substituted with 1-3 substituents independently selected from $C_{1-4}$alkyl, halo$C_{1-4}$ alkyl, $C_{1-4}$alkoxy, halo$C_{1-4}$alkoxy, $C_{1-4}$alkyl-OH, halo$C_{1-4}$ alkyl-OH, OH, halogen, CN, —$NR^aR^b$, $C_{1-4}$alkyl-$NR^aR^b$ and oxo group (=O). In yet other embodiments, two adjacent $R^1$ groups, together with the carbon atoms to which they are attached, form a 5-6-membered heterocyclic ring optionally substituted with 1-3 substituents independently selected from $C_{1-4}$alkyl, halo$C_{1-4}$alkyl, $C_{1-4}$alkoxy, halo$C_{1-4}$alkoxy, $C_{1-4}$alkyl-OH, halo$C_{1-4}$alkyl-OH, OH, halogen, CN, —$NR^aR^b$, $C_{1-4}$alkyl-$NR^aR^b$ and oxo group (═O).

In some embodiments of any of the compounds herein, Q together with its substituents $(R^1)_n$,

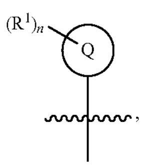

at each occurrence independently has the structure of

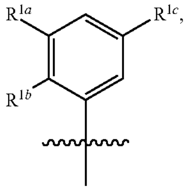

wherein: $R^{1a}$ at each occurrence is independently hydrogen, halogen, $C_{1-6}$alkyl, halo$C_{1-6}$alkyl, $C_{1-6}$alkenyl, $C_{1-6}$alkynyl, OH, $C_{1-6}$alkyl-OH, halo$C_{1-6}$alkyl-OH, $C_{1-6}$alkoxy, halo$C_{1-6}$ alkoxy, CN, $C_{3-7}$cycloalkyl, $C_{3-7}$cycloalkyl-OH, $C_{3-7}$cycloalkoxy, —$S(O)_t$—$C_{1-6}$alkyl, —$S(O)_t$—$NR^aR^b$, or 3-7-membered heterocyclyl, wherein the 3-7-membered heterocyclyl are optionally substituted with 1-4 substituents independently selected from $C_{1-4}$alkyl, halo$C_{1-4}$alkyl, $C_{1-4}$alkoxy, halo$C_{1-4}$alkoxy, $C_{1-4}$alkyl-OH, halo$C_{1-4}$alkyl-OH, OH, halogen, CN, —$S(O)_t$—$C_{1-6}$alkyl, —$S(O)_t$—$NR^aR^b$, —$NR^aR^b$, and $C_{1-4}$alkyl-$NR^aR^b$;

$R^{1b}$ at each occurrence is independently hydrogen, halogen, $C_{1-4}$alkyl or $C_{3-6}$cycloalkyl;

or $R^{1a}$ and $R^{1b}$, at each occurrence, together with the carbon atoms to which they are attached, form a 5-7-membered carbocyclic or heterocyclic ring optionally substituted with 1-3 substituents independently selected from $C_{1-4}$alkyl, halo$C_{1-4}$alkyl, $C_{1-4}$alkoxy, halo$C_{1-4}$alkoxy, $C_{1-4}$alkyl-OH, halo$C_{1-4}$alkyl-OH, OH, halogen, CN, —$NR^aR^b$, $C_{1-4}$alkyl-$NR^aR^b$, and oxo group (═O); and $R^{1c}$ at each occurrence is independently hydrogen, halogen, $NH_2$, or $C_{1-4}$alkyl.

In some embodiments, the compound of Formula (I) includes a compound of Formula IAa, (IAa)

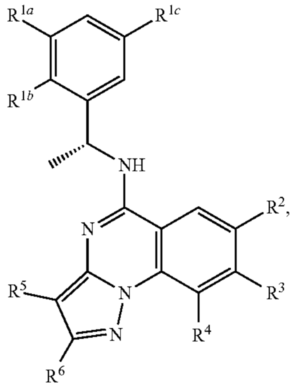

or a pharmaceutically acceptable salt thereof, and/or a tautomer thereof, and/or a stereoisomer thereof, wherein $R^{1a}$, $R^{1b}$, $R^{1c}$, $R^2$, $R^3$, $R^4$, $R^5$, $R^6$, $R^8$, $R^a$, $R^b$, and t are each as defined above, or may have any of the values disclosed herein.

In some embodiments, the compound of Formula I includes a compound of Formula IBa, (IBa)

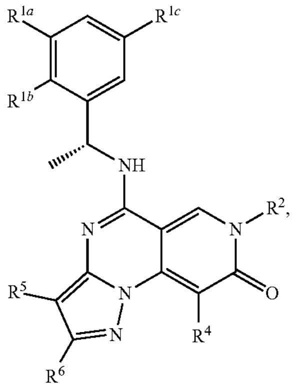

or a pharmaceutically acceptable salt thereof, and/or a tautomer thereof, and/or a stereoisomer thereof, wherein $R^{1a}$, $R^{1b}$, $R^{1c}$, $R^2$, $R^4$, $R^5$, $R^6$, $R^8$, $R^a$, $R^b$, and t are each as defined above, or may have any of the values disclosed herein.

In some embodiments, the compound of Formula (II) includes a compound of Formula IIAa, (IIAa)

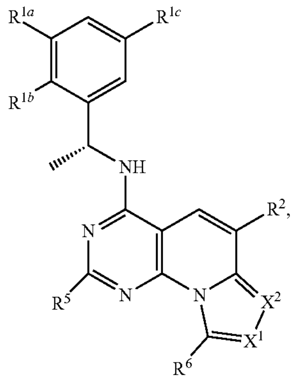

or a pharmaceutically acceptable salt thereof, and/or a tautomer thereof, and/or a stereoisomer thereof, wherein $X^1$, $X^2$, $R^{1a}$, $R^{1b}$, $R^{1c}$, $R^2$, $R^5$, $R^6$, $R^7$, $R^8$, $R^9$, $R^a$, $R^b$, and t are each as defined above, or may have any of the values disclosed herein.

In some embodiments, the compound of Formula II includes a compound of Formula IIBa, (IIBa)

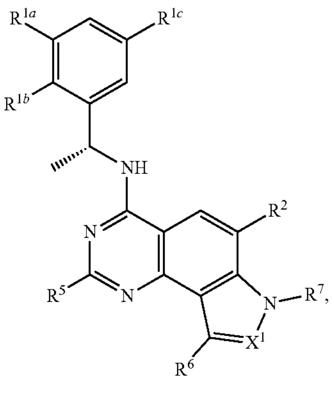

or a pharmaceutically acceptable salt thereof, and/or a tautomer thereof, and/or a stereoisomer thereof, wherein $X^1$, $R^{1a}$, $R^{1b}$, $R^{1c}$, $R^2$, $R^5$, $R^6$, $R^7$, $R^8$, $R^9$, $R^a$, $R^b$, and t are each as defined above, or may have any of the values disclosed herein.

In some embodiments, the present technology relates to a compound of Formula IICa:

(IICa)

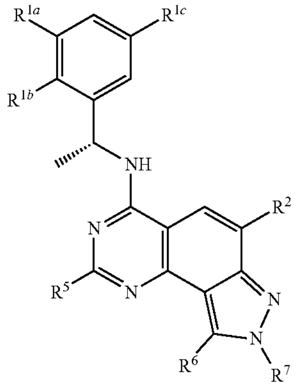

or a pharmaceutically acceptable salt thereof, and/or a tautomer thereof, and/or a stereoisomer thereof, wherein $R^{1a}$, $R^{1b}$, $R^{1c}$, $R^2$, $R^5$, $R^6$, $R^7$, $R^8$, and t are defined as above or may have any value disclosed herein.

In any embodiments, $R^{1a}$ at each occurrence is independently hydrogen, halogen, $C_{1-6}$alkyl, halo$C_{1-6}$alkyl, $C_{1-6}$alkenyl, $C_{1-6}$alkynyl, OH, $C_{1-6}$alkyl-OH, halo$C_{1-6}$alkyl-OH, $C_{1-6}$alkoxy, halo$C_{1-6}$alkoxy, CN, $C_{3-7}$cycloalkyl, $C_{3-7}$cycloalkyl-OH, $C_{3-7}$cycloalkoxy, —$S(O)_t$—$C_{1-6}$alkyl, or —$S(O)_t$—$NR^aR^b$. In certain other embodiments, $R^{1a}$ at each occurrence is independently 3-7-membered heterocyclyl optionally substituted with 1-4 substituents independently selected from $C_{1-4}$alkyl, halo$C_{1-4}$alkyl, $C_{1-4}$alkoxy, halo$C_{1-4}$ alkoxy, $C_{1-4}$alkyl-OH, halo$C_{1-4}$alkyl-OH, OH, halogen, CN, —$S(O)_t$—$C_{1-6}$alkyl, —$S(O)_t$—$NR^aR^b$, —$NR^aR^b$, and $C_{1-4}$alkyl-$NR^aR^b$. In yet other embodiments, $R^{1a}$ at each occurrence is independently $CHF_2$, $CH_2F$, $CF_3$, $CF_2CH_3$ or $CF_2CH_2OH$. In yet other embodiments, $R^{1a}$ and $R^{1b}$, at each occurrence, together with the carbon atoms to which they are attached, form a 5- or 6-membered carbocyclic ring optionally substituted with 1-3 halogen. In yet other embodiments, $R^{1a}$ and $R^{1b}$, at each occurrence, together with the carbon atoms to which they are attached, form a carbocyclic ring having the structure of

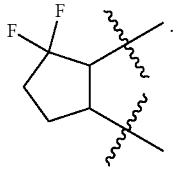 [SMILES: *C1CCC(F)(F)C1*]

In any embodiments, $R^{1b}$ at each occurrence is independently hydrogen. In certain other embodiments, $R^{1b}$ at each occurrence is independently halogen. In yet other embodiments, $R^{1b}$ at each occurrence is independently $C_{1-4}$alkyl. In yet other embodiments, $R^{1b}$ at each occurrence is independently F or methyl.

In any embodiments, $R^{1c}$ at each occurrence is independently hydrogen. In certain other embodiments, $R^{1c}$ at each occurrence is independently halogen. In yet other embodiments, $R^{1c}$ at each occurrence is independently $NH_2$. In yet other embodiments, $R^{1c}$ at each occurrence is independently $C_{1-4}$alkyl.

In any embodiments, Q together with its substituents $(R^1)_n$,

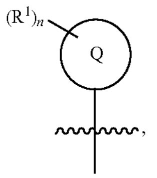

at each occurrence independently has the structure of

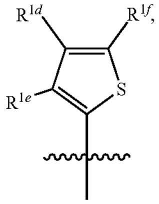

wherein:

$R^{1d}$ and $R^{1e}$ at each occurrence are independently hydrogen, halogen, $C_{1-4}$alkyl, or halo$C_{1-4}$alkyl; and $R^{1f}$ at each occurrence is independently phenyl, 5-6-membered heteroaryl, or 3-7-membered heterocyclyl, wherein the phenyl, 5-6-membered heteroaryl, and 3-7-membered heterocyclyl are optionally substituted with 1-4 substituents independently selected from $C_{1-4}$alkyl, halo$C_{1-4}$alkyl, $C_{1-4}$alkoxy, halo$C_{1-4}$alkoxy, $C_{1-4}$alkyl-OH, halo$C_{1-4}$alkyl-OH, OH, halogen, CN, —$NR^aR^b$ and $C_{1-4}$alkyl-$NR^aR^b$.

In some embodiments, the compound of Formula (I) includes a compound of Formula IAb, (IAb)

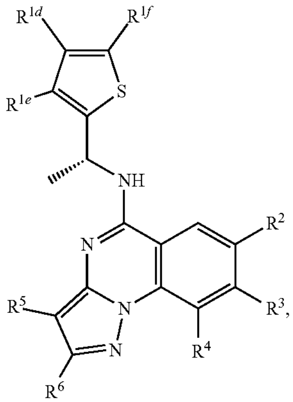

or a pharmaceutically acceptable salt thereof, and/or a tautomer thereof, and/or a stereoisomer thereof, wherein $R^{1d}$, $R^{1e}$, $R^{1f}$, $R^2$, $R^3$, $R^4$, $R^5$, $R^6$, $R^8$, $R^a$, $R^b$, and t are each as defined above, or may have any of the values disclosed herein.

In some embodiments, the compound of Formula I includes a compound of Formula IBb, (IBb)

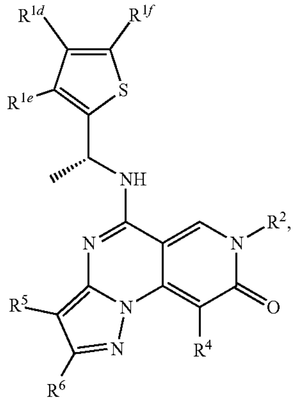

or a pharmaceutically acceptable salt thereof, and/or a tautomer thereof, and/or a stereoisomer thereof, wherein $R^{1d}$, $R^{1e}$, $R^{1f}$, $R^2$, $R^4$, $R^5$, $R^6$, $R^8$, $R^a$, $R^b$, and t are each as defined above, or may have any of the values disclosed herein.

In some embodiments, the compound of Formula I includes a compound of Formula ICb, (ICb)

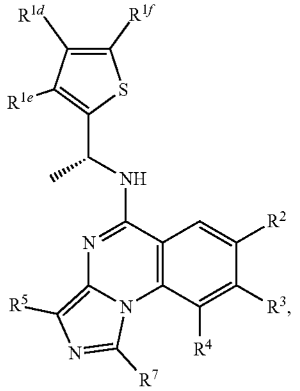

or a pharmaceutically acceptable salt thereof, and/or a tautomer thereof, and/or a stereoisomer thereof, wherein $R^{1d}$, $R^{1e}$, $R^{1f}$, $R^2$, $R^4$, $R^5$, $R^7$, $R^8$, $R^a$, $R^b$, and t are each as defined above, or may have any of the values disclosed herein.

In some embodiments, the compound of Formula I includes a compound of Formula IDb, (IDb)

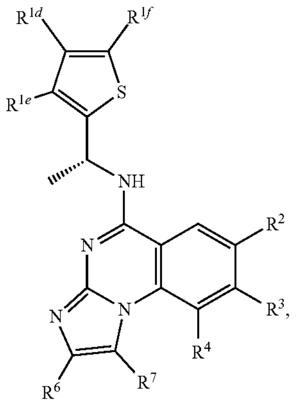

or a pharmaceutically acceptable salt thereof, and/or a tautomer thereof, and/or a stereoisomer thereof, wherein $R^{1d}$, $R^{1e}$, $R^{1f}$, $R^2$, $R^3$, $R^4$, $R^6$, $R^7$, $R^8$, $R^a$, $R^b$, and t are each as defined above, or may have any of the values disclosed herein.

In some embodiments, the compound of Formula II includes a compound of Formula (IIIb), IIAb

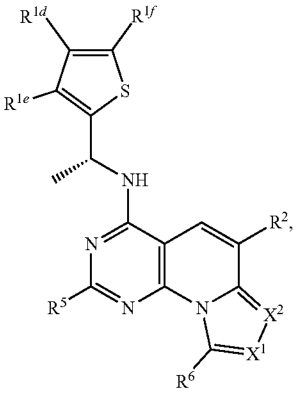

or a pharmaceutically acceptable salt thereof, and/or a tautomer thereof, and/or a stereoisomer thereof, wherein $X^1$, $X^2$, $R^{1d}$, $R^{1e}$, $R^{1f}$, $R^2$, $R^5$, $R^6$, $R^7$, $R^8$, $R^9$, $R^a$, $R^b$, and t are each as defined above, or may have any of the values disclosed herein.

In some embodiments, the compound of Formula II includes a compound of Formula IIBb, (IIBb)

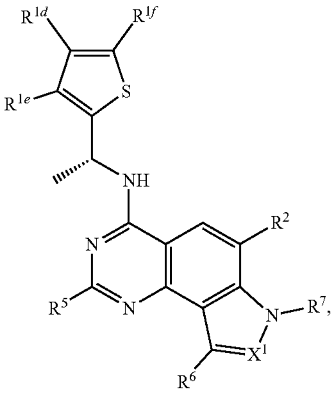

or a pharmaceutically acceptable salt thereof, and/or a tautomer thereof, and/or a stereoisomer thereof, wherein $X^1$, $R^{1d}$, $R^{1e}$, $R^{1f}$, $R^2$, $R^5$, $R^6$, $R^7$, $R^8$, $R^9$, $R^a$, $R^b$, and t are each as defined above, or may have any of the values disclosed herein.

In some embodiments, the present technology relates to a compound of Formula IICb:

(IICb)

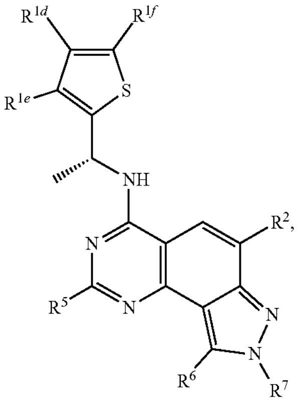

or a pharmaceutically acceptable salt thereof, and/or a tautomer thereof, and/or a stereoisomer thereof, wherein $R^{1d}$, $R^{1e}$, $R^{1f}$, $R^2$, $R^5$, $R^6$, $R^7$, $R^8$, and t are defined as above or may have any value disclosed herein.

In any embodiments, $R^{1d}$ and $R^{1e}$ at each occurrence are independently hydrogen or methyl. In certain other embodiments, $R^{1d}$ and $R^{1e}$ at each occurrence are independently hydrogen.

In any embodiments, $R^{1f}$ at each occurrence is independently phenyl optionally substituted with 1-4 substituents independently selected from $C_{1-4}$alkyl, halo$C_{1-4}$alkyl, $C_{1-4}$alkoxy, halo$C_{1-4}$alkoxy, $C_{1-4}$alkyl-OH, halo$C_{1-4}$alkyl-OH, OH, halogen, CN, —$NR^aR^b$ and $C_{1-4}$alkyl-$NR^aR^b$. In certain other embodiments, $R^{1f}$ at each occurrence is independently phenyl optionally substituted with $C_{1-4}$alkyl-$NR^aR^b$. In yet other embodiments, $R^{1f}$ at each occurrence is independently phenyl optionally substituted with $C_{1-4}$alkyl-NH—$C_{1-4}$alkyl. In yet other embodiments, $R^{1f}$ at each occurrence is independently phenyl optionally substituted with $C_{1-3}$alkyl-NH—$C_{1-3}$alkyl. In yet other embodiments, $R^{1f}$ at each occurrence is independently phenyl optionally substituted with $C_{1-2}$alkyl-NH—$C_{1-2}$alkyl. In yet other embodiments, $R^{1f}$ at each occurrence is independently phenyl optionally substituted with $C_{1-2}$alkyl-N($C_{1-2}$alkyl)-$C_{1-2}$ alkyl.

In any embodiments, $R^2$ at each occurrence is independently hydrogen, halogen, CN, —$OR^a$, —$NR^aR^b$, $C_{1-6}$alkyl, or halo$C_{1-6}$alkyl, wherein each of the $C_{1-6}$alkyl and halo$C_{1-6}$ alkyl is optionally substituted with 1-5 $R^8$. For example, $R^2$ may be tetrahydrofuranyloxy, pyrrolidinyloxy, piperidinyloxy, each optionally substituted with 1-5 $R^8$. In certain other embodiments, $R^2$ at each occurrence is independently $C_{3-7}$cycloalkyl optionally substituted with 1-5 $R^8$. For example, $R^2$ may be cyclopropyl, cyclobutyl, or cyclohexyl, each optionally substituted with 1-5 $R^8$. In yet other embodiments, $R^2$ at each occurrence is independently 3-7-membered heterocyclyl optionally substituted with 1-5 $R^8$. For example, $R^2$ may be pyrrolidinyl, tetrahydrofuranyl, morpholinyl, dihydropyranyl, tetrahydropyranyl, pyridinonyl, piperidinyl, each optionally substituted with 1-5 $R^8$. In yet other embodiments, $R^2$ at each occurrence is independently phenyl optionally substituted with 1-5 $R^8$. In yet other embodiments, $R^2$ at each occurrence is independently 5-membered heteroaryl optionally substituted with 1-5 $R^8$. In yet other embodiments, $R^2$ at each occurrence is independently 6-membered heteroaryl optionally substituted with 1-5 $R^8$. In some embodiments, $R^2$ may be substituted with 1 or 2 $R^8$.

In any embodiments, $R^3$ at each occurrence is independently hydrogen, halogen, $C_{1-6}$alkyl, halo$C_{1-6}$alkyl, or CN. In certain other embodiments, $R^3$ at each occurrence is independently $C_{1-6}$alkoxy, halo$C_{1-6}$alkoxy, or $C_{1-6}$alkyl-OH. In yet other embodiments, $R^3$ at each occurrence is independently $C_{3-7}$cycloalkyl or $C_{3-7}$cycloalkyl-OH. In yet other embodiments, $R^3$ at each occurrence is independently —$NH_2$, —$NHC_{1-4}$alkyl, —N($C_{1-4}$alkyl)$_2$, or 3-7-membered cyclic amine.

In any embodiments, $R^4$ at each occurrence is independently hydrogen. In certain other embodiments, $R^4$ at each occurrence is independently halogen or $C_{1-6}$alkyl.

In any embodiments, $R^5$ at each occurrence is independently hydrogen or $C_{1-4}$alkyl. In certain other embodiments, $R^5$ at each occurrence is independently hydrogen. In yet other embodiments, $R^5$ at each occurrence is independently methyl.

In any embodiments, $R^6$ at each occurrence is independently hydrogen. In yet other embodiments, $R^6$ at each occurrence is independently methyl.

In any embodiments (including, e.g., embodiments of Formulae II, IIA, IIAa, IIAb, IIB, IIBa, and IIBb), $X^1$ is N or $CR^9$. In some embodiments, $X^1$ is N. In certain other embodiments, $X^1$ is $CR^9$. In some embodiments, $X^1$ is $NR^7$ (provided that the 5-member ring is still aromatic, e.g., as in Formulae IIC, IICa, and IICb).

In any embodiments, $X^2$ is N or $CR^7$. In some embodiments, $X^2$ is N. In certain other embodiments, $X^2$ is $CR^7$. In some embodiments, $X^2$ is $NR^7$ (provided that the 5-member ring is aromatic, e.g., as in Formula IIB, IIBa, and 1IBb).

In any embodiments, $R^7$ at each occurrence is independently hydrogen. In certain other embodiments, $R^7$ at each occurrence is independently methyl.

In any embodiments, $R^9$ at each occurrence is independently hydrogen. In certain other embodiments, $R^9$ at each occurrence is independently methyl.

In any embodiments, $X^3$ is N. In any embodiments, $X^3$ is C.

In any embodiments, $R^8$ at each occurrence is independently hydrogen, halogen, $C_{1-4}$alkyl, halo$C_{1-4}$alkyl, or $C_{1-4}$alkoxy. In certain other embodiments, $R^8$ at each occurrence is independently $C_{3-7}$cycloalkyl or 3-7-membered heterocyclyl. In yet other embodiments, $R^8$ at each occurrence is independently phenyl or 5-6-membered heteroaryl. In yet other embodiments, $R^8$ at each occurrence is independently —$OR^a$, —$SR^a$, —$S(O)_tR^a$, —$S(O)_t$—$NR^aR^b$, —OC(O)—$R^a$, —$NR^aR^b$, —C(O)$R^a$, —C(O)O$R^a$, —OC(O)$NR^aR^b$, —C(O)$NR^aR^b$, —N($R^a$)C(O)O$R^a$, —N($R^a$)C(O)$R^a$, —N($R^a$)C(O)$NR^aR^b$, —N($R^a$)C(N$R^a$)$NR^aR^b$, —N($R^a$)$S(O)_tNR^aR^b$, —P(═O)($R^a$)($R^b$), —O—P(═O)(O$R^a$)(O$R^b$), or oxo group (═O). In yet other embodiments, $R^8$ at each occurrence is independently oxo group (═O). In yet other embodiments, $R^8$ at each occurrence is independently —$NR^aR^b$. In yet other embodiments, $R^8$ at each occurrence is independently —$NR^aR^b$, wherein said —$NR^aR^b$ is independently $NH_2$, —$NHC_{1-4}$alkyl, —N($C_{1-4}$ alkyl)$_2$, or 3-7-membered cyclic amine. In yet other embodiments, $R^8$ at each occurrence is independently —$S(O)_t$—$C_{1-4}$alkyl.

In any embodiments, the compound is selected from:

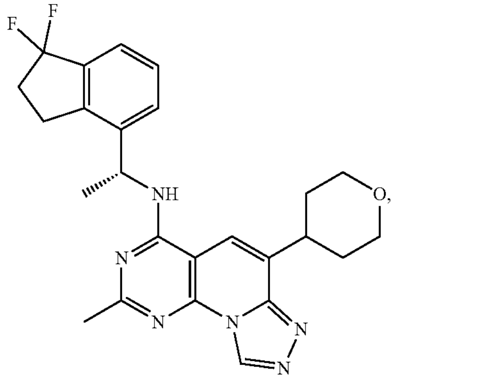

,

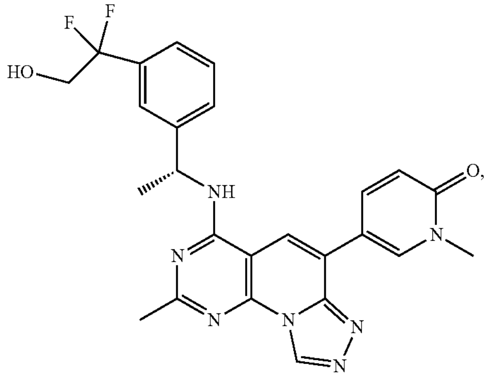

,

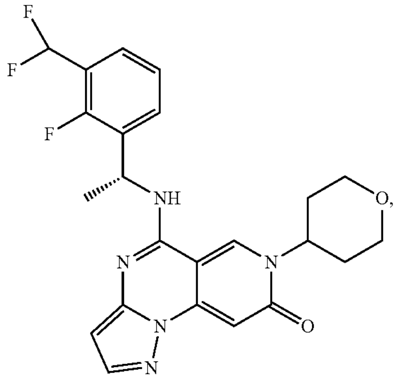

,

-continued
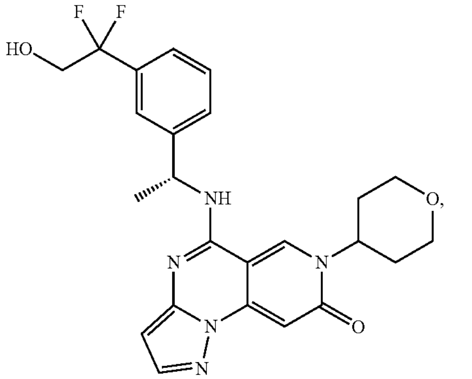
and
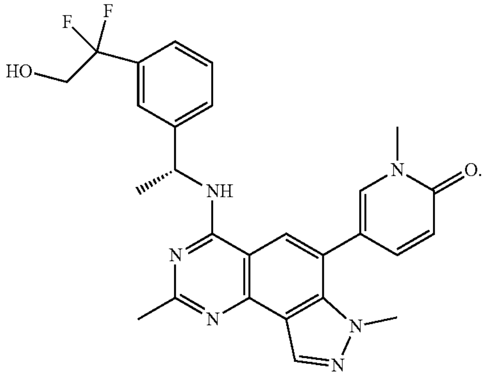
In any embodiments, the compound is selected from:
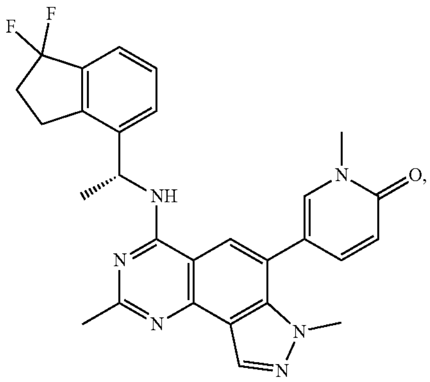
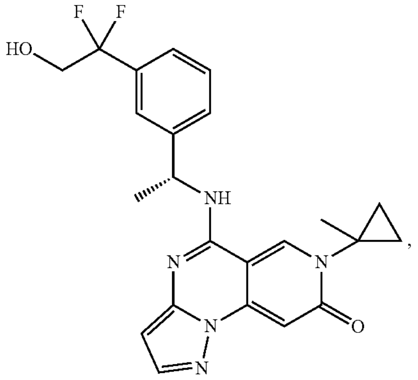
-continued
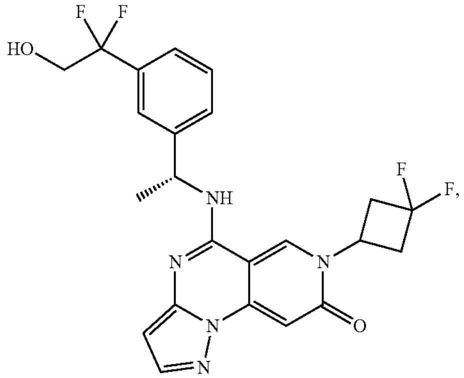
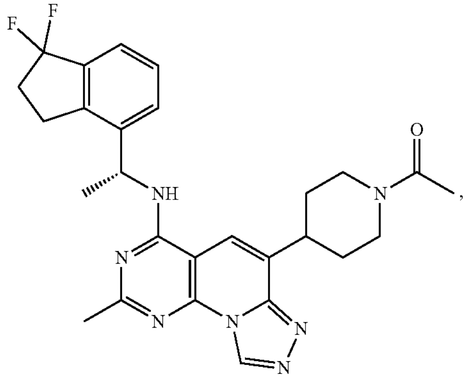
and
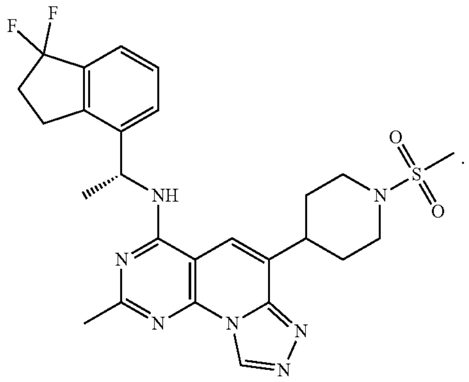
In any embodiments, the compound is selected from:
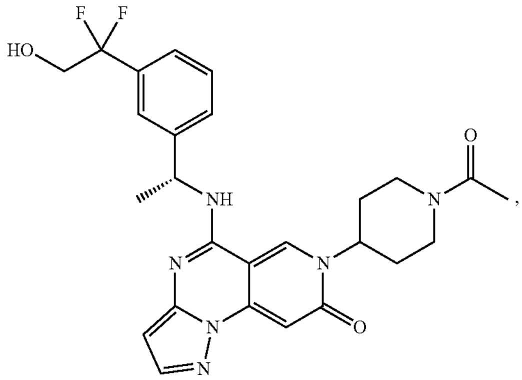

-continued

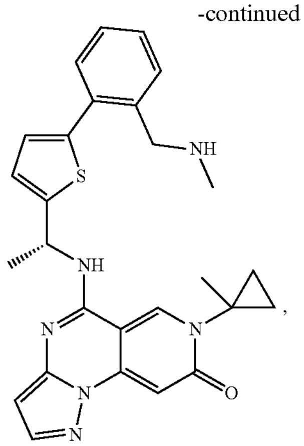

and

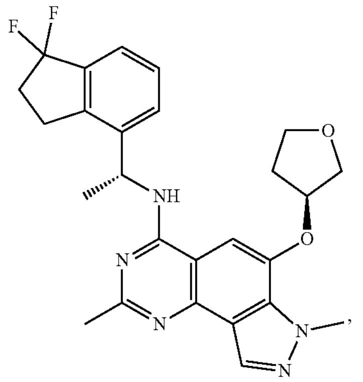

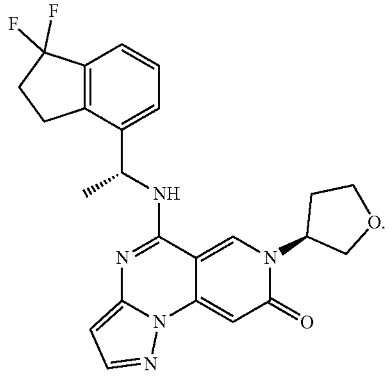

In some embodiments, the present technology relates to a compound of Formulae (I), (Ia), (Ib), (II), (IIa), (IIb), (III), (IIIa), (IIIb), (IV), (IVa), and (IVb), including each exemplified compound, wherein at least one hydrogen (H) is replaced with deuterium (D). Enriching for deuterium may afford certain therapeutic advantages, such as increasing in vivo half-life or reducing dosage requirements, or may provide a compound useful as a standard for characterization of biological samples. In some other embodiments, a compound provided herein may have an isotopic enrichment factor for each deuterium present at a site designated as a potential site of deuteration on the compound of at least 3500 (52.5% deuterium incorporation), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In another aspect, the present technology relates to a pharmaceutical composition comprising a compound disclosed herein, and a pharmaceutically acceptable carrier.

In yet another aspect, the present technology relates to a method for treating or preventing a disease or condition mediated by mammalian Ras family proteins in a subject in need thereof, comprising administering an effective amount of a compound disclosed herein to the subject.

In yet another aspect, the present technology relates to a method for treating or preventing cancer in a subject in need thereof, comprising administering an effective amount of a compound disclosed herein to the subject. In some embodiments, the cancer is breast cancer, leukemia, prostate cancer, ovarian cancer, pancreatic cancer, colon cancer, lung cancer, endometrial cancer, thyroid cancer, cholangiocarcinoma, multiple myeloma, melanoma, uterine cancer, head and neck squamous cell carcinoma, diffuse large B cell lymphoma, esophageal cancer, hepatocellular cancer, glioblastoma, renal cancer, sarcoma, bladder cancer, urothelial cancer, gastric cancer, or cervical cancer.

In yet another aspect, the present technology relates to a method for treating or preventing RASopathies caused by aberrant RAS signaling activities in a subject in need thereof, comprising administering an effective amount of a compound disclosed herein to the subject.

In yet another aspect, the present technology relates to a method for disorder or condition in a subject in need thereof, comprising administering an effective amount of a compound disclosed herein to the subject, wherein the disorder or condition is selected from neurofibromatosis type 1, Noonan syndrome, Noonan syndrome with multiple lentigines, Costello syndrome, cardiofaciocutaneous syndrome, and capillary malformation-arteriovenous syndrome.

In yet another aspect, the present technology relates to a method for treating or preventing renal dysfunction associated with fibrosis in a subject in need thereof, comprising administering an effective amount of a compound disclosed herein to the subject.

In yet another aspect, the present technology relates to a process of making a compound of Formulae (I), (Ia), (Ib), (II), (IIa), (IIb), (III), (IIIa), (IIIb), (IV), (IVa), and (IVb), including each exemplified compound and intermediate described herein.

General Synthetic Methods

The compounds of the present technology can be synthesized using the methods described herein, together with synthetic methods known in the art of synthetic organic chemistry, or by variations thereon as appreciated by those skilled in the art. Proffered methods include, but are not limited to, those exemplary schemes and working examples described below. All substituents are as defined hereinabove unless otherwise indicated. The reactions are performed in a solvent or solvent mixture appropriate to the reagents and materials employed and suitable for the transformations proposed. This will sometimes require a judgment to modify the order of synthetic steps or to select on particular process scheme over another in order to obtain a desired compound of the technology.

It will be recognized that another major consideration in the planning of any synthetic route in this field is the judicious choice of the protecting group used for protection of the reactive functional groups present in the compounds described in this technology. An authoritative account describing the many alternatives to the trained practitioner is by Greene et al., Greene's Protective Groups in Organic Synthesis, Fifth Edition, Wiley (2014). It will also be recognized that the compound names referred to in the descriptions of Schemes 1-5 are for convenience only, and do not necessarily reflect the actual chemical names of those compounds.

Scheme 1

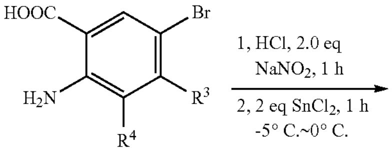

1

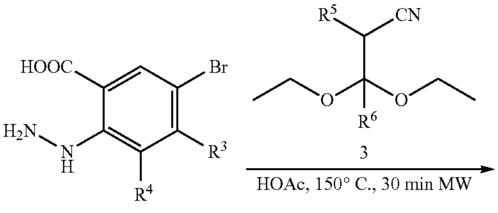

2 3

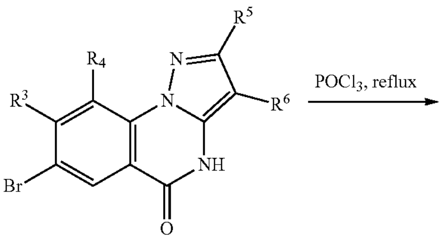

4

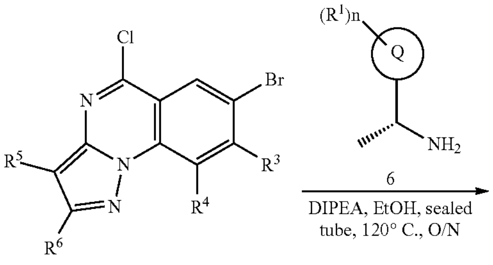

5 6

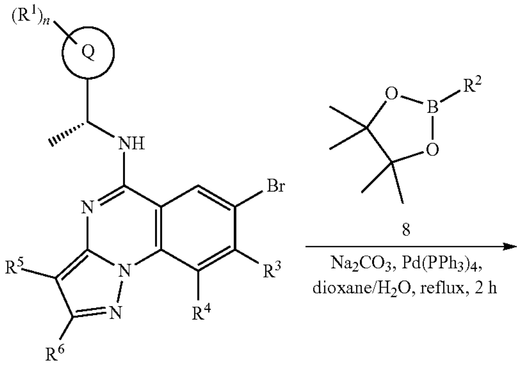

7 8

-continued

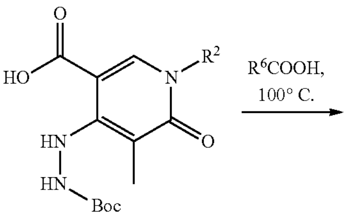

15

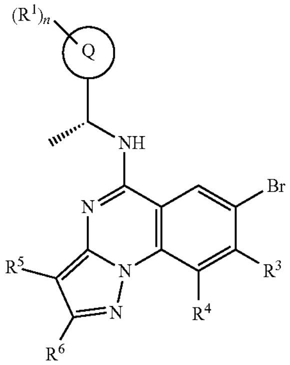

9

Scheme 1 describes the synthesis of tricyclic derivative 9. Aniline 1 is converted to phenyl hydrazine 2 under standard conditions ($NaNO_2$/HCl and $SnCl_2$). Treatment of 2 with cyano substituted acetal or ketal 3under high temperature or microwave conditions gives tricyclic core 4. Chloronation of 4 with $POCl_3$ affords 5, which undergoes nucleophilic substitution of 5 with amine 6, provides 7. Suzuki coupling reaction of 7 with $R^2$-bonic ester or acid 8, finally gives the desired compound 9.

Scheme 2

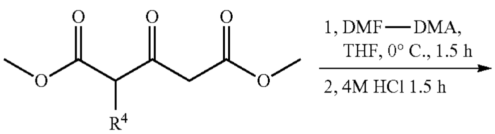

10

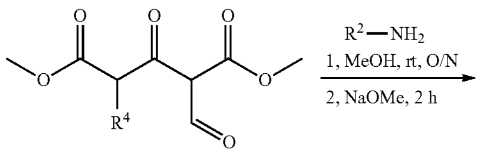

11

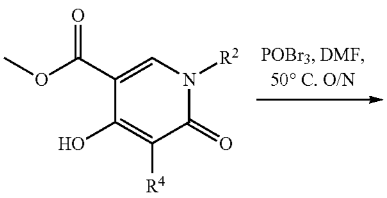

12

-continued

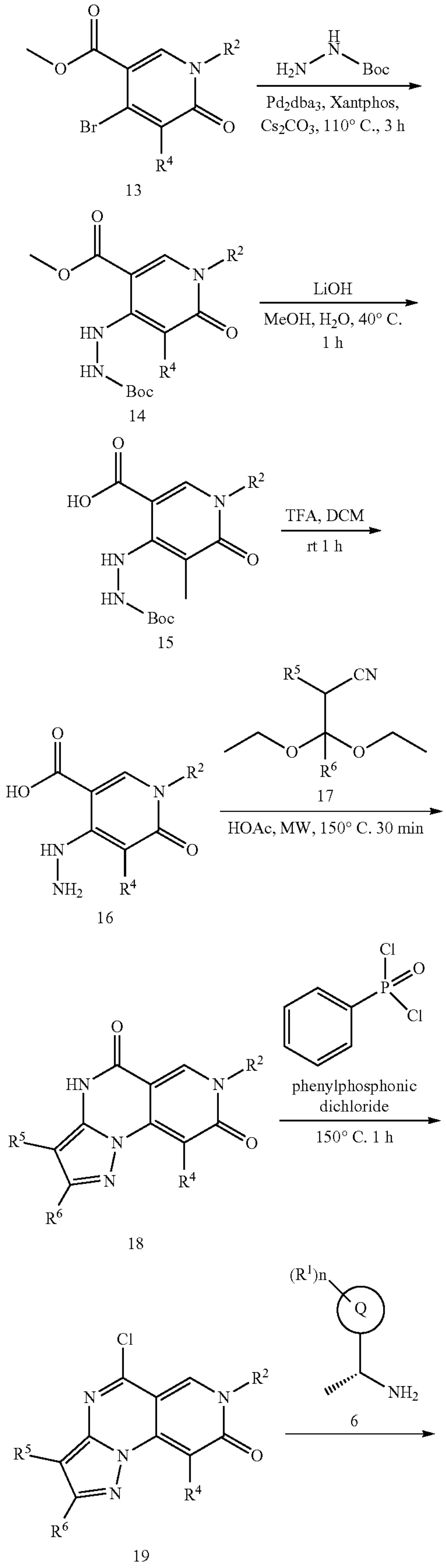

13, 14, 15, 16, 17, 18, 6, 19

-continued

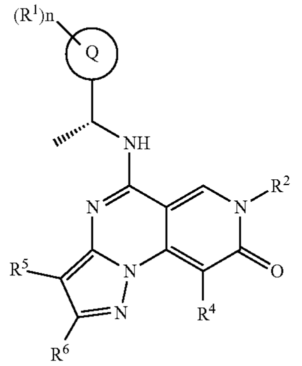

20

Scheme 2 describes a general synthetic route to the tricyclic analogs 20. Treatment of ketoacetic ester with DMF-DMA and followed by aqueous HCl, gives the aldehyde intermediate 11, which is reacted with $R^2$—$NH_2$ and subsequent reaction with NaOMe to afford hydroxypyridone 12. Conversion of 12 to bromide 13 is done under the condition of POBr3 with DMF. Boc-protected hydrazine derivative is obtained under Buckwald conditions with appropriately catalyst (e.g., Pd2(dba)$_3$/Xantphos). After base hydrolysis and de-protection of Boc group with TFA, the resulting hydrazine-acid is reacted with cyano-acetal or ketal to give rise to tricyclic core 18. Upon treatment of 18 with phenylphosphonic dichloride, the resulting chloride 19 is reacted with amine 6 to afford the desired product 20.

Scheme 3

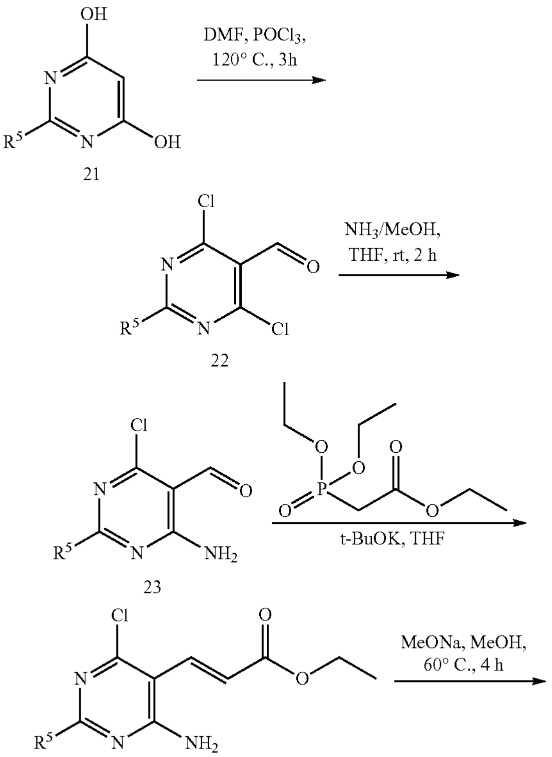

21, 22, 23, 24

-continued

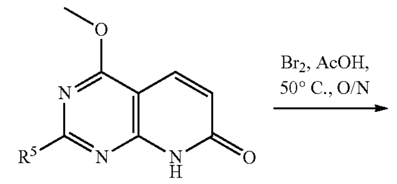

25

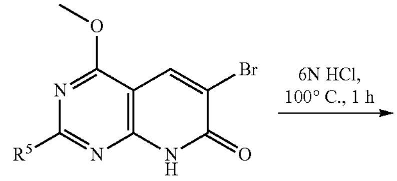

26

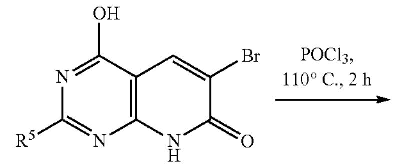

27

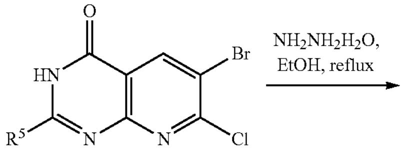

28

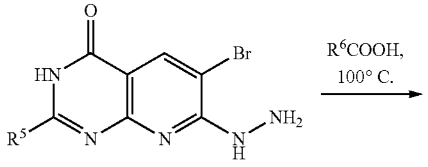

29

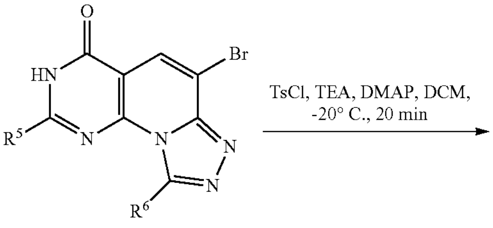

30

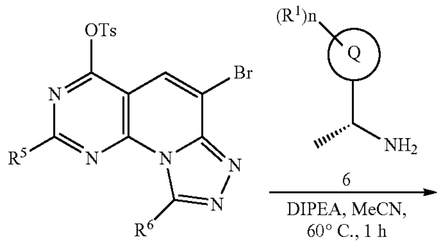

6

31

-continued

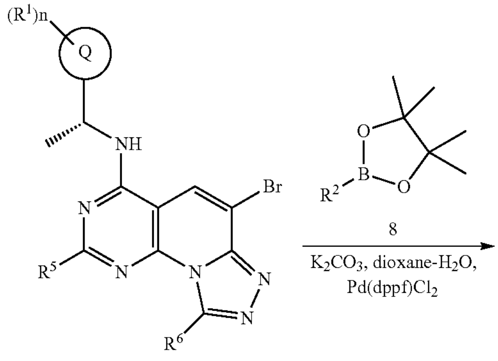

8

32

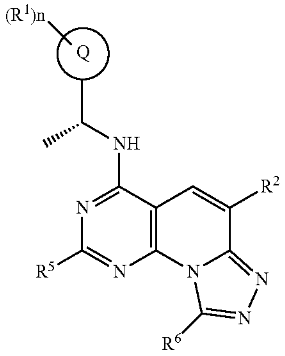

33

Scheme 3 describes a general synthetic route to the tricyclic analog 33. Treatment of substituted dihydroxypyrimidine 21 in presence of POCl3 and DMF at elevated temperature gives dichloropyrimidine aldehyde 22. Mono-nucleophilic substitution of ammonia of 22 affords 23 which undergoes Horner-Wittig reaction to afford 24. Upon treatment of 24 with NaOMe, cyclized intermediate 25 is obtained. Bromination of 25, followed by acidic cleavage of MeO group, affords 27. Selective mono-chloronation of 27 under the condition of POCl3 at elevated temperature gives rise to 28. Nucleophilic substitution of 28 with hydrazine in ethanol under reflux provides 29 which undergoes cyclization with carboxylic acid ($R_6COOH$), gives tricyclic core 30. Treatment of 30 with TsCl in the presence of base generates tosylate intermediate 31. Nucleophilic displacement of tosylate 31 with amine 6, affords intermediate 32, which can be further substituted with $R^2$ group under Suzuki coupling condition using $R^2$-boronic esters or Buckwald coupling condition using $R^2$-amine to finish the target compound 33.

Scheme 4

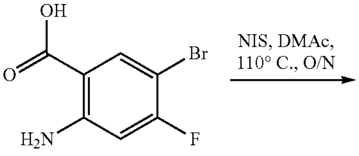

34

-continued

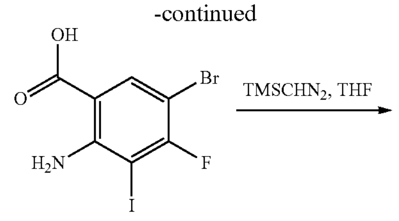

35

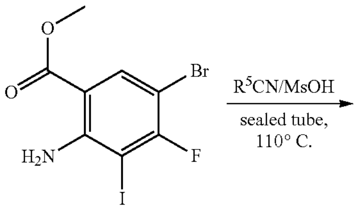

36

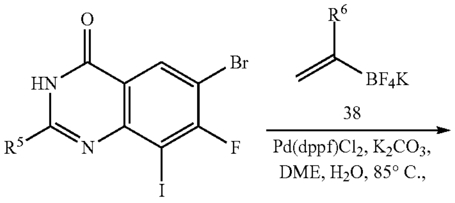

37

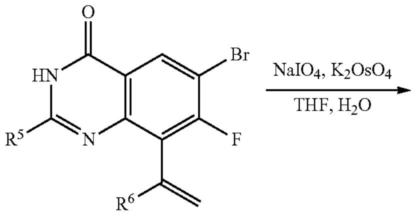

39

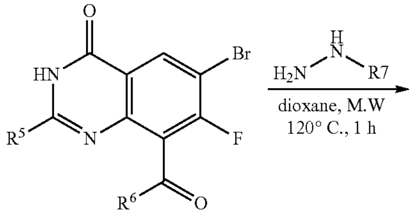

40

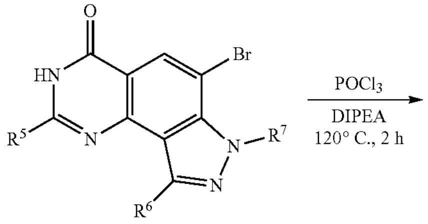

41

-continued

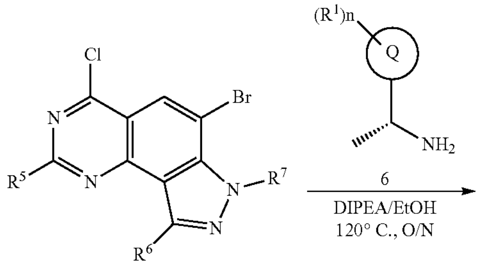

42

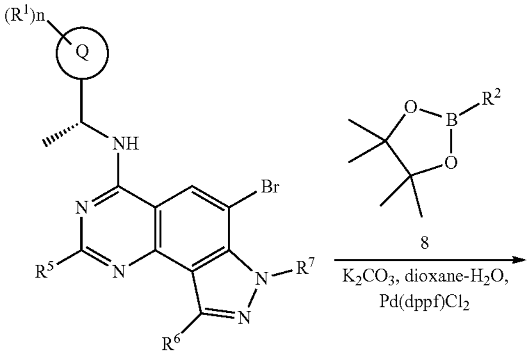

43

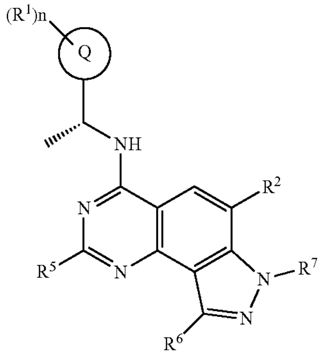

44

Scheme 4 describes the synthesis of tricyclic compound 44. Iodonation of aniline 34 with NIS under heated condition gives iodo-acid intermediate 35, which is converted to methyl ester by treatment of TMS diazomethane. Condensation of 36 with $R^5CN$ at elevated intermediate 40. temperature affords quinazolinone 37. Suzuki coupling reaction of 37 with vinyl boron reagent 38 gives 39. Oxidative leavage of vinyl group with $NaIO_4$ in the presence of $K_2OsO_4$, generates Carbointermediate 40. Nucleophilic displacement of 40 with $R_7$-substituted hydrazine and subsequent cyclization, affords pyrazolo-quinazolinone 41. After treatment of 41 with POCl3 in presence of DIPEA at elevated temperature, 42 is obtained. Nucleophilic displacement of pyrimidine chloride 42 with amine 6 gives 43, which can further undergo Suzuki coupling reaction with $R^2$-boronic acid or ester to finish the target compounds 44, or undergo Buckwald coupling an amine to give 44.

Pharmaceutical Compositions and Methods

The compounds utilized in the methods described herein may be formulated together with a pharmaceutically acceptable carrier or adjuvant into pharmaceutically acceptable compositions prior to be administered to a subject. In another embodiment, such pharmaceutically acceptable compositions further comprise additional therapeutic agents in amounts effective for achieving a modulation of disease or disease symptoms, including those described herein.

The term "pharmaceutically acceptable carrier or adjuvant" refers to a carrier or adjuvant that may be administered to a subject, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-□-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-o-cyclodextrins, or other solubilized derivatives may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

The pharmaceutical compositions described above comprising a compound of formulae (I)-(V) may further comprise another therapeutic agent useful for treating or preventing a disease or condition mediated by mammalian Ras family proteins. In particular, such combination may be useful for treating or preventing cancer, including breast cancer, leukemia, prostate cancer, ovarian cancer, pancreatic cancer, colon cancer, lung cancer, endometrial cancer, thyroid cancer, cholangiocarcinoma, multiple myeloma, melanoma, uterine cancer, head and neck squamous cell carcinoma, diffuse large B cell lymphoma, esophageal cancer, hepatocellular cancer, glioblastoma, renal cancer, sarcoma, bladder cancer, urothelial cancer, gastric cancer, or cervical cancer.

All publications, patents, and patent applications mentioned in this specification are herein incorporated by reference to the same extent as if each individual publication, patent, or patent application was specifically and individually indicated to be incorporated by reference. In case of conflict, the present application, including any definitions herein, will control.

The examples herein are provided to illustrate advantages of the present technology and to further assist a person of ordinary skill in the art with preparing or using the compounds of the present technology or salts, pharmaceutical compositions, derivatives, solvates, metabolites, prodrugs, racemic mixtures or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

Abbreviations used herein are as follows:

| Abbrv. | Full Name | Abbrv. | Full Name |
|---|---|---|---|
| anhy. | anhydrous | aq. | aqueous |
| min | minute(s) | satd. | saturated |
| mL | milliliter | hrs | hours |
| mmol | millimole(s) | mol | mole(s) |
| MS | mass spectrometry | NMR | nuclear magnetic resonance |
| TLC | thin layer chromatography | HPLC | high-performance liquid chromatography |
| LCMS | Liquid chromatography-mass spectrometry | PPTS | Pyridinium p-Toluenesulfonate |
| DCE | 1,2-dichloroethane | $CHCl_3$ | chloroform |
| DCM | dichloromethane | DMF | dimethylformamide |
| $Et_2O$ | diethyl ether | EtOH | ethyl alcohol |
| EtOAc | ethyl acetate | MeOH | methyl alcohol |
| MeCN | acetonitrile | PE | petroleum ether |
| THF | tetrahydrofuran | DMSO | dimethyl sulfoxide |
| AcOH | acetic acid | HCl | hydrochloric acid |
| $H_2SO_4$ | sulfuric acid | $NH_4Cl$ | ammonium chloride |
| KOH | potassium hydroxide | NaOH | sodium hydroxide |
| $K_2CO_3$ | potassium carbonate | $Na_2CO_3$ | sodium carbonate |
| TFA | trifluoroacetic acid | $Na_2SO_4$ | sodium sulfate |
| $NaBH_4$ | sodium borohydride | $NaHCO_3$ | sodium bicarbonate |
| LiHMDS | lithium hexamethyldisilylamide | $NaBH_4$ | sodium borohydride |
| $Et_3N$ or TEA | Triethylamine | Py or Pyr | pyridine |
| TBAF | Tetrabutylammonium fluoride | MsCl | Methanesulfonyl chloride |
| BnBr | Benzyl bromide | DHP | 3,4-Dihydro-2H-pyran |
| Cbz | carbobenzyloxy | m-CPBA | 3-Chloro-peroxybenzoic acid |
| Dess-Martin | 1,1,1-Triacetoxy-1,1-Dihydro-1,2-Benziodoxol-3(1H)-On | DIAD | Diisopropyl azodicarboxylate |
| DMAP | 4-(dimethyl-amino)pyridine | DIPEA | N,N-diisopropylethylamine |
| TMSCHN2 | (Trimethylsilyl)di-azomethane | TMSCH2N3 | Trimethylsilylmethyl azide |
| Ruphos | 2-Dicyclohexylphosphino-2',6'-diisopropoxybiphenyl | | |
| RuPhosPd G3 | Methanesulfonato(2-dicyclohexylphosphino-2',6'-di-i-propoxy-1,1'-biphenyl)(2'-amino-1,1'-biphenyl-2-yl)palladium(II) | | |

General Conditions and Procedures

In the following examples, the chemical reagents were purchased from commercial sources (such as Alfa, Acros, Sigma Aldrich, TCI and Shanghai Chemical Reagent Company), and used without further purification. THF was continuously refluxed and freshly distilled from sodium and benzophenone under nitrogen, dichloromethane was continuously refluxed and freshly distilled from $CaH_2$ under nitrogen.

Flash chromatography was performed on an Ez Purifier III via column with silica gel particles of 200-300 mesh. Analytical and preparative thin layer chromatography plates (TLC) were HSGF 254 (0.15-0.2 mm thickness, Shanghai Anbang Company, China). Nuclear magnetic resonance (NMR) spectra were recorded using Brucker AMX-300 or AMX-400 NMR (Brucker, Switzerland) at around 20-30° C. unless otherwise specified. The following abbreviations are used: s, singlet; d, doublet; t, triplet; q, quartet; m, multiplet; dd, doublet of doublets; ddd, doublet of doublet of doublet; dt, doublet of triplets; bs, broad signal. Chemical shifts were reported in parts per million (ppm, 6) downfield from tetramethylsilane. Mass spectra were run with electrospray ionization (ESI) from a Waters LCT TOF Mass Spectrometer (Waters, USA). Compound purification was carried out as needed using a variety of traditional methods including, but not limited to, preparative chromatography under acidic, neutral, or basic conditions using either normal phase or reverse phase HPLC or flash columns or Prep-TLC plates.

Preparative HPLC: unless otherwise described, the compounds were purified using a WATERS Fractionlynx system equipped with a YMC Pack Pro ds Column (5 μm, 120A, 50×20 mm) and the following solvent system: $H_2O$, AcCN, and 2% TFA in $H_2O$. Specific elution gradients were based on the retention times obtained with an analytical LC-MS, however, in general all elution gradients of $H_2O$ and MeCN were run over a 7 minute run time with a flow rate of 35 mL/min. An autoblend method was used to ensure a concentration of 0.1% TFA throughout each run. Specific elution gradients were based on the retention times obtained with an analytical LC-MS, however, in general, all elution gradients of $H_2O$ and MeCN were run over at 8 minute run time with a flow rate of 50 mL/min.

Analytical LC-MS: analytical LC-MS was performed on a WATERS Acquity UPLC-MS instrument equipped with a ACQUITY UPLC BEH $Ci_8$ Column (2.1×50 mm, 1.7μιη), a column temperature of 45° C. and using the following solvent system: Solvent A: 0.1% HCOOH in $H_2O$; and Solvent B: 0.1% HCOOH in AcCN. All compounds were run using the same elution gradient, i.e., 5% to 95% Solvent B over a 1.5 min run time with a flow rate of 0.6 mL/min.

Preparative Chiral SFC Separation: stereoisomer mixtures were separated using a Berger Minigram SFC instrument on one of the following columns: ChiralPak AS-H (10×250 mm), ChiralPak IA (10×250 mm), ChiralPak AD-H (21×250 mm), Phenomenex Lux-2 (21.2×250 mm), or ChiralPak IC (10×250 mm); eluting with either 0.1% diethylamine in $MeOH/CO_2$, or 0.1% diethylamine in $EtOH/CO_2$ or 0.1% diethylamine in isopropanol/$CO_2$ with a flow rate of 2.5 mL/min and a column temperature of 35° C.

Analytical Chiral SFC Separation: stereoisomer mixtures or single enantiomers were analyzed using a JASCO analytical SFC instrument on one of the following columns: ChiralPak AS-H (4.6×250 mm), ChiralPak IA (4.6×250 mm), ChiralPak AD-H (4.6×250 mm), Phenomenex Lux-2 (4.6×250 mm), or ChiralPak IC (4.6×250 mm); eluting with either 0.1% diethylamine in $MeOH/CO_2$, or 0.1% diethylamine in $EtOH/CO_2$ or 0.1% diethylamine in isopropanol/$CO_2$, with a flow rate of 6.0 imL/min and a column temperature of 35° C.

Intermediate 1: Synthesis of (R)-1-(2-methyl-3-(trifluoromethyl)phenyl)ethanamine

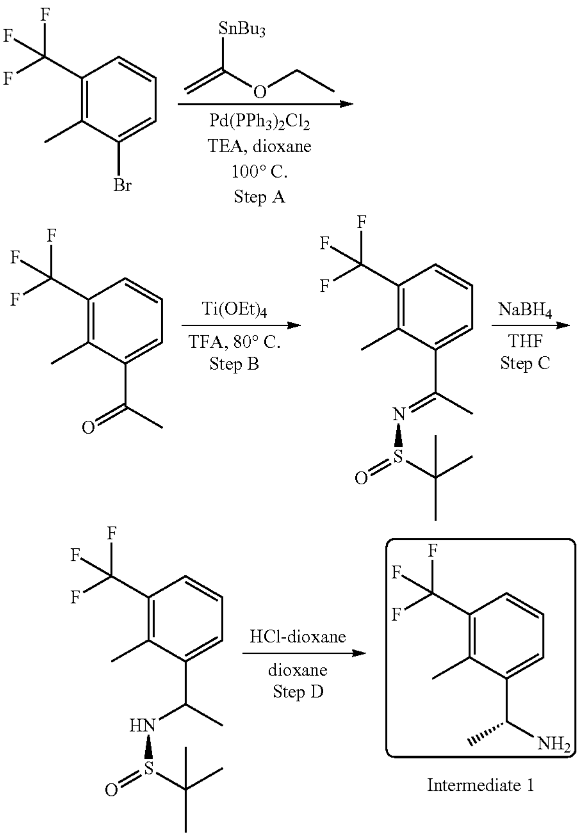

Intermediate 1

Step A. 1-(2-methyl-3-(trifluoromethyl)phenyl)ethan-1-one

To a solution of 1-bromo-2-methyl-3-(trifluoromethyl)benzene (1.3 mL, 8.4 mmol) in dry dioxane (20 mL) is added Tributyl(1-ethoxyvinyl)stannane (3.3 g, 9.2 mmol), TEA (3.5 mL, 25.1 mmol) and $Pd(PPh_3)_2Cl_2$ (0.3 g, 0.4 mmol). After stirred at 100° C. for 2 h. 12 N HCl (15 mL) was added. When complete conversion of starting material, the cooled mixture was poured into water (50 mL) and extracted with EtOAc (50 mL*2). The combine organic phase was washed with brine and dried over $Na_2SO_4$ and concentrated. The crude product was purified by chromatography (silica gel, 0-25%, EtOAc in PE) to give 1-[2-methyl-3-(trifluoromethyl) phenyl]ethan-1-one (1.4 g, 7.1 mmol, 85.1%) as a brown oil. LC-MS (ESI) m/z 196 $(M+H)^+$.

Step B. (S,E)-2-methyl-N-(1-(2-methyl-3-(trifluoromethyl)phenyl)ethylidene)propane-2-sulfinamide To a stirred solution of 1-[2-methyl-3-(trifluoromethyl) phenyl]ethan-1-one (1.44 g, 7.1 mmol) in THF (15 mL) was added (R)-2-methylpropane-2-sulfonamide (1.29 g, 10.7 mmol) and Titanium ethoxide (3 mL, 14.2 mmol) at rt. After stirred at 80° C. overnight, the cooled mixture was poured into water (50 mL) and filtered. The filtrate was extracted with EtOAc (50 mL*2). The combined organic phase was washed with brine, dried over $Na_2SO_4$, filtered and concentrated. The crude product was purified by chromatography (silica gel, 0-50%, EtOAc in PE) to give 2-methyl-N-[(1E)-1-[2-methyl-3-(trifluoromethyl)phenyl]ethylidene] propane-2-sulfinamide (1.2 g, 3.9 mmol, 55.2%) as a brown oil.

Step C. (S)-2-methyl-N-(1-(2-methyl-3-(trifluoromethyl)phenyl)ethyl)propane-2-sulfinamide To a stirred solution of 2-methyl-N-[(1E)-1-[2-methyl-3-(trifluoromethyl)phenyl]ethylidene]propane-2-sulfinamide (1.2 g, 3.9 mmol) in THF (64 mL) was added $NaBH_4$ (0.26 g, 7.07 mmol) at 0° C. After stirred at rt for 3.5 h, the mixture was poured into water (20 mL) and extracted with EtOAc (20 mL*2). The combined organic phase was washed with brine, dried over $Na_2SO_4$, filtered and concentrated. The crude product was purified by chromatography (silica gel, 0-60%, EtOAc in PE) to give 2-methyl-N-{1-[2-methyl-3-(trifluoromethyl)phenyl]ethyl}propane-2-sulfinamide (0.6 g, 1.95 mmol, 49.7%) as a yellow oil.

Step D. (R)-1-(2-methyl-3-(trifluoromethyl)phenyl) ethan-1-amine

To a stirred solution of 2-methyl-N-{1-[2-methyl-3-(trifluoromethyl)phenyl]ethyl}propane-2-sulfinamide (60 mg, 0.2 mmol) in dioxane (5 mL) was added dioxane/HCl (5 mL, 4 mol/L) at rt. After stirred at rt for 1 h, the mixture was concentrated to give crude of (1R)-1-[2-methyl-3-(trifluoromethyl)phenyl]ethan-1-amine (100 mg, 0.15 mmol, 75.6%) as a yellow solid. LC-MS (ESI) m/z 204 $(M+H)^+$.

Intermediate 2: Synthesis of (1R)-1-[3-(1,1-difluoroethyl)-2-fluorophenyl]ethan-1-amine

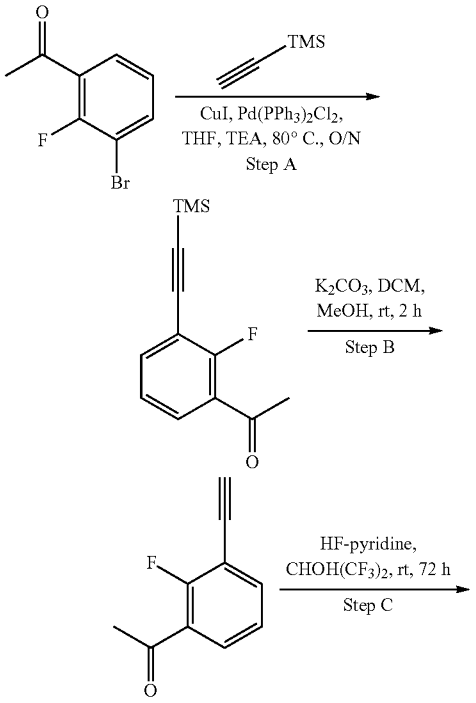

-continued

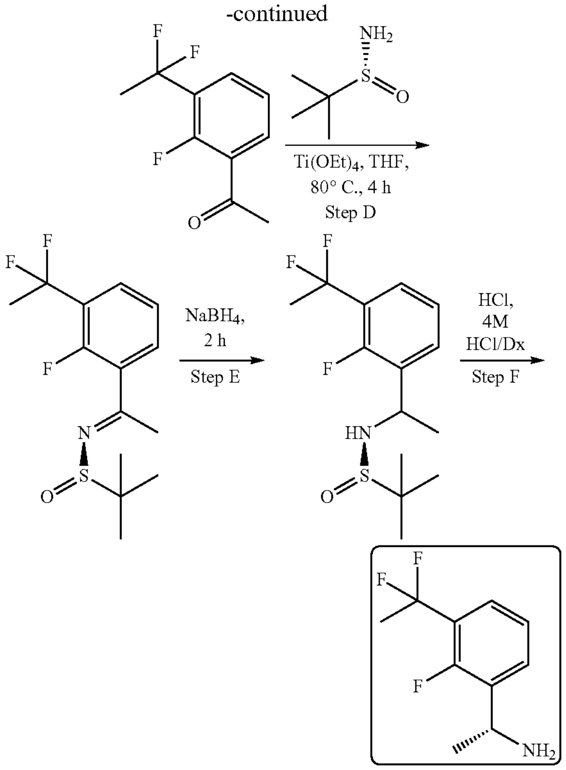

Intermediate 2

Step A. 1-{2-fluoro-3-[2-(trimethylsilyl)ethynyl] phenyl}ethan-1-one

To a stirred solution of 1-(3-bromo-2-fluorophenyl)ethan-1-one (5 g, 23.1 mmol) in THF (30 mL) was added ethynyltrimethylsilane (5 mL, 34.5 mmol), CuI (880 mg, 4.6 mmol), $Pd(dppf)Cl_2$ (1.7 g, 2.3 mmol) and TEA (9.6 mL, 69.1 mmol) at rt. After stirred at 80° C. overnight, the cooled mixture was poured into water (30 ml) and extracted with DCM (20 ml*2). The combined organic phase was washed with brine, dried over $Na_2SO_4$, filtered and concentrated. The residue was purified by chromatography (silica gel, 0-20%, EtOAc in PE) to give 1-{2-fluoro-3-[2-(trimethylsilyl)ethynyl]phenyl}ethan-1-one (5 g, 21.3 mmol, 92%) as a yellow oil. LCMS: m/z 235 $(M+H)^+$.

Step B. 1-(3-ethynyl-2-fluorophenyl)ethan-1-one

To a stirred solution of 1-{2-fluoro-3-[2-(trimethylsilyl)ethynyl]phenyl}ethan-1-one (5 g, 21.3 mmol) in DCM (20 mL)/MeOH (20 mL) was added $K_2CO_3$ (8.8 g, 64.1 mmol) at rt. After stirred at rt for 2 h, the cooled mixture was poured into water (30 ml) and extracted with DCM (20 ml*2). The combined organic phase was washed with brine, dried over $Na_2SO_4$, filtered and concentrated to give 1-(3-ethynyl-2-fluorophenyl)ethan-1-one (3.2 g, 19.7 mmol, 92%) as a brown solid. LCMS: m/z 163 $(M+H)^+$.

Step C. 1-[3-(1,1-difluoroethyl)-2-fluorophenyl] ethan-1-one

To a stirred solution of 1-(3-ethynyl-2-fluorophenyl) ethan-1-one (2.7 g, 16.6 mmol) in $CHOH(CF_3)_2$ (8 mL) was added HF 70% in pyridine (8 mL) at rt. After stirred at rt over the weekend, the cooled mixture was poured into water (30 ml) and extracted with DCM (20 ml*2). The combined organic phase was washed with brine, dried over $Na_2SO_4$, filtered and concentrated. The residue was purified by chromatography (silica gel, 0-20%, EtOAc in PE) to give 1-[3-(1,1-difluoroethyl)-2-fluorophenyl]ethan-1-one (1.4 g, 6.9 mmol, 41%) as a brown solid. LCMS: m/z 203 $(M+H)^+$.

Step D. N-[(1E)-1-[3-(1,1-difluoroethyl)-2-fluorophenyl]ethylidene]-2-methylpropane-2-sulfonamide To a stirred solution of 1-[3-(1,1-difluoroethyl)-2-fluorophenyl]ethan-1-one (700 mg, 3.4 mmol) in THE (10 mL) was added 2-methylpropane-2-sulfonamide (629 mg, 5.2 mmol) and $Ti(OEt)_4$ (2 mL) at rt. After stirred at 80° C. for 4 h, the cooled mixture was poured into water (30 ml) and extracted with DCM (20 ml*2). The combined organic phase was washed with brine, dried over $Na_2SO_4$, filtered and concentrated. The residue was purified by chromatography (silica gel, 0-30%, EtOAc in PE) to give N-[(1E)-1-[3-(1,1-difluoroethyl)-2-fluorophenyl]ethylidene]-2-methylpropane-2-sulfonamide (700 mg, 2.3 mmol, 66%) as a yellow oil. LCMS: m/z 236 $(M+H)^+$.

Step E. N-{1-[3-(1,1-difluoroethyl)-2-fluorophenyl]ethyl}-2-methylpropane-2-sulfonamide To a stirred solution of N-[(1E)-1-[3-(1,1-difluoroethyl)-2-fluorophenyl]ethylidene]-2-methylpropane-2-sulfonamide (700 mg, 2.3 mmol) in THE (5 mL) was added $NaBH_4$ (116 mg, 3.44 mmol) at 0° C. After stirred at rt for 2 h, the cooled mixture was poured into water (30 ml) and extracted with DCM (20 ml*2). The combined organic phase was washed with brine, dried over $Na_2SO_4$, filtered and concentrated. The residue was purified by chromatography (silica gel, 0-30%, EtOAc in PE) to give N-{1-[3-(1,1-difluoroethyl)-2-fluorophenyl]ethyl}-2-methylpropane-2-sulfonamide (380 mg, 1.2 mmol, 54%) as a yellow solid. LCMS: m/z 308 $(M+H)^+$. $^1H$ NMR (400 MHz, DMSO) δ 7.70 (s, 1H), 7.45 (d, J=7.3 Hz, 1H), 7.31 (t, J=7.7 Hz, 1H), 5.86 (d, J=7.7 Hz, 1H), 4.75-4.62 (m, 1H), 2.00 (dd, J=21.9, 16.3 Hz, 3H), 1.42 (d, J=6.8 Hz, 3H), 1.11 (s, 9H).

Step F. (1R)-1-[3-(1,1-difluoroethyl)-2-fluorophenyl]ethan-1-amine

To a stirred mixture of N-{1-[3-(1,1-difluoroethyl)-2-fluorophenyl]ethyl}-2-methyl propane-2-sulfonamide (100 mg, 0.32 mmol) in dioxane (3 mL) was added HCl/dioxane (3 mL) at rt. After stirred at rt for 2 h, the mixture was concentrated to give crude (1R)-1-[3-(1,1-difluoroethyl)-2-fluorophenyl]ethan-1-amine (60 mg, 0.29 mmol, 91%) as a yellow solid. LCMS: m/z 204 $(M+H)^+$.

Intermediate 3: Synthesis of (R)-1-(6-(trifluoromethyl)pyridin-2-yl)ethanamine

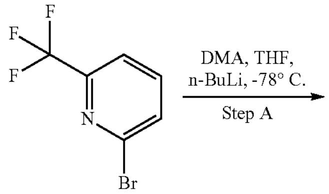

-continued

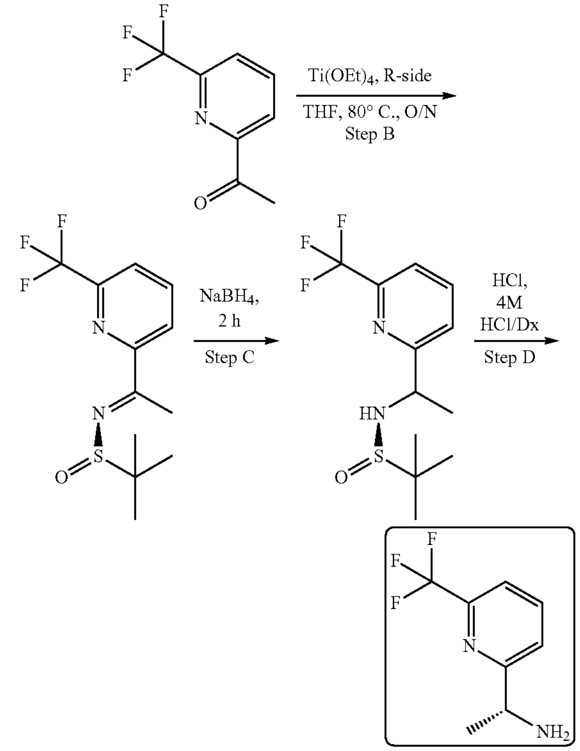

Intermediate 3

Step A: 1-(6-(trifluoromethyl)pyridin-2-yl)ethan-1-one

To a solution of 2-bromo-6-(trifluoromethyl)pyridine (0.5 g, 2.2 mmol) in THF (5 mL) was added DMA (0.23 mL, 2.4 mmol) at rt. The mixture was colded to −60° C. and n-BuLi (0.23 g, 3.54 mmol) was dropwise. The reaction was stirred at −20° C. over 3 h and quenched with saturated $NH_4Cl$ solution and extracted with EtOAc. The organic layers was washed with brine and dried over $Na_2SO_4$ then concentrated under reduced pressure. The crude product was purified by column chromatography on silica gel (gradient elution: 0-10% EtOAc in PE) to give the product of 1-[6-(trifluoromethyl)pyridin-2-yl]ethan-1-one (0.09 g, 0.48 mmol, 21.5%) as a yellow oil. LCMS (ESI) m/z 190 $(M+H)^+$ Step B: (S,E)-2-methyl-N-(1-(6-(trifluoromethyl)pyridin-2-yl)ethylidene)propane-2-sulfinamide To a stirred solution of 1-[6-(trifluoromethyl)pyridin-2-yl]ethan-1-one (0.7 g, 3.7 mmol) in THF (15 mL) was added (R)-2-methylpropane-2-sulfonamide (0.67 g, 5.55 mmol) and Titanium ethoxide (2.33 mL, 11.1 mmol) at rt. After stirred at 80° C. overnight, the cooled mixture was poured into ice water (25 mL) and filtered. The filtrate was extracted with EtOAc (25 mL*2). The combined organic phase was washed with brine, dried over $Na_2SO_4$, filtered and concentrated. The crude product was purified by chromatography (silica gel, 0-100%, EtOAc in PE) to give 2-methyl-N-[(1E)-1-[6-(trifluoromethyl)pyridin-2-yl]ethylidene] propane-2-sulfinamide (0.74 g, 2.53 mmol, 68.4%) as a brown oil.

Step C: (S)-2-methyl-N-(1-(6-(trifluoromethyl)pyridin-2-yl)ethyl)propane-2-sulfinamide To a stirred solution of 2-methyl-N-[(1E)-1-[6-(trifluoromethyl)pyridin-2-yl]ethylidene]propane-2-sulfinamide (0.7 g, 2.4 mmol) in THE (7 mL) was added $NaBH_4$ (0.14 mL, 4.31 mmol) at 0° C. After stirred at rt for 3 h, the mixture was poured into water (20 mL) and extracted with EtOAc (20 mL*2). The combined organic phase was washed with brine, dried over $Na_2SO_4$, filtered and concentrated. The crude product was purified by chromatography (silica gel, 0-60%, EtOAc in PE) to give 2-methyl-N-{1-[6-(trifluoromethyl)pyridin-2-yl]ethyl}propane-2-sulfinamide (0.3 g, 1.0 mmol, 42.6%) as a yellow oil.

Step D: (R)-1-(6-(trifluoromethyl)pyridin-2-yl) ethan-1-amine

To a solution of 2-methyl-N-{1-[6-(trifluoromethyl)pyridin-2-yl]ethyl}propane-2-sulfinamide (0.08 g, 0.27 mmol) in dioxane (5 mL) was added dioxane/HCl (3 mL, 4 mol/L) at rt. After stirred at rt for 1 h, the mixture was concentrated to give crude of (1R)-1-[6-(trifluoromethyl)pyridin-2-yl] ethan-1-amine (60 mg, 0.25 mmol, 93%) as a yellow solid. LC-MS (ESI) m/z 191 $(M+H)^+$.

Intermediate 4: Synthesis of (R)-benzyl 2-(5-(1-aminoethyl)thiophen-2-yl)benzyl (methyl)carbamate

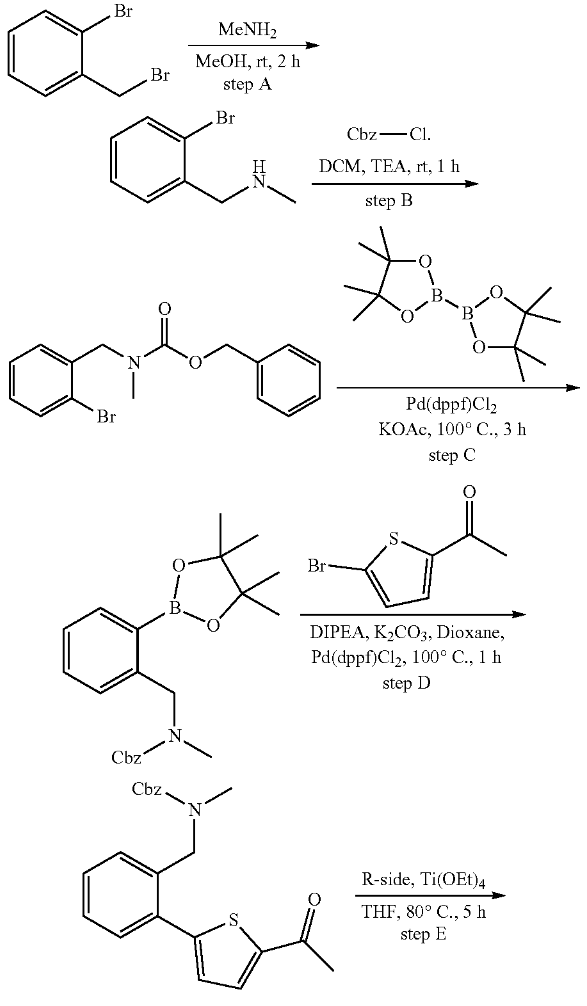

-continued

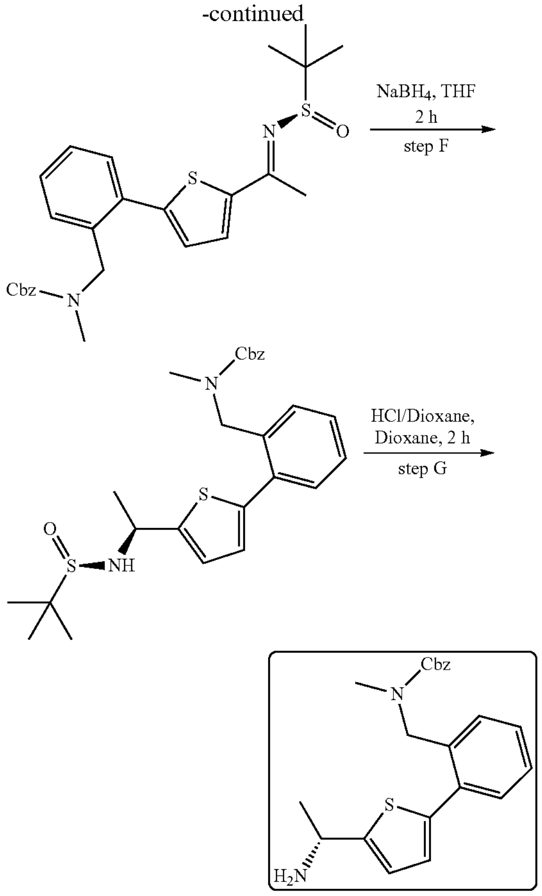

Intermediate 4

Step A: 1-(2-bromophenyl)-N-methylmethanamine

To a solution of MeNH2 (10.8 g, 160 mmol) in MeOH was added a solution of 1-bromo-2-(bromomethyl)benzene (10 g, 40.0 mmol) in MeOH over 30 min at rt. After stirred at rt for 2 h, the mixture was concentrated and extracted with EtOAc. The organic layers was washed with brine and dried over $Na_2SO_4$. The crude product was purified by column chromatography on silica gel (gradient elution: 0-20% MeOH in DCM) to give the product of [(2-bromophenyl) methyl](methyl)amine (2.7 g, 13.5 mmol, 33.7%). LC-MS (ESI) m/z: $249^+$.

Step B: benzyl N-[(2-bromophenyl)methyl]-N-methylcarbamate

To a solution of [(2-bromophenyl)methyl](methyl)amine (2.7 g, 13.5 mmol) in DCM (30 mL) was added TEA (5.6 mL, 40.5 mmol) at rt. A solution of Cbz-Cl (2.76 g, 16.2 mmol) in DCM (20 mL) was added dropwise. After stirred at rt for 1.5 h, the reaction was quenched by saturated solution of $NaHCO_3$and extracted with DCM. The organic layers was washed with brine and dried over $Na_2SO_4$ then concentrated under reduced pressure. The crude product was purified by column chromatography on silica gel (gradient elution: 0-10% EtOAc in PE) to give the product of benzyl N-[(2-bromophenyl)methyl]-N-methylcarbamate (3 g, 8.976 mmol, 66.5%) as colourless oil. LC-MS (ESI) m/z: $334^+$ Step C: benzyl N-methyl-N-{[2-(tetramethyl-1,3,2-dioxaborolan-2-yl)phenyl]methyl}carbamate To a solution of benzyl N-[(2-bromophenyl)methyl]-N-methylcarbamate (4 g, 11.9 mmol) in dioxane (40 mL) was added 4,4,4',4',5,5,5',5'-octamethyl-2,2'-bi(1,3,2-dioxaborolane) (3.95 g, 15.6 mmol), Pd(dppf)$Cl_2$ (0.44 g, 0.598 mmol) and KOAc (3.52 g, 35.9 mmol) under $N_2$ at rt. after stirred at 100° C. overnight, the cooled mixture was filtered. The filtrate was diluted with water and then extracted with EtOAc. The organic layers was washed with brine and dried over $Na_2SO_4$ then concentrated. The residue was purified by chromatography (silica gel, 0-50%, EtOAc in PE) to give the product of benzyl N-methyl-N-{[2-(tetramethyl-1,3,2-dioxaborolan-2-yl)phenyl]methyl}carbamate (4.35 g, 11.4 mmol, 95.3%) as a green oil. LC-MS (ESI) m/z 382 $(M+H)^+$.

Step D: benzyl N-{[2-(5-acetylthiophen-2-yl)phenyl]methyl}-N-methylcarbamate

To a solution of benzyl N-methyl-N-{[2-(tetramethyl-1,3,2-dioxaborolan-2-yl)phenyl]methyl}carbamate (4.35 g, 11.4 mmol) in dioxane (40 mL) and $H_2O$ (10 mL) was added 1-(5-bromothiophen-2-yl)ethan-1-one (1.87 g, 9.13 mmol), Pd(dppf)$Cl_2$ (0.83 g, 1.14 mmol) and $K_2CO_3$ (6.31 g, 45.636 mmol) at rt. After stirred at 100° C. for 1.5 h, the mixture was filtered. The filtrate was extracted with EtOAc. The organic layers was washed with brine and dried over $Na_2SO_4$ then concentrated. The mixture was purified by chromatography (silica gel, 0-50%, EtOAc in PE) to give the product of benzyl N-{[2-(5-acetylthiophen-2-yl)phenyl]methyl}-N-methylcarbamate (0.38 g, 1.00 mmol, 8.78%) as a white solid. LC-MS (ESI) m/z 380 $(M+H)^+$.

Step E: benzyl N-methyl-N-[(2-{5-[(1E)-1-[(2-methylpropane-2-sulfinyl)imino]ethyl]thiophen-2-yl}phenyl)methyl]carbamate To a solution of benzyl N-{[2-(5-acetylthiophen-2-yl)phenyl]methyl}-N-methylcarbamate (2.45 g, 6.46 mmol) in THE (30 mL) was added (R)-2-methylpropane-2-sulfonamide (1.17 g, 9.68 mmol), titanium ethoxide (4.061 mL, 19.369 mmol) at rt. After stirred at 80° C. for 5 h, the mixture was quenched with ice water and filtered. The filtrate was extracted with EtOAc. The organic layers was washed with brine and dried over $Na_2SO_4$ then concentrated under reduced pressure. The mixture was purified by chromatography (silica gel, 0-80%, EtOAc in PE) to give the product of benzyl N-methyl-N-[(2-{5-[(1E)-1-[(2-methylpropane-2-sulfinyl) imino]ethyl]thiophen-2-yl}phenyl)methyl]carbamate (2 g, 4.14 mmol, 64.2%) as a white solid.

Step F: benzyl N-methyl-N-[(2-{5-[(1R)-1-[(2-methylpropane-2-sulfinyl)amino]ethyl]thiophen-2-yl}phenyl)methyl]carbamate To a solution of benzyl N-methyl-N-[(2-{5-[(1E)-1-[(2-methylpropane-2-sulfinyl)imino]ethyl]thiophen-2-yl}phenyl)methyl]carbamate (2 g, 4.14 mmol) in THE (20 mL) was added $NaBH_4$ (0.541 mL, 16.6 mmol) at 0° C. After stirred at rt for 2 h, the mixture was quenched with ice water and extracted with EtOAc. The organic layers was washed with brine and dried over $Na_2SO_4$ then concentrated under reduced pressure. The mixture was purified by chromatography (silica gel, 0-100%, EtOAc in PE) to give the product of benzyl N-methyl-N-[(2-{5-[(1R)-1-[(2-methylpropane-2-sulfinyl)amino]ethyl]thiophen-2-yl}phenyl)methyl] carbamate (1.76 g, 3.63 mmol, 87.6%) as white solid.

Step G: benzyl N-[(2-{5-[(1R)-1-aminoethyl]thiophen-2-yl}phenyl)methyl]-N-methylcarbamate To a solution of benzyl N-methyl-N-{[2-(5-{1-[(2-methylpropane-2-sulfinyl)amino]ethyl}thiophen-2-yl)phenyl] methyl}carbamate (180 mg, 0.371 mmol) in dioxane (5 mL) was added HCl-dioxane (2 mL) at rt. After stirred at rt for 1 h, the mixture was concentrated under reduced pressure to give the crude of benzyl N-[(2-{5-[(1R)-1-aminoethyl]thiophen-2-yl}phenyl)methyl]-N-methylcarbamate (165 mg, 0.325 mmol, 87.6%) as white solid. LC-MS (ESI) m/z: 381'.

Intermediate 5: Synthesis of (R)-2-(3-(1-aminoethyl)-5-(trifluoromethyl)phenyl)propan-2-ol

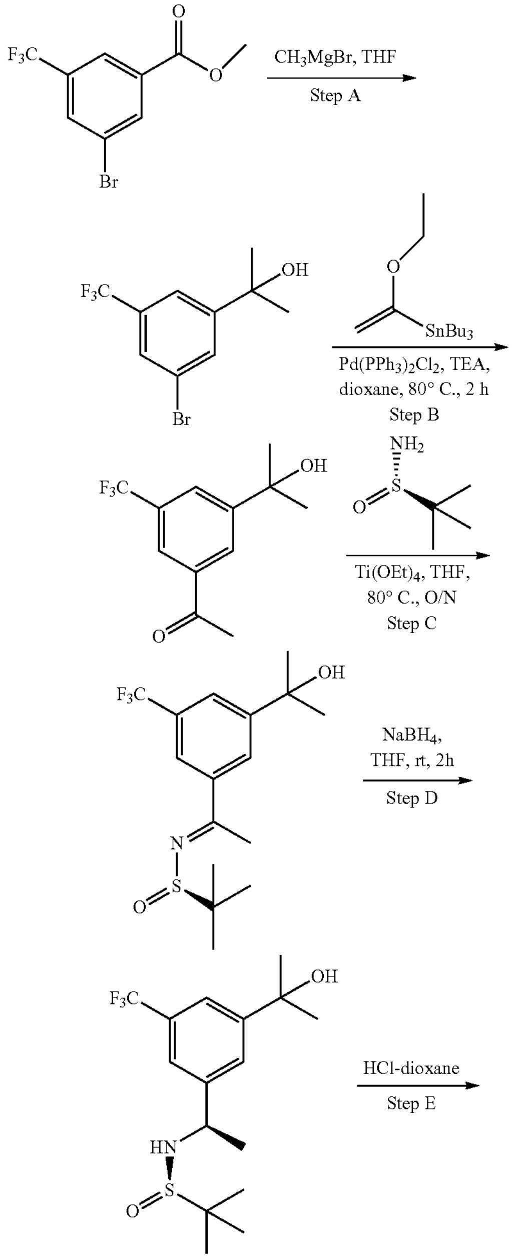

-continued

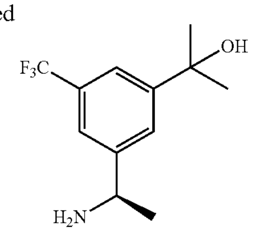

Step A. 2-[3-bromo-5-(trifluoromethyl)phenyl]propan-2-ol

To a stirred solution of methyl 3-bromo-5-(trifluoromethyl)benzoate (10 g, 35.3 mmol) in THF (100 mL) at 0° C. was added $CH_3MgBr$ (4.21 g, 35.3 mmol) slowly. The reaction mixture was stirred at room temperature for 2 h under nitrogen atmosphere. The reaction mixture was diluted with water (50 mL) and extracted with EtOAc (50 mL×3). The combined organic phase was washed by water and brine. The organic phase was dried over anhydrous $Na_2SO_4$, filtered and concentrated to give the crude product which was purified by column chromatography on silica gel (PE:EtOAc=10:1 to 3:1) to obtain 2-[3-bromo-5-(trifluoromethyl)phenyl]propan-2-ol (9 g, 31.8 mmol, 89.9%) as a colorless oil. LC-MS (ESI) m/z 283 $(M+H)^+$.

Step B. 1-[3-(2-hydroxypropan-2-yl)-5-(trifluoromethyl)phenyl]ethan-1-one

To a stirred solution of 2-[3-bromo-5-(trifluoromethyl)phenyl]propan-2-ol (9 g, 31.8 mmol) and tributyl (1-ethoxyethenyl) stannane (13.8 g, 38.2 mmol) in dioxane (90 mL) at room temperature was added TEA (13.3 mL, 95.4 mmol) and $Pd(PPh_3)_2Cl_2$ (1.98 g, 3.18 mmol) slowly. The reaction mixture was stirred at 80° C. for 2 h under nitrogen atmosphere. The reaction mixture was diluted with water (50 ml) and extracted with EtOAc (50 mL×3). The combined organic phase was washed by water and brine. The organic phase was dried over anhydrous $Na_2SO_4$, filtered and concentrated to give the crude product which was purified by column chromatography on silica gel (PE:EtOAc=10:1 to 3:1) to obtain 1-[3-(2-hydroxypropan-2-yl)-5-(trifluoromethyl)phenyl]ethan-1-one (6 g, 24.4 mmol, 76.7%) as a colorless oil. LC-MS (ESI) m/z 247 $(M+H)^+$.

Step C. (R)—N-[(1E)-1-[3-(2-hydroxypropan-2-yl)-5-(trifluoromethyl)phenyl]ethylidene]-2-methylpropane-2-sulfonamide To a stirred solution of 1-[3-(2-hydroxypropan-2-yl)-5-(trifluoromethyl)phenyl]ethan-1-one (6 g, 24.4 mmol) and (R)-2-methylpropane-2-sulfonamide (3.54 g, 29.2 mmol) in THF (50 mL) at room temperature was added $Ti(OEt)_4$ (11.1 g, 48.7 mmol) slowly, the reaction mixture was stirred at 80° C. for 12 h under nitrogen atmosphere. The reaction mixture was diluted with water (50 mL), and extracted with EtOAc (50 mL×3). The combined organic phase was washed by water and brine. The organic phase was dried over anhydrous $Na_2SO_4$, filtered and concentrated to give the crude product which was purified by column chromatography on silica gel (PE:EtOAc=10:1 to 3:1) to obtain (R)—N-[(1E)-1-[3-(2-hydroxypropan-2-yl)-5-(trifluoromethyl)phenyl]ethylidene]-2-methylpropane-2-sulfonamide (5 g, 14.3 mmol, 58.7%) as a colorless oil. LC-MS (ESI) m/z 350 $(M+H)^+$.

Step D. N-{1-[3-(2-hydroxypropan-2-yl)-5-(trifluoromethyl)phenyl]ethyl}-2-methylpropane-2-sulfonamide To a stirred solution of (R)—N-[(1E)-1-[3-(2-hydroxypropan-2-yl)-5-(trifluoromethyl) phenyl]ethylidene]-2-methylpropane-2-sulfonamide (5 g, 14.3 mmol) in THE (50 mL) at room temperature was added $NaBH_4$ (0.935 mL, 28.6 mmol) slowly. The reaction mixture was stirred at room temperature for 2 h under nitrogen atmosphere. The reaction mixture was diluted with water (50 mL) and extracted with EtOAc (50 mL×3). The combined organic phase was washed by water and brine, dried over anhydrous $Na_2SO_4$, filtered and concentrated to give the crude product which was purified by column chromatography on silica gel (PE:EtOAc=10:1 to 3:1) to obtain N-{1-[3-(2-hydroxypropan-2-yl)-5-(trifluoromethyl)phenyl]ethyl}-2-methylpropane-2-sulfonamide (3 g, 8.54 mmol, 59.7%) as a colorless oil. LC-MS (ESI) m/z 352 $(M+H)^+$.

Step E. 2-[3-(1-aminoethyl)-5-(trifluoromethyl)phenyl]propan-2-ol

A stirred solution of N-{1-[3-(2-hydroxypropan-2-yl)-5-(trifluoromethyl)phenyl]ethyl}-2-methylpropane-2-sulfonamide (3 g, 8.54 mmol) in HCl-dioxane (30 mL) was stirred at room temperature for 1 h under nitrogen atmosphere. The reaction mixture was concentrated to obtain 2-[3-(1-aminoethyl)-5-(trifluoromethyl)phenyl]propan-2-ol (1.4 g, 5.66 mmol, 66.3%) as a colorless oil. LC-MS (ESI) m/z 248 $(M+H)^+$.

Intermediate 6: Synthesis of (R)-5-(4-((1-(3-(1,1-difluoro-2-methoxyethyl)phenyl)ethyl) amino)-2,7-dimethyl-7H-pyrazolo[3,4-h]quinazolin-6-yl)-1-methylpyridin-2(1H)-one

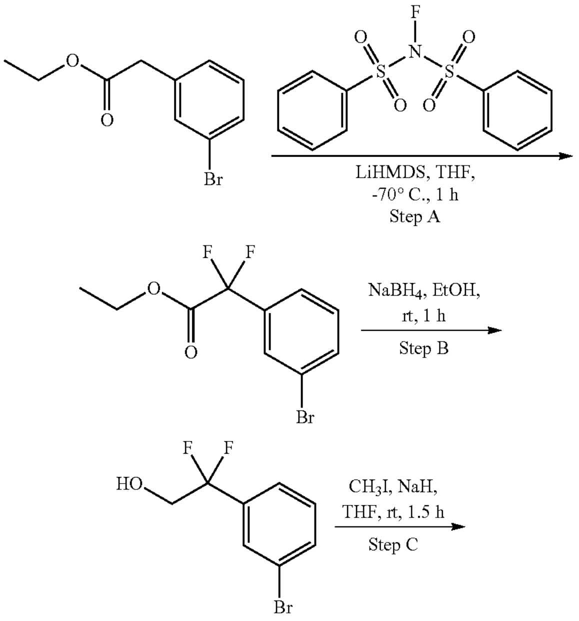

-continued

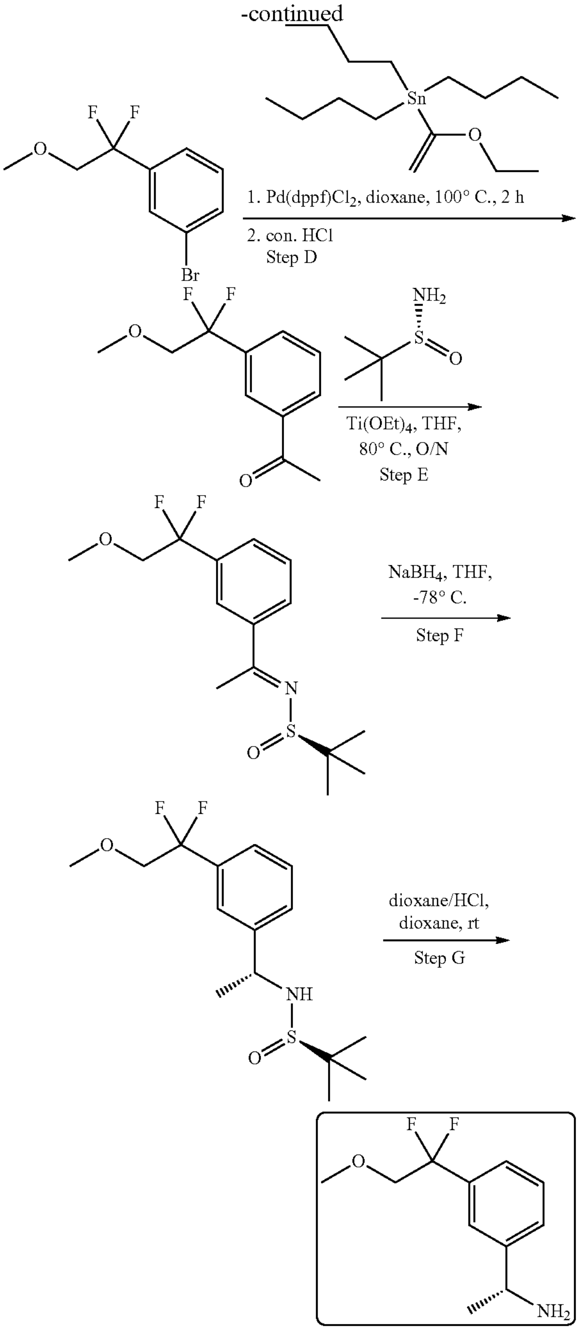

Step A: ethyl 2-(3-bromophenyl)-2,2-difluoroacetate

To a solution of ethyl 2-(3-bromophenyl)acetate (22.8 g, 93.8 mmol) in dry THF (150 mL) cooled to −65° C. was added dropwise LiHMDS (127 mL, 1 mol/L). The reaction mixture was stirred at −65° C. for 30 min. A solution of N-fluoro-N-(phenylsulfonyl)benzenesulfonamide (59.1 g, 188 mmol) in dry THF (150 mL) is added dropwise. The reaction mixture was slowly allowed to warm to 0° C. and stirred for 1 h. After complete consumption of starting material, the mixture was quenched with solution of $NH_4Cl$ and extracted with EtOAc. The combined organic phase was washed with brine and dried over $Na_2SO_4$ then concentrated. The crude product was purified by chromatography to give the desired product of ethyl 2-(3-bromophenyl)-2,2-difluoroacetate (13.5 g. 48.4 mmol. 51.6%) as a colorless oil.

Step B: 2-(3-bromophenyl)-2,2-difluoroethan-1-ol

To a solution of ethyl 2-(3-bromophenyl)-2,2-difluoroacetate (13.5 g, 48.4 mmol) in EtOH (140 mL) was added $NaBH_4$ (3.16 mL, 96.7 mmol) at 0° C. and the mixture was stirred at rt for 1 h. The reaction quenched with water and extracted with EtOAc. The combined organic phase was washed with brine and dried over $Na_2SO_4$ then concentrated to give crude product of 2-(3-bromophenyl)-2,2-difluoroethan-1-ol (13.5 g, 39.9 mmol, 82.4%) as colorless oil.

Step C: 1-bromo-3-(1,1-difluoro-2-methoxyethyl)benzene

To a solution of 2-(3-bromophenyl)-2,2-difluoroethan-1-ol (2.8 g, 11.8 mmol) in dry THE (13 mL) cooled to 0° C. was added dropwise NaH (0.94 g, 23.6 mmol). The reaction mixture was stirred at 0° C. for 30 min, then a solution of $CH_3I$ (1.1 mL, 17.7 mmol) in THE (20 mL) is added dropwise. The reaction mixture is slowly allowed to warm to rt and stirred for 1.5 h. After complete consumption of starting material, the mixture was quenched with solution of $NH_4Cl$ and extracted with EtOAc. The combine organic phase was washed with brine, dried over $Na_2SO_4$ and then concentrated. The crude product was purified by chromatography to give the desired product 1-bromo-3-(1,1-difluoro-2-methoxyethyl)benzene (1.7 g, 6.77 mmol, 57.3%) as colorless oil.

Step D: 1-(3-(1,1-difluoro-2-methoxyethyl)phenyl) ethan-1-one

To a solution of 1-bromo-3-(1,1-difluoro-2-methoxyethyl)benzene (1.3 g, 5.2 mmol) is added Tributyl(1-ethoxyvinyl)stannane (2.06 g, 5.7 mmol), TEA (2.16 mL, 15.5 mmol) and $Pd(dppf)Cl_2$ (0.19 g, 0.259 mmol). The reaction was stirred at 100° C. for 2 h under $N_2$. After complete conversation of starting material, HCl (12 N, 1.3 mL) was added and stirred for 10 min. The reaction quenched with water and extracted with EtOAc (25 mL*2). The combined organic layer was washed with brine, dried over $Na_2SO_4$ and then concentrated. The residue was purified by chromatography (silica gel, EtOAc in PE 0-30%) to give the product of 1-[3-(1,1-difluoro-2-methoxyethyl)phenyl]ethan-1-one (1 g, 4.67 mmol, 90.1%) as a brown oil.

Step E: (R,E)-N-(1-(3-(1,1-difluoro-2-methoxyethyl)phenyl)ethylidene)-2-methylpropane-2-sulfonamide To a stirred solution of 1-[3-(1,1-difluoro-2-methoxyethyl)phenyl]ethan-1-one (1.3 g, 6.07 mmol) in THE (13 mL) was added (R)-2-methylpropane-2-sulfonamide (1.10 g, 9.104 mmol) and $Ti(OEt)_4$ (4.15 g, 18.2 mmol) at rt. After stirred at 80° C. overnight, the cooled mixture was poured into water (50 mL) and filtrated. The mixture was extracted with EtOAc (25 mL*2). The combined organic layers was washed with brine, dried over $Na_2SO_4$, filtered and concentrated. The crude product was purified by chromatography (silica gel, 0-50%, EtOAc in PE) to give product of (R)—N-[(1E)-1-[3-(1,1-difluoro-2-methoxyethyl)phenyl] ethylidene]-2-methylpropane-2-sulfonamide (1.3 g, 4.1 mmol, 67.5%) as a brown oil. LC-MS (ESI) m/z 318 $(M+H)^+$.

Step F: (R)—N—((R)-1-(3-(1,1-difluoro-2-methoxyethyl)phenyl)ethyl)-2-methylpropane-2-sulfonamide To a stirred solution of (R)—N-[(1E)-1-[3-(1,1-difluoro-2-methoxyethyl)phenyl]ethylidene]-2-methylpropane-2-sulfonamide (1 g, 3.15 mmol) and THE (10 mL) was added $NaBH_4$ (0.206 mL, 6.3 mmol) at −60° C. After stirred at 0° C. for 1 h, the mixture was poured into water (30 mL) and extracted with EtOAc (15 mL*2). The combined organic phase was washed with brine, dried over $Na_2SO_4$, filtered and concentrated. The crude product was purified by chromatography (silica gel, 0-100%, EtOAc in PE) to give the product of (R)—N-[(1R)-1-[3-(1,1-difluoro-2-methoxyethyl)phenyl]ethyl]-2-methylpropane-2-sulfonamide (0.7 g, 2.19 mmol, 69.6%) as a white oil. LC-MS (ESI) m/z 320 $(M+H)^+$.

Step G: (R)-1-(3-(1,1-difluoro-2-methoxyethyl)phenyl)ethan-1-amine

To a solution of (R)—N-[(1R)-1-[3-(1,1-difluoro-2-methoxyethyl)phenyl]ethyl]-2-methylpropane-2-sulfonamide (0.7 g, 2.19 mmol) in dioxane (5 mL) was added HCl/dioxane (4 mol/L, 5 mL) at rt. After stirred at rt for 1 h, the mixture was concentrated under reduced pressure to give the crude of (R)-1-[3-(1,1-difluoro-2-methoxyethyl)phenyl]ethan-1-amine (0.5 g, 1.86 mmol, 84.8%) as a white solid. LC-MS (ESI) m/z: $216^+$.

Intermediate 7 & 8: Synthesis of 3-[(1R)-1-aminoethyl]-5-(trifluoromethyl)aniline

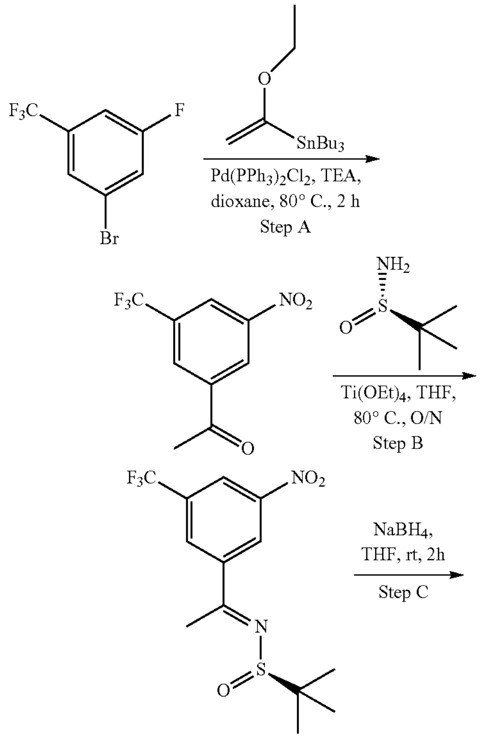

-continued

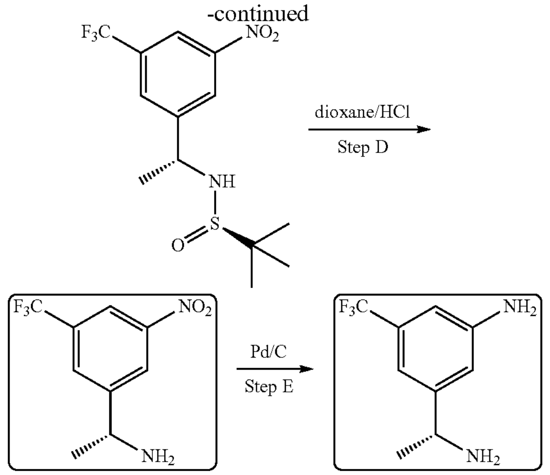

Intermediate 7

Intermediate 8

Step A. 1-[3-nitro-5-(trifluoromethyl)phenyl]ethan-1-one

To a stirred solution of 1-bromo-3-nitro-5-(trifluoromethyl)benzene (10 g, 37.0 mmol) in dioxane (100 mL) was added tributyl(1-ethoxyethenyl)stannane (20.1 g, 55.5 mmol), TEA (15.4 mL, 111 mmol) and $Pd(dppf)Cl_2$ (1.36 g, 1.85 mmol) at rt. After stirred at 100° C. for 2 h, the cooled mixture was acidified by con. HCl to PH=3. After stirred at rt for 30 min, the mixture was poured into water (100 mL) and extracted with EtOAc (100 mL*2). The combined organic phase was washed with brine, dried over $Na_2SO_4$, filtered and concentrated. The crude product was purified by chromatography (silica gel, 0-50%, EtOAc in PE) to give 1-[3-nitro-5-(trifluoromethyl)phenyl]ethan-1-one (7 g, 30.0 mmol, 81%) as a yellow oil.

Step B. (R)-2-methyl-N-[(1E)-1-[3-nitro-5-(trifluoromethyl)phenyl]ethylidene]propane-2-sulfinamide To a stirred solution of 1-[3-nitro-5-(trifluoromethyl)phenyl]ethan-1-one (7 g, 30.0 mmol) in THF (100 mL) was added (R)-2-methylpropane-2-sulfonamide (5.46 g, 45.0 mmol) and $Ti(OEt)_4$ (17.1 g, 75.0 mmol) at rt. After stirred at 80° C. overnight, the cooled mixture was poured into water (100 mL) and filtered. The filtrate was extracted with EtOAc (100 mL*2). The combined organic phase was washed with brine, dried over $Na_2SO_4$, filtered and concentrated. The crude product was purified by chromatography (silica gel, 0-50%, EtOAc in PE) to give (R)-2-methyl-N-[(1E)-1-[3-nitro-5-(trifluoromethyl)phenyl]ethylidene]propane-2-sulfinamide (7.8 g, 23.2 mmol, 77%) as a brown oil. LC-MS (ESI) m/z 337 $(M+H)^+$.

Step C. (R)-2-methyl-N-[(1R)-1-[3-nitro-5-(trifluoromethyl)phenyl]ethyl]propane-2-sulfinamide To a stirred solution of (R)-2-methyl-N-[(1E)-1-[3-nitro-5-(trifluoromethyl)phenyl]ethylidene]propane-2-sulfinamide (7.8 g, 23.2 mmol) in THF (100 mL) was added $NaBH_4$ (1.57 g, 46.4 mmol) at 0° C. After stirred at rt for 2 h, the mixture was poured into water (100 mL) and extracted with EtOAc (100 mL*2). The combined organic phase was washed with brine, dried over $Na_2SO_4$, filtered and concentrated. The crude product was purified by chromatography (silica gel, 0-50%, EtOAc in PE) to give (R)-2-methyl-N-[(1R)-1-[3-nitro-5-(trifluoromethyl)phenyl]ethyl]propane-2-sulfinamide (5 g, 14.8 mmol, 63%) as a yellow solid. LC-MS (ESI) m/z 339 $(M+H)^+$.

Step D. (1R)-1-[3-nitro-5-(trifluoromethyl)phenyl]ethan-1-amine

To a stirred solution of (R)-2-methyl-N-[(1R)-1-[3-nitro-5-(trifluoromethyl)phenyl]ethyl]propane-2-sulfinamide (2 g, 5.91 mmol) in dioxane (10 mL) was added dioxane/HCl (10 mL, 40 mmol, 4 mol/L) at rt. After stirred at rt for 1 h, the mixture was concentrated to give (1R)-1-[3-nitro-5-(trifluoromethyl)phenyl]ethan-1-amine (1.6 g, 5.91 mmol, 100%) as a brown solid. LC-MS (ESI) m/z 235 $(M+H)^+$.

Step E. 3-[(1R)-1-aminoethyl]-5-(trifluoromethyl)aniline

To a stirred solution of (1R)-1-[3-nitro-5-(trifluoromethyl)phenyl]ethan-1-amine (1 g, 4.27 mmol) in MeOH (10 mL) was added Pd/C (0.1 g, 10%) at rt. After stirred at rt using a $H_2$ balloon for 2 h, the mixture was filtered and concentrated to give 3-[(1R)-1-aminoethyl]-5-(trifluoromethyl)aniline (0.8 g, 3.92 mmol, 92%) as a brown oil. LC-MS (ESI) m/z 205 $(M+H)^+$.

Intermediate 9: Synthesis of (R)—N—((R)-1-(3-(1,1-difluoro-2-hydroxyethyl)-5-fluorophenyl)ethyl)-2-methylpropane-2-sulfonamide

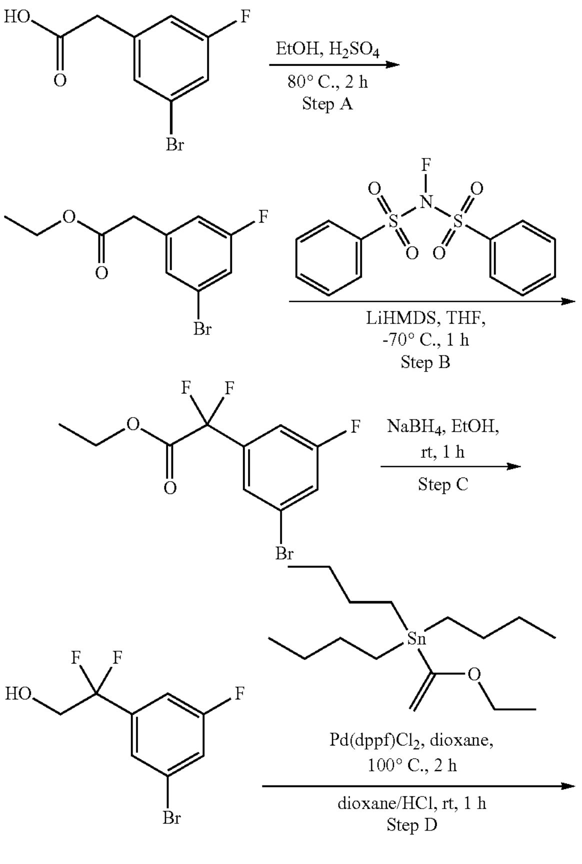

-continued

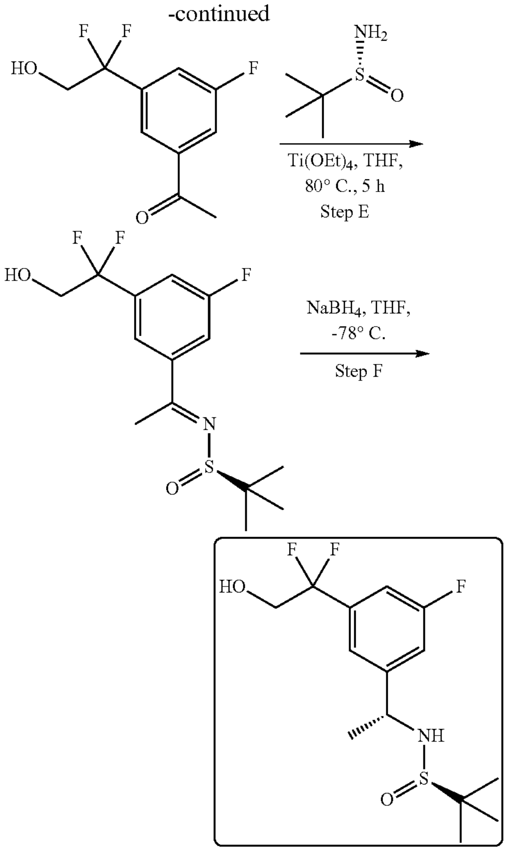

Step A: ethyl 2-(3-bromo-5-fluorophenyl)acetate

To a solution of 2-(3-bromo-5-fluorophenyl)acetic acid (7.5 g, 32.2 mmol) in EtOH (100 mL) was added $H_2SO_4$ (2 mL) at rt. After stirred at 80° C. for 2 h, the reaction was quenched with water and washed with $NaHCO_3$. The mixture was extracted with EtOAc, washed with brine and dried over $Na_2SO_4$ then concentrated to give the product of ethyl 2-(3-bromo-5-fluorophenyl)acetate (7.5 g, 28.7 mmol, 89.3%) as a white oil.

Step B: ethyl 2-(3-bromo-5-fluorophenyl)-2,2-difluoroacetate

To a solution of ethyl 2-(3-bromo-5-fluorophenyl)acetate (6.4 g, 24.5 mmol) in dry THF (80 mL) was cooled to −65° C. and LiHMDS (34.3 mL) was added dropwise. The reaction mixture was stirred at −65° C. for 30 min, then a solution of N-fluoro-N-(phenylsulfonyl)benzenesulfonamide (15.4 g, 49 mmol) in dry THF (80 mL) was added dropwise. The reaction mixture is slowly allowed to warm to 0° C. and stirred for 1 h. After complete consumption of starting material, the mixture was quenched with solution of $NH_4Cl$ and extracted with EtOAc. The combine organic phase was washed with brine and dried over $Na_2SO_4$ then concentrated. The crude product was purified by chromatography giving the desired product of ethyl 2-(3-bromo-5-fluorophenyl)-2,2-difluoroacetate (2.6 g, 8.75 mmol, 35.7%) as a colorless oil.

Step C: 2-(3-bromo-5-fluorophenyl)-2,2-difluoroethan-1-ol

To a solution of ethyl 2-(3-bromo-5-fluorophenyl)-2,2-difluoroacetate (2.6 g, 8.8 mmol) in EtOH (30 mL) was added $NaBH_4$ (0.857 mL, 26.3 mmol) at 0° C. and the mixture was stirred at rt for 1 h. The reaction quenched with water and extracted with EtOAc. The combined organic phase was washed with brine and dried over $Na_2SO_4$ then concentrated to give crude product of 2-(3-bromo-5-fluorophenyl)-2,2-difluoroethan-1-ol (2.6 g, 7.1 mmol, 81.5%) as a colorless oil.

Step D: 1-[3-(1,1-difluoro-2-hydroxyethyl)-5-fluorophenyl]ethan-1-one

To a solution of 2-(3-bromo-5-fluorophenyl)-2,2-difluoroethan-1-ol (2.5 g, 9.8 mmol) was added tributyl(1-ethoxyvinyl)stannane (3.89 g, 10.8 mmol) and $Pd(dppf)Cl_2$ (0.72 g, 0.98 mmol). The reaction was stirred at 100° C. for 1 h under $N_2$. After complete conversation of starting material, HCl (12 N, 2.5 mL) was added and stirred for 10 min. The reaction was quenched with water and extracted with EtOAc (25 mL*2). The combined organic layer was washed with brine and dried over $Na_2SO_4$ then concentrated. The residue was purified by chromatography (silica gel, EtOAc in PE 0-50%) to give the product of 1-[3-(1,1-difluoro-2-hydroxyethyl)-5-fluorophenyl]ethan-1-one (1.5 g, 6.87 mmol, 70.1%) as a brown oil.

Step E: (R)—N-[(1E)-1-[3-(1,1-difluoro-2-hydroxyethyl)-5-fluorophenyl]ethylidene]-2-methylpropane-2-sulfonamide To a stirred solution of 1-[3-(1,1-difluoro-2-hydroxyethyl)-5-fluorophenyl]ethan-1-one (1.5 g, 6.87 mmol) in THF (15 mL) was added (R)-2-methylpropane-2-sulfinamide (1.25 g, 10.3 mmol) and $Ti(OEt)_4$ (4.7 g, 20.6 mmol) at rt. After stirred at 80° C. overnight, the cooled mixture was poured into water (50 mL) and filtrated. The mixture was extracted with EtOAc (25 mL*2) and the combined organic layers was washed with brine, dried over $Na_2SO_4$, filtered and concentrated. The crude product was purified by chromatography (silica gel, 0-50% EtOAc in PE) to give product of (R)—N-[(1E)-1-[3-(1,1-difluoro-2-hydroxyethyl)-5-fluorophenyl] ethylidene]-2-methylpropane-2-sulfonamide (1.5 g, 4.67 mmol, 67.9%) as a brown oil. LC-MS (ESI) m/z 322 $(M+H)^+$.

Step F: 1-{3-[(10-{[(1R)-1-(1,1-difluoro-2,3-dihydro-1H-inden-4-yl)ethyl]amino}-12-methyl-2,4,5,11,13-pentaazatricyclo[7.4.0.0^{2,6}]trideca-1(9),3,5,7,10,12-hexaen-7-yl)oxy]pyrrolidin-1-yl}ethan-1-one To a stirred solution of (R)—N-[(1E)-1-[3-(1,1-difluoro-2-hydroxyethyl)-5-fluorophenyl]ethylidene]-2-methylpropane-2-sulfonamide (1.5 g, 4.7 mmol) in THE (15 mL) was added $NaBH_4$ (0.152 mL, 4.67 mmol) at 0° C. After stirred at 0° C. for 1 h, the mixture was poured into water (20 mL) and extracted with EtOAc (20 mL*2). The combined organic phase was washed with brine, dried over $Na_2SO_4$, filtered and concentrated. The crude product was purified by chromatography (silica gel, 0-100% EtOAc in PE) to give the product of (R)—N-[(1R)-1-[3-(1,1-difluoro-2-hydroxyethyl)-5-fluorophenyl]ethyl]-2-methylpropane-2-sulfonamide (1 g, 3.1 mmol, 66.3%) as a white oil. LC-MS (ESI) m/z 324 $(M+H)^+$. $^1H$ NMR (400 MHz, DMSO) δ 7.48-7.35 (m, 1H), 7.22 (d, J=9.2 Hz, 1H), 5.84 (d, J=7.9 Hz, 1H), 5.66 (t, J=6.4 Hz, 1H), 4.46 (s, 1H), 3.86 (td, J=14.1, 6.4 Hz, 1H), 1.40 (d, J=6.8 Hz, 2H), 1.24-1.07 (m, 5H).

Intermediate 10: Synthesis of 1-(difluoromethyl)cyclopropan-1-amine

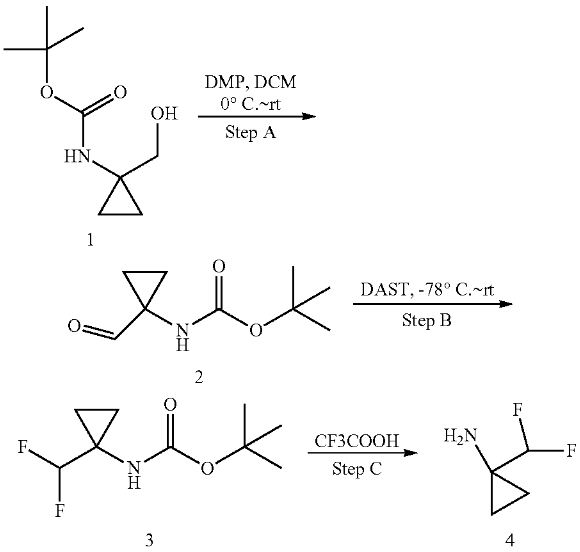

1
2
3
4

Step A: tert-butyl (1-formylcyclopropyl)carbamate

To a stirred solution of tert-butyl N-[1-(hydroxymethyl) cyclopropyl]carbamate (23 g, 123 mmol) in DCM (250 mL) at 0° C. was added Dess-Martin periodinane (62.5 g, 147 mmol) slowly. The reaction mixture was allowed to warm to room temperature and stirred at room temperature for 2 h. The reaction mixture was diluted with ice-water (50 mL), basified to pH=8-9 with $NaHCO_3$. The mixture was filtered and the filtrate was extracted with DCM (100 mL×3). The combined organic phase was washed by water and brine, dried over anhydrous $Na_2SO_4$, filtered and concentrated to give a crude product which was purified by column chromatography on silica gel (PE:EtOAc=50:1 to 10:1) to obtain tert-butyl N-(1-formylcyclopropyl)carbamate (19 g, 102 mmol, 83.5%) as a light yellow solid. LC/MS (ESI) m/z: 186 $(M+H)^+$.

Step B: tert-butyl (1-(difluoromethyl)cyclopropyl)carbamate

To a stirred solution of tert-butyl N-(1-formylcyclopropyl)carbamate (11 g, 59.4 mmol) in anhydrous DCM (200 mL) at −78° C. was added Diethylaminosulfur trifluoride (22 g, 137 mmol) slowly. The reaction mixture was allow to warm to room temperature and stirred for 2 h under nitrogen atmosphere. The reaction mixture was diluted with saturated $NaHCO_3$solution (150 mL), extracted with DCM (100 mL×3). The combined organic phase was washed by water and brine, dried over anhydrous $Na_2SO_4$, filtered and concentrated to give a crude product which was purified by column chromatography on silica gel (PE:EtOAc=100:1 to 10:1) to obtain tert-butyl N-[1-(difluoromethyl)cyclopropyl] carbamate (2.6 g, 12.6 mmol, 21.0%) as a white solid. LC/MS (ESI) m/z: 208 $(M+H)^+$.

Step C: 1-(difluoromethyl)cyclopropan-1-amine

To a stirred solution of tert-butyl N-[1-(difluoromethyl) cyclopropyl]carbamate (1.6 g, 7.7 mmol) in DCM (30 mL)

was added $CF_3COOH$ (6 mL, 80 mmol) slowly. The reaction mixture was stirred at room temperature for 2 h. The reaction mixture was concentrated to give a crude product 1-(difluoromethyl)cyclopropan-1-amine (1.2 g 7.5 mmol, 96.7%) as a trifluoroacetic acid salt which was used directly for next step without purification.

Intermediate 10: Synthesis of 2-methoxy-1-[4-(tetramethyl-1,3,2-dioxaborolan-2-yl)-1,2,3,6-tetrahydropyridin-1-yl]ethan-1-one

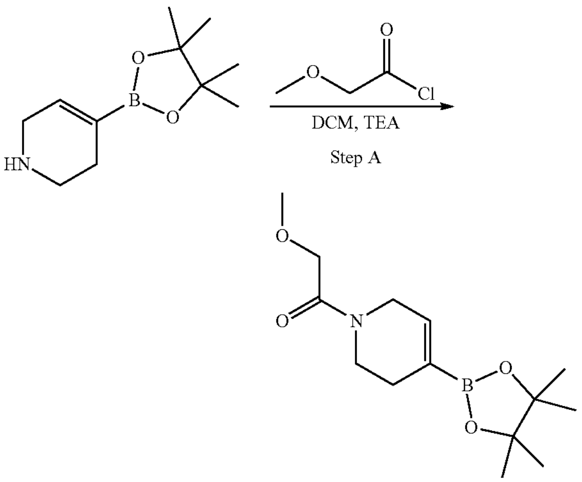

Step A: 2-methoxy-1-[4-(tetramethyl-1,3,2-dioxaborolan-2-yl)-1,2,3,6-tetrahydropyridin-1-yl]ethan-1-one To a stirred solution of 4-(tetramethyl-1,3,2-dioxaborolan-2-yl)-1,2,3,6-tetrahydropyridine (300 mg, 1.44 mmol) in DCM (5 mL) at room temperature was added TEA (0.199 mL, 1.44 mmol) and 2-methoxyacetyl chloride (0.131 mL, 1.44 mmol) slowly. The reaction mixture was stirred at room temperature for 2 h under nitrogen atmosphere. The reaction mixture was diluted with water (50 mL), extracted with EtOAc (50 mL×3). The combined organic phase was washed by water and brine, dried over anhydrous $Na_2SO_4$, filtered and concentrated to give the crude product which was purified by column chromatography on silica gel (PE: EtOAc=10:1 to 3:1) to obtain 2-methoxy-1-[4-(tetramethyl-1,3,2-dioxaborolan-2-yl)-1,2,3,6-tetrahydropyridin-1-yl]ethan-1-one (270 mg, 0.960 mmol, 66.9%) as a colorless oil. LC/MS (ESI) m/z: 282 $(M+H)^+$.

Example 1: Synthesis of N-[(1R)-1-(1,1-difluoro-2,3-dihydro-1H-inden-4-yl)ethyl]-12-methyl-7-(oxan-4-yl)-2,4,5,11,13-pentaazatricyclo[7.4.0.0^{2,6}]trideca-1(9),3,5,7,10,12-hexaen-10-amine

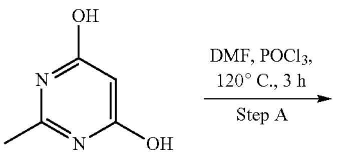

-continued

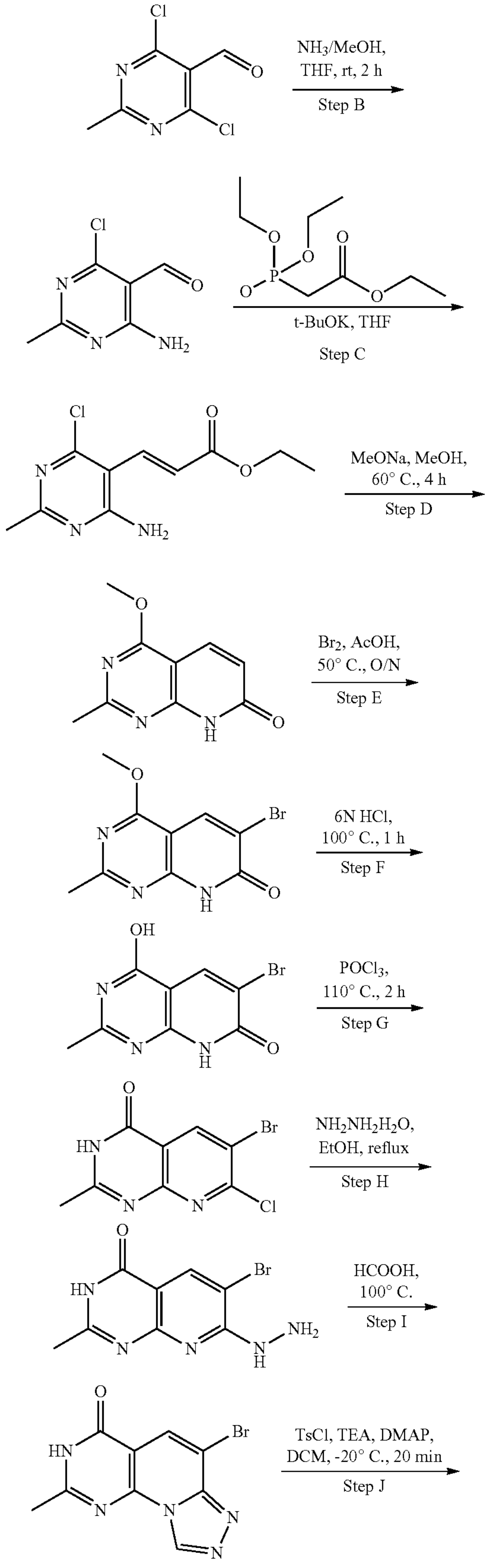

10

-continued

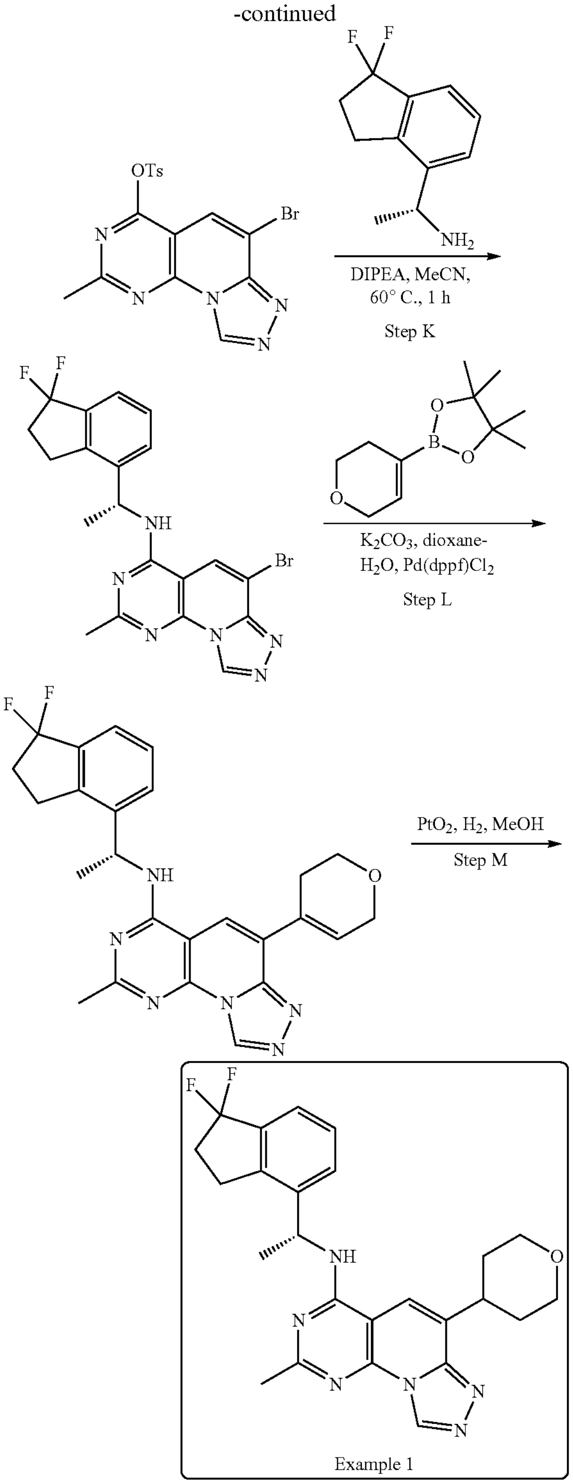

Example 1

Step A. 4,6-dichloro-2-methylpyrimidine-5-carbaldehyde

A stirred mixture of DMF (6.2 mL, 39.26 mmol) was added $POCl_3$ (100 g, 652 mmol) at 0° C. After stirred at rt for 10 min. 2-methylpyrimidine-4,6-diol (10 g, 79.3 mmol) was added at 0° C. After stirred at 120° C. for 3 h, the cooled mixture was concentrated. The crude product was poured into cooled $NaHCO_3$ (100 mL, aq) and extracted with EtOAc twice. The combined organic phase was washed with $NaHCO_3$ (100 mL, aq), brine, dried over $Na_2SO_4$, filtered and concentrated. The crude product was purified by chromatography (silica gel, 0-20%, EtOAc in PE) to give 4,6-dichloro-2-methylpyrimidine-5-carbaldehyde (7.5 g, 39 mmol, 49.5%) as a white solid. LC-MS (ESI) m/z 190 $(M+H)^+$.

Step B. 4-amino-6-chloro-2-methylpyrimidine-5-carbaldehyde

To a stirred solution of 4,6-dichloro-2-methylpyrimidine-5-carbaldehyde (6 g, 31.4 mmol) in THF (50 mL) was added $NH_3$/MeOH (9 mL, 62.8 mmol, 7 mol/L) at 0° C. After stirred at rt for 2 h, the mixture was concentrated. The crude product was purified by chromatography (silica gel, 0-100%, EtOAc in PE) to give 4-amino-6-chloro-2-methylpyrimidine-5-carbaldehyde (4.4 g, 25.64 mmol, 81%) as a yellow solid. LC-MS (ESI) m/z 172 $(M+H)^+$.

Step C. ethyl (2E)-3-(4-amino-6-chloro-2-methylpyrimidin-5-yl)prop-2-enoate

To a stirred mixture of t-BuOK (4.35 g, 35.61 mmol) in THF (100 mL) was added ethyl 2-(diethoxyphosphoryl) acetate (6.5 mL, 32.87 mmol) at 0° C. After stirred at 0° C. for 1 h, the mixture was added 4-amino-6-chloro-2-methylpyrimidine-5-carbaldehyde (4.7 g, 27.39 mmol) at 0° C. After stirred at rt overnight, the mixture was poured into water (200 mL) and extracted with EtOAc (200 mL*2). The combined organic phase was washed with brine, dried over $Na_2SO_4$, filtered and concentrated. The crude product was purified by chromatography (silica gel, 0-50%, EtOAc in PE) to give ethyl (2E)-3-(4-amino-6-chloro-2-methylpyrimidin-5-yl)prop-2-enoate (6.4 g, 26.5 mmol, 96%) as a yellow solid. LC-MS (ESI) m/z 242 $(M+H)^+$.

Step D. 4-methoxy-2-methyl-7H,8H-pyrido[2,3-d]pyrimidin-7-one

To a stirred solution of ethyl (2E)-3-(4-amino-6-chloro-2-methylpyrimidin-5-yl)prop-2-enoate (6.4 g, 26.48 mmol) in MeOH (100 mL) was added MeONa (10.6 mL, 52.9 mmol, 5 mol/L in MeOH) at rt. After stirred at 60° C. for 4 h, the cooled mixture was concentrated. The crude product was purified by chromatography (silica gel, 0-100%, EtOAc in PE) to give 4-methoxy-2-methyl-7H,8H-pyrido[2,3-d]pyrimidin-7-one (4 g, 20.9 mmol, 79%) as a yellow solid. LC-MS (ESI) m/z 192 $(M+H)^+$.

Step E. 6-bromo-4-methoxy-2-methyl-7H,8H-pyrido[2,3-d]pyrimidin-7-one

To a stirred solution of 4-methoxy-2-methyl-7H,8H-pyrido[2,3-d]pyrimidin-7-one (4 g, 20.9 mmol) in AcOH (40 mL) was added $Br_2$ (2.2 mL, 41.8 mmol) at rt. After stirred at 50° C. overnight, the cooled mixture was added DCM (100 mL) and stirred at rt for 30 min. The mixture was filtered. The filter cake was washed with DCM (50 mL) and dried to give 6-bromo-4-methoxy-2-methyl-7H,8H-pyrido[2,3-d]pyrimidin-7-one (4.4 g, 16.23 mmol, 78%) as a yellow solid. LC-MS (ESI) m/z 270 $(M+H)^+$.

Step F. 6-bromo-4-hydroxy-2-methyl-7H,8H-pyrido[2,3-d]pyrimidin-7-one

A stirred mixture of 6-bromo-4-methoxy-2-methyl-7H,8H-pyrido[2,3-d]pyrimidin-7-one (4.4 g, 16.3 mmol) was added HCl (25 mL, 36%) and water (25 mL) at rt. After stirred at 100° C. for 1 h, the cooled mixture was concentrated to give 6-bromo-4-hydroxy-2-methyl-7H,8H-pyrido[2,3-d]pyrimidin-7-one (4 g, 15.6 mmol, 96%) as a yellow solid. LC-MS (ESI) m/z 256 $(M+H)^+$.

Step G. 6-bromo-7-chloro-2-methylpyrido[2,3-d]pyrimidin-4-ol

A stirred solution of 6-bromo-4-hydroxy-2-methyl-7H,8H-pyrido[2,3-d]pyrimidin-7-one (4 g, 15.62 mmol) was added $POCl_3$ (40 mL) at rt. After stirred at 100° C. for 2 h, the cooled mixture was concentrated. The crude product was purified by chromatography (silica gel, 0-20%, MeOH in DCM) to give 6-bromo-7-chloro-2-methylpyrido[2,3-d]pyrimidin-4-ol (1.9 g, 6.92 mmol, 44%) as a yellow solid. LC-MS (ESI) m/z 275 $(M+H)^+$.

Step H. 6-bromo-7-hydrazinyl-2-methyl-3H,4H-pyrido[2,3-d]pyrimidin-4-one

To a stirred solution of 6-bromo-7-chloro-2-methyl-3H,4H-pyrido[2,3-d]pyrimidin-4-one (1.9 g, 6.92 mmol) in EtOH (20 mL) was added $NH_2NH_2 \cdot H_2O$ (4.2 mL, 69.2 mmol) at rt. After stirred at 100° C. for 2 h, the cooled mixture was concentrated. The crude product was added water (20 mL) and stirred at rt for 10 min. The mixture was filtered. The filter cake was dried to give 6-bromo-7-hydrazinyl-2-methyl-3H,4H-pyrido[2,3-d]pyrimidin-4-one (1.2 g, 4.44 mmol, 64%) as a yellow solid. LC-MS (ESI) m/z 270 $(M+H)^+$.

Step I. 7-bromo-12-methyl-2,4,5,11,13-pentaazatricyclo[7.4.0.0^{2,6}]trideca-1(9),3,5,7,12-pentaen-10-one A stirred solution of 6-bromo-7-hydrazinyl-2-methyl-3H,4H-pyrido[2,3-d]pyrimidin-4-one (1.2 g, 4.44 mmol) was added formic acid (15 mL) at rt. After stirred at 100° C. for 2 h, the cooled mixture was concentrated. The crude product was purified by chromatography (silica gel, 0-20%, MeOH in DCM) to give 7-bromo-12-methyl-2,4,5,11,13-pentaazatricyclo[7.4.0.0^{2,6}]trideca-1(9),3,5,7,12-pentaen-10-one (700 mg, 2.50 mmol, 56%) as a yellow solid. LC-MS (ESI) m/z 280 $(M+H)^+$.

Step J. 7-bromo-12-methyl-2,4,5,11,13-pentaazatricyclo[7.4.0.0^{2,6}]trideca-1(9),3,5,7,10,12-hexaen-10-yl 4-methylbenzene-1-sulfonate To a stirred solution of 7-bromo-12-methyl-2,4,5,11,13-pentaazatricyclo[7.4.0.0^{2,6}]trideca-1(9),3,5,7,10,12-hexaen-10-ol (40 mg, 0.14 mmol) in DCM (5 mL) was added TEA (44 mg, 0.43 mmol), TsCl (33 mg, 0.17 mmol) at −20° C. After stirred at −20° C. for 20 min, the mixture was poured into water (10 mL) and extracted with DCM (10 mL*2). The combined organic phase was washed with brine, dried over $Na_2SO_4$, filtered and concentrated. The crude product was purified by chromatography (silica gel, 0-20%, MeOH in DCM) to give 7-bromo-12-methyl-2,4,5,11,13-pentaazatricyclo[7.4.0.0^{2,6}]trideca-1(9),3,5,7,10,12-hexaen-10-yl 4-methylbenzene-1-sulfonate (24 mg, 0.055 mmol, 38%) as a yellow solid. LC-MS (ESI) m/z 435 $(M+H)^+$.

Step K. 7-bromo-N-[(1R)-1-(1,1-difluoro-2,3-dihydro-1H-inden-4-yl)ethyl]-12-methyl-2,4,5,11,13-pentaazatricyclo[7.4.0.0^{2,6}]trideca-1(9),3,5,7,10,12-hexaen-10-amine To a stirred solution of 7-bromo-12-methyl-2,4,5,11,13-pentaazatricyclo[7.4.0.0^{2,6}]trideca-1(9),3,5,7,10,12-hexaen-10-yl 4-methylbenzene-1-sulfonate (24 mg, 0.055 mmol) in MeCN (5 mL) was added DIPEA (22 mg, 0.17 mmol) and (1R)-1-(1,1-difluoro-2,3-dihydro-1H-inden-4-yl)ethan-1-amine (17 mg, 0.083 mmol) at rt. After stirred at 60° C. for 2 h, the cooled mixture was concentrated. The crude product was purified by chromatography (silica gel, 0-20%, MeOH in DCM) to give 7-bromo-N-[(1R)-1-(1,1-difluoro-2,3-dihydro-1H-inden-4-yl)ethyl]-12-methyl-2,4,5,11,13-pentaazatricyclo[7.4.0.0^{2,6}]trideca-1(9),3,5,7,10,12-hexaen-10-amine (20 mg, 0.044 mmol, 78%) as a yellow solid. LC-MS (ESI) m/z 460 $(M+H)^+$.

Step L. N-[(1R)-1-(1,1-difluoro-2,3-dihydro-1H-inden-4-yl)ethyl]-7-(3,6-dihydro-2H-pyran-4-yl)-12-methyl-2,4,5,11,13-pentaazatricyclo[7.4.0.0^{2,6}]trideca-1(9),3,5,7,10,12-hexaen-10-amine To a stirred solution of 7-bromo-N-[(1R)-1-(1,1-difluoro-2,3-dihydro-1H-inden-4-yl)ethyl]-12-methyl-2,4,5,11,13-pentaazatricyclo[7.4.0.0^{2,6}]trideca-1(9),3,5,7,10,12-hexaen-10-amine (20 mg, 0.044 mmol) in dioxane (2 mL) and water (0.5 mL) was added 2-(3,6-dihydro-2H-pyran-4-yl)-4,4,5,5-tetramethyl-1,3,2-dioxaborolane (13.72 mg, 0.065 mmol) (1R)-1-(1,1-difluoro-2,3-dihydro-1H-inden-4-yl)ethan-1-amine (17 mg, 0.083 mmol), $K_2CO_3$ (18 mg, 0.131 mmol) and Pd(dppf)$Cl_2$ (7 mg, 0.009 mmol) at rt. After stirred at 80° C. for 2 h, the cooled mixture was filtered and concentrated. The crude product was purified by chromatography (silica gel, 0-20%, MeOH in DCM) to give crude N-[(1R)-1-(1,1-difluoro-2,3-dihydro-1H-inden-4-yl)ethyl]-7-(3,6-dihydro-2H-pyran-4-yl)-12-methyl-2,4,5,11,13-pentaazatricyclo [7.4.0.0^{2,6}]trideca-1(9),3,5,7,10,12-hexaen-10-amine (20 mg, 0.043 mmol, 99%) as a yellow solid. LC-MS (ESI) m/z 463 $(M+H)^+$.

Step M. N-[(1R)-1-(1,1-difluoro-2,3-dihydro-1H-inden-4-yl)ethyl]-12-methyl-7-(oxan-4-yl)-2,4,5,11,13-pentaazatricyclo[7.4.0.0^{2,6}]trideca-1(9),3,5,7,10,12-hexaen-10-amine To a stirred solution of N-[(1R)-1-(1,1-difluoro-2,3-dihydro-1H-inden-4-yl)ethyl]-7-(3,6-dihydro-2H-pyran-4-yl)-12-methyl-2,4,5,11,13-pentaazatricyclo[7.4.0.0^{2,6}]trideca-1(9),3,5,7,10,12-hexaen-10-amine (20 mg, 0.043 mmol) in MeOH (5 mL) was added $PtO_2$ (20 mg, 0.088 mmol) at rt. After stirred at 60° C. using a $H_2$ balloon for 2 h, the cooled mixture was filtered and concentrated. The crude product was purified by prep-HPLC (C18, 30~70% MeCN in $H_2O$ with 0.1% HCOOH) to give N-[(1R)-1-(1,1-difluoro-2,3-dihydro-1H-inden-4-yl)ethyl]-12-methyl-7-(oxan-4-yl)-2,4,5,11,13-pentaazatricyclo[7.4.0.0^{2,6}]trideca-1(9),3,5,7,10,12-hexaen-10-amine (1.2 mg, 0.003 mmol, 6%) as a white solid. LC-MS (ESI) m/z 465 $(M+H)^+$. 1H NMR (400 MHz, DMSO) δ 9.55 (s, 1H), 8.68 (d, J=7.1 Hz, 1H), 8.02 (s, 1H), 7.65 (d, J=4.6 Hz, 1H), 7.43 (s, 2H), 5.62-5.55 (m, 1H), 4.05 (d, J=10.9 Hz, 2H), 3.56 (s, 3H), 3.18 (s, 2H), 2.64 (dd, J=14.2, 6.8 Hz, 2H), 2.45 (s, 3H), 1.97 (s, 4H), 1.62 (d, J=6.8 Hz, 3H).

The examples in the following Table 1 were prepared by using a method analogous to that used to prepare the examples as described herein.

TABLE 1

| Ex# | Structure & name | Analytical data | Method |
|---|---|---|---|
| Example 2 | 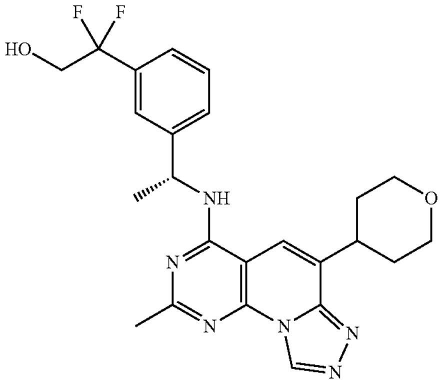 [SMILES: Cc1nc(N[C@H](C)c2cccc(C(F)(F)CO)c2)c2cc(C3CCOCC3)c3nncn3c2n1] (R)-2,2-difluoro-2-(3-(1-((2-methyl-6-(tetrahydro-2H-pyran-4-yl)-[1,2,4]triazolo[4',3':1,6]pyrido[2,3-d]pyrimidin-4-yl)amino)ethyl)phenyl)ethanol | LC-MS (ESI) m/z 469 $(M + H)^+$. 1H NMR (400 MHz, MeOD) δ 9.58 (s, 1H), 7.98 (s, 1H), 7.67 (s, 1H), 7.59 (d, J = 7.2 Hz, 1H), 7.42 (p, J = 7.7 Hz, 2H), 5.71 (d, J = 7.0 Hz, 1H), 4.12 (d, J = 9.9 Hz, 2H), 3.87 (t, J = 13.5 Hz, 2H), 3.70 (dd, J = 12.6, 10.3 Hz, 2H), 3.56-3.49 (m, 1H), 2.54 (s, 3H), 2.03 (dt, J = 12.6, 10.6 Hz, 4H), 1.69 (d, J = 7.1 Hz, 3H). | Example 1 |
| Example 3 | 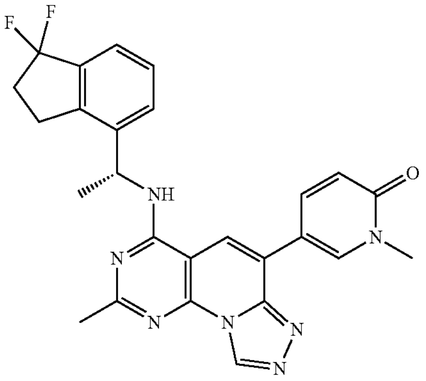 [SMILES: Cc1nc(N[C@H](C)c2cccc3c2CCC3(F)F)c2cc(-c3ccc(=O)n(C)c3)c3nncn3c2n1] (R)-5-(4-((1-(1,1-difluoro-2,3-dihydro-1H-inden-4-yl)ethyl)amino)-2-methyl-[1,2,4]triazolo[4',3':1,6]pyrido[2,3-d]pyrimidin-6-yl)-1-methylpyridin-2(1H)-one | LC-MS (ESI) m/z 488 $(M + H)^+$. $^1H$ NMR (400 MHz, MeOD) δ 9.64 (s, 1H), 8.89 (d, J = 2.5 Hz, 1H), 8.31 (s, 1H), 8.28 (dd, J = 9.4, 2.6 Hz, 1H), 7.60 (d, J = 6.9 Hz, 1H), 7.38 (dd, J = 12.2, 7.0 Hz, 2H), 6.73 (d, J = 9.4 Hz, 1H), 5.67 (q, J = 7.0 Hz, 1H), 3.71 (s, 3H), 3.13 (s, 2H), 2.66-2.57 (m, 2H), 2.53 (s, 3H), 1.68 (d, J = 7.0 Hz, 3H). | Example 1 |
| Example 4 | 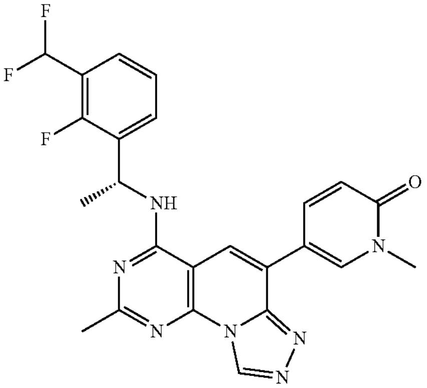 [SMILES: Cc1nc(N[C@H](C)c2cccc(C(F)F)c2F)c2cc(-c3ccc(=O)n(C)c3)c3nncn3c2n1] (R)-5-(4-((1-(3-(difluoromethyl)-2-fluorophenyl)ethyl)amino)-2-methyl-[1,2,4]triazolo[4',3':1,6]pyrido[2,3-d]pyrimidin-6-yl)-1-methylpyridin-2(1H)-one | LC-MS (ESI) m/z 480 $(M + H)^+$. $^1H$ NMR (400 MHz, MeOD) δ 9.64 (s, 1H), 8.90 (d, J = 2.5 Hz, 1H), 8.34 (s, 1H), 8.29 (dd, J = 9.5, 2.6 Hz, 1H), 7.65 (t, J = 7.1 Hz, 2H), 7.49 (t, J = 7.0 Hz, 1H), 7.25 (t, J = 7.8 Hz, 1H), 7.01 (t, J = 54.8 Hz, 1H), 6.73 (d, J = 9.5 Hz, 1H), 5.86 (q, J = 7.1 Hz, 1H), 3.72 (s, 4H), 2.52 (s, 3H), 1.72 (d, J = 7.1 Hz, 4H). | Example 1 |

TABLE 1-continued

| Ex# | Structure & name | Analytical data | Method |
|---|---|---|---|
| Example 5 | 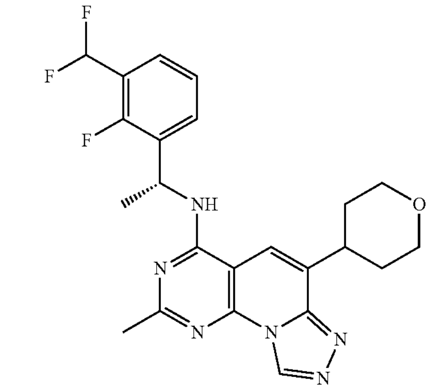 [SMILES: Cc1nc(N[C@H](C)c2cccc(C(F)F)c2F)c2cc(C3CCOCC3)c3nncn3c2n1] (R)-N-(1-(3-(difluoromethyl)-2-fluorophenyl)ethyl)-2-methyl-6-(tetrahydro-2H-pyran-4-yl)-[1,2,4]triazolo[4',3':1,6]pyrido[2,3-d]pyrimidin-4-amine | LC-MS (ESI) m/z 457 $(M + H)^+$. $^1H$ NMR (400 MHz, MeOD) δ 9.57 (s, 1H), 8.03 (s, 1H), 7.62 (t, J = 7.4 Hz, 1H), 7.48 (t, J = 6.9 Hz, 1H), 7.24 (t, J = 7.7 Hz, 1H), 7.01 (t, J = 54.9 Hz, 1H), 5.84 (q, J = 7.0 Hz, 1H), 4.17-4.10 (m, 2H), 3.71 (td, J = 11.5, 2.1 Hz, 2H), 3.56-3.48 (m, 1H), 2.49 (s, 3H), 2.04 (dd, J = 26.7, 11.8 Hz, 4H), 1.70 (d, J = 7.1 Hz, 3H). | Example 1 |
| Example 6 | 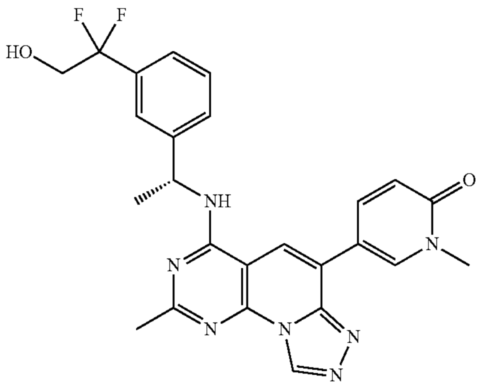 [SMILES: Cc1nc(N[C@H](C)c2cccc(C(F)(F)CO)c2)c2cc(-c3ccc(=O)n(C)c3)c3nncn3c2n1] (R)-5-(4-((1-(3-(1,1-difluoro-2-hydroxyethyl)phenyl)ethyl)amino)-2-methyl-[1,2,4]triazolo[4',3':1,6]pyrido[2,3-d]pyrimidin-6-yl)-1-methylpyridin-2(1H)-one | LC-MS (ESI) m/z 492 $(M + H)^+$. $^1H$ NMR (400 MHz, MeOD) δ 9.64 (s, 1H), 8.88 (d, J = 2.6 Hz, 1H), 8.30 (s, 1H), 8.27 (dd, J = 9.5, 2.7 Hz, 1H), 7.68 (s, 1H), 7.59 (s, 1H), 7.43 (d, J = 7.4 Hz, 2H), 6.72 (d, J = 9.5 Hz, 1H), 5.72 (d, J = 7.0 Hz, 1H), 4.58 (s, 1H), 3.88 (t, J = 13.4 Hz, 2H), 3.71 (s, 3H), 2.57 (s, 3H), 1.71 (d, J = 7.1 Hz, 3H). | Example 1 |
| Example 7 | 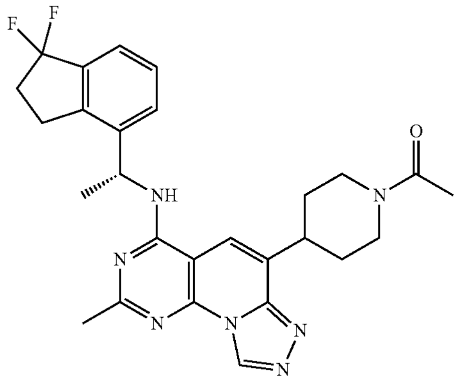 [SMILES: CC(=O)N1CCC(c2cc3c(N[C@H](C)c4cccc5c4CCC5(F)F)nc(C)nc3n3cnnc23)CC1] (R)-1-(4-(4-((1-(1,1-difluoro-2,3-dihydro-1H-inden-4-yl)ethyl)amino)-2-methyl-[1,2,4]triazolo[4',3':1,6]pyrido[2,3-d]pyrimidin-6-yl)piperidin-1-yl)ethanone | LC-MS (ESI) m/z 506 $(M + H)^+$. $^1H$ NMR (400 MHz, DMSO) δ 9.56 (s, 1H), 8.64 (d, J = 7.1 Hz, 1H), 8.05 (s, 1H), 7.65 (d, J = 5.4 Hz, 1H), 7.45-7.39 (m, 2H), 5.63-5.55 (m, 1H), 3.78 (d, J = 11.5 Hz, 2H), 3.18 (s, 3H), 2.98-2.92 (m, 5H), 2.69-2.62 (m, 2H), 2.46 (s, 3H), 2.16 (d, J = 11.2 Hz, 2H), 1.97 (d, J = 12.3 Hz, 2H), 1.62 (d, J = 6.9 Hz, 3H). | Example 1 |

TABLE 1-continued

| Ex# | Structure & name | Analytical data | Method |
|---|---|---|---|
| Example 8 | 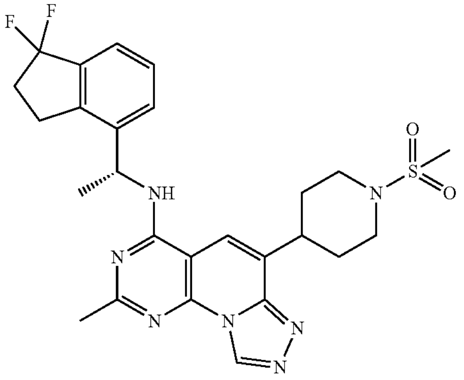 [SMILES: Cc1nc(N[C@H](C)c2cccc3c2CCC3(F)F)c2cc(C3CCN(S(C)(=O)=O)CC3)c3nncn3c2n1]<br>(R)-N-(1-(1,1-difluoro-2,3-dihydro-1H-inden-4-yl)ethyl)-2-methyl-6-(1-(methylsulfonyl)piperidin-4-yl)-[1,2,4]triazolo[4',3':1,6]pyrido[2,3-d]pyrimidin-4-amine | LC-MS (ESI) m/z 542 $(M + H)^+$. $^1H$ NMR (400 MHz, DMSO) δ 9.56 (s, 1H), 8.64 (d, J = 7.1 Hz, 1H), 8.05 (s, 1H), 7.65 (d, J = 5.4 Hz, 1H), 7.45-7.39 (m, 2H), 5.63-5.55 (m, 1H), 3.78 (d, J = 11.5 Hz, 2H), 3.18 (s, 3H), 2.98-2.92 (m, 5H), 2.69-2.62 (m, 2H), 2.46 (s, 3H), 2.16 (d, J = 11.2 Hz, 2H), 1.97 (d, J = 12.3 Hz, 2H), 1.62 (d, J = 6.9 Hz, 3H) | Example 1 |
| Example 9 | 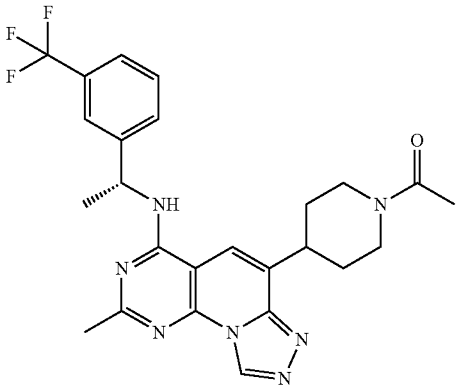 [SMILES: CC(=O)N1CCC(c2cc3c(N[C@H](C)c4cccc(C(F)(F)F)c4)nc(C)nc3n3cnnc23)CC1]<br>(R)-1-(4-(2-methyl-4-((1-(3-(trifluoromethyl)phenyl)ethyl)amino)-[1,2,4]triazolo[4',3':1,6]pyrido[2,3-d]pyrimidin-6-yl)piperidin-1-yl)ethan-1-one | LC-MS (ESI) m/z 498 $(M + H)^+$. $^1H$ NMR (400 MHz, MeOD) δ 9.54 (s, 1H), 7.96 (s, 1H), 7.78 (s, 1H), 7.76-7.71 (m, 1H), 7.57-7.48 (m, 2H), 5.72-5.63 (m, 1H), 4.77 (dd, J = 13.3, 1.9 Hz, 1H), 4.12 (dd, J = 13.7, 1.8 Hz, 1H), 3.52 (ddd, J = 12.1, 8.9, 3.3 Hz, 1H), 3.38 (dd, J = 13.1, 11.2 Hz, 1H), 2.85 (td, J = 12.9, 2.3 Hz, 1H), 2.52 (s, 3H), 2.26-2.11 (m, 5H), 1.85 (ddd, J = 17.3, 12.7, 7.5 Hz, 2H), 1.70 (d, J = 7.1 Hz, 3H). | Example 1 |
| Example 10 | 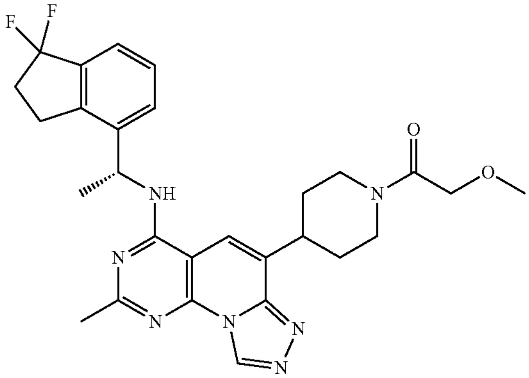 [SMILES: COCC(=O)N1CCC(c2cc3c(N[C@H](C)c4cccc5c4CCC5(F)F)nc(C)nc3n3cnnc23)CC1]<br>(R)-1-(4-(4-((1-(1,1-difluoro-2,3-dihydro-1H-inden-4-yl)ethyl)amino)-2-methyl-[1,2,4]triazolo[4',3':1,6]pyrido[2,3-d]pyrimidin-6-yl)piperidin-1-yl)-2-methoxyethan-1-one | LC-MS (ESI) m/z 536 $(M + H)^+$. $^1H$ NMR (400 MHz, MeOD) δ 9.52 (s, 1H), 7.98 (s, 1H), 7.58 (d, J = 6.9 Hz, 1H), 7.43-7.26 (m, 2H), 5.62 (d, J = 6.7 Hz, 1H), 4.74 (d, J = 13.1 Hz, 1H), 4.23 (q, J = 13.0 Hz, 2H), 4.05 (d, J = 12.7 Hz, 1H), 3.58-3.34 (m, 6H), 3.14 (s, 1H), 2.89 (t, J = 12.7 Hz, 1H), 2.61 (s, 2H), 2.48 (s, 3H), 2.25-2.12 (m, 2H), 1.86 (d, J = 7.0 Hz, 2H), 1.66 (d, J = 6.9 Hz, 3H). | Example 1 |

TABLE 1-continued

| Ex# | Structure & name | Analytical data | Method |
|---|---|---|---|
| Example 11 | 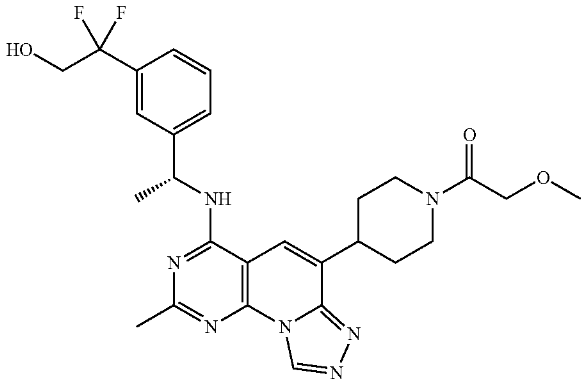 [SMILES: COCC(=O)N1CCC(c2cc3c(N[C@H](C)c4cccc(C(F)(F)CO)c4)nc(C)nc3n3cnnc23)CC1] (R)-1-(4-(4-((1-(3-(1,1-difluoro-2-hydroxyethyl)phenyl)ethyl)amino)-2-methyl-[1,2,4]triazolo[4',3':1,6]pyrido[2,3-d]pyrimidin-6-yl)piperidin-1-yl)-2-methoxyethan-1-one | LC-MS (ESI) m/z 540 $(M + H)^+$. $^1H$ NMR (400 MHz, MeOD) δ 9.62 (s, 1H), 8.06 (s, 1H), 7.66 (s, 1H), 7.58 (d, J = 7.0 Hz, 1H), 7.42 (q, J = 7.9 Hz, 2H), 5.70 (q, J = 6.7 Hz, 1H), 4.74 (d, J = 13.5 Hz, 1H), 4.22 (q, J = 13.4 Hz, 2H), 4.06 (d, J = 13.1 Hz, 1H), 3.87 (t, J = 13.5 Hz, 2H), 3.55-3.35 (m, 5H), 2.89 (t, J = 12.3 Hz, 1H), 2.55 (s, 3H), 2.18 (dd, J = 20.4, 12.8 Hz, 2H), 1.86 (d, J = 6.7 Hz, 2H), 1.69 (d, J = 7.1 Hz, 3H). | Example 1 |
| Example 12 | 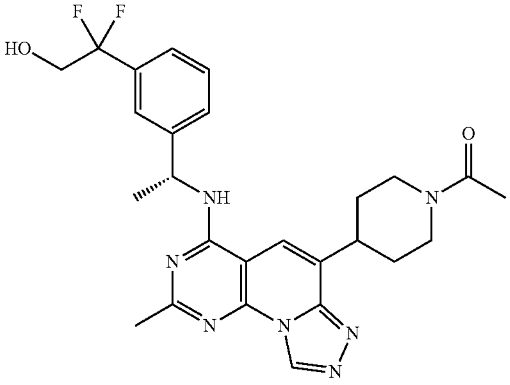 [SMILES: CC(=O)N1CCC(c2cc3c(N[C@H](C)c4cccc(C(F)(F)CO)c4)nc(C)nc3n3cnnc23)CC1] (R)-1-(4-(4-((1-(3-(1,1-difluoro-2-hydroxyethyl)phenyl)ethyl)amino)-2-methyl-[1,2,4]triazolo[4',3':1,6]pyrido[2,3-d]pyrimidin-6-yl)piperidin-1-yl)ethan-1-one | LC-MS (ESI) m/z 510 $(M + H)^+$. $^1H$ NMR (400 MHz, MeOD) δ 9.56 (d, J = 2.3 Hz, 1H), 7.96 (s, 1H), 7.66 (s, 1H), 7.58 (d, J = 7.0 Hz, 1H), 7.45-7.38 (m, 2H), 5.73-5.66 (m, 1H), 4.76 (d, J = 11.4 Hz, 1H), 4.11 (d, J = 12.4 Hz, 1H), 3.87 (t, J = 13.4 Hz, 2H), 3.53 (t, J = 12.0 Hz, 1H), 3.38 (t, J = 12.4 Hz, 1H), 2.84 (t, J = 11.8 Hz, 1H), 2.54 (s, 3H), 2.25-2.10 (m, 5H), 1.91-1.78 (m, 2H), 1.68 (d, J = 7.1 Hz, 3H). | Example 1 |
| Example 13 | 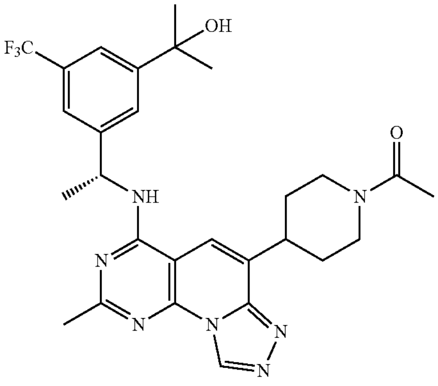 [SMILES: CC(=O)N1CCC(c2cc3c(N[C@H](C)c4cc(C(C)(C)O)cc(C(F)(F)F)c4)nc(C)nc3n3cnnc23)CC1] (R)-1-(4-(4-((1-(3-(2-hydroxypropan-2-yl)-5-(trifluoromethyl)phenyl)ethyl)amino)-2-methyl-[1,2,4]triazolo[4',3':1,6]pyrido[2,3-d]pyrimidin-6-yl)piperidin-1-yl)ethan-1-one | LC/MS (ESI) m/z: 556 $(M + H)^+$. $^1H$ NMR (400 MHz, MeOD) δ 9.53 (s, 1H), 7.95 (d, J = 0.5 Hz, 1H), 7.88 (s, 1H), 7.65 (d, J = 5.5 Hz, 2H), 5.67 (d, J = 7.0 Hz, 1H), 4.77 (dd, J = 13.3, 2.0 Hz, 1H), 4.12 (dd, J = 13.7, 1.9 Hz, 1H), 3.52 (s, 1H), 3.38 (d, J = 2.0 Hz, 1H), 2.85 (td, J = 12.9, 2.4 Hz, 1H), 2.52 (s, 3H), 2.27-2.20 (m, 1H), 2.17 (d, J = 2.1 Hz, 3H), 2.12 (s, 1H), 1.84 (s, 2H), 1.71 (d, J = 7.1 Hz, 3H), 1.54 (d, J = 4.0 Hz, 6H). | Example 1 |

TABLE 1-continued

| Ex# | Structure & name | Analytical data | Method |
|---|---|---|---|
| Example 14 | 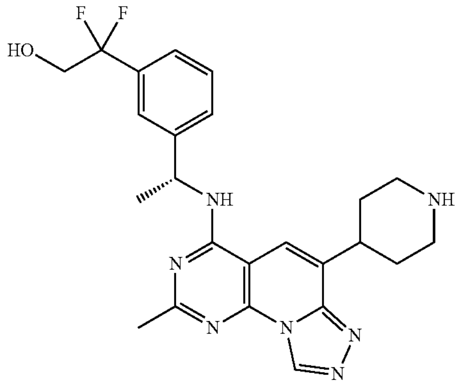 [SMILES: Cc1nc(N[C@H](C)c2cccc(C(F)(F)CO)c2)c2cc(C3CCNCC3)c3nncn3c2n1] (R)-2,2-difluoro-2-(3-(1-((2-methyl-6-(piperidin-4-yl)-[1,2,4]triazolo[4',3':1,6]pyrido[2,3-d]pyrimidin-4-yl)amino)ethyl)phenyl)ethan-1-ol | LC-MS (ESI) m/z 468 $(M + H)^+$. $^1H$ NMR (400 MHz, MeOD) δ 9.65-9.47 (m, 1H), 7.94 (s, 1H), 7.67 (s, 1H), 7.59 (d, J = 7.2 Hz, 1H), 7.45-7.39 (m, 2H), 5.72 (q, J = 6.8 Hz, 1H), 3.87 (t, J = 13.5 Hz, 2H), 3.39 (d, J = 11.6 Hz, 1H), 3.23 (d, J = 12.4 Hz, 2H), 2.90 (t, J = 12.1 Hz, 2H), 2.54 (s, 3H), 2.13 (d, J = 13.6 Hz, 2H), 1.87 (d, J = 12.7 Hz, 2H), 1.70 (d, J = 7.1 Hz, 3H). | Example 1 |
| Example 15 | 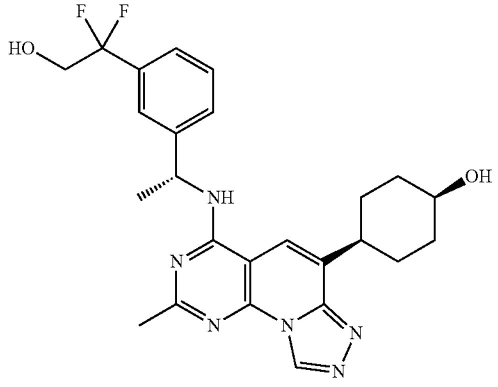 [SMILES: Cc1nc(N[C@H](C)c2cccc(C(F)(F)CO)c2)c2cc([C@H]3CC[C@@H](O)CC3)c3nncn3c2n1] Cis-(R)-4-(4-((1-(3-(1,1-difluoro-2-hydroxyethyl)phenyl)ethyl)amino)-2-methyl-[1,2,4]triazolo[4',3':1,6]pyrido[2,3-d]pyrimidin-6-yl)cyclohexan-1-ol | LC-MS (ESI) m/z 483 $(M + H)^+$. SW-N191149-197-1 $^1H$ NMR (400 MHz, MeOD) δ 9.52 (s, 1H), 7.95 (s, 1H), 7.67 (s, 1H), 7.59 (d, J = 7.1 Hz, 1H), 7.45-7.38 (m, 2H), 5.69 (q, J = 7.0 Hz, 1H), 4.14 (s, 1H), 3.88 (t, J = 13.5 Hz, 2H), 3.27 (t, J = 7.5 Hz, 1H), 2.53 (d, J = 3.5 Hz, 3H), 2.11-1.94 (m, 4H), 1.92-1.79 (m, 4H), 1.69 (d, J = 7.1 Hz, 3H). | Example 1 |
| Example 16 | 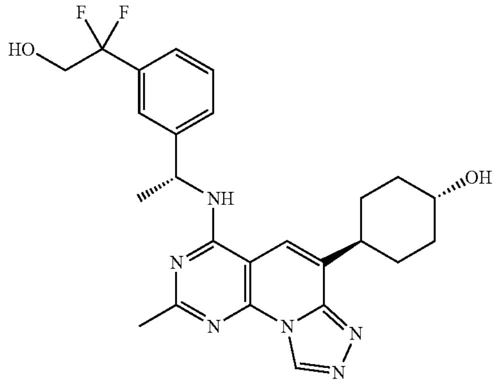 [SMILES: Cc1nc(N[C@H](C)c2cccc(C(F)(F)CO)c2)c2cc([C@H]3CC[C@H](O)CC3)c3nncn3c2n1] Trans-(R)-4-(4-((1-(3-(1,1-difluoro-2-hydroxyethyl)phenyl)ethyl)amino)-2-methyl-[1,2,4]triazolo[4',3':1,6]pyrido[2,3-d]pyrimidin-6-yl)cyclohexan-1-ol | LC-MS (ESI) m/z 483 $(M + H)^+$. SW-N191149-197-2 $^1H$ NMR (400 MHz, MeOD) δ 9.55 (s, 1H), 7.96 (s, 1H), 7.66 (s, 1H), 7.58 (d, J = 7.1 Hz, 1H), 7.42 (q, J = 8.0 Hz, 2H), 5.70 (q, J = 7.0 Hz, 1H), 3.87 (t, J = 13.5 Hz, 2H), 3.74-3.63 (m, 1H), 3.22 (t, J = 12.3 Hz, 1H), 2.53 (s, 3H), 2.15 (s, 4H), 1.81 (d, J = 13.3 Hz, 2H), 1.69 (d, J = 7.1 Hz, 3H), 1.56 (dd, J = 23.2, 9.9 Hz, 2H). | |

Example 17: Synthesis of 12-methyl-7-(oxolan-3-yloxy)-N-[(1R)-1-[3-(trifluoromethyl) phenyl]ethyl]-2,4,5,11,13-pentaazatricyclo[7.4.0.0^{2,6}]trideca-1(9),3,5,7,10,12-hexaen-10-amine. (The title compound was synthesized from Compound 10 in Example 1.)

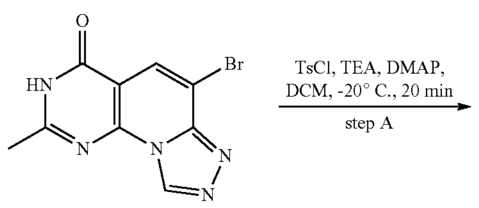

10

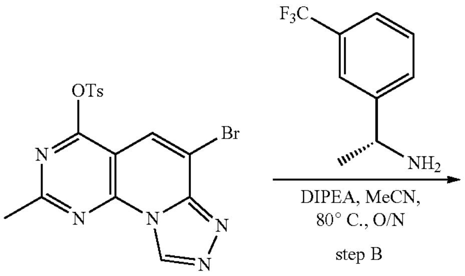

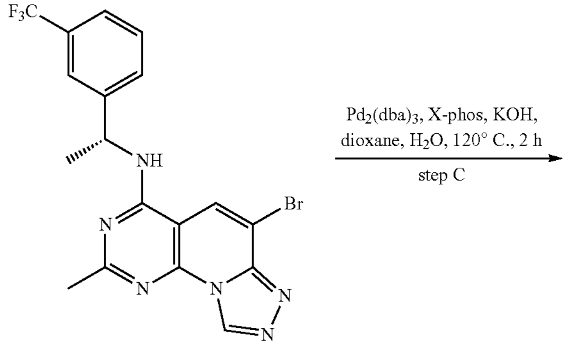

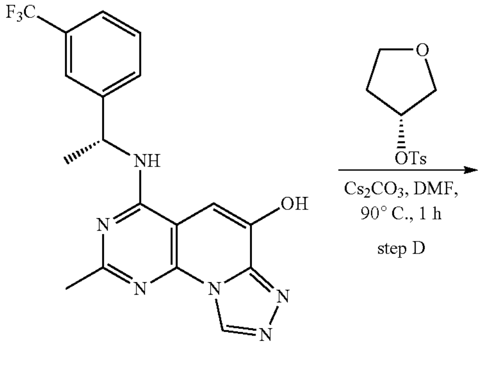

-continued

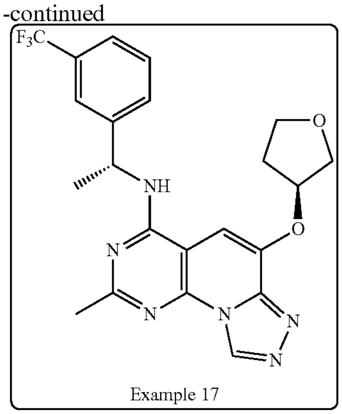

Example 17

Step A. 7-bromo-12-methyl-2,4,5,11,13-pentaazatricyclo[7.4.0.0^{2,6}]trideca-1(9),3,5,7,10,12-hexaen-10-yl 4-methylbenzene-1-sulfonate To a stirred solution of 7-bromo-12-methyl-2,4,5,11,13-pentaazatricyclo [7.4.0.0^{2,6}]trideca-1(9),3,5,7,10,12-hexaen-10-ol (200 mg, 0.71 mmol) in DCM (10 mL) was added TEA (0.3 mL, 2.14 mmol) and TsCl (163 mg, 0.86 mmol) at −20° C. After stirred at −20° C. for 20 min, the mixture was purified directly by chromatography (silica gel, 0-50%, EtOAc in DCM) to give 7-bromo-12-methyl-2,4,5,11,13-pentaazatricyclo[7.4.0.0^{2,6}]trideca-1(9),3,5,7,10,12-hexaen-10-yl 4-methylbenzene-1-sulfonate (110 mg, 0.25 mmol, 35%) as a yellow solid. LC-MS (ESI) m/z 434 & 436 $(M+H)^+$.

Step B. 7-bromo-12-methyl-N-[(1R)-1-[3-(trifluoromethyl)phenyl]ethyl]-2,4,5,11,13-pentaazatricyclo [7.4.0.0^{2,6}]trideca-1(9),3,5,7,10,12-hexaen-10-amine To a stirred solution of 7-bromo-12-methyl-2,4,5,11,13-pentaazatricyclo [7.4.0.0^{2,6}]trideca-1(9),3,5,7,10,12-hexaen-10-yl 4-methylbenzene-1-sulfonate (130 mg, 0.30 mmol) in MeCN (5 mL) was added DIPEA (0.3 mL, 1.68 mmol) and (1R)-1-(1,1-difluoro-2,3-dihydro-1H-inden-4-yl)ethan-1-amine (118 mg, 0.60 mmol) at rt. After stirred at 80° C. overnight, the cooled mixture was concentrated. The crude product was purified by chromatography (silica gel, 0-20%, MeOH in DCM) to give 7-bromo-N-[(1R)-1-(1,1-difluoro-2,3-dihydro-1H-inden-4-yl)ethyl]-12-methyl-2,4,5,11,13-pentaazatricyclo [7.4.0.0^{2,6}]trideca-1(9),3,5,7,10,12-hexaen-10-amine (110 mg, 0.24 mmol, 80%) as a yellow solid. LC-MS (ESI) m/z 459 & 461 $(M+H)^+$.

Step C. 12-methyl-10-{[(1R)-1-[3-(trifluoromethyl) phenyl]ethyl]amino}-2,4,5,11,13-pentaazatricyclo [7.4.0.0^{2,6}]trideca-1(9),3,5,7,10,12-hexaen-7-ol To a stirred solution of 7-bromo-12-methyl-N-[(1R)-1-[3-(trifluoromethyl)phenyl]ethyl]-2,4,5,11,13-pentaazatricyclo [7.4.0.0^{2,6}]trideca-1(9),3,5,7,10,12-hexaen-10-amine (50 mg, 0.11 mmol) in dioxane (2 mL) and water (0.5 mL) was added X-phos (11 mg, 0.022 mmol), Pd2(dba)$_3$ (20 mg, 0.022 mmol), KOH (12 mg, 0.22 mmol) at rt. After stirred at 110° C. for 2 h, the cooled mixture was filtered and concentrated. The crude product was purified by prep-TLC (10% MeOH in DCM) to give 12-methyl-10-{[(1R)-1-[3-(trifluoromethyl)phenyl]ethyl]amino}-2,4,5,11,13-pentaazatricyclo[7.4.0.0^{2,6}]trideca-1(9),3,5,7,10,12-hexaen-7-ol (20 mg, 0.05 mmol, 46%) as a brown solid. LC-MS (ESI) m/z 389 $(M+H)^+$.

Step D. 12-methyl-7-(oxolan-3-yloxy)-N-[(1R)-1-[3-(trifluoromethyl)phenyl]ethyl]-2,4,5,11,13-pentaazatricyclo[7.4.0.0^{2,6}]trideca-1(9),3,5,7,10,12-hexaen-10-amine To a stirred solution of 12-methyl-10-{[(1R)-1-[3-(trifluoromethyl)phenyl]ethyl]amino}-2,4,5,11,13-pentaazatricyclo[7.4.0.0^{2,6}]trideca-1(9),3,5,7,10,12-hexaen-7-ol (20 mg, 0.05 mmol) in DMF (5 mL) was added (3R)-oxolan-3-yl 4-methylbenzene-1-sulfonate (25 mg, 0.10 mmol) and $Cs_2CO_3$ (97 mg, 0.30 mmol) at rt. After stirred at 90° C. for 1 h, the cooled mixture was poured into water (30 mL) and extracted with EtOAc (30 mL*2). The combined organic phase was washed with brine, dried over $Na_2SO_4$, filtered and concentrated. The crude product was purified by chromatography (silica gel, 0-20%, MeOH in DCM) and then by prep-HPLC (C18, 30~80% MeCN in $H_2O$ with 0.1% HCOOH) to give 12-methyl-7-(oxolan-3-yloxy)-N-[(1R)-1-[3-(trifluoromethyl)phenyl]ethyl]-2,4,5,11,13-pentaazatricyclo[7.4.0.0^{2,6}]trideca-1(9),3,5,7,10,12-hexaen-10-amine (2.6 mg, 0.006 mmol, 11%) as a white solid. LC-MS (ESI) m/z 459 $(M+H)^+$. $^1H$ NMR (400 MHz, MeOD) δ 9.56 (s, 1H), 7.77 (s, 1H), 7.73 (d, J=4.4 Hz, 1H), 7.52 (d, J=5.7 Hz, 2H), 7.40 (s, 1H), 5.71-5.64 (m, 1H), 5.38 (s, 1H), 4.17-4.05 (m, 3H), 3.99-3.93 (m, 1H), 2.50 (s, 3H), 2.37 (ddd, J=18.5, 10.8, 6.4 Hz, 2H), 1.71 (d, J=7.1 Hz, 3H).

Example 18: Synthesis of N-[(1R)-1-[3-amino-5-(trifluoromethyl)phenyl]ethyl]-12-methyl-7-(oxolan-3-yloxy)-2,4,5,11,13-pentaazatricyclo[7.4.0.0^{2,6}]trideca-1(9),3,5,7,10,12-hexaen-10-amine. (the Title Compound was Synthesized from Compound 10 in Example 1.)

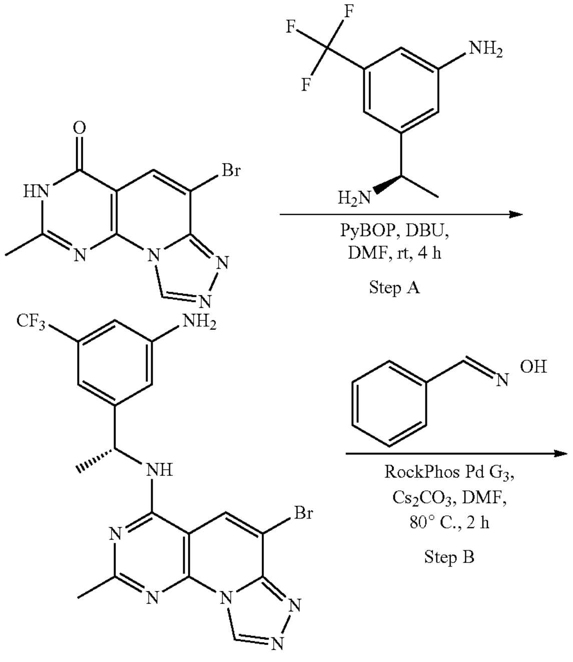

-continued

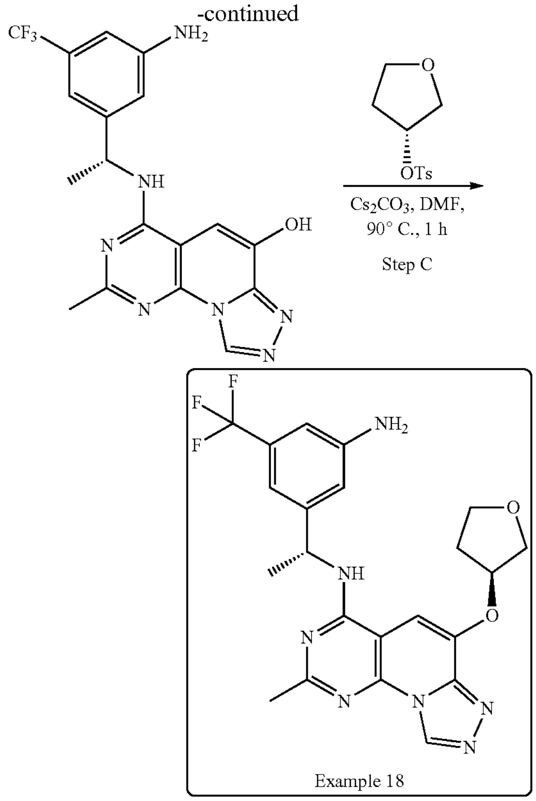

Example 18

Step A. N-[(1R)-1-[3-amino-5-(trifluoromethyl)phenyl]ethyl]-7-bromo-12-methyl-2,4,5,11,13-pentaazatricyclo[7.4.0.0^{2,6}]trideca-1(9),3,5,7,10,12-hexaen-10-amine To a stirred solution of 7-bromo-12-methyl-2,4,5,11,13-pentaazatricyclo [7.4.0.0^{2,6}]trideca-1(9),3,5,7,10,12-hexaen-10-ol (100 mg, 0.36 mmol) in DMF (10 mL) was added 3-[(1R)-1-aminoethyl]-5-(trifluoromethyl)aniline (146 mg, 0.71 mmol), PyBOP (279 mg, 0.54 mmol) and DBU (163 mg, 1.07 mmol) at rt. After stirred at rt for 4 h, the mixture was poured into water (50 mL) and extracted with EtOAc (50 mL*2). The combined organic phase was washed with brine, dried over $Na_2SO_4$, filtered and concentrated. The crude product was purified by chromatography (silica gel, 0-20%, MeOH in DCM) to give N-[(1R)-1-[3-amino-5-(trifluoromethyl)phenyl]ethyl]-7-bromo-12-methyl-2,4,5,11,13-pentaazatricyclo [7.4.0.0^{2,6}]trideca-1(9),3,5,7,10,12-hexaen-10-amine (60 mg, 0.13 mmol, 36%) as a yellow solid. LC-MS (ESI) m/z 466 $(M+H)^+$.

Step B. 10-{[(1R)-1-[3-amino-5-(trifluoromethyl)phenyl]ethyl]amino}-12-methyl-2,4,5,11,13-pentaazatricyclo[7.4.0.0^{2,6}]trideca-1(9),3,5,7,10,12-hexaen-7-ol To a stirred solution of N-[(1R)-1-[3-amino-5-(trifluoromethyl)phenyl]ethyl]-7-bromo-12-methyl-2,4,5,11,13-pentaazatricyclo[7.4.0.0^{2,6}]trideca-1(9),3,5,7,10,12-hexaen-10-amine (60 mg, 0.13 mmol) in DMF (3 mL) was added (E)-N-(phenylmethylidene)hydroxylamine (24 mg, 0.19 mmol), 2009020-38-4 (32 mg, 0.039 mmol) and $Cs_2CO_3$ (126 mg, 0.39 mmol) at rt. After stirred at 100° C. for 2 h, the cooled mixture was poured into water (20 mL)

and extracted with EtOAc (20 mL*2). The combined organic phase was washed with brine, dried over $Na_2SO_4$, filtered and concentrated. The crude product was purified by prep-TLC (10% MeOH in DCM) to give 10-{[(1R)-1-[3-amino-5-(trifluoromethyl)phenyl]ethyl]amino}-12-methyl-2,4,5,11,13-pentaazatricyclo[7.4.0.0^{2,6}]trideca-1(9),3,5,7,10,12-hexaen-7-ol (30 mg, 0.074 mmol, 57%) as a gray solid. LC-MS (ESI) m/z 404 $(M+H)^+$.

Step C. N-[(1R)-1-[3-amino-5-(trifluoromethyl)phenyl]ethyl]-12-methyl-7-(oxolan-3-yloxy)-2,4,5,11,13-pentaazatricyclo[7.4.0.0^{2,6}]trideca-1(9),3,5,7,10,12-hexaen-10-amine To a stirred solution of 10-{[(1R)-1-[3-amino-5-(trifluoromethyl)phenyl]ethyl]amino}-12-methyl-2,4,5,11,13-pentaazatricyclo[7.4.0.0^{2,6}]trideca-1(9),3,5,7,10,12-hexaen-7-ol (30 mg, 0.074 mmol) in DMF (5 mL) was added (3R)-oxolan-3-yl 4-methylbenzene-1-sulfonate (36 mg, 0.15 mmol) and $Cs_2CO_3$ (73 mg, 0.22 mmol) at rt. After stirred at 90° C. for 1 h, the cooled mixture was poured into water (30 mL) and extracted with EtOAc (30 mL*2). The combined organic phase was washed with brine, dried over $Na_2SO_4$, filtered and concentrated. The crude product was purified by prep-TLC (10%, MeOH in DCM) and then by prep-HPLC (C18, ~80% MeCN in $H_2O$ with 0.1% HCOOH) to give N-[(1R)-1-[3-amino-5-(trifluoromethyl)phenyl]ethyl]-12-methyl-7-(oxolan-3-yloxy)-2,4,5,11,13-pentaazatricyclo[7.4.0.0^{2,6}]trideca-1(9),3,5,7,10,12-hexaen-10-amine (2 mg, 0.004 mmol, 6%) as a white solid. LC-MS (ESI) m/z 474 $(M+H)^+$. $^1H$ NMR (400 MHz, MeOD) δ 9.59 (s, 1H), 7.42 (s, 1H), 6.99 (s, 2H), 6.80 (s, 1H), 5.62 (q, J=7.0 Hz, 1H), 5.38 (s, 1H), 4.12 (dd, J=7.6, 3.4 Hz, 2H), 4.09-4.04 (m, 1H), 3.96 (td, J=8.1, 4.4 Hz, 1H), 2.54 (s, 3H), 2.42-2.32 (m, 2H), 1.65 (d, J=7.1 Hz, 3H).

The examples in the following Table 2 were prepared by using a method analogous to that used to prepare the examples as described herein.

TABLE 2

| Ex# | Structure & name | Analytical data | Method |
|---|---|---|---|
| Example 19 | 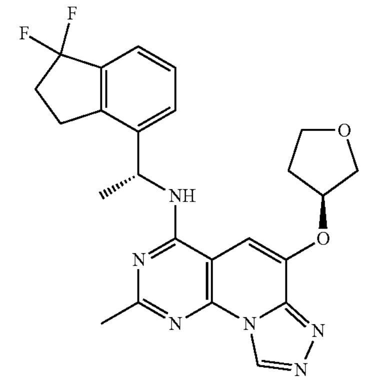 [SMILES: Cc1nc(N[C@H](C)c2cccc3c2CCC3(F)F)c2cc(O[C@H]3CCOC3)c3nncn3c2n1] N-((R)-1-(1,1-difluoro-2,3-dihydro-1H-inden-4-yl)ethyl)-2-methyl-6-(((S)-tetrahydrofuran-3-yl)oxy)-[1,2,4]triazolo[4',3':1,6]pyrido[2,3-d]pyrimidin-4-amine | LC-MS (ESI) m/z 467 $(M + H)^+$. $^1H$ NMR (400 MHz, MeOD) δ 9.57 (s, 1H), 7.58 (d, J = 7.3 Hz, 1H), 7.43 (s, 1H), 7.40-7.32 (m, 2H), 5.65 (q, J = 7.0 Hz, 1H), 5.39 (s, 1H), 4.15-4.05 (m, 3H), 3.97 (dt, J = 8.3, 4.2 Hz, 1H), 3.19-2.99 (m, 2H), 2.66-2.56 (m, 2H), 2.49 (s, 3H), 2.42-2.32 (m, 2H), 1.67 (d, J = 7.0 Hz, 3H). | Example 18 |
| Example 20 | 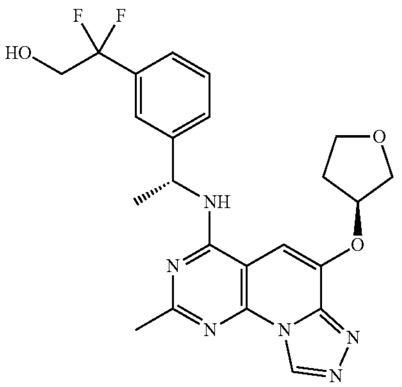 [SMILES: Cc1nc(N[C@H](C)c2cccc(C(F)(F)CO)c2)c2cc(O[C@H]3CCOC3)c3nncn3c2n1] 2,2-difluoro-2-(3-((R)-1-((2-methyl-6-(((S)-tetrahydrofuran-3-yl)oxy)-[1,2,4]triazolo[4',3':1,6]pyrido[2,3-d]pyrimidin-4-yl)amino)ethyl)phenyl)ethan-1-ol | LC-MS (ESI) m/z 471 $(M + H)^+$. $^1H$ NMR (400 MHz, MeOD) δ 9.59 (d, J = 2.4 Hz, 1H), 7.66 (s, 1H), 7.58 (d, J = 6.9 Hz, 1H), 7.45-7.39 (m, 3H), 5.74-5.68 (m, 1H), 5.39 (s, 1H), 4.15-4.06 (m, 3H), 3.96 (dt, J = 12.7, 6.4 Hz, 1H), 3.87 (t, J = 13.4 Hz, 2H), 2.53 (s, 3H), 2.39-2.35 (m, 1H), 1.69 (d, J = 7.1 Hz, 3H), 1.29 (s, 1H). | Example 18 |

TABLE 2-continued

| Ex# | Structure & name | Analytical data | Method |
|---|---|---|---|
| Example 21 | 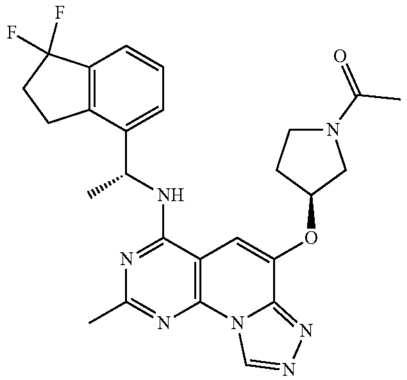 [SMILES: CC(=O)N1CC[C@H](Oc2cc3c(N[C@H](C)c4cccc5c4CCC5(F)F)nc(C)nc3n3cnnc23)C1] 1-((S)-3-((4-(((R)-1-(1,1-difluoro-2,3-dihydro-1H-inden-4-yl)ethyl)amino)-2-methyl-[1,2,4]triazolo[4',3':1,6]pyrido[2,3-d]pyrimidin-6-yl)oxy)pyrrolidin-1-yl)ethan-1-one | LC/MS (ESI) m/z: 509 $(M + H)^+$. $^1H$ NMR (400 MHz, MeOD) δ 9.61 (d, J = 2.3 Hz, 1H), 7.58 (t, J = 6.3 Hz, 2H), 7.41-7.31 (m, 2H), 5.62 (dd, J = 12.3, 7.0 Hz, 1H), 5.42 (d, J = 25.8 Hz, 1H), 3.98-3.60 (m, 4H), 3.38 (dd, J = 13.8, 5.7 Hz, 1H), 3.19-3.09 (m, 1H), 2.71-2.50 (m, 3H), 2.49 (s, 3H), 2.43-2.29 (m, 1H), 2.11 (d, J = 7.9 Hz, 3H), 1.67 (s, 3H). | Example 18 |
| Example 22 | 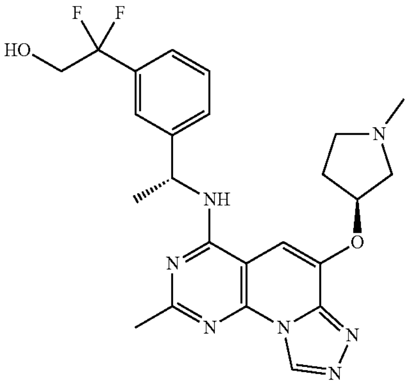 [SMILES: Cc1nc(N[C@H](C)c2cccc(C(F)(F)CO)c2)c2cc(O[C@H]3CCN(C)C3)c3nncn3c2n1] 2,2-difluoro-2-(3-((R)-1-((2-methyl-6-(((S)-1-methylpyrrolidin-3-yl)oxy)-[1,2,4]triazolo[4',3':1,6]pyrido[2,3-d]pyrimidin-4-yl)amino)ethyl)phenyl)ethan-1-ol | LC-MS (ESI) m/z 484 $(M + H)^+$. $^1H$ NMR (400 MHz, MeOD) δ 9.51 (s, 1H), 7.58 (s, 1H), 7.54-7.46 (m, 2H), 7.34 (q, J = 7.7 Hz, 2H), 5.60 (q, J = 6.8 Hz, 1H), 5.44 (s, 1H), 4.01 (s, 1H), 3.80 (t, J = 13.4 Hz, 3H), 3.51 (d, J = 36.6 Hz, 2H), 3.02 (s, 3H), 2.68 (s, 1H), 2.44 (s, 4H), 1.62 (d, J = 6.8 Hz, 3H). | Example 18 |

Example 23: Synthesis of N-[(1R)-1-(1,1-difluoro-2,3-dihydro-1H-inden-4-yl)ethyl]-12-methyl-7-(morpholin-4-yl)-2,4,5,11,13-pentaazatricyclo[7.4.0.0^{2,6}]trideca-1(9),3,5,7,10,12-hexaen-10-amine

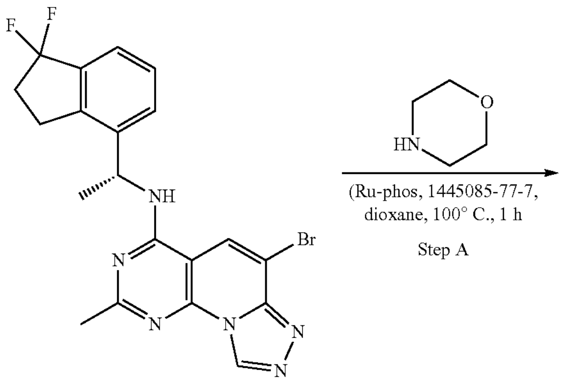

-continued

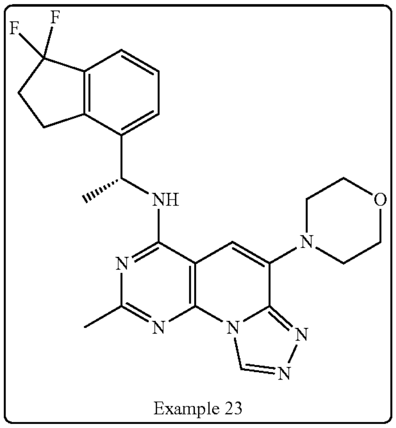
Example 23

Step A. N-[(1R)-1-(1,1-difluoro-2,3-dihydro-1H-inden-4-yl)ethyl]-12-methyl-7-(morpholin-4-yl)-2,4,5,11,13-pentaazatricyclo[7.4.0.0^{2,6}]trideca-1(9),3,5,7,10,12-hexaen-10-amine To a stirred solution of 7-bromo-N-[(1R)-1-(1,1-difluoro-2,3-dihydro-1H-inden-4-yl)ethyl]-12-methyl-2,4,5,11,13-pentaazatricyclo[7.4.0.0^{2,6}]trideca-1(9),3,5,7,10,12-hexaen-10-amine (30 mg, 0.065 mmol) in dioxane (2 mL) was added morpholine (17 mg, 0.196 mmol), Ru-phos (6 mg, 0.013 mmol), RuPhos Pd G3 (6 mg, 0.007 mmol) and $Cs_2CO_3$ (64 mg, 0.196 mmol) at rt. After stirred at 100° C. for 1 h, the cooled mixture was filtered and concentrated. The crude product was purified by pre-TLC (EtOAc:PE 2:1) and then by prep-HPLC (C18, 30~80% MeOH in $H_2O$ with 0.1% HCOOH) to give N-[(1R)-1-(1,1-difluoro-2,3-dihydro-1H-inden-4-yl)ethyl]-12-methyl-7-(morpholin-4-yl)-2,4,5,11,13-pentaazatricyclo [7.4.0.0^{2,6}]trideca-1(9),3,5,7,10,12-hexaen-10-amine (2.8 mg, 0.006 mmol, 9%) as a white solid. LC-MS (ESI) m/z 466 $(M+H)^+$. $^1$H NMR (400 MHz, MeOD) δ 9.53 (s, 1H), 7.58 (d, J=7.2 Hz, 1H), 7.35 (dt, J=14.9, 7.4 Hz, 2H), 7.23 (s, 1H), 5.62 (q, J=7.0 Hz, 1H), 3.95 (t, J=4.5 Hz, 4H), 3.58-3.49 (m, 4H), 3.38 (s, 1H), 3.13 (s, 1H), 2.66-2.56 (m, 2H), 2.46 (s, 3H), 1.66 (d, J=7.0 Hz, 3H).

Example 24: Synthesis of (R)-5-(4-((1-(3-(1,1-difluoro-2-hydroxyethyl)phenyl)ethyl)amino)-2,7-dimethyl-7H-pyrazolo[3,4-h]quinazolin-6-yl)-1-methylpyridin-2(1H)-one

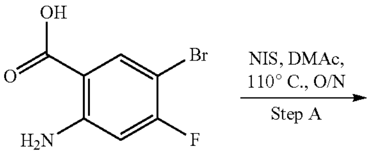

1

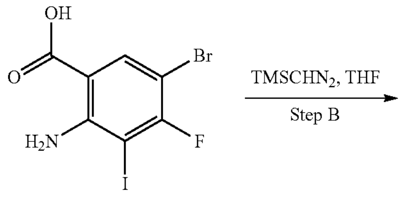

2

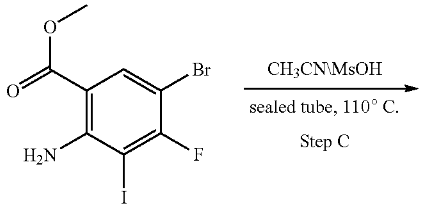

3

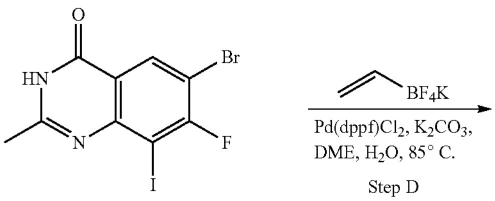

4

-continued

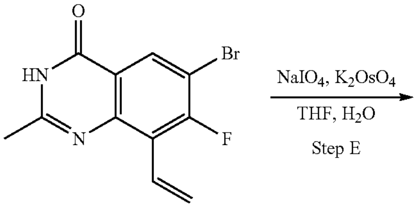

5

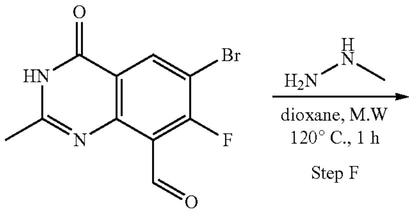

6

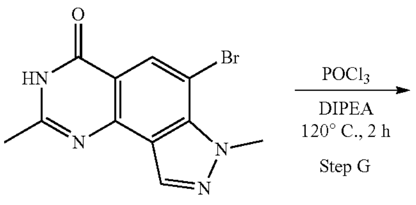

7

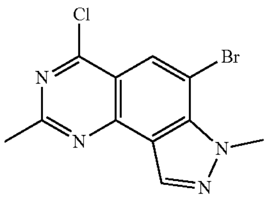

8

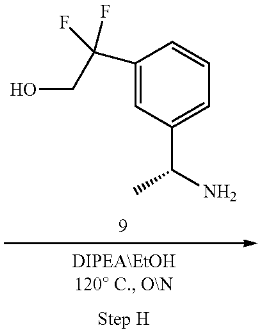

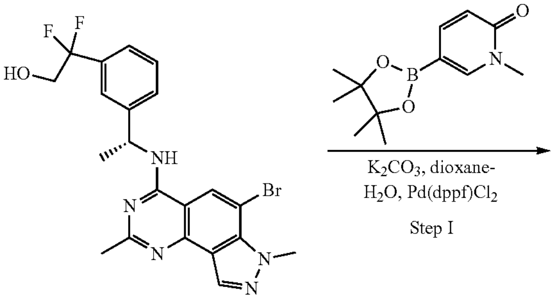

10

-continued

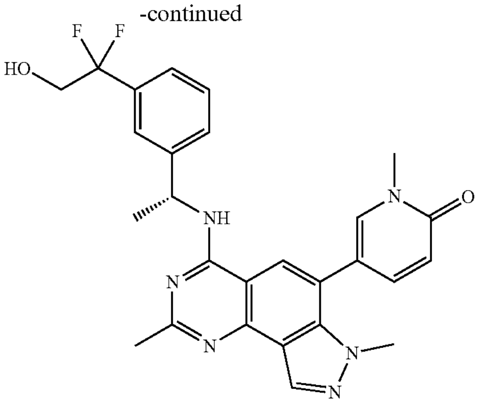

Example 24

Step A: 2-amino-5-bromo-4-fluoro-3-iodobenzoic acid

To a stirred solution of 2-amino-5-bromo-4-fluorobenzoic acid (5.0 g, 21.4 mmol) in N,N-dimethylacetamide (60 mL) was added N-iodosuccinimide (4.81 g, 21.4 mmol) slowly. The reaction mixture was stirred at 120° C. for 16 h under nitrogen atmosphere. The reaction mixture was cooled to room temperature and diluted with water (50 mL), extracted with EtOAc (50 mL×3). The combined organic phase was washed by sat. $Na_2S_2O_3$ and brine, the organic phase was dried over anhydrous $Na_2SO_4$, filtered and concentrated to give the crude product which was purified by column chromatography on silica gel (PE:EtOAc=10:1 to 1:1) to obtain 2-amino-5-bromo-4-fluoro-3-iodobenzoic acid (2.6 g, 7.2 mmol, 33.8%) as a brown solid. LC/MS (ESI) m/z: 360 $(M+H)^+$.

Step B: methyl 2-amino-5-bromo-4-fluoro-3-iodobenzoate

To a stirred solution of 2-amino-5-bromo-4-fluoro-3-iodobenzoic acid (2.4 g, 6.7 mmol) in THE (10 mL) and MeOH (10 mL) at room temperature was added dropwise (Trimethylsilyl)diazomethane solution (6.7 mL, 13.4 mmol, 2 M in hexane). The reaction mixture was stirred at room temperature for 2 h under nitrogen atmosphere before HOAc (1 mL) was added slowly. The reaction mixture was concentrated and the residue was diluted with water (50 mL), extracted with EtOAc (50 mL×3). The combined organic phase was washed by water and brine, dried over anhydrous $Na_2SO_4$, filtered and concentrated to give the crude product which was purified by column chromatography on silica gel (PE:EtOAc=10:1 to 3:1) to obtain methyl 2-amino-5-bromo-4-fluoro-3-iodobenzoate (2.3 g, 6.1 mmol, 91%) as a brown solid. LC/MS (ESI) m/z: 374 $(M+H)^+$.

Step C: 6-bromo-7-fluoro-8-iodo-2-methylquinazolin-4(3H)-one

To a stirred solution of methyl 2-amino-5-bromo-4-fluoro-3-iodobenzoate (1.3 g, 3.5 mmol) in $CH_3CN$ (9 mL) was added methanesulfonic acid (2 mL). The reaction mixture was stirred in a sealed tube at 110° C. for 16 h. The reaction mixture was concentrated and the residue was diluted with sat.$NaHCO_3$ (30 mL), extracted with EtOAc (30 mL×3). The combined organic phase was washed by water and brine, the organic phase was dried over anhydrous $Na_2SO_4$, filtered and concentrated to give the crude product which was triturated with 10 ml PE:EtOAc=10:1 to obtain 6-bromo-7-fluoro-8-iodo-2-methyl-3,4-dihydroquinazolin-4-one (1.0 g, 2.6 mmol, 75.1%) as a brown solid. LC/MS (ESI) m/z: 383 $(M+H)^+$.

Step D: 6-bromo-7-fluoro-2-methyl-8-vinylquinazolin-4(3H)-one

To a stirred solution of 6-bromo-7-fluoro-8-iodo-2-methyl-3,4-dihydroquinazolin-4-one (600 mg, 1.6 mmol), Potassium Vinyltrifluoroborate (70 mg, 0.5 mmol) and $K_2CO_3$ (649 mg, 4.7 mmol) in 1,2-dimethoxyethane (20 mL) and $H_2O$ (5 mL) was added $Pd(dppf)Cl_2 \cdot CH_2Cl_2$ (128 mg, 0.2 mmol). The reaction mixture was stirred at 85° C. for 16 h under nitrogen atmosphere. The reaction mixture was diluted with water (20 mL), extracted with EtOAc (20 mL×3). The combined organic phase was washed by water and brine, the organic phase was dried over anhydrous $Na_2SO_4$, filtered and concentrated to give the crude product which was purified by column chromatography on silica gel (PE:EtOAc=10:1 to 3:1) to obtain 6-bromo-8-ethenyl-7-fluoro-2-methyl-3,4-dihydroquinazolin-4-one (300 mg, 1.1 mmol, 67.6%) as a brown solid. LC/MS (ESI) m/z: 284 $(M+H)^+$.

Step E: 6-bromo-7-fluoro-2-methyl-4-oxo-3,4-dihydroquinazoline-8-carbaldehyde

To a stirred solution of 6-bromo-8-ethenyl-7-fluoro-2-methyl-3,4-dihydroquinazolin-4-one (300 mg, 1.1 mmol) and sodium periodate (1.1 g, 5.5 mmol) in THE (20 mL) and $H_2O$ (20 mL) at 0° C. was added Potassium osmate (VI) dihydrate (22 mg, 0.1 mmol). The reaction mixture was stirred at room temperature for 16 h. The reaction mixture was diluted with water (50 mL), extracted with EtOAc (50 mL×3). The combined organic phase was washed by water and brine, the organic phase was dried over anhydrous $Na_2SO_4$, filtered and concentrated to give the crude product which was purified by column chromatography on silica gel (PE:EtOAc=10:1 to 3:1) to obtain 6-bromo-7-fluoro-2-methyl-4-oxo-3,4-dihydroquinazoline-8-carbaldehyde (200 mg, 0.7 mmol, 66.2%) as a brown solid. LC/MS (ESI) m/z: 286 $(M+H)^+$.

Step F: 6-bromo-2,7-dimethyl-3,7-dihydro-4H-pyrazolo[3,4-h]quinazolin-4-one

To a stirred solution of 6-bromo-7-fluoro-2-methyl-4-oxo-3,4-dihydroquinazoline-8-carbaldehyde (130 mg, 0.7 mmol) in dioxane (4 mL) was added 40% Methylhydrazine (800 mg, 7.0 mmol). The reaction mixture was stirred at 120° C. for 1 h under microwave. The reaction mixture was concentrated to give a crude product which was triturated with 4 ml EtOAc to obtain 6-bromo-2,7-dimethyl-3H,4H, 7H-pyrazolo[3,4-h]quinazolin-4-one (130 mg, 0.4 mmol, 63%) as a off-white solid. LC/MS (ESI) m/z: =294 $(M+H)^+$.

Step G: 6-bromo-4-chloro-2,7-dimethyl-7H-pyrazolo[3,4-h]quinazoline

To a stirred solution of 6-bromo-2,7-dimethyl-7H-pyrazolo[3,4-h]quinazolin-4-ol (130 mg, 0.4 mmol) in $POCl_3$ (4 mL) at room temperature was added N,N-Diisopropylethylamine (0.7 mL) slowly. The reaction mixture was stirred at 120° C. for 3 h under nitrogen atmosphere. The reaction mixture was cooled and poured into ice-water (5 mL), the mixture was adjusted pH to 7-8 with $NaHCO_3$and extracted with EtOAc (10 mL×3). The combined organic phase was washed by water and brine, the organic phase was dried over anhydrous $Na_2SO_4$, filtered and concentrated to give the crude product which was purified by column chromatography flash (EtOAc in PE from 0% to 80%) to obtain 6-bromo-4-chloro-2,7-dimethyl-7H-pyrazolo[3,4-h]quinazoline (30 mg, 0.09 mmol, 21.7%) as an off-white solid. LC/MS (ESI) m/z: =313 $(M+H)^+$.

Step H: (R)-2-(3-(1-((6-bromo-2,7-dimethyl-7H-pyrazolo[3,4-h]quinazolin-4-yl)amino)ethyl) phenyl)-2,2-difluoroethan-1-ol To a stirred solution of 6-bromo-4-chloro-2,7-dimethyl-7H-pyrazolo[3,4-h]quinazoline (30 mg, 0.09 mmol) and 2-{3-[(1R)-1-aminoethyl]phenyl}-2,2-difluoroethan-1-ol (38 mg, 0.2 mmol) in EtOH (3 mL) was added N,N-Diisopropylethylamine (40 mg, 0.3 mmol). The reaction mixture was stirred at 120° C. in a sealed tube for 16 h. The reaction mixture was concentrated and the residue diluted with water (5 mL), extracted with EtOAc (5 mL×3). The combined organic phase was washed by water and brine, the organic phase was dried over anhydrous $Na_2SO_4$, filtered and concentrated to give the crude product which was purified by silica gel flash chromatography (gradient 0%-10% MeOH in DCM) to obtain 2-{3-[(1R)-1-({6-bromo-2,7-dimethyl-7H-pyrazolo[3,4-h]quinazolin-4-yl}amino)ethyl]phenyl}-2,2-difluoroethan-1-ol (40 mg, 0.08 mmol, 87%) as a off-white solid. LC/MS (ESI) m/z: 475.9 $(M+H)^+$.

Step I: (R)-5-(4-((1-(3-(1,1-difluoro-2-hydroxyethyl)phenyl)ethyl)amino)-2,7-dimethyl-7H-pyrazolo[3,4-h]quinazolin-6-yl)-1-methylpyridin-2(1H)-one To a stirred solution of 2-{3-[(1R)-1-({6-bromo-2,7-dimethyl-7H-pyrazolo[3,4-h]quinazolin-4-yl}amino)ethyl]phenyl}-2,2-difluoroethan-1-ol (40 mg, 0.08 mmol) and 1-methyl-5-(tetramethyl-1,3,2-dioxaborolan-2-yl)-1,2-dihydropyridin-2-one (40 mg, 0.168 mmol), $Na_2CO_3$ (27 mg, 0.25 mmol) in dioxane/water (4:1, 3 mL) was added $Pd(PPh_3)_4$ (9 mg, 0.008 mmol). The reaction mixture was stirred at 110° C. for 3 h under nitrogen atmosphere. The reaction mixture was diluted with water (5 mL), extracted with EtOAc (5 mL×3). The combined organic phase was washed by water and brine, dried over anhydrous $Na_2SO_4$, filtered and concentrated to give the crude product which was purified by prep-TLC (DCM:MeOH=20:1) to obtain 5-(4-{[(1R)-1-[3-(1,1-difluoro-2-hydroxyethyl)phenyl]ethyl]amino}-2,7-dimethyl-7H-pyrazolo[3,4-h]quinazolin-6-yl)-1-methyl-1,2-dihydropyridin-2-one (20 mg, 0.04 mmol, 47.2%) as a off-white solid. LC/MS (ESI) m/z: 505 $(M+H)^+$. $^1H$ NMR (400 MHz, DMSO) δ 8.51 (s, 1H), 8.38 (d, J=7.8 Hz, 1H), 8.17 (s, 1H), 8.10 (d, J=2.4 Hz, 1H), 7.77 (dd, J=9.3, 2.6 Hz, 1H), 7.71 (s, 1H), 7.66 (d, J=7.6 Hz, 1H), 7.49 (t, J=7.6 Hz, 1H), 7.43 (d, J=7.8 Hz, 1H), 6.60 (d, J=9.3 Hz, 1H), 5.79-5.71 (m, 1H), 5.68 (t, J=6.3 Hz, 1H), 3.96-3.83 (m, 5H), 3.61 (s, 3H), 2.55 (s, 3H), 1.66 (d, J=7.0 Hz, 3H).

The examples in the following Table 3 were prepared by using a method analogous to that used to prepare the examples as described herein.

TABLE 3

| Ex# | Structure & name | Analytical data | Method |
|---|---|---|---|
| Example 25 | 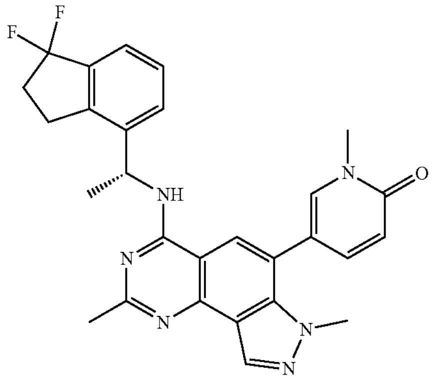 [SMILES: Cc1nc(N[C@H](C)c2cccc3c2CCC3(F)F)c2cc(-c3ccc(=O)n(C)c3)c3c(cnn3C)c2n1] (R)-5-(4-((1-(1,1-difluoro-2,3-dihydro-1H-inden-4-yl)ethyl)amino)-2,7-dimethyl-7H-pyrazolo[3,4-h]quinazolin-6-yl)-1-methylpyridin-2(1H)-one | LC/MS (ESI) m/z: 501 $(M + H)^+$. $^1H$ NMR (400 MHz, DMSO) δ 8.43 (s, 1H), 8.39 (d, J = 7.4 Hz, 1H), 8.12 (s, 1H), 8.04 (d, J = 2.5 Hz, 1H), 7.77-7.61 (m, 2H), 7.46-7.33 (m, 2H), 6.54 (d, J = 9.2 Hz, 1H), 5.61 (p, J = 6.9 Hz, 1H), 3.87 (s, 3H), 3.55 (s, 3H), 3.39 (s, 1H), 3.22-3.13 (m, 1H), 2.71-2.60 (m, 2H), 2.45 (s, 3H), 1.58 (d, J = 7.0 Hz, 3H). | Example 24 |

TABLE 3-continued

| Ex# | Structure & name | Analytical data | Method |
| --- | --- | --- | --- |
| Example 26 | 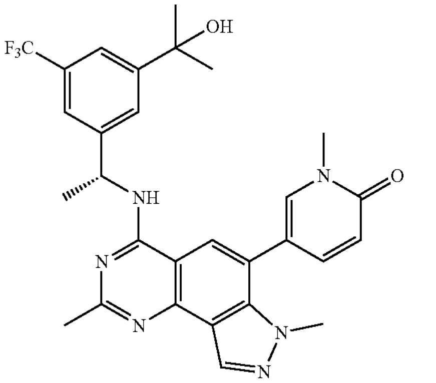 [SMILES: Cc1nc(N[C@H](C)c2cc(C(C)(C)O)cc(C(F)(F)F)c2)c2cc(-c3ccc(=O)n(C)c3)c3c(cnn3C)c2n1] (R)-5-(4-((1-(3-(2-hydroxypropan-2-yl)-5-(trifluoromethyl)phenyl)ethyl)amino)-2,7-dimethyl-7H-pyrazolo[3,4-h]quinazolin-6-yl)-1-methylpyridin-2(1H)-one | LC-MS (ESI) m/z 551 $(M + H)^+$. $^1H$ NMR (400 MHz, MeOD) δ 8.62 (s, 1H), 8.04 (s, 1H), 7.95 (d, J = 2.5 Hz, 1H), 7.88 (s, 1H), 7.80-7.56 (m, 4H), 6.71 (d, J = 9.2 Hz, 1H), 16.39-3.41 (m, 65H), 5.73 (q, J = 7.4 Hz, 1H), 4.85 (s, 47H), 3.93 (s, 3H), 3.67 (d, J = 12.2 Hz, 3H), 3.31 (dt, J = 3.2, 1.6 Hz, 50H), 2.57 (d, J = 7.4 Hz, 3H), 1.70 (t, J = 9.9 Hz, 3H), 1.53 (d, J = 5.6 Hz, 6H), 0.05--0.04 (m, 15H). | Example 24 |
| Example 27 | 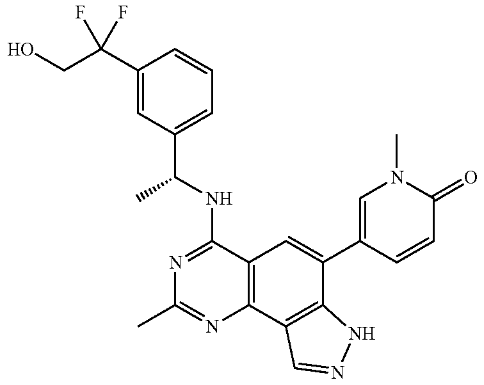 (R)-5-(4-((1-(3-(1,1-difluoro-2-hydroxyethyl)phenyl)ethyl)amino)-2-methyl-7H-pyrazolo[3,4-h]quinazolin-6-yl)-1-methylpyridin-2(1H)-one | LCMS: m/z 477 $(M + H)^+$. $^1H$ NMR (400 MHz, MeOD) δ 8.79 (s, 1H), 8.32 (s, 1H), 8.11 (d, J = 9.0 Hz, 2H), 7.70 (s, 1H), 7.63 (d, J = 6.6 Hz, 1H), 7.49-7.44 (m, 2H), 6.75 (d, J = 10.0 Hz, 1H), 5.92 (q, J = 7.0 Hz, 1H), 3.89 (t, J = 13.3 Hz, 2H), 2.76 (s, 3H), 1.78 (d, J = 7.1 Hz, 3H). | Example 24 |
| Example 28 | 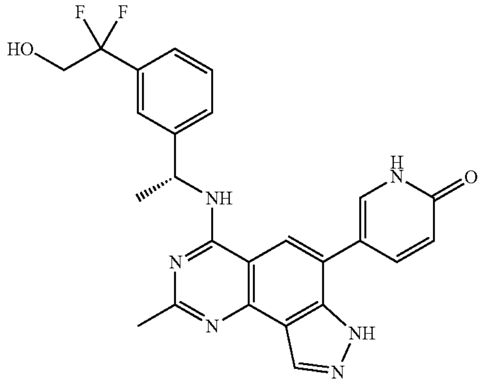 (R)-5-(4-((1-(3-(1,1-difluoro-2-hydroxyethyl)phenyl)ethyl)amino)-2-methyl-7H-pyrazolo[3,4-h]quinazolin-6-yl)pyridin-2(1H)-one | LCMS: m/z 491 $(M + H)^+$. $^1H$ NMR (400 MHz, MeOD) δ 8.78 (s, 1H), 8.33 (s, 2H), 8.04 (d, J = 8.6 Hz, 1H), 7.70 (s, 1H), 7.65-7.62 (m, 1H), 7.47 (d, J = 6.6 Hz, 2H), 6.76 (d, J = 9.4 Hz, 1H), 5.92 (t, J = 7.0 Hz, 1H), 3.89 (t, J = 13.3 Hz, 2H), 3.71 (s, 3H), 2.77 (s, 3H), 1.79 (d, J = 7.1 Hz, 3H). | Example 24 |

TABLE 3-continued

| Ex# | Structure & name | Analytical data | Method |
| --- | --- | --- | --- |
| Example 29 | 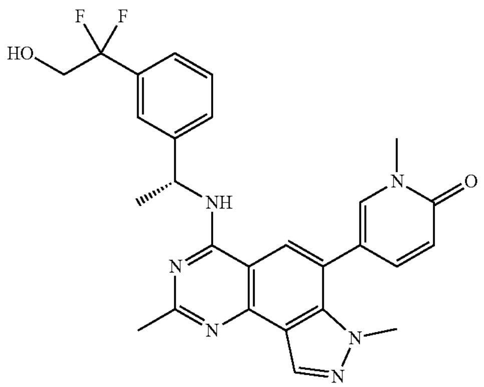 (R)-5-(4-((1-(3-(1,1-difluoro-2-hydroxyethyl)phenyl)ethyl)amino)-2,7-dimethyl-7H-pyrazolo[3,4-h]quinazolin-6-yl)pyridin-2(1H)-one | LCMS: m/z 491(M + H)$^+$. $^1$H NMR (400 MHz, MeOD) δ 8.68 (s, 1H), 8.22 (s, 1H), 7.79 (dd, J = 9.4, 2.6 Hz, 1H), 7.73 (d, J = 2.0 Hz, 1H), 7.68 (s, 1H), 7.63-7.59 (m, 1H), 7.46 (dd, J = 8.5, 5.2 Hz, 2H), 6.71 (dd, J = 9.3, 0.6 Hz, 1H), 5.90 (d, J = 7.1 Hz, 1H), 3.98 (s, 3H), 3.89 (t, J = 13.3 Hz, 2H), 2.76 (s, 3H), 1.75 (d, J = 7.1 Hz, 3H). | Example 24 |
| Example 30 | 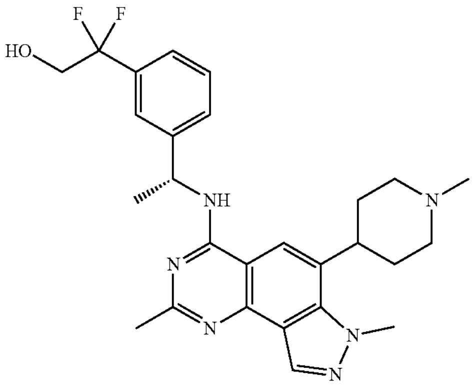 [SMILES: Cc1nc(N[C@H](C)c2cccc(C(F)(F)CO)c2)c2cc(C3CCN(C)CC3)c3c(cnn3C)c2n1] (R)-2-(3-(1-((2,7-dimethyl-6-(1-methylpiperidin-4-yl)-7H-pyrazolo[3,4-h]quinazolin-4-yl)amino)ethyl)phenyl)-2,2-difluoroethan-1-ol | LCMS: m/z 495 (M+H)+. 1H NMR (400 MHZ, MeOD) 8 8.55 (s, 1H), 7.92 (s, 1H), 7.69 (s, 1H), 7.60 (d, J = 7.1 Hz, 1H), 7.41 (p, J = 7.8 Hz, 2H), 5.78 (d, J = 7.1 Hz, 1H), 4.36 (s, 3H), 3.87 (t, J = 13.6 Hz, 2H), 3.46 (dd, J = 12.8, 5.0 Hz, 1H), 3.12 (d, J = 11.3 Hz, 2H), 2.54 (s, 3H), 2.42 (s, 3H), 2.35 (s, 2H), 2.05 (t, J = 6.7 Hz, 4H), 1.71 (d, J = 7.1 Hz, 3H). | Example 24 |
| Example 31 | 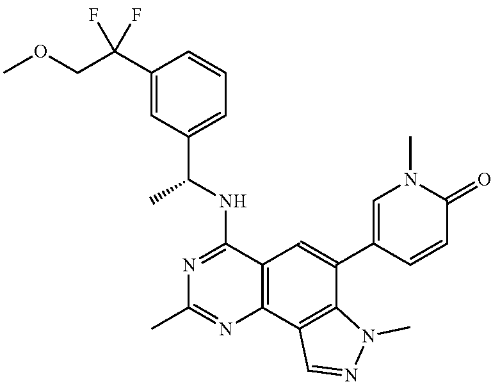 [SMILES: COCC(F)(F)c1cccc([C@@H](C)Nc2nc(C)nc3c2cc(-c2ccc(=O)n(C)c2)c2c3cnn2C)c1] (R)-5-(4-((1-(3-(1,1-difluoro-2-methoxyethyl)phenyl)ethyl)amino)-2,7-dimethyl-7H-pyrazolo[3,4-h]quinazolin-6-yl)-1-methylpyridin-2(1H)-one | LC/MS (ESI) m/z: 519 (M + H)$^+$ $^1$H NMR (400 MHz, MeOD) δ 8.60 (s, 1H), 8.04 (s, 1H), 7.95 (d, J = 2.4 Hz, 1H), 7.74 (dd, J = 9.2, 2.5 Hz, 1H), 7.65 (s, 1H), 7.58 (d, J = 7.2 Hz, 1H), 7.44-7.34 (m, 2H), 6.70 (d, J = 9.2 Hz, 1H), 5.73 (q, J = 7.1 Hz, 1H), 3.91 (s, 3H), 3.80 (s, 2H), 3.68 (s, 3H), 2.57 (s, 3H), 1.67 (d, J = 7.1 Hz, 3H). | Example 24 |

Example 32: Synthesis of (R)-5-(4-((1-(3-(1,1-difluoro-2-hydroxyethyl)phenyl)ethyl)amino)-7-methyl-2-(trifluoromethyl)-7H-pyrazolo[3,4-h]quinazolin-6-yl)-1-methylpyridin-2(1H)-one

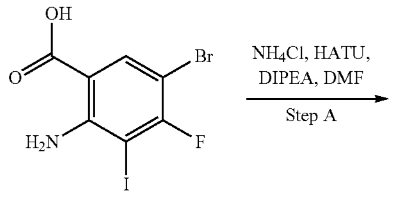

1

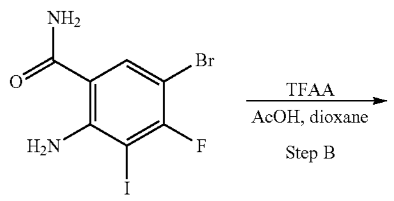

2

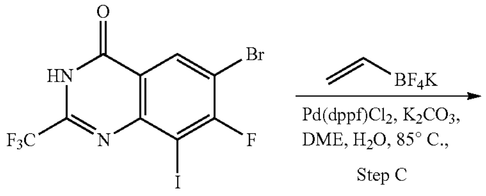

3

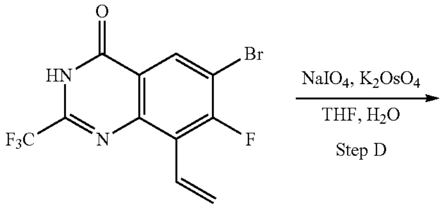

4

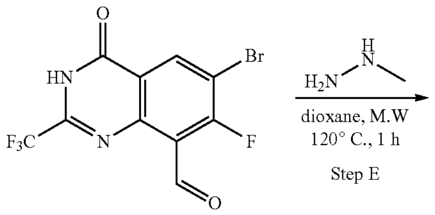

5

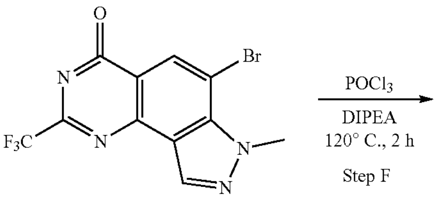

6

-continued

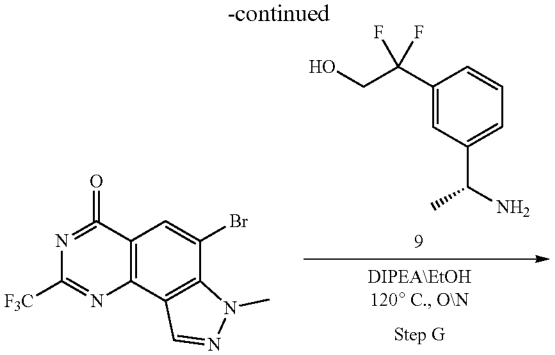

9

7

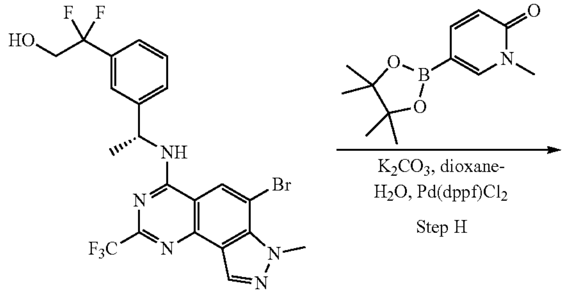

8

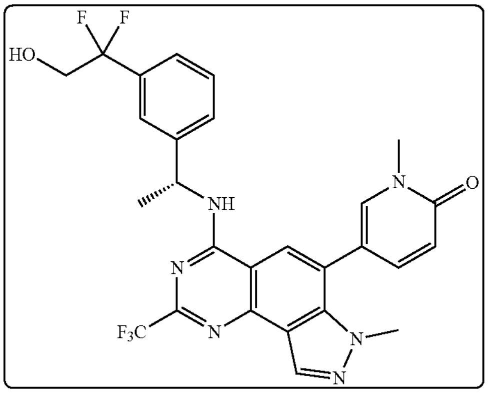

Example 32

Step A. 2-amino-5-bromo-4-fluoro-3-iodobenzamide

To a stirred solution of 2-amino-5-bromo-4-fluoro-3-iodobenzoic acid (5.5 g, 15.2 mmol) in DMF (5 mL) was added $NH_4Cl$ (1.1 mL, 30.5 mmol), HATU (8.7 g, 22.9 mmol) and DIEA (7.5 mL, 45.8 mmol). The reaction mixture was stirred at room temperature for 1 h. The reaction mixture was poured into water, extracted with EtOAc. The organic layer was washed with brine, dried over $Na_2SO_4$ and concentrated in vacuum to give the residue and the residue was purified by column chromatography (silica gel, 20 g, 0~50% PE in EtOAc) to give 2-amino-5-bromo-4-fluoro-3-iodobenzamide (4.0 g, 11.1 mmol, 72.9%) as a light yellow solid. LCMS: m/z 359 $(M+H)^+$.

Step B. 6-bromo-7-fluoro-8-iodo-2-(trifluoromethyl)quinazolin-4(3H)-one

To a stirred solution of 2-amino-5-bromo-4-fluoro-3-iodobenzamide (5.5 g, 15.3 mmol) in dioxane (15 mL) was added TFAA (5 mL). The reaction mixture was stirred at room temperature for 1 h. The reaction mixture was concentrated in vacuum to remove dioxane and dissolved in AcOH (10 mL). The reaction mixture was stirred at 120° C. for 2 h. The reaction mixture was concentrated in vacuum to give the residue and the residue was purified by column chromatography (silica gel, 10 g, 0~3% MeOH in DCM) to give 6-bromo-7-fluoro-8-iodo-2-(trifluoromethyl)-3,4-dihydroquinazolin-4-one (4 g, 9.1 mmol, 59.7%) as a light yellow solid. LCMS: m/z 437 $(M+H)^+$.

Step C. 6-bromo-7-fluoro-2-(trifluoromethyl)-8-vinylquinazolin-4(3H)-one

To a stirred solution of 6-bromo-7-fluoro-8-iodo-2-(trifluoromethyl)-3,4-dihydroquinazolin-4-one (1.0 g, 2.2 mmol) in dioxane (5 mL) and $H_2O$ (2 mL) was added Potassium Vinyltrifluoroborate (306.6 mg, 2.3 mmol), $K_2CO_3$ (632.6 mg, 4.5 mmol) and Pd(dppf)$Cl_2$ (120 mg). The reaction mixture was stirred at 85° C. for 16 h. The reaction mixture was filtered and the filtrate was concentrated in vacuum to give the residue and the residue was purified column chromatography (silica gel, 10 g, 0~70% EtOAc in PE) to give 6-bromo-8-ethenyl-7-fluoro-2-(trifluoromethyl)-3,4-dihydroquinazolin-4-one (180 mg, 0.53 mmol, 25%) as a light yellow solid. LCMS: m/z 337 $(M+H)^+$.

Step D. 6-bromo-7-fluoro-4-oxo-2-(trifluoromethyl)-3,4-dihydroquinazoline-8-carbaldehyde To a stirred solution of 6-bromo-8-ethenyl-7-fluoro-2-(trifluoromethyl)-3,4-dihydroquinazolin-4-one (180 mg, 0.5 mmol) in THE (2 mL) and $H_2O$ (2 mL) was added sodium periodate (571 mg, 2.7 mmol) and potassium citrate (16.3 mg, 0.1 mmol). The reaction mixture was stirred at room temperature for 1 h. The reaction mixture was poured into water, extracted with DCM and the organic layer was washed with brine, dried over $Na_2SO_4$ and concentrated in vacuum to give the residue and the residue was purified by column chromatography (silica gel, 10 g, 0~3% MeOH in DCM) to give 6-bromo-7-fluoro-4-oxo-2-(trifluoromethyl)-3,4-dihydroquinazoline-8-carbaldehyde (150 mg, 0.4 mmol, 82.8%) as a light yellow solid. LCMS: m/z 339 $(M+H)^+$.

Step E. 6-bromo-7-methyl-2-(trifluoromethyl)-7H-pyrazolo[3,4-h]quinazolin-4-ol

To a stirred solution of 6-bromo-7-fluoro-4-oxo-2-(trifluoromethyl)-3,4-dihydroquinazoline-8-carbaldehyde (150 mg, 0.4 mmol) in dioxane (5 mL) was added methylhydrazine (0.3 mL, 4.4 mmol). The reaction mixture was stirred at 120° C. for 3 h. The reaction mixture was concentrated in vacuum to give the residue and the residue was purified by prep-TLC (100% EtOAc) to give 6-bromo-7-methyl-2-(trifluoromethyl)-7H-pyrazolo[3,4-h]quinazolin-4-ol (100 mg, 0.3 mmol, 65.1%) as a light yellow solid. LCMS: m/z 347 $(M+H)^+$.

Step F. 6-bromo-4-chloro-7-methyl-2-(trifluoromethyl)-7H-pyrazolo[3,4-h]quinazoline To a stirred solution of 6-bromo-7-methyl-2-(trifluoromethyl)-7H-pyrazolo[3,4-h]quinazolin-4-ol (100 mg, 0.3 mmol) in $POCl_3$ (3 mL) was added DIEA (0.3 mL, 1.4 mmol). The reaction mixture was stirred at 120° C. for 1 h. The reaction mixture was concentrated in vacuum to give the residue and the residue was purified by prep-TLC (30% EtOAc in PE) to give 6-bromo-4-chloro-7-methyl-2-(trifluoromethyl)-7H-pyrazolo[3,4-h]quinazoline (70 mg, 0.2 mmol, 66.4%) as a light yellow solid. LCMS: m/z 365 $(M+H)^+$.

Step G. (R)-2-(3-(1-((6-bromo-7-methyl-2-(trifluoromethyl)-7H-pyrazolo[3,4-h]quinazolin-4-yl)amino)ethyl)phenyl)-2,2-difluoroethan-1-ol To a stirred solution of 6-bromo-4-chloro-7-methyl-2-(trifluoromethyl)-7H-pyrazolo[3,4-h]quinazoline (60 mg, 0.16 mmol) in EtOH (3 mL) was added 2-{3-[(1R)-1-aminoethyl]phenyl}-2,2-difluoroethan-1-ol (49.5 mg, 0.2 mmol) and DIPEA (106 mg, 0.8 mmol). The reaction mixture was stirred at 120° C. for 3 h. The reaction mixture was concentrated in vacuum to give the residue and the residue was purified by prep-TLC (60% EtOAc in PE) to give 2-{3-[(1R)-1-{[6-bromo-7-methyl-2-(trifluoromethyl)-7H-pyrazolo[3,4-h]quinazolin-4-yl]amino}ethyl] phenyl}-2,2-difluoroethan-1-ol (40 mg, 0.1 mmol, 45.9%) as a light yellow solid. LCMS: m/z 530 $(M+H)^+$.

Step H. (R)-5-(4-((1-(3-(1,1-difluoro-2-hydroxyethyl)phenyl)ethyl)amino)-7-methyl-2-(trifluoromethyl)-7H-pyrazolo[3,4-h]quinazolin-6-yl)-1-methylpyridin-2(1H)-one To a stirred solution of 2-{3-[(1R)-1-{[6-bromo-7-methyl-2-(trifluoromethyl)-7H-pyrazolo[3,4-h]quinazolin-4-yl]amino}ethyl]phenyl}-2,2-difluoroethan-1-ol (40 mg, 0.07 mmol) in dioxane (5 mL) and $H_2O$ (2 mL) was added 1-methyl-5-(tetramethyl-1,3,2-dioxaborolan-2-yl)-1,2-dihydropyridin-2-one (26.6 mg, 0.1 mmol) Pd(dppf)$Cl_2$ (11.0 mg, 0.01 mmol) and $K_2CO_3$ (31.2 mg, 0.2 mmol). The reaction mixture was stirred at 100° C. for 5 h. The reaction mixture was filtered and the filtrate was concentrated in vacuum to give the residue and the residue was purified by prep-TLC (5% MeOH in DCM) and SFC to give 5-(4-{[(1R)-1-[3-(1,1-difluoro-2-hydroxyethyl)phenyl]ethyl]amino}-7-methyl-2-(trifluoromethyl)-7H-pyrazolo[3,4-h]quinazolin-6-yl)-1-methyl-1,2-dihydropyridin-2-one (27 mg, 0.05 mmol, 64.1%) as a light white solid. $^1H$ NMR (400 MHz, MeOD) δ 8.64 (s, 1H), 8.11 (s, 1H), 7.99 (d, J=2.4 Hz, 1H), 7.78 (dd, J=9.2, 2.5 Hz, 1H), 7.68 (s, 1H), 7.61 (d, J=6.6 Hz, 1H), 7.44-7.37 (m, 2H), 6.72 (d, J=9.2 Hz, 1H), 5.70 (q, J=7.0 Hz, 2H), 3.95 (s, 4H), 3.85 (td, J=13.4, 3.6 Hz, 2H), 3.70 (s, 4H), 1.71 (d, J=7.1 Hz, 4H). LCMS: m/z 559 $(M+H)^+$.

Example 33: Synthesis of (R)-5-(4-((1-(3-(1,1-difluoro-2-hydroxyethyl)-5-fluorophenyl) ethyl) amino)-7-methyl-2-(trifluoromethyl)-7H-pyrazolo[3,4-h]quinazolin-6-yl)-1-methylpyridin-2(1H)-one. (The Title Compound was Synthesized from Compound 7 in Example 30.)

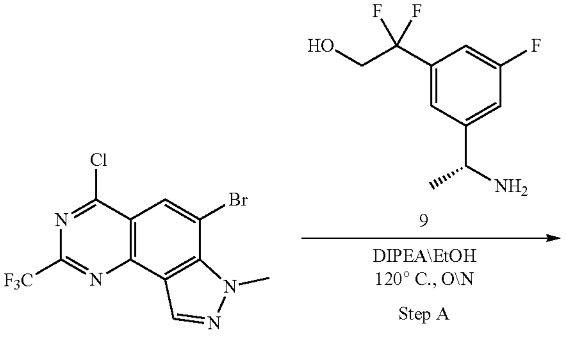

7

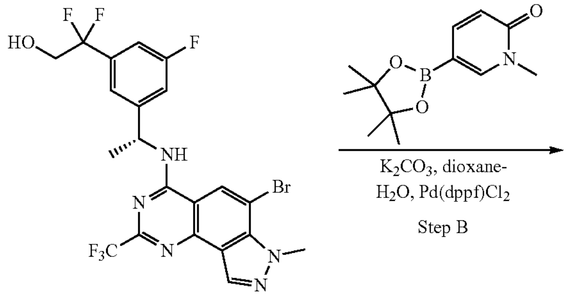

8

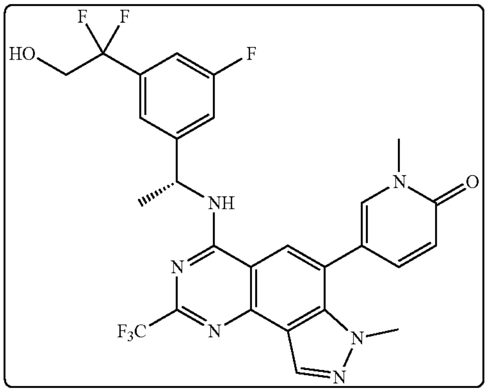
Example 33

Step A. (R)-2-(3-(1-((6-bromo-7-methyl-2-(trifluoromethyl)-7H-pyrazolo[3,4-h]quinazolin-4-yl) amino)ethyl)-5-fluorophenyl)-2,2-difluoroethan-1-ol To a stirred solution of 6-bromo-4-chloro-7-methyl-2-(trifluoromethyl)-7H-pyrazolo[3,4-h]quinazoline (70 mg, 0.2 mmol) in EtOH (3 mL) was added 2-{3-[(1R)-1-aminoethyl]-5-fluorophenyl}-2,2-difluoroethan-1-ol (62.9 mg, 0.3 mmol) and DIEA (0.1 mL, 0.6 mmol). The reaction mixture was stirred at 120° C. for 3 h. The reaction mixture was concentrated in vacuum to give the residue and the residue was purified by prep-TLC (60% EtOAc in PE) to give 2-{3-[(1R)-1-{[6-bromo-7-methyl-2-(trifluoromethyl)-7H-pyrazolo[3,4-h]quinazolin-4-yl]amino}ethyl]-5-fluorophenyl}-2,2-difluoroethan-1-ol (55 mg, 0.1 mmol, 52.3%) as a light yellow solid. LCMS: m/z 548 $(M+H)^+$.

Step B. (R)-5-(4-((1-(3-(1,1-difluoro-2-hydroxyethyl)-5-fluorophenyl)ethyl)amino)-7-methyl-2-(trifluoromethyl)-7H-pyrazolo[3,4-h]quinazolin-6-yl)-1-methylpyridin-2(1H)-one To a stirred solution of 2-{3-[(1R)-1-{[6-bromo-7-methyl-2-(trifluoromethyl)-7H-pyrazolo[3,4-h]quinazolin-4-yl]amino}ethyl]-5-fluorophenyl}-2,2-difluoroethan-1-ol (15 mg, 0.02 mmol) in dioxane (2 mL) and $H_2O$ (0.5 mL) was added 1-methyl-5-(tetramethyl-1,3,2-dioxaborolan-2-yl)-1,2-dihydropyridin-2-one (9.65 mg, 0.041 mmol), Pd(dppf)$Cl_2$ (4.00 mg) and $K_2CO_3$ (11.3 mg). The reaction mixture was stirred at 100° C. for 3 h. The reaction mixture was filtered and the filtrate was concentrated in vacuum to give the residue and the residue was purified prep-HPLC to give 5-(4-{[(1R)-1-[3-(1,1-difluoro-2-hydroxyethyl)-5-fluorophenyl]ethyl]amino}-7-methyl-2-(trifluoromethyl)-7H-pyrazolo[3,4-h]quinazolin-6-yl)-1-methyl-1,2-dihydropyridin-2-one (6.3 mg, 0.01 mmol, 39.9%) as a white solid. $^1H$ NMR (400 MHz, MeOD) δ 8.60 (s, 1H), 8.07 (s, 1H), 8.01 (d, J=2.1 Hz, 1H), 7.78 (dd, J=9.2, 2.5 Hz, 1H), 7.51 (s, 1H), 7.35 (d, J=9.5 Hz, 1H), 7.14 (d, J=9.0 Hz, 1H), 6.72 (d, J=9.2 Hz, 1H), 5.65 (q, J=7.0 Hz, 1H), 3.92 (s, 3H), 3.86 (td, J=13.3, 3.4 Hz, 2H), 3.71 (s, 3H), 1.71 (d, J=7.1 Hz, 3H). LCMS: m/z 577 $(M+H)^+$.

Example 34: Synthesis of 5-(4-{[(1R)-1-[3-(1,1-difluoro-2-hydroxyethyl)phenyl]ethyl]amino}-2-methyl-8-(trifluoromethyl)-8H-pyrazolo[3,4-h]quinazolin-6-yl)-1-methyl-1,2-dihydropyridin-2-one

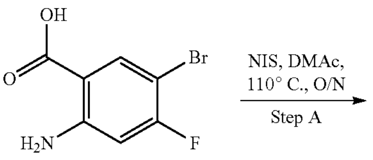

1

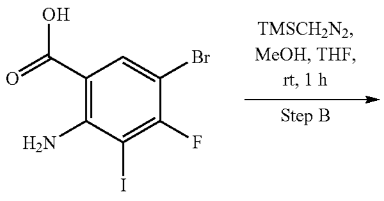

2

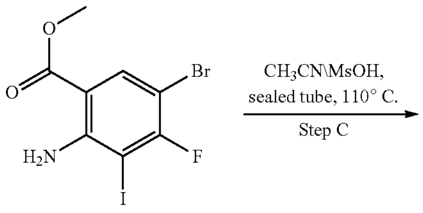

3

-continued

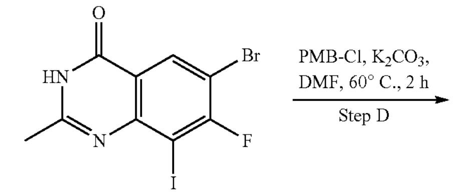

4

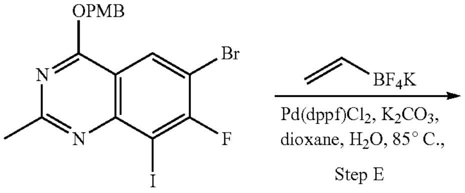

5

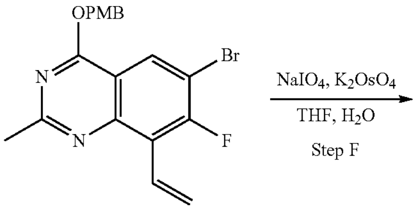

6

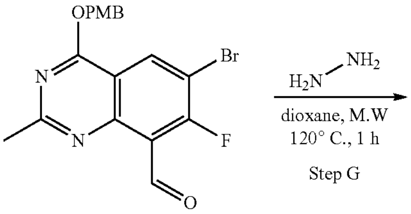

7

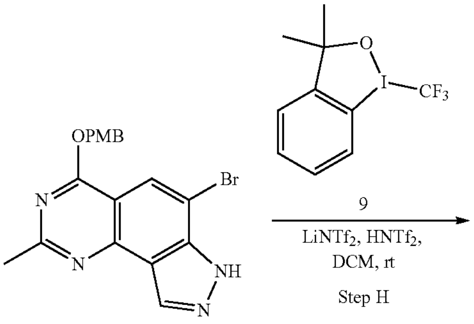

8

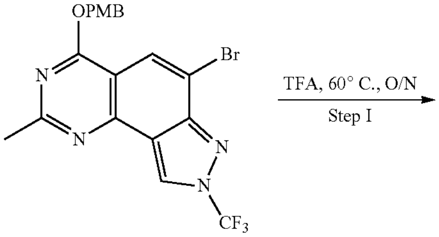

10

-continued

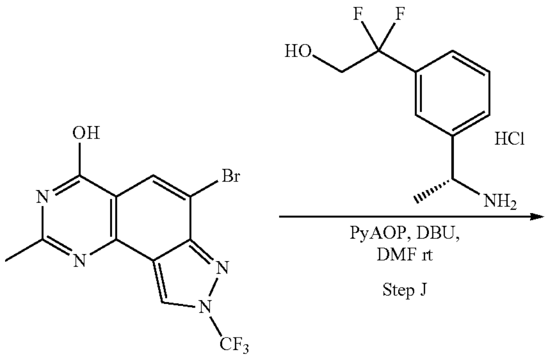

11

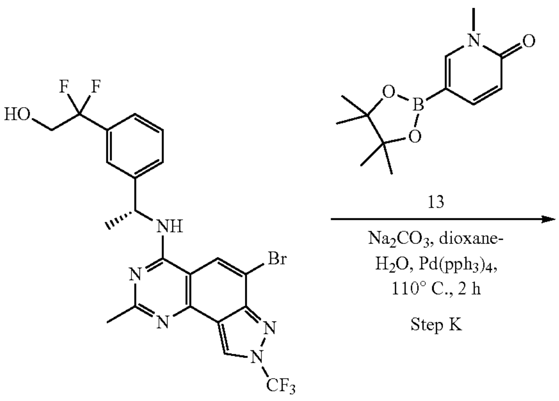

12

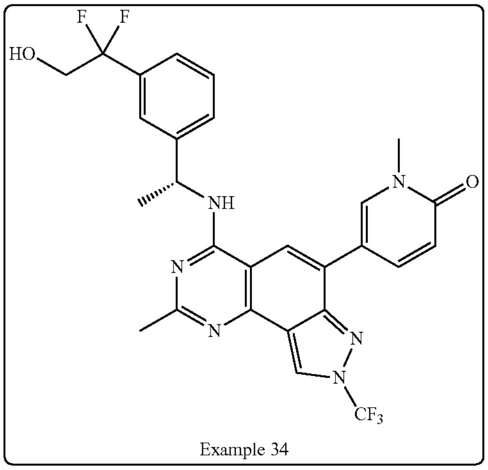 [SMILES: Cc1nc(N[C@H](C)c2cccc(C(F)(F)CO)c2)c2cc(-c3ccc(=O)n(C)c3)c3nn(C(F)(F)F)cc3c2n1]

Example 34

Step A. 2-amino-5-bromo-4-fluoro-3-iodobenzoic acid

To a stirred solution of 2-amino-5-bromo-4-fluorobenzoic acid (31 g, 132 mmol) in DMAc (100 mL) was added NIS (44.7 g, 198 mmol) slowly at rt. The reaction mixture was stirred at 110° C. for 16 h under nitrogen atmosphere. The reaction mixture was cooled to room temperature and diluted with water (50 mL), extracted with EtOAc (50 mL×3). The combined organic phase was washed by brine, dried over anhydrous $Na_2SO_4$, filtered and concentrated to give the crude product which was purified by column chromatography on silica gel (PE:EtOAc=5:1 to 1:1) to obtain 2-amino-5-bromo-4-fluoro-3-iodobenzoic acid (20 g, 55.6 mmol, 42%) as a brown solid. LC/MS (ESI) m/z: 361 $(M+H)^+$.

Step B. methyl 2-amino-5-bromo-4-fluoro-3-iodobenzoate

To a stirred solution of 2-amino-5-bromo-4-fluoro-3-iodobenzoic acid (13 g, 36 mmol) in THE (50 mL)/MeOH (50 mL) was added $TMSCHN_2$ (8.1 mL, 63 mmol) at rt. After stirred at rt for 1 h, the mixture was poured into water (80 mL) and extracted with EtOAc (8 mL*3). The combined organic phase was washed with brine, dried over $Na_2SO_4$, filtered and concentrated. The residue was purified by chromatography (silica gel, 0-10%, EtOAc in PE) to give methyl 2-amino-5-bromo-4-fluoro-3-iodobenzoate (7.6 g, 20 mmol, 56%) as a brown solid. LCMS: m/z 375 $(M+H)^+$.

Step C. 6-bromo-7-fluoro-8-iodo-2-methyl-3,4-dihydroquinazolin-4-one

To a stirred solution of methyl 2-amino-5-bromo-4-fluoro-3-iodobenzoate (7.6 g, 20.3 mmol) in $CH_3CN$ (40 mL) was added MsOH (8 mL) at rt. After stirred at 110° C. overnight, the cooled mixture was poured into water (40 ml) and extracted with EtOAc (20 ml*3). The combined organic phase was washed with brine, dried over $Na_2SO_4$, filtered and concentrated. The residue was purified by chromatography (silica gel, 0-80%, EtOAc in PE) to give 6-bromo-7-fluoro-8-iodo-2-methyl-3,4-dihydroquinazolin-4-one (6.1 g, 15.9 mmol, 78%) as a yellow solid. LCMS: m/z 384 $(M+H)^+$.

Step D. 6-bromo-7-fluoro-8-iodo-4-[(4-methoxyphenyl)methoxy]-2-methylquinazoline To a stirred solution of 6-bromo-7-fluoro-8-iodo-2-methyl-3,4-dihydroquinazolin-4-one (6.1 g, 16 mmol) in DMF (20 mL) was added PMBCl (3.7 g, 23.9 mmol) and $K_2CO_3$ (2.2 g, 15.9 mmol) at rt. After stirred at 60° C. for 2 h, the cooled mixture was poured into water (50 ml) and extracted with EtOAc (15 mL*3). The combined organic phase was washed with brine, dried over $Na_2SO_4$, filtered and concentrated. The residue was purified by chromatography (silica gel, 0-40%, EtOAc in PE) to give 6-bromo-7-fluoro-8-iodo-4-[(4-methoxyphenyl)methoxy]-2-methylquinazoline (7.1 g, 14.1 mmol, 88%) as a yellow solid. LCMS: m/z 504 $(M+H)^+$.

Step E. 6-bromo-8-ethenyl-7-fluoro-4-[(4-methoxyphenyl)methoxy]-2-methylquinazoline To a stirred solution of 6-bromo-7-fluoro-8-iodo-4-[(4-methoxyphenyl)methoxy]-2-methylquinazoline (7 g, 13.9 mmol) in dioxane (150 mL)/$H_2O$ (35 mL) was added $Pd(dppf)Cl_2$ (0.8 g, 1.1 mmol), $K_2CO_3$ (16.8 g, 32.8 mmol) and trifluoro(vinyl)-14-borane (2 g, 14 mmol) at rt. After stirred at 85° C. overnight, the cooled mixture was poured into water (50 ml) and extracted with EtOAc (20 mL*3). The combined organic phase was washed with brine, dried over $Na_2SO_4$, filtered and concentrated. The residue was purified by chromatography (silica gel, 0-80%, EtOAc in PE) to give 6-bromo-8-ethenyl-7-fluoro-4-[(4-methoxyphenyl)methoxy]-2-methylquinazoline (2.8 g, 6.9 mmol, 50%) as a yellow solid. LCMS: m/z 404 $(M+H)^+$.

Step F. 6-bromo-7-fluoro-4-[(4-methoxyphenyl)methoxy]-2-methylquinazoline-8-carbaldehyde To a stirred solution of 6-bromo-8-ethenyl-7-fluoro-4-[(4-methoxyphenyl)methoxy]-2-methylquinazoline (2.6 g, 6.5 mmol) and sodium periodate (22 g, 33 mmol) in THE (40 mL)/$H_2O$ (40 mL) at 0° C. was added potassium osmate dihydrate (46 mg, 0.14 mmol) slowly. The reaction mixture was stirred at room temperature for 4 h. The reaction mixture was diluted with water (50 mL), the mixture was extracted with EtOAc (50 mL×3). The combined organic phase was washed by water and brine, dried over anhydrous $Na_2SO_4$, filtered and concentrated to give the crude product which was purified by column chromatography on silica gel (PE:EtOAc=10:1 to 3:1) to obtain 6-bromo-7-fluoro-4-[(4-methoxyphenyl)methoxy]-2-methylquinazoline-8-carbaldehyde (2 g, 4.9 mmol, 76%) as a brown solid. LCMS: m/z 406 $(M+H)^+$.

Step G. 6-bromo-4-[(4-methoxyphenyl)methoxy]-2-methyl-7H-pyrazolo[3,4-h]quinazoline To a stirred solution of 6-bromo-7-fluoro-4-[(4-methoxyphenyl)methoxy]-2-methylquinazoline-8-carbaldehyde (2 g, 4.9 mmol) in dioxane (50 mL) was added hydrazine (0.32 g, 9.8 mmol) slowly. The reaction mixture was stirred at 120° C. for 1 h under microwave. The reaction mixture was concentrated to give the crude product which was purified by column chromatography on silica gel (PE:EtOAc=10:1 to 3:1) to obtain 6-bromo-4-[(4-methoxyphenyl)methoxy]-2-methyl-7H-pyrazolo[3,4-h]quinazoline (1.2 g, 3.1 mmol, 61%) as a yellow solid. LC/MS (ESI) m/z: =400 $(M+H)^+$.

Step H. 6-bromo-4-[(4-methoxyphenyl)methoxy]-2-methyl-7-(trifluoromethyl)-7H-pyrazolo[3,4-h]quinazoline To a stirred solution of 6-bromo-4-[(4-methoxyphenyl)methoxy]-2-methyl-7H-pyrazolo[3,4-h]quinazoline (600 mg, 1.5 mmol) in DCM (5 mL) was added $LiNTf_2$ (22 mg, 0.07 mmol) at rt. After stirred at rt for 10 min, 3,3-dimethyl-1-(trifluoromethyl)-3H-1λ^3,2-benziodaoxole (749 mg, 2.3 mmol) and $HNTf_2$ (127 mg, 0.45 mmol) was added at rt. After stirred at 35° C. for 3 h, the mixture was purified by chromatography (silica gel, 0-30%, MeOH in DCM) and then prep-TLC (PE:EtOAc=3:1) to give 6-bromo-4-[(4-methoxyphenyl)methoxy]-2-methyl-7-(trifluoromethyl)-7H-pyrazolo[3,4-h]quinazoline (60 mg, 0.13 mmol, 8%) as a yellow solid. LCMS: m/z 468 $(M+H)^+$.

Step I. 6-bromo-2-methyl-8-(trifluoromethyl)-8H-pyrazolo[3,4-h]quinazolin-4-ol

After 6-bromo-4-[(4-methoxyphenyl)methoxy]-2-methyl-8-(trifluoromethyl)-8H-pyrazolo[3,4-h]quinazoline (60 mg, 0.13 mmol) was added to TFA (5 mL) and the mixture was stirred at 60° C. overnight. The cooled mixture was concentrated in vacuo and azeotroped with toluene. The residue was purified by prep-TLC (DCM:MeOH=15:1) to give 6-bromo-2-methyl-8-(trifluoromethyl)-8H-pyrazolo[3,4-h]quinazolin-4-ol (40 mg, 0.12 mmol, 89%) as a yellow solid. LCMS: m/z 348 $(M+H)^+$.

Step J. 2-{3-[(1R)-1-{[6-bromo-2-methyl-8-(trifluoromethyl)-8H-pyrazolo[3,4-h]quinazolin-4-yl]amino}ethyl]phenyl}-2,2-difluoroethan-1-ol To a stirred solution of 6-bromo-2-methyl-8-(trifluoromethyl)-8H-pyrazolo[3,4-h]quinazolin-4-ol (40 mg, 0.12 mmol) in DMF (5 mL) was added 2-{3-[(1R)-1-aminoethyl] phenyl}-2,2-difluoroethan-1-ol (58 mg, 0.28 mmol), PyAOP (90 mg, 0.17 mmol) and DBU (0.1 mL, 0.57 mmol) at rt. After stirred at rt for 3 h, the cooled mixture was poured into water (20 mL) and extracted with EtOAc (8 mL*3). The combined organic phase was washed with brine, dried over $Na_2SO_4$, filtered and concentrated. The residue was purified by prep-TLC (DCM:MeOH=20:1) to give 2-{3-[(1R)-1-{[6-bromo-2-methyl-8-(trifluoromethyl)-8H-pyrazolo[3,4-h] quinazolin-4-yl]amino}ethyl]phenyl}-2,2-difluoroethan-1-ol (10 mg, 0.02 mmol, 16%) as a yellow solid. LCMS: m/z 531 $(M+H)^+$.

Step K. 5-(4-{[(1R)-1-[3-(1,1-difluoro-2-hydroxy-ethyl)phenyl]ethyl]amino}-2-methyl-8-(trifluoromethyl)-8H-pyrazolo[3,4-h]quinazolin-6-yl)-1-methyl-1,2-dihydropyridin-2-one To a stirred solution of 2-{3-[(1R)-1-{[6-bromo-2-methyl-8-(trifluoromethyl)-8H-pyrazolo[3,4-h]quinazolin-4-yl]amino}ethyl]phenyl}-2,2-difluoroethan-1-ol (10 mg, 0.02 mmol) in dioxane (8 mL)/$H_2O$ (2 mL) was added $Pd(PPh_3)_4$ (20 mg, 0.02 mmol), $Na_2CO_3$ (92 mg, 0.86 mmol) and 1-methyl-5-(tetramethyl-1,3,2-dioxaborolan-2-yl)-1,2-dihydropyridin-2-one (13 mg, 0.06 mmol) at rt. After stirred at 110° C. for 1 h, the cooled mixture was poured into water (10 mL) and extracted with EtOAc (5 ml*3). The combined organic phase was washed with brine, dried over $Na_2SO_4$, filtered and concentrated. The residue was purified by prep-TLC (DCM:MeOH=8:1) to give 5-(4-{[(1R)-1-[3-(1,1-difluoro-2-hydroxyethyl)phenyl]ethyl]amino}-2-methyl-8-(trifluoromethyl)-8H-pyrazolo[3,4-h]quinazolin-6-yl)-1-methyl-1,2-dihydropyridin-2-one (2 mg, 0.004 mmol, 22%) as a yellow solid. LCMS: m/z 559 $(M+H)^+$. $^1H$ NMR (400 MHz, MeOD) δ 9.26 (s, 1H), 8.68 (d, J=2.5 Hz, 1H), 8.36 (dd, J=9.5, 2.6 Hz, 1H), 8.25 (s, 1H), 7.69 (s, 1H), 7.61 (d, J=7.4 Hz, 1H), 7.41 (dd, J=10.6, 7.8 Hz, 2H), 6.72 (d, J=9.5 Hz, 1H), 5.72 (d, J=7.0 Hz, 1H), 3.88 (t, J=13.5 Hz, 2H), 3.71 (s, 3H), 2.55 (s, 3H), 1.72 (d, J=7.1 Hz, 3H).

Example 35: Synthesis of 2,7-dimethyl-6-(oxolan-3-yloxy)-N-[(1R)-1-[3-(trifluoromethyl) phenyl] ethyl]-7H-pyrazolo[3,4-h]quinazolin-4-amine. (The Title Compound was Synthesized from Compound 7 in Example 24.)

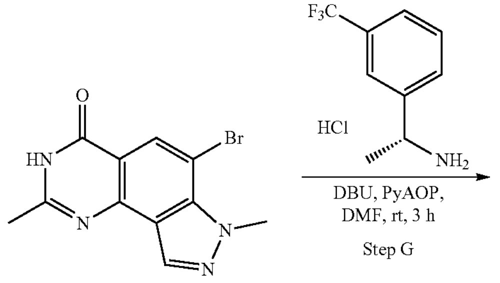

-continued

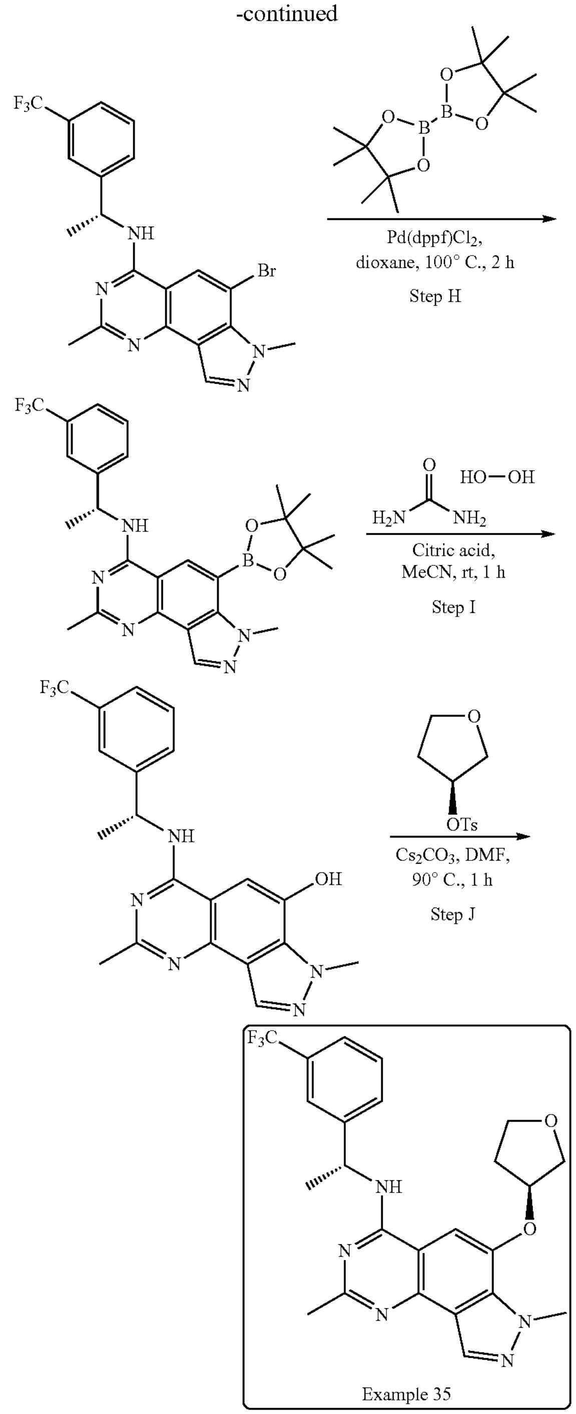

Example 35

Step G. 6-bromo-2,7-dimethyl-N-[(1R)-1-[3-(trifluoromethyl)phenyl]ethyl]-7H-pyrazolo[3,4-h]quinazolin-4-amine To a stirred solution of 6-bromo-2,7-dimethyl-3H,4H,7H-pyrazolo[3,4-h]quinazolin-4-one (200 mg, 0.68 mmol) in DMF (10 mL) was added (1R)-1-[3-(trifluoromethyl)phenyl]ethan-1-amine (193 mg, 1.02 mmol), PyAOP (711 mg, 1.36 mmol) and DBU (0.5 mL, 3.41 mmol) at rt. After stirred at rt for 3 h, the cooled mixture was poured into water (20 ml) and extracted with EtOAc (8 mL*3). The combined organic phase was washed with brine, dried over $Na_2SO_4$, filtered and concentrated. The residue was purified by prep-TLC (DCM:MeOH=15:1) to give 6-bromo-2,7-dimethyl-N-[(1R)-1-[3-(trifluoromethyl)phenyl]ethyl]-7H-pyrazolo[3,4-h]quinazolin-4-amine (80 mg, 0.17 mmol, 25%) as a yellow solid. LCMS: m/z 318 $(M+H)^+$.

Step H. 2,7-dimethyl-6-(tetramethyl-1,3,2-dioxaborolan-2-yl)-N-[(1R)-1-[3-(trifluoromethyl)phenyl]ethyl]-7H-pyrazolo[3,4-h]quinazolin-4-amine To a stirred solution of 6-bromo-2,7-dimethyl-N-[(1R)-1-[3-(trifluoromethyl)phenyl]ethyl]-7H-pyrazolo[3,4-h]quinazolin-4-amine (80 mg, 0.172 mmol) in dioxane (5 mL) was added 4,4,5,5-tetramethyl-2-(tetramethyl-1,3,2-dioxaborolan-2-yl)-1,3,2-dioxaborolane (0.1 mL, 0.345 mmol), $Pd(dppf)Cl_2$ (25.2 mg, 0.034 mmol) and KOAc (50 mg, 0.51 mmol) at rt. After stirred at 100° C. for 3 h, the cooled mixture was poured into water (10 ml) and extracted with EtOAc (10 mL*3). The combined organic phase was washed with brine, dried over $Na_2SO_4$, filtered and concentrated to give crude 2,7-dimethyl-6-(tetramethyl-1,3,2-dioxaborolan-2-yl)-N-[(1R)-1-[3-(trifluoromethyl)phenyl]ethyl]-7H-pyrazolo[3,4-h]quinazolin-4-amine (80 mg, 0.15 mmol, 90.8%) as a yellow oil. LCMS: m/z 512 $(M+H)^+$.

Step I. 2,7-dimethyl-4-{[(1R)-1-[3-(trifluoromethyl)phenyl]ethyl]amino}-7H-pyrazolo[3,4-h]quinazolin-6-ol To a stirred solution of 2,7-dimethyl-6-(tetramethyl-1,3,2-dioxaborolan-2-yl)-N-[(1R)-1-[3-(trifluoromethyl)phenyl]ethyl]-7H-pyrazolo[3,4-h]quinazolin-4-amine (80 mg, 0.15 mmol) in MeCN (5 mL) was added citric acid (30 mg, 0.15 mmol) and HPU (73 mg, 0.78 mmol) at rt. After stirred at rt for 1 h, the mixture was poured into water (10 ml) and extracted with DCM (5 mL*3). The combined organic phase was washed with brine, dried over $Na_2SO_4$, filtered and concentrated. The residue was purified by chromatography (silica gel, 0-20%, MeOH in DCM) to give 2,7-dimethyl-4-{[(1R)-1-[3-(trifluoromethyl)phenyl]ethyl]amino}-7H-pyrazolo[3,4-h]quinazolin-6-ol (20 mg, 0.05 mmol, 31%) as a yellow solid. LCMS: m/z 402 $(M+H)^+$.

Step J. 2,7-dimethyl-6-(oxolan-3-yloxy)-N-[(1R)-1-[3-(trifluoromethyl)phenyl]ethyl]-7H-pyrazolo[3,4-h]quinazolin-4-amine To a stirred solution of 2,7-dimethyl-4-{[(1R)-1-[3-(trifluoromethyl)phenyl]ethyl]amino}-7H-pyrazolo[3,4-h]quinazolin-6-ol (25 mg, 0.06 mmol) in DMF (3 mL) was added $Cs_2CO_3$ (101 mg, 0.31 mmol) and oxolan-3-yl 4-methylbenzene-1-sulfonate (22 mg, 0.09 mmol) at rt. After stirred at 90° C. for 1 h, the cooled mixture was poured into water (10 ml) and extracted with EtOAc (5 ml*3). The combined organic phase was washed with brine, dried over $Na_2SO_4$, filtered and concentrated. The residue was purified by prep-TLC (DCM:MeOH=10:1) then prep-HPLC (C18, 40~90% MeCN in $H_2O$ with 0.1% $CF_3COOH$) to give 2,7-dimethyl-6-(oxolan-3-yloxy)-N-[(1R)-1-[3-(trifluoromethyl)phenyl]ethyl]-7H-pyrazolo[3,4-h]quinazolin-4-amine (5 mg, 0.01 mmol, 17%) as a white solid. LCMS: m/z 472 $(M+H)^+$. $^1H$ NMR (400 MHz, MeOD) δ 8.55 (s, 1H), 7.82-7.76 (m, 2H), 7.58 (d, J=7.2 Hz, 3H), 5.93 (t, J=7.0 Hz, 1H), 5.44 (s, 1H), 4.39 (s, 3H), 4.18-4.05 (m, 3H), 4.01 (dt, J=8.5, 4.2 Hz, 1H), 2.71 (s, 3H), 2.50-2.41 (m, 1H), 2.39-2.31 (m, 1H), 1.79 (d, J=7.1 Hz, 3H).

The examples in the following Table 4 were prepared by using a method analogous to that used to prepare the examples as described herein.

TABLE 4

| Ex# | Structure & name | Analytical data | Method |
|---|---|---|---|
| Example 36 | 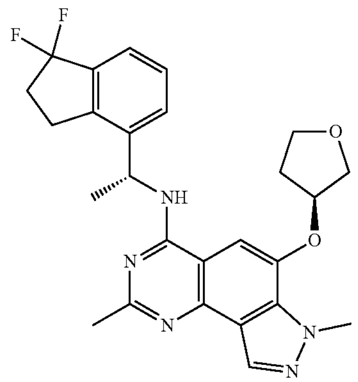 [SMILES: Cc1nc(N[C@H](C)c2cccc3c2CCC3(F)F)c2cc(O[C@H]3CCOC3)c3c(cnn3C)c2n1] N-((R)-1-(1,1-difluoro-2,3-dihydro-1H-inden-4-yl)ethyl)-2,7-dimethyl-6-(((S)-tetrahydrofuran-3-yl)oxy)-7H-pyrazolo[3,4-h]quinazolin-4-amine | LCMS: m/z 480 $(M + H)^+$. $^1H$ NMR (400 MHz, MeOD) δ 8.54 (s, 1H), 7.63 (d, J = 7.7 Hz, 2H), 7.45-7.38 (m, 2H), 5.86 (q, J = 7.1 Hz, 1H), 5.44 (t, J = 4.7 Hz, 1H), 4.38 (s, 3H), 4.18-4.06 (m, 3H), 4.00 (td, J = 8.5, 4.2 Hz, 1H), 3.30-3.26 (m, 1H), 3.20-3.11 (m, 1H), 2.68 (s, 3H), 2.66-2.55 (m, 2H), 2.42 (ddt, J = 32.0, 19.3, 6.8 Hz, 2H), 1.76 (d, J = 7.1 Hz, 3H). | Example 35 |

TABLE 4-continued

| Ex# | Structure & name | Analytical data | Method |
|---|---|---|---|
| Example 37 | 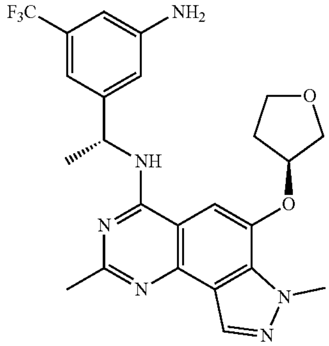 [SMILES: Cc1nc(N[C@H](C)c2cc(N)cc(C(F)(F)F)c2)c2cc(O[C@H]3CCOC3)c3c(cnn3C)c2n1] N-((R)-1-(3-amino-5-(trifluoromethyl)phenyl)ethyl)-2,7-dimethyl-6-(((S)-tetrahydrofuran-3-yl)oxy)-7H-pyrazolo[3,4-h]quinazolin-4-amine | LC/MS (ESI) m/z: 487 (M + H)$^+$. $^1$H NMR (400 MHz, MeOD) δ 8.51 (s, 1H), 7.43 (s, 1H), 7.00 (d, J = 5.2 Hz, 2H), 6.81 (s, 1H), 5.71 (q, J = 7.1 Hz, 1H), 5.41 (s, 1H), 4.58 (s, 2H), 4.34 (s, 3H), 4.19-3.90 (m, 4H), 2.58 (s, 3H), 2.40 (ddt, J = 19.2, 13.5, 8.2 Hz, 2H), 1.68 (d, J = 7.1 Hz, 3H). | Example 35 (using Intermediate 7) |
| Example 38 | 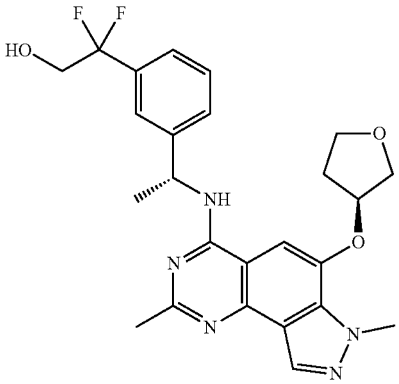 [SMILES: Cc1nc(N[C@H](C)c2cccc(C(F)(F)CO)c2)c2cc(O[C@H]3CCOC3)c3c(cnn3C)c2n1] 2-(3-((R)-1-((2,7-dimethyl-6-(((S)-tetrahydrofuran-3-yl)oxy)-7H-pyrazolo[3,4-h]quinazolin-4-yl)amino)ethyl)phenyl)-2,2-difluoroethan-1-ol | LCMS: m/z 484 (M + H)$^+$. $^1$H NMR (400 MHz, MeOD) δ 8.54 (s, 1H), 7.69 (s, 1H), 7.60 (dd, J = 11.4, 5.3 Hz, 2H), 7.50-7.44 (m, 2H), 5.91 (t, J = 7.1 Hz, 1H), 5.43 (s, 1H), 4.38 (d, J = 0.5 Hz, 3H), 4.17-3.97 (m, 4H), 3.89 (t, J = 13.3 Hz, 2H), 2.72 (s, 3H), 2.42 (ddd, J = 34.0, 21.1, 5.6 Hz, 2H), 1.78 (d, J = 7.1 Hz, 3H) | Example 35 |
| Example 39 | 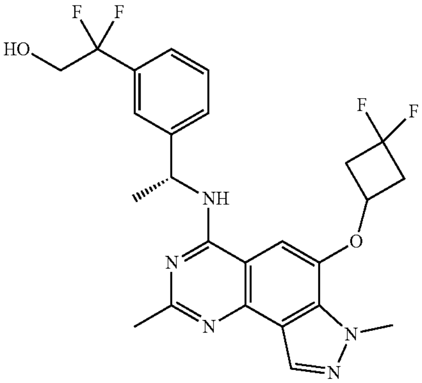 [SMILES: Cc1nc(N[C@H](C)c2cccc(C(F)(F)CO)c2)c2cc(OC3CC(F)(F)C3)c3c(cnn3C)c2n1] (R)-2-(3-(1-((6-(3,3-difluorocyclobutoxy)-2,7-dimethyl-7H-pyrazolo[3,4-h]quinazolin-4-yl)amino)ethyl)phenyl)-2,2-difluoroethan-1-ol | LCMS: m/z 504 (M + H)$^+$. $^1$H NMR (400 MHz, MeOD) δ 8.56 (s, 1H), 7.68 (s, 1H), 7.61 (d, J = 6.9 Hz, 1H), 7.46 (dd, J = 6.2, 4.6 Hz, 3H), 5.91 (q, J = 7.0 Hz, 1H), 5.12 (dd, J = 7.4, 4.8 Hz, 1H), 4.41 (s, 3H), 3.90 (dd, J = 16.8, 9.7 Hz, 2H), 3.42-3.33 (m, 2H), 3.02-2.89 (m, 2H), 2.72 (s, 3H), 1.78 (d, J = 7.1 Hz, 3H). | Example 35 |

TABLE 4-continued

| Ex# | Structure & name | Analytical data | Method |
|---|---|---|---|
| Example 40 | 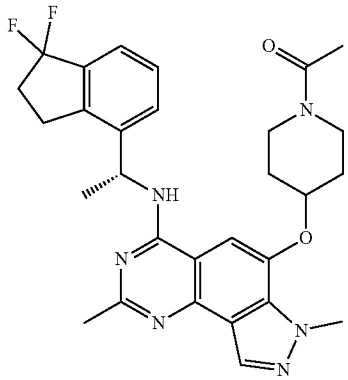 [SMILES: CC(=O)N1CCC(Oc2cc3c(N[C@H](C)c4cccc5c4CCC5(F)F)nc(C)nc3c3cnn(C)c23)CC1] (R)-1-(4-((4-((1-(1,1-difluoro-2,3-dihydro-1H-inden-4-yl)ethyl)amino)-2,7-dimethyl-7H-pyrazolo[3,4-h]quinazolin-6-yl)oxy)piperidin-1-yl)ethan-1-one | LC/MS (ESI) m/z: 536 $(M + H)^+$. $^1H$ NMR (400 MHz, MeOD) δ 8.54 (s, 2H), 8.54 (s, 1H), 7.69 (d, J = 2.3 Hz, 1H), 7.69 (d, J = 2.3 Hz, 1H), 7.62 (d, J = 7.3 Hz, 1H), 7.62 (d, J = 7.3 Hz, 1H), 7.45-7.39 (m, 2H), 7.42 (dt, J = 14.7, 7.4 Hz, 3H), 5.88-5.84 (m, 1H), 5.89-5.83 (m, 1H), 5.10 (s, 2H), 5.10 (s, 1H), 4.42 (s, 3H), 4.42 (s, 3H), 3.85 (s, 2H), 3.63 (s, 2H), 3.18 (s, 2H), 2.68 (d, J = 1.6 Hz, 3H), 2.64 (d, J = 11.8 Hz, 2H), 2.17 (s, 5H), 1.99 (s, 2H), 1.76 (d, J = 7.0 Hz, 3H). | Example 35 |
| Example 41 | 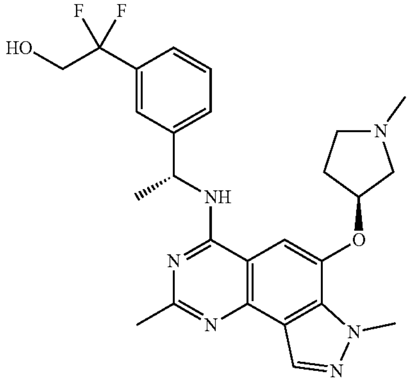 [SMILES: Cc1nc(N[C@H](C)c2cccc(C(F)(F)CO)c2)c2cc(O[C@H]3CCN(C)C3)c3c(cnn3C)c2n1] 2-(3-((R)-1-((2,7-dimethyl-6-(((S)-1-methylpyrrolidin-3-yl)oxy)-7H-pyrazolo[3,4-h]quinazolin-4-yl)amino)ethyl)phenyl)-2,2-difluoroethan-1-ol | LCMS: m/z 497 $(M + H)^+$. $^1H$ NMR (400 MHz, MeOD) δ 8.56 (s, 1H), 7.69 (s, 1H), 7.64-7.58 (m, 2H), 7.47 (d, J = 6.3 Hz, 2H), 5.91 (q, J = 7.1 Hz, 1H), 5.56 (s, 1H), 4.41 (s, 3H), 4.22 (s, 1H), 3.93 (s, 1H), 3.88 (d, J = 13.3 Hz, 2H), 3.51 (dd, J = 27.2, 25.6 Hz, 2H), 3.08 (s, 3H), 2.88 (s, 1H), 2.72 (s, 3H), 2.56 (s, 1H), 1.79 (d, J = 7.1 Hz, 3H). | Example 35 |

Example 42: Synthesis of 1-(4-{[(1R)-1-[3-(1,1-difluoro-2-hydroxyethyl)phenyl] ethyl]amino}-2,7-dimethyl-7H-pyrazolo[3,4-h]quinazolin-6-y)pyrrolidin-3-ol. (The title compound was synthesized from Compound 7 in Example 24.)

-continued

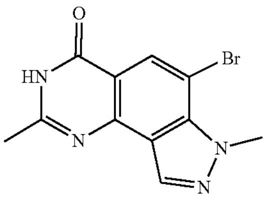

1

$POCl_3$, DIPEA,
120 C., 1 h
Step A

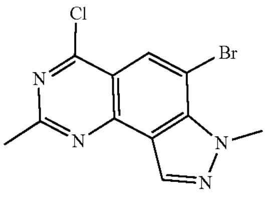

2

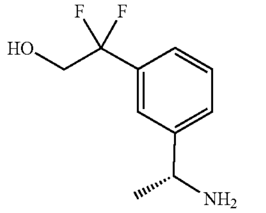

3

EtOH, DIPEA,
120° C., O/N
Step B

-continued

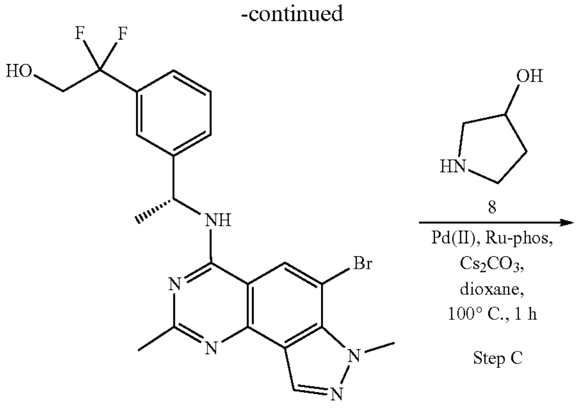

4

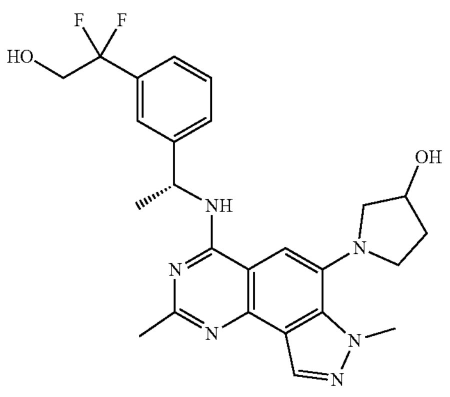

Example 42

Step A. 6-bromo-4-chloro-2,7-dimethyl-7H-pyrazolo[3,4-h]quinazoline

To a stirred solution of 6-bromo-2,7-dimethyl-3H,4H,7H-pyrazolo[3,4-h]quinazolin-4-one (450 mg, 1.5 mmol) in $POCl_3$ (10 mL) was added DIPEA (2 mL) at rt. After stirred at 120° C. for 1 h, the cooled mixture was concentrated. The residue was poured into $NaHCO_3$ (aq, 20 mL) and extracted with EtOAc (10 mL*3). The combined organic phase was washed with brine, dried over $Na_2SO_4$, filtered and concentrated. The residue was purified by chromatography (silica gel, 0-50%, EtOAc in PE) to give 6-bromo-4-chloro-2,7-dimethyl-7H-pyrazolo[3,4-h]quinazoline (130 mg, 0.42 mmol, 27%) as a yellow solid. LCMS: m/z 311 $(M+H)^+$.

Step B. 2-{3-[(1R)-1-({6-bromo-2,7-dimethyl-7H-pyrazolo[3,4-h]quinazolin-4-yl}amino)ethyl]phenyl}-2,2-difluoroethan-1-ol To a stirred solution of 6-bromo-4-chloro-2,7-dimethyl-7H-pyrazolo[3,4-h]quinazoline (130 mg, 0.42 mmol) in EtOH (10 mL) was added DIPEA (434 mg, 3.3 mmol) and 2-{3-[(1R)-1-aminoethyl]phenyl}-2,2-difluoroethan-1-ol (203 mg, 1.01 mmol) at rt. After stirred at 120° C. overnight, the cooled mixture was poured into water (20 ml) and extracted with EtOAc (10 mL*2). The combined organic phase was washed with brine, dried over $Na_2SO_4$, filtered and concentrated. The residue was purified by chromatography (silica gel, 0-15%, MeOH in DCM) to give 2-{3-[(1R)-1-({6-bromo-2,7-dimethyl-7H-pyrazolo[3,4-h]quinazolin-4-yl}amino)ethyl]phenyl}-2,2-difluoroethan-1-ol (160 mg, 0.34 mmol, 80%) as a yellow solid. LCMS: m/z 476 $(M+H)^+$.

Step C. 1-(4-{[(1R)-1-[3-(1,1-difluoro-2-hydroxyethyl)phenyl]ethyl]amino}-2,7-dimethyl-7H-pyrazolo[3,4-h]quinazolin-6-yl)pyrrolidin-3-ol To a stirred solution of 2-{3-[(1R)-1-({6-bromo-2,7-dimethyl-7H-pyrazolo[3,4-h]quinazolin-4-yl}amino)ethyl]phenyl}-2,2-difluoroethan-1-ol (100 mg, 0.21 mmol) in dioxane (5 mL) was added pyrrolidin-3-ol (28 mg, 0.32 mmol), PD(II) MESO-TETRA(4-CARBOXYPHENYL)PORPHINE (19 mg, 0.02 mmol), Ru-phos (20 mg, 0.04 mmol) and $Cs_2CO_3$ (205 mg, 0.63 mmol) at rt. After stirred at 100° C. for 1 h, the cooled mixture was poured into water (10 mL) and extracted with EtOAc (5 mL*3). The combined organic phase was washed with brine, dried over $Na_2SO_4$, filtered and concentrated. The residue was purified by prep-TLC (DCM:MeOH=8:1) then prep-HPLC (C18, 40~90% MeCN in $H_2O$ with 0.1% $CF_3COOH$) to give 1-(4-{[(1R)-1-[3-(1,1-difluoro-2-hydroxyethyl)phenyl]ethyl]amino}-2,7-dimethyl-7H-pyrazolo[3,4-h]quinazolin-6-yl)pyrrolidin-3-ol (10 mg, 0.02 mmol, 10%) as a white solid. LCMS: m/z 483 $(M+H)^+$. $^1H$ NMR (400 MHz, MeOD) δ 8.55 (s, 1H), 7.68 (d, J=3.2 Hz, 2H), 7.59 (d, J=7.2 Hz, 1H), 7.43-7.37 (m, 2H), 5.74 (d, J=7.1 Hz, 1H), 4.62-4.58 (m, 1H), 4.41 (s, 3H), 3.87 (t, J=13.5 Hz, 2H), 3.48-3.42 (m, 1H), 3.37 (dd, J=9.5, 5.0 Hz, 1H), 3.22 (dt, J=10.2, 2.8 Hz, 1H), 3.15 (dt, J=12.3, 4.5 Hz, 1H), 2.52 (s, 3H), 2.41 (dt, J=13.6, 6.8 Hz, 1H), 1.97 (ddd, J=13.4, 9.3, 4.0 Hz, 1H), 1.69 (d, J=7.1 Hz, 3H).

Example 43: Synthesis of (3S)-1-(4-{[(1R)-1-[3-(1,1-difluoro-2-hydroxyethyl)phenyl]ethyl]amino}-2,7-dimethyl-7H-pyrazolo[3,4-h]quinazolin-6-yl)pyrrolidin-3-ol. (The title compound was synthesized from Compound 4 in Example 42.)

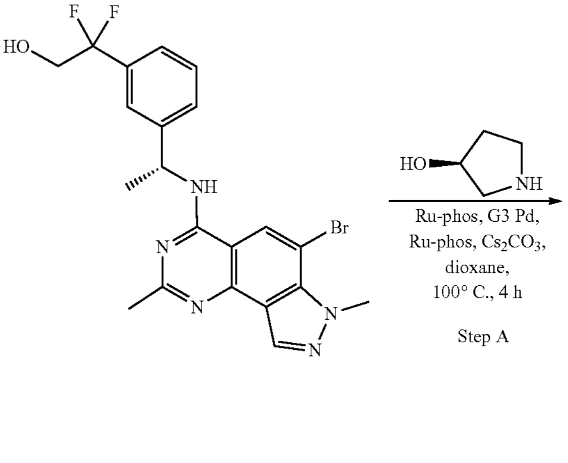

-continued

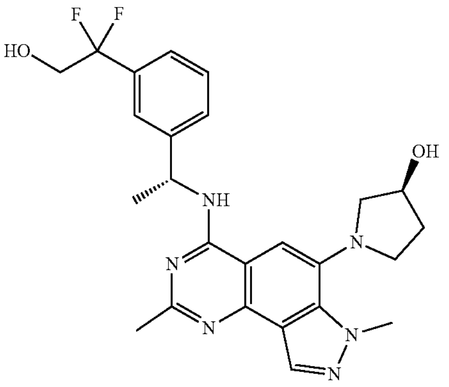

Example 43

Step A. (3S)-1-(4-{[(1R)-1-[3-(1,1-difluoro-2-hydroxyethyl)phenyl]ethyl]amino}-2,7-dimethyl-7H-pyrazolo[3,4-h]quinazolin-6-yl)pyrrolidin-3-ol To a stirred solution of 2-{3-[(1R)-1-({6-bromo-2,7-dimethyl-7H-pyrazolo[3,4-h]quinazolin-4-yl}amino)ethyl]phenyl}-2,2-difluoroethan-1-ol (350 mg, 0.73 mmol) in dioxane (10 mL) was added (3S)-pyrrolidin-3-ol (128 mg, 1.47 mmol), Ru-phos (69 mg, 0.15 mmol), Ru-phos Pd G3 (62 mg, 0.073 mmol) and $Cs_2CO_3$ (718 mg, 2.20 mmol) at rt. After stirred at 100° C. for 4 h. The cool mixture was filtered and concentrated. The crude product was purified by pre-TLC (10% MeOH in DCM) and then by prep-SFC to give (3S)-1-(4-{[(1R)-1-[3-(1,1-difluoro-2-hydroxyethyl)phenyl]ethyl]amino}-2,7-dimethyl-7H-pyrazolo[3,4-h]quinazolin-6-yl)pyrrolidin-3-ol (40 mg, 0.083 mmol, 11%) as a yellow solid. LC-MS (ESI) m/z 485 $(M+H)^+$. $^1H$ NMR (400 MHz, MeOD) δ 8.45 (s, 1H), 7.58 (s, 2H), 7.48 (s, 1H), 7.34-7.22 (m, 2H), 5.64 (d, J=6.9 Hz, 1H), 4.50 (s, 1H), 4.30 (s, 3H), 3.77 (t, J=13.4 Hz, 2H), 3.34 (dd, J=14.6, 7.9 Hz, 1H), 3.27 (dd, J=10.3, 5.5 Hz, 1H), 3.13 (d, J=9.7 Hz, 1H), 3.09-3.00 (m, 1H), 2.43 (s, 3H), 2.30 (dt, J=13.9, 6.9 Hz, 1H), 1.88 (d, J=5.4 Hz, 1H), 1.59 (d, J=6.9 Hz, 3H).

Example 44: Synthesis of (3R)-1-(4-{[(1R)-1-[3-(1,1-difluoro-2-hydroxyethyl)phenyl]ethyl]amino}-2,7-dimethyl-7H-pyrazolo[3,4-h]quinazolin-6-yl)pyrrolidin-3-ol. (The title compound was synthesized from Compound 4 in Example 42.)

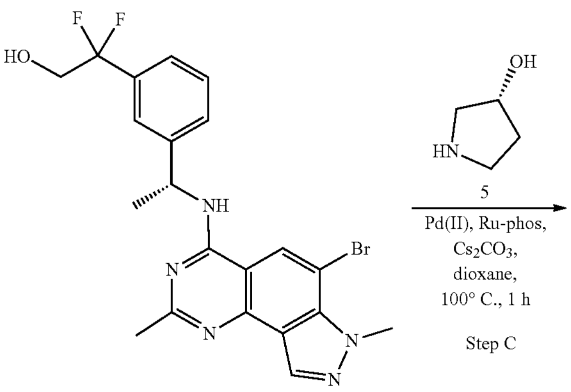

4

-continued

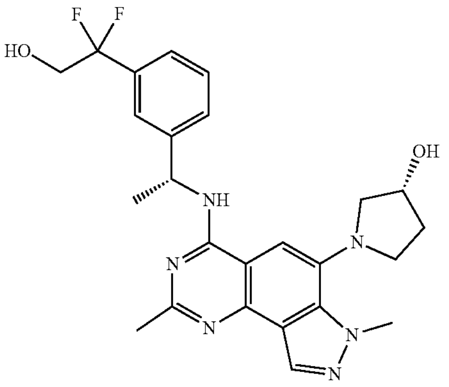

Example 44

Step C. (3R)-1-(4-{[(1R)-1-[3-(1,1-difluoro-2-hydroxyethyl)phenyl]ethyl]amino}-2,7-dimethyl-7H-pyrazolo[3,4-h]quinazolin-6-yl)pyrrolidin-3-ol To a stirred solution of 2-{3-[(1R)-1-({6-bromo-2,7-dimethyl-7H-pyrazolo[3,4-h]quinazolin-4-yl}amino)ethyl]phenyl}-2,2-difluoroethan-1-ol (450 mg, 0.95 mmol) in dioxane (30 mL) was added (3R)-pyrrolidin-3-ol (400 mg, 2.8 mmol), RuPhos Pd G3 (79 mg, 0.1 mmol), Ru-phos (95 mg, 0.19 mmol) and $Cs_2CO_3$ (1.3 g, 3.8 mmol) at rt. After stirred at 100° C. for 3 h, the cooled mixture was poured into water (10 mL) and extracted with EtOAc (5 mL*3). The combined organic phase was washed with brine, dried over $Na_2SO_4$, filtered and concentrated. The residue was purified by chromatography (silica gel, 0-12%, MeOH in DCM) and then prep-TLC (DCM:MeOH=9:1) to give (3R)-1-(4-{[(1R)-1-[3-(1,1-difluoro-2-hydroxyethyl)phenyl]ethyl]amino}-2,7-dimethyl-7H-pyrazolo[3,4-h]quinazolin-6-yl)pyrrolidin-3-ol (63 mg, 0.13 mmol, 14%) as a yellow solid. LCMS: m/z 483 $(M+H)^+$. $^1H$ NMR (400 MHz, MeOD) δ 8.56 (s, 1H), 7.71 (s, 1H), 7.68 (s, 1H), 7.59 (d, J=7.1 Hz, 1H), 7.44-7.39 (m, 2H), 5.78 (d, J=7.1 Hz, 1H), 4.62-4.58 (m, 1H), 4.41 (s, 3H), 3.87 (t, J=13.5 Hz, 2H), 3.47 (d, J=7.8 Hz, 1H), 3.40 (dd, J=10.4, 5.5 Hz, 1H), 3.23 (dd, J=10.4, 2.7 Hz, 1H), 3.18-3.12 (m, 1H), 2.57 (s, 3H), 2.42 (dd, J=13.4, 5.8 Hz, 1H), 1.98 (dt, J=13.5, 5.3 Hz, 1H), 1.72 (d, J=7.1 Hz, 3H).

Example 45: Synthesis of (R)-5-(5-((1-(3-(1,1-difluoro-2-hydroxyethyl)phenyl)ethyl)amino)-8-methoxypyrazolo[1,5-a]quinazolin-7-yl)-1-methylpyridin-2(1H)-one

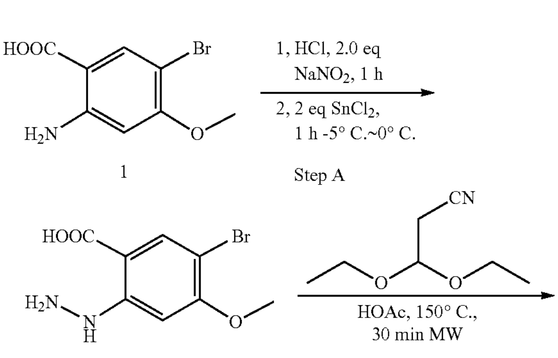

-continued

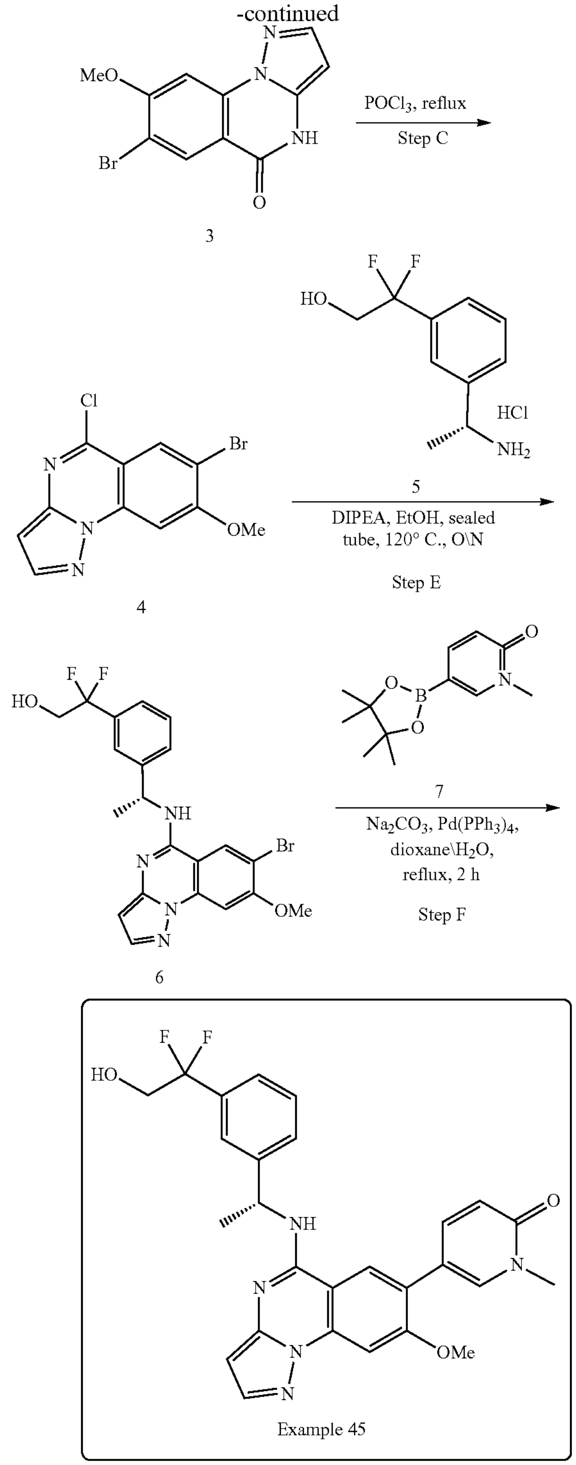

Step A. 5-bromo-2-hydrazinyl-4-methoxybenzoic acid

To a stirred solution of 2-amino-5-bromo-4-methoxybenzoic acid (3.0 g, 12.2 mmol) in 6N HCl (60 mL) at −5° C. was added a solution of $NaNO_2$ (1.68 g, 24.4 mmol) in $H_2O$ (5 mL) slowly. The reaction mixture was stirred at −5~0° C. for 1 h before Tin(II) chloride (4.62 g, 24.38 mmol) in 6N HCl (20 mL) was added. The result solution was stirred at −5~0° C. another 1 h and the reaction mixture was filtered. The filter cake was dried to give 5-bromo-2-hydrazinyl-4-methoxybenzoic acid (2.6 g, 9.95 mmol, 81.6%) as a brown solid. LC/MS (ESI) m/z: 260.8\262.8 $(M+H)^+$.

Step B. 7-bromo-8-methoxypyrazolo[1,5-a]quinazolin-5(4H)-one

To a stirred solution of 5-bromo-2-hydrazinyl-4-methoxybenzoic acid (1.2 g, 4.5 mmol) in HOAc (15 mL) at room temperature was added 3,3-diethoxypropanenitrile (660 mg, 4.59 mmol). The reaction mixture was heated to 150° C. by microwave and stirred at 150° C. for 30 min. The reaction mixture was concentrated to give a crude product which was purified by column chromatography on silica gel (DCM: MeOH=100:1 to 20:1) to obtain 7-bromo-8-methoxy-4H,5H-pyrazolo[1,5-a]quinazolin-5-one (930 mg, 3.16 mmol, 68.7%) as a yellow solid. LC/MS (ESI) m/z: 294\296 $(M+H)^+$.

Step C. 7-bromo-5-chloro-8-methoxypyrazolo[1,5-a]quinazoline

A solution of 7-bromo-8-methoxy-4H,5H-pyrazolo[1,5-a]quinazolin-5-one (930 mg, 3.16 mmol) in $POCl_3$ (14.7 mL, 158.1 mmol) was stirred at 120° C. for 3 h under nitrogen atmosphere. The reaction mixture was concentrated to dryness and the residue was diluted with ice-water (40 mL), adjust pH to 7-8 with aqueous $NaHCO_3$. The mixture was extracted with EtOAc (20 mL*3). The combined organic phase was washed by water and brine, dried over anhydrous $Na_2SO_4$, filtered and concentrated to give a crude product which was purified by column chromatography on silica gel (PE:EtOAc=10:1 to 3:1) to obtain 7-bromo-5-chloro-8-methoxypyrazolo[1,5-a]quinazoline (520 mg, 1.66 mmol, 52.6%) as a brown solid. LC/MS (ESI) m/z: 312/314 $(M+H)^+$.

Step D. (R)-2-(3-(1-aminoethyl)phenyl)-2,2-difluoroethan-1-ol

A solution of (R)—N-(1-(3-(1,1-difluoro-2-hydroxyethyl)phenyl)ethyl)pivalamide (200 mg, 0.7 mmol) in 4M HCl\dioxane (5 mL) was stirred at room temperature for 1 h. The reaction mixture was concentrated to dryness to obtain (R)-2-(3-(1-aminoethyl)phenyl)-2,2-difluoroethan-1-ol (160 mg, 0.7 mmol, 100%) which was used directly for next step without purification.

Step E (R)-2-(3-(1-((7-bromo-8-methoxypyrazolo[1,5-a]quinazolin-5-yl)amino)ethyl) phenyl)-2,2-difluoroethan-1-ol To a stirred solution of 7-bromo-5-chloro-8-methoxypyrazolo[1,5-a]quinazoline (80 mg, 0.25 mmol) and DIPEA (33 mg, 0.25 mmol) in EtOH (3 mL) was added 2-{3-[(1R)-1-aminoethyl]phenyl}-2,2-difluoroethan-1-ol (51.5 mg, 0.25 mmol). The reaction mixture was stirred at 120° C. for 16 h in a sealed tube. The reaction mixture was concentrated to give a crude product which was purified by column chromatography on silica gel (PE:EtOAc=10:1 to 1:1) to obtain 2-{3-[(1R)-1-({7-bromo-8-methoxypyrazolo[1,5-a]quinazolin-5-yl}amino)ethyl] phenyl}-2,2-difluoroethan-1-ol (30 mg, 0.06 mmol, 24.5%) as a yellow solid. LC/MS (ESI) m/z: 476.8\477.8 $(M+H)^+$ Step F (R)-5-(5-((1-(3-(1,1-difluoro-2-hydroxyethyl)phenyl)ethyl)amino)-8-methoxypyrazolo[1,5-a]quinazolin-7-yl)-1-methylpyridin-2(1H)-one To a stirred solution of 2-{3-[(1R)-1-({7-bromo-8-methoxypyrazolo[1,5-a]quinazolin-5-yl}amino)ethyl]phenyl}-2,2-difluoroethan-1-ol (20 mg, 0.04 mmol), $Na_2CO_3$ (13.3 mg, 0.12 mmol) and 1-methyl-5-(tetramethyl-1,3,2-dioxaborolan-2-yl)-1,2-dihydropyridin-2-one (19.70 mg, 0.08 mmol) in 1,4-dioxane-water (2-0.5 mL) at room temperature was added $Pd(PPh_3)_4$ (4.84 mg, 0.004 mmol). The reaction mixture was stirred at 120° C. for 3 h under nitrogen atmosphere. The reaction mixture was diluted with water (10 mL), extracted with EtOAc (10 mL×3). The combined organic phase was washed by water and brine, dried over anhydrous $Na_2SO_4$, filtered and concentrated to give a crude product which was purified by column chromatography on silica gel (DCM:MeOH=100:1 to 20:1) to obtain 5-(5-{[(1R)-1-[3-(1,1-difluoro-2-hydroxyethyl)phenyl]ethyl]amino}-8-methoxypyrazolo[1,5-a]quinazolin-7-yl)-1-methyl-1,2-dihydropyridin-2-one (3 mg, 0.006 mmol, 14.2) as a off-white solid. LC/MS (ESI) m/z: 506.1 $(M+H)^+$. $^1H$ NMR (400 MHz, DMSO) δ 8.43 (s, 1H), 8.09 (d, J=7.6 Hz, 1H), 7.98 (d, J=2.3 Hz, 1H), 7.80 (d, J=2.0 Hz, 1H), 7.73 (s, 1H), 7.69 (dd, J=9.3, 2.6 Hz, 1H), 7.64-7.56 (m, 2H), 7.43 (t, J=7.6 Hz, 1H), 7.36 (d, J=8.2 Hz, 1H), 6.50 (d, J=9.4 Hz, 1H), 6.04 (d, J=2.0 Hz, 1H), 5.65-5.51 (i, 2H), 3.99 (s, 3H), 3.82 (d, J=6.1 Hz, 1H), 3.53 (s, 3H), 1.60 (d, J=7.0 Hz, 3H)

The examples in the following Table 5 were prepared by using a method analogous to that used to prepare the examples as described herein.

TABLE 5

| Ex# | Structure & name | Analytical data | Method |
| --- | --- | --- | --- |
| Example 46 | 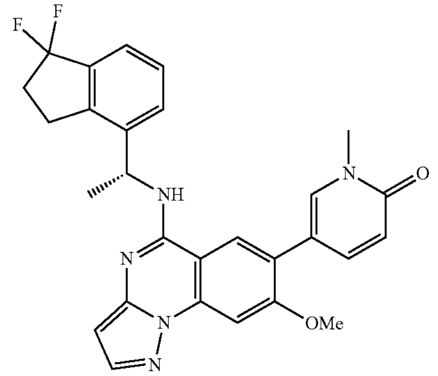 [SMILES: COc1cc2c(cc1-c1ccc(=O)n(C)c1)c(N[C@H](C)c1cccc3c1CCC3(F)F)nc1ccnn12] (R)-5-(5-((1-(1,1-difluoro-2,3-dihydro-1H-inden-4-yl)ethyl)amino)-8-methoxypyrazolo[1,5-a]quinazolin-7-yl)-1-methylpyridin-2(1H)-one | LC/MS (ESI) m/z: 501 $(M + H)^+$. $^1H$ NMR (400 MHz, DMSO) δ 8.48 (s, 1H), 8.19 (d, J = 7.3 Hz, 1H), 8.04 (d, J = 2.5 Hz, 1H), 7.86 (d, J = 2.0 Hz, 1H), 7.78-7.70 (m, 3H), 7.49-7.40 (m, 2H), 6.56 (d, J = 9.4 Hz, 1H), 6.08 (d, J = 2.0 Hz, 1H), 5.58 (t, J = 7.1 Hz, 1H), 4.05 (s, 3H), 3.60 (s, 3H), 3.43 (s, 1H), 3.22 (d, J = 4.0 Hz, 1H), 2.70 (dq, J = 21.4, 7.2 Hz, 2H), 1.65 (d, J = 7.0 Hz, 3H). | Example 45 |
| Example 47 | 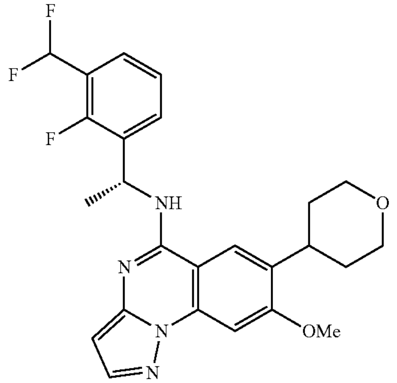 [SMILES: COc1cc2c(cc1C1CCOCC1)c(N[C@H](C)c1cccc(C(F)F)c1F)nc1ccnn12] (R)-N-(1-(3-(difluoromethyl)-2-fluorophenyl)ethyl)-8-methoxy-7-(tetrahydro-2H-pyran-4-yl)pyrazolo[1,5-a]quinazolin-5-amine | LC/MS (ESI) m/z: 471.2 $(M + H)^+$. $^1H$ NMR (400 MHz, DMSO) δ 8.27 (s, 1H), 8.07 (d, J = 7.4 Hz, 1H), 7.68 (d, J = 2.0 Hz, 1H), 7.65-7.56 (m, 2H), 7.43 (t, J = 6.9 Hz, 1H), 7.21 (dt, J = 66.0, 40.9 Hz, 2H), 5.93 (d, J = 2.0 Hz, 1H), 5.69 (t, J = 7.1 Hz, 1H), 4.00-3.91 (m, 5H), 3.44 (t, J = 11.0 Hz, 2H), 1.88 (td, J = 12.4, 6.3 Hz, 2H), 1.63 (d, J = 12.9 Hz, 2H), 1.55 (d, J = 7.0 Hz, 3H). | Example 45 |

TABLE 5-continued

| Ex# | Structure & name | Analytical data | Method |
|---|---|---|---|
| Example 48 | 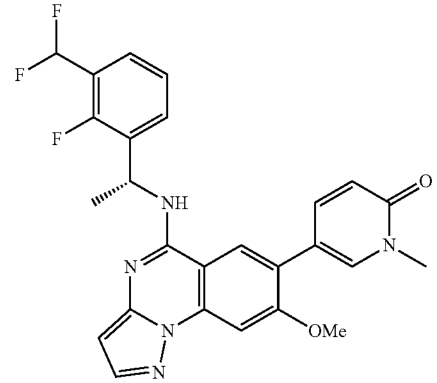 [SMILES: COc1cc2c(cc1-c1ccc(=O)n(C)c1)c(N[C@H](C)c1cccc(C(F)F)c1F)nc1ccnn12] (R)-5-(5-((1-(3-(difluoromethyl)-2-fluorophenyl)ethyl)amino)-8-methoxypyrazolo[1,5-a]quinazolin-7-yl)-1-methylpyridin-2(1H)-one | LC-MS (ESI) m/z 494 $(M + H)^+$. $^1H$ NMR (400 MHz, DMSO) δ 8.46 (s, 1H), 8.12 (d, J = 7.5 Hz, 1H), 8.01 (d, J = 2.5 Hz, 1H), 7.80 (d, J = 2.0 Hz, 1H), 7.75-7.66 (m, 3H), 7.50 (t, J = 6.8 Hz, 1H), 7.27 (dt, J = 61.4, 43.4 Hz, 2H), 6.52 (d, J = 9.4 Hz, 1H), 6.04 (d, J = 2.0 Hz, 1H), 5.77 (t, J = 7.2 Hz, 1H), 4.00 (s, 3H), 3.55 (s, 3H), 1.61 (d, J = 7.0 Hz, 3H). | Example 45 |
| Example 49 | 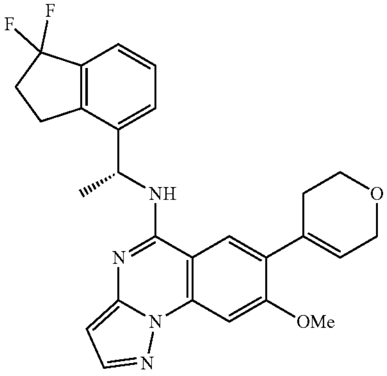 [SMILES: COc1cc2c(cc1C1=CCOCC1)c(N[C@H](C)c1cccc3c1CCC3(F)F)nc1ccnn12] (R)-N-(1-(1,1-difluoro-2,3-dihydro-1H-inden-4-yl)ethyl)-7-(3,6-dihydro-2H-pyran-4-yl)-8-methoxypyrazolo[1,5-a]quinazolin-5-amine | LC/MS (ESI) m/z: 477.2(M+H)+ . 1H NMR (400 MHz, DMSO) & 8.27 (s, 1H), 8.16 (d, J = 7.4 Hz, 1H), 7.77 (d, J = 2.0 Hz, 1H), 7.71-7.61 (m, 2H), 7.45-7.35 (m, 2H), 6.03-5.96 (m, 2H), 5.51 (t, J = 7.1 Hz, 1H), 4.26 (d, J = 2.7 Hz, 2H), 3.97 (s, 3H), 3.84 (t, J = 5.4 Hz, 2H), 3.29-3.23 (m, 1H), 3.19-3.09 (m, 1H), 2.69-2.60 (m, 2H), 2.49-2.42 (m, 2H), 1.59 (d, J = 7.0 Hz, 3H). | Example 45 |
| Example 50 | 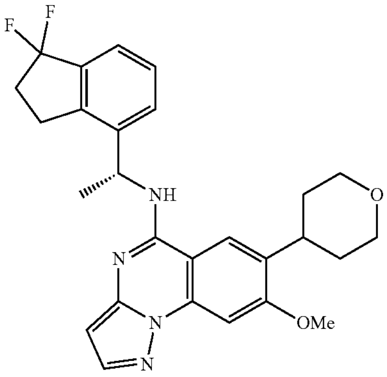 [SMILES: COc1cc2c(cc1C1CCOCC1)c(N[C@H](C)c1cccc3c1CCC3(F)F)nc1ccnn12] (R)-N-(1-(1,1-difluoro-2,3-dihydro-1H-inden-4-yl)ethyl)-8-methoxy-7-(tetrahydro-2H-pyran-4-yl)pyrazolo[1,5-a]quinazolin-5-amine | LC/MS (ESI) m/z: 479.2$(M + H)^+$. $^1H$ NMR (400 MHz, DMSO) δ 8.35 (s, 1H), 8.20 (d, J = 7.2 Hz, 1H), 7.81 (d, J = 2.0 Hz, 1H), 7.71 (t, J = 4.3 Hz, 1H), 7.69 (s, 1H), 7.52-7.40 (m, 2H), 6.04 (d, J = 2.0 Hz, 1H), 5.59 (t, J = 7.0 Hz, 1H), 4.16-3.97 (m, 5H), 3.56 (t, J = 11.2 Hz, 2H), 3.32 (dd, J = 9.6, 6.1 Hz, 2H), 3.24-3.16 (m, 1H), 2.70 (tt, J = 14.0, 6.8 Hz, 2H), 2.02 (dd, J = 16.8, 8.6 Hz, 2H), 1.74 (d, J = 12.9 Hz, 2H), 1.66 (d, J = 7.0 Hz, 3H). | Example 45 |

TABLE 5-continued

| Ex# | Structure & name | Analytical data | Method |
|---|---|---|---|
| Example 51 | 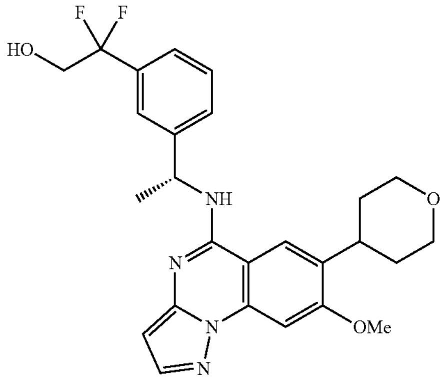 [SMILES: COc1cc2c(cc1C1CCOCC1)c(N[C@H](C)c1cccc(C(F)(F)CO)c1)nc1ccnn12] (R)-2,2-difluoro-2-(3-(1-((8-methoxy-7-(tetrahydro-2H-pyran-4-yl)pyrazolo[1,5-a]quinazolin-5-yl)amino)ethyl)phenyl)ethanol | LC/MS (ESI) m/z: 483 $(M + H)^+$. $^1H$ NMR (400 MHz, DMSO) δ 8.31 (s, 1H), 8.12 (d, J = 7.8 Hz, 1H), 7.76 (d, J = 2.0 Hz, 1H), 7.64 (d, J = 6.3 Hz, 2H), 7.59 (d, J = 7.7 Hz, 1H), 7.45 (t, J = 7.7 Hz, 1H), 7.38 (d, J = 7.7 Hz, 1H), 6.01 (d, J = 2.0 Hz, 1H), 5.62 (dd, J = 10.6, 4.4 Hz, 2H), 4.09-3.95 (m, 5H), 3.83 (td, J = 14.3, 6.2 Hz, 2H), 3.50 (t, J = 11.0 Hz, 3H), 1.98-1.86 (m, 2H), 1.69 (d, J = 11.4 Hz, 2H), 1.62 (d, J = 7.0 Hz, 3H). | Example 45 |
| Example 52 | 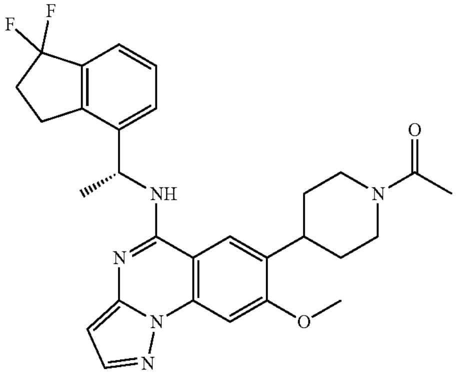 [SMILES: COc1cc2c(cc1C1CCN(C(C)=O)CC1)c(N[C@H](C)c1cccc3c1CCC3(F)F)nc1ccnn12] (R)-1-(4-(5-((1-(1,1-difluoro-2,3-dihydro-1H-inden-4-yl)ethyl)amino)-8-methoxypyrazolo[1,5-a]quinazolin-7-yl)piperidin-1-yl)ethanone | LC-MS (ESI) m/z 520 $(M + H)^+$. $^1H$ NMR (400 MHz, MeOD) δ 8.14 (d, J = 1.1 Hz, 1H), 7.77 (d, J = 2.1 Hz, 1H), 7.70 (s, 1H), 7.59 (d, J = 7.1 Hz, 1H), 7.35 (dt, J = 14.9, 7.5 Hz, 2H), 6.06-6.02 (m, 1H), 5.62-5.54 (m, 1H), 4.73 (d, J = 13.0 Hz, 1H), 4.60 (s, 1H), 4.07 (d, J = 13.8 Hz, 1H), 4.03 (s, 3H), 3.44-3.35 (m, 2H), 3.10 (dd, J = 16.3, 5.7 Hz, 1H), 2.75 (dd, J = 12.8, 10.4 Hz, 1H), 2.59 (tt, J = 12.8, 6.5 Hz, 2H), 2.16 (d, J = 1.6 Hz, 3H), 1.92 (dd, J = 23.3, 12.6 Hz, 2H), 1.80 (ddd, J = 12.5, 8.8, 4.5 Hz, 2H), 1.65 (d, J = 7.0 Hz, 3H), 1.29 (s, 1H). | Example 45 |
| Example 53 | 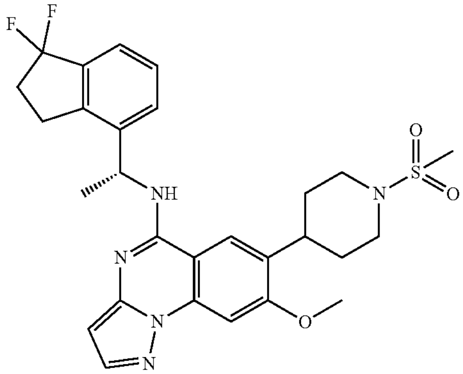 [SMILES: COc1cc2c(cc1C1CCN(S(C)(=O)=O)CC1)c(N[C@H](C)c1cccc3c1CCC3(F)F)nc1ccnn12] (R)-N-(1-(1,1-difluoro-2,3-dihydro-1H-inden-4-yl)ethyl)-8-methoxy-7-(1-(methylsulfonyl)piperidin-4-yl)pyrazolo[1,5-a]quinazolin-5-amine | LCMS (ESI) m/z 556 $(M + H)^+$. $^1H$ NMR (400 MHz, MeOD) δ 8.19 (s, 1H), 7.77 (d, J = 2.1 Hz, 1H), 7.71 (s, 1H), 7.60 (d, J = 6.7 Hz, 1H), 7.34 (dd, J = 12.9, 5.5 Hz, 2H), 6.03 (d, J = 2.1 Hz, 1H), 5.58 (d, J = 7.0 Hz, 1H), 4.03 (s, 3H), 3.89 (d, J = 11.7 Hz, 2H), 3.48 (s, 2H), 3.13 (s, 1H), 2.91 (s, 1H), 2.88 (s, 3H), 2.61 (dt, J = 20.8, 6.9 Hz, 2H), 2.00 (dd, J = 13.4, 7.9 Hz, 5H), 1.66 (d, J = 7.0 Hz, 3H), 1.28 (s, 1H). | Example 45 |

Example 54: Synthesis of 8-methoxy-7-[(3 S)-oxolan-3-yloxy]-N-[(1R)-1-[3-(trifluoromethyl) phenyl] ethyl]pyrazolo[1,5-α]quinazolin-5-amine. (The Title Compound was Synthesized from Compound 4 in Example 14.)

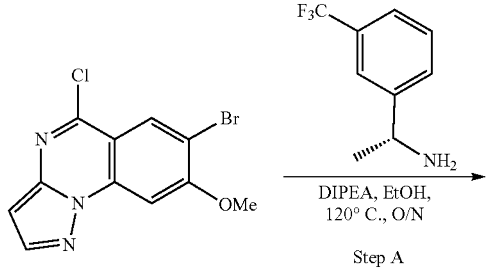

4

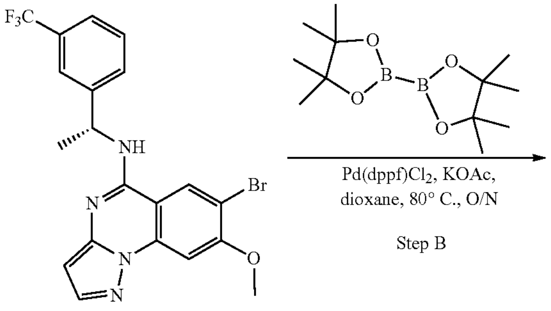

5

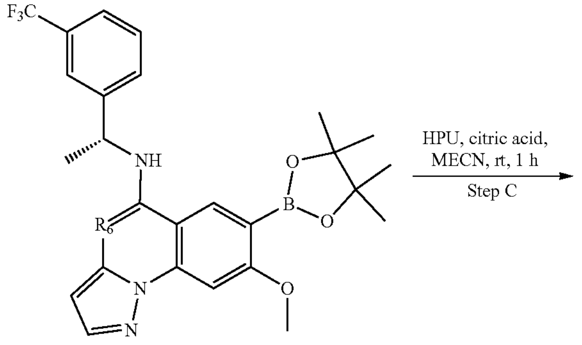

6

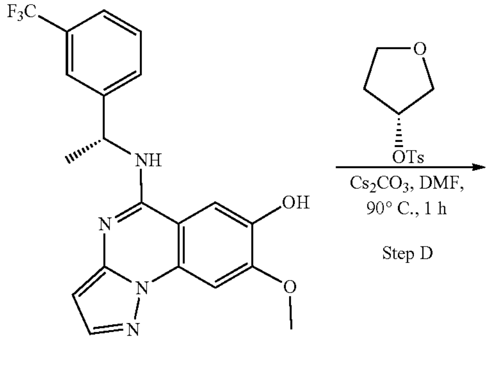

7

-continued

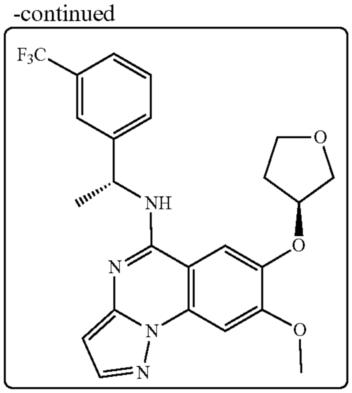

Example 54

Step A. 7-bromo-8-methoxy-N-[(1R)-1-[3-(trifluoromethyl)phenyl]ethyl]pyrazolo[1,5-a]quinazolin-5-amine To a stirred solution of 7-bromo-5-chloro-8-methoxy-pyrazolo[1,5-a]quinazoline (140 mg, 0.45 mmol) in EtOH (10 mL) was added DIPEA (0.5 mL, 2.81 mmol) and (1R)-1-[3-(trifluoromethyl)phenyl]ethan-1-amine (127 mg, 0.67 mmol) at rt. After stirred at 120° C. overnight, the cooled mixture was concentrated. The crude product was purified by chromatography (silica gel, 0-20%, MeOH in DCM) to give 7-bromo-8-methoxy-N-[(1R)-1-[3-(trifluoromethyl)phenyl]ethyl]pyrazolo[1,5-a]quinazolin-5-amine (80 mg, 0.17 mmol, 38%) as a yellow solid. LC-MS (ESI) m/z 465 & 467 $(M+H)^+$.

Step B. 8-methoxy-7-(tetramethyl-1,3,2-dioxaborolan-2-yl)-N-[(1R)-1-[3-(trifluoromethyl) phenyl] ethyl]pyrazolo[1,5-a]quinazolin-5-amine To a stirred solution of 7-bromo-8-methoxy-N-[(1R)-1-[3-(trifluoromethyl)phenyl]ethyl]pyrazolo[1,5-a]quinazolin-5-amine (70 mg, 0.150 mmol) in dioxane (2 mL) was added 4,4,5,5-tetramethyl-2-(tetramethyl-1,3,2-dioxaborolan-2-yl)-1,3,2-dioxaborolane (68 mg, 0.30 mmol), KOAc (44 mg, 0.45 mmol) and Pd(dppf)$Cl_2$ (22 mg, 0.030 mmol) at rt. After stirred at 80° C. overnight, the cooled mixture was filtered and concentrated. The crude product was purified by chromatography (silica gel, 0-20%, MeOH in DCM) to give 8-methoxy-7-(tetramethyl-1,3,2-dioxaborolan-2-yl)-N-[(1R)-1-[3-(trifluoromethyl)phenyl]ethyl]pyrazolo[1,5-a]quinazolin-5-amine (50 mg, 0.098 mmol, 65%) as a yellow solid. LC-MS (ESI) m/z 513 $(M+H)^+$.

Step C. 8-methoxy-5-{[(1R)-1-[3-(trifluoromethyl) phenyl]ethyl]amino}pyrazolo[1,5-a]quinazolin-7-ol To a stirred solution of 8-methoxy-7-(tetramethyl-1,3,2-dioxaborolan-2-yl)-N-[(1R)-1-[3-(trifluoromethyl)phenyl]ethyl]pyrazolo[1,5-a]quinazolin-5-amine (50 mg, 0.098 mmol) in $CH_3CN$ (5 mL) was added HPU (23 mg, 0.24 mmol) and citric acid (38 mg, 0.20 mmol) at rt. After stirred at rt for 1 h, the mixture was poured into water (20 mL) and extracted with EtOAc (20 mL*2). The combined organic phase was washed with brine, dried over $Na_2SO_4$, filtered and concentrated to give 8-methoxy-5-{[(1R)-1-[3-(trifluoromethyl)phenyl]ethyl]amino}pyrazolo[1,5-a]quinazolin-7-ol (40 mg, 0.099 mmol, 100%) as a yellow solid. LC-MS (ESI) m/z 403 $(M+H)^+$.

Step D. 8-methoxy-7-[(3S)-oxolan-3-yloxy]-N-[(1R)-1-[3-(trifluoromethyl)phenyl]ethyl]pyrazolo[1,5-a]quinazolin-5-amine To a stirred solution of 8-methoxy-5-{[(1R)-1-[3-(trifluoromethyl)phenyl]ethyl]amino}pyrazolo[1,5-a]quinazolin-7-ol (40 mg, 0.099 mmol) in DMF (10 mL) was added (3R)-oxolan-3-yl 4-methylbenzene-1-sulfonate (48 mg, 0.20 mmol) and $Cs_2CO_3$ (97 mg, 0.30 mmol) at rt. After stirred at 90° C. for 1 h, the cooled mixture was poured into water (50 mL) and extracted with EtOAc (50 mL*2). The combined organic phase was washed with brine, dried over $Na_2SO_4$, filtered and concentrated. The crude product was purified by prep-HPLC (C18, 30~80% MeCN in $H_2O$ with 0.1% HCOOH) to give 8-methoxy-7-[(3S)-oxolan-3-yloxy]-N-[(1R)-1-[3-(trifluoromethyl)phenyl]ethyl]pyrazolo[1,5-a]quinazolin-5-amine (10 mg, 0.021 mmol, 21%) as a white solid. LC-MS (ESI) m/z 473 $(M+H)^+$. $^1H$ NMR (400 MHz, DMSO) δ 8.03 (d, J=7.6 Hz, 1H), 7.94 (s, 1H), 7.81 (s, 1H), 7.76 (t, J=5.9 Hz, 2H), 7.70 (s, 1H), 7.58 (d, J=5.8 Hz, 2H), 6.00 (d, J=1.8 Hz, 1H), 5.69-5.54 (m, 1H), 5.24 (s, 1H), 3.98 (s, 3H), 3.97-3.75 (m, 4H), 2.29 (dt, J=14.3, 7.1 Hz, 1H), 2.09-2.02 (m, 1H), 1.64 (d, J=7.0 Hz, 3H).

Example 55: Synthesis of N-[(1R)-1-[3-amino-5-(trifluoromethyl)phenyl]ethyl]-8-methoxy-7-[(3S)-oxolan-3-yloxy]pyrazolo[1,5-a]quinazolin-5-amine (optimization method)

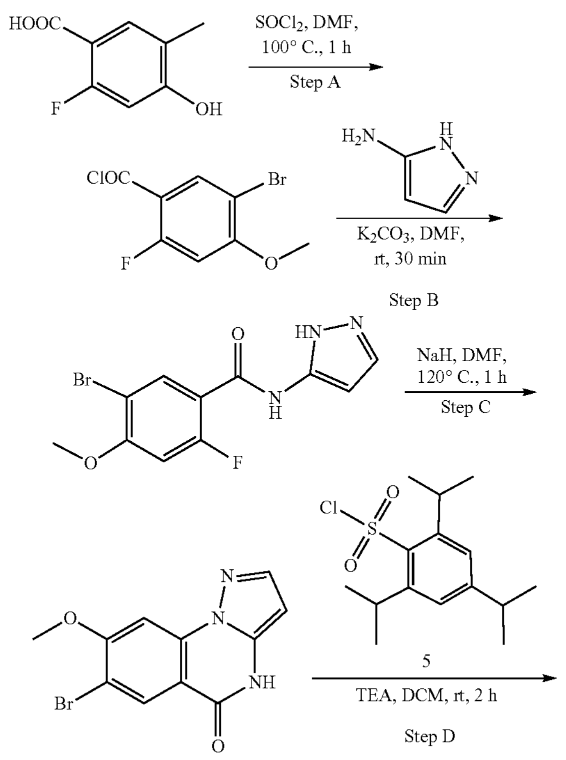

-continued

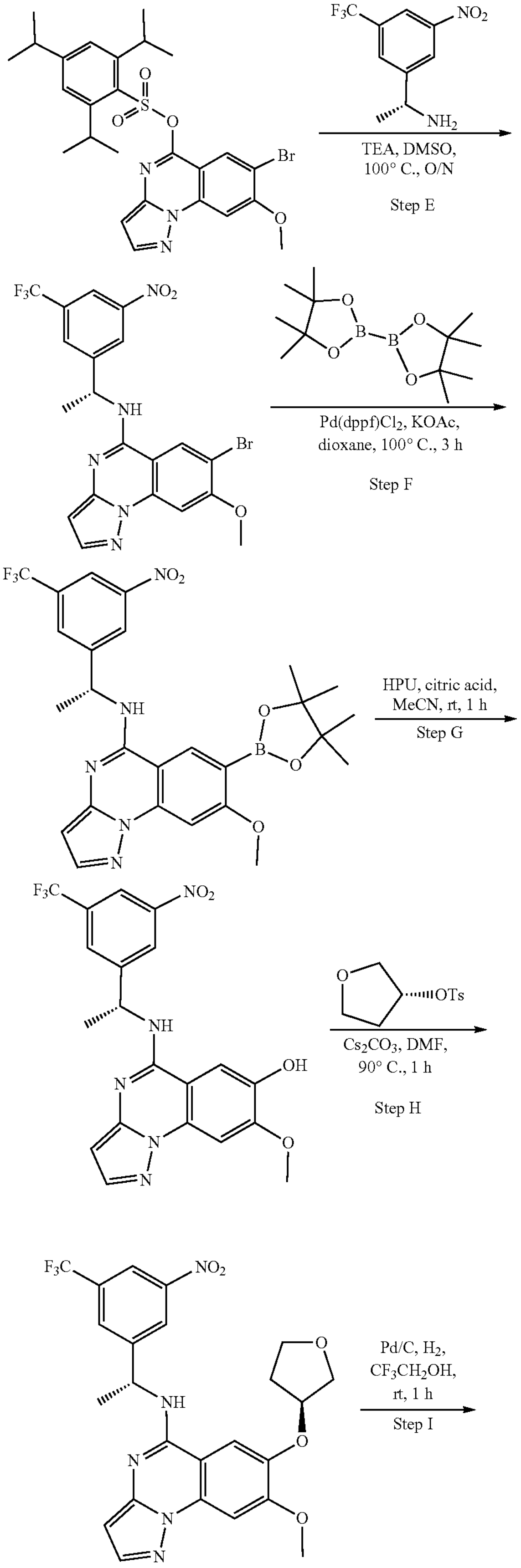

-continued

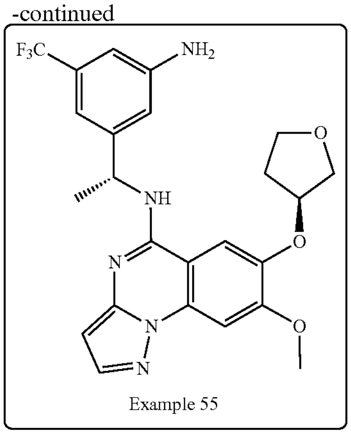

Example 55

Step A. 5-bromo-2-fluoro-4-methoxybenzoyl chloride

To a stirred solution of 5-bromo-2-fluoro-4-methoxybenzoic acid (1 g, 4.02 mmol) in $SOCl_2$ (10 mL, 137.85 mmol) was added DMF (0.2 mL, 2.01 mmol) at rt. After stirred at 100° C. for 30 min, the mixture was concentrated to give crude 5-bromo-2-fluoro-4-methoxybenzoyl chloride (1 g, 3.74 mmol, 93%) as a yellow solid.

Step B. 5-bromo-2-fluoro-4-methoxy-N-(1H-pyrazol-5-yl)benzamide

To a stirred solution of 1H-pyrazol-5-amine (0.5 mL, 5.61 mmol) in DMF (10 mL) was added $K_2CO_3$ (1.55 g, 11.22 mmol) and 5-bromo-2-fluoro-4-methoxybenzoyl chloride (1 g, 3.74 mmol, dissolved in DMF) slowly at rt. After stirred at rt for 30 min, the cooled mixture was poured into water (30 ml) and extracted with DCM (20 ml*2). The combined organic phase was washed with brine, dried over $Na_2SO_4$, filtered and concentrated. The residue was washed by mixture (20 ml, PE:EtOAc=15:1) to give 5-bromo-2-fluoro-4-methoxy-N-(1H-pyrazol-5-yl)benzamide (800 mg, 2.55 mmol, 68%) as a white solid. LCMS: m/z 315 $(M+H)^+$.

Step C. 7-bromo-8-methoxy-4H,5H-pyrazolo[1,5-a]quinazolin-5-one

To a stirred solution of 5-bromo-2-fluoro-4-methoxy-N-(1H-pyrazol-5-yl)benzamide (800 mg, 2.55 mmol) in DMF (30 mL) was added NaH 60% (150 mg, 3.82 mmol) at rt. After stirred at 120° C. for 30 min, the mixture was poured into water (20 ml). The mixture was filtered. The filter cake was washed by mixture (22 ml, PE:EtOAc=10:1) to give crude 7-bromo-8-methoxy-4H,5H-pyrazolo[1,5-a]quinazolin-5-one (400 mg, 1.36 mmol, 53%) as a yellow solid. LCMS: m/z 295 $(M+H)^+$.

Step D. 7-bromo-8-methoxypyrazolo[1,5-a]quinazolin-5-yl 2,4,6-tris(propan-2-yl)benzene-1-sulfonate To a stirred solution of 7-bromo-8-methoxy-4H,5H-pyrazolo[1,5-a]quinazolin-5-one (400 mg, 1.36 mmol) in DCM (10 mL) was added 2,4,6-tris(propan-2-yl)benzene-1-sulfonyl chloride (0.6 mL, 2.04 mmol) and TEA (0.9 mL, 6.8 mmol) at rt. After stirred at rt for 2 h, the mixture was purified directly by chromatography (silica gel, 0-40%, EtOAc in PE) to give 7-bromo-8-methoxypyrazolo[1,5-a]quinazolin-5-yl 2,4,6-tris(propan-2-yl)benzene-1-sulfonate (260 mg, 0.46 mmol, 34%) as a yellow solid. LCMS: m/z 561 $(M+H)^+$.

Step E. 7-bromo-8-methoxy-N-[(1R)-1-[3-nitro-5-(trifluoromethyl)phenyl]ethyl]pyrazolo[1,5-a]quinazolin-5-amine To a stirred solution of 7-bromo-8-methoxypyrazolo[1,5-a]quinazolin-5-yl 2,4,6-tris(propan-2-yl)benzene-1-sulfonate (200 mg, 0.36 mmol) in DMSO (3 mL) was added (1R)-1-[3-nitro-5-(trifluoromethyl)phenyl]ethan-1-amine (125 mg, 0.53 mmol) and TEA (0.2 mL, 1.07 mmol) at rt. After stirred at 100° C. overnight, the cooled mixture was poured into water (20 ml) and extracted with EtOAc (8 ml*3). The combined organic phase was washed with brine, dried over $Na_2SO_4$, filtered and concentrated. The residue was purified by chromatography (silica gel, 0-20%, MeOH in DCM) to give 7-bromo-8-methoxy-N-[(1R)-1-[3-nitro-5-(trifluoromethyl)phenyl]ethyl]pyrazolo[1,5-a]quinazolin-5-amine (70 mg, 0.14 mmol, 38%) as a yellow solid. LCMS: m/z 511 $(M+H)^+$.

Step F. 7-(4,4-dimethyl-1,3,2-dioxaborolan-2-yl)-8-methoxy-N-[(1R)-1-[3-nitro-5-(trifluoromethyl)phenyl]ethyl]pyrazolo[1,5-a]quinazolin-5-amine To a stirred solution of 7-bromo-8-methoxy-N-[(1R)-1-[3-nitro-5-(trifluoromethyl)phenyl]ethyl]pyrazolo[1,5-a]quinazolin-5-amine (70 mg, 0.14 mmol) in dioxane (3 mL) was added 4,4,5,5-tetramethyl-2-(tetramethyl-1,3,2-dioxaborolan-2-yl)-1,3,2-dioxaborolane (0.1 mL, 0.21 mmol), $Pd(dppf)Cl_2$ (10 mg, 0.01 mmol) and KOAc (41 mg, 0.41 mmol) at rt. After stirred at 100° C. for 3 h, the cooled mixture was poured into water (10 ml) and extracted with EtOAc (10 ml*3). The combined organic phase was washed with brine, dried over $Na_2SO_4$, filtered and concentrated to give crude 7-(4,4-dimethyl-1,3,2-dioxaborolan-2-yl)-8-methoxy-N-[(1R)-1-[3-nitro-5-(trifluoromethyl)phenyl]ethyl]pyrazolo[1,5-a]quinazolin-5-amine (35 mg, 0.06 mmol, 48%) as a yellow oil. LCMS: m/z 530 $(M+H)^+$.

Step G. 8-methoxy-5-{[(1R)-1-[3-nitro-5-(trifluoromethyl)phenyl]ethyl]amino}pyrazolo[1,5-a]quinazolin-7-ol To a stirred solution of 8-methoxy-N-[(1R)-1-[3-nitro-5-(trifluoromethyl)phenyl]ethyl]-7-(tetramethyl-1,3,2-dioxaborolan-2-yl)pyrazolo[1,5-a]quinazolin-5-amine (35 mg, 0.06 mmol) in MeCN (1 mL) was added citric acid (0.2 mL, 0.4 mmol, 2 mol/L) and HPU (12 mg, 0.13 mmol) at rt. After stirred at rt for 1 h, the mixture was poured into water (10 ml) and extracted with DCM (5 ml*3). The combined organic phase was washed with brine, dried over $Na_2SO_4$, filtered and concentrated. The residue was purified by chromatography (silica gel, 0-20%, MeOH in DCM) to give 8-methoxy-5-{[(1R)-1-[3-nitro-5-(trifluoromethyl) phenyl]ethyl]amino}pyrazolo[1,5-a]quinazolin-7-ol (20 mg, 0.05 mmol, 71%) as a yellow solid. LCMS: m/z 448 $(M+H)^+$.

Step H. 8-methoxy-N-[(1R)-1-[3-nitro-5-(trifluoromethyl)phenyl]ethyl]-7-[(3S)-oxolan-3-yloxy]pyrazolo[1,5-a]quinazolin-5-amine To a stirred solution of 8-methoxy-5-{[(1R)-1-[3-nitro-5-(trifluoromethyl)phenyl]ethyl]amino}pyrazolo[1,5-a]quinazolin-7-ol (20 mg, 0.05 mmol) in DMF (3 mL) was added $Cs_2CO_3$ (44 mg, 0.14 mmol) and (3R)-oxolan-3-yl 4-methylbenzene-1-sulfonate (16 mg, 0.07 mmol) at rt. After stirred at 90° C. for 1 h, the cooled mixture was poured into water (10 ml) and extracted with EtOAc (5 ml*3). The combined organic phase was washed with brine, dried over $Na_2SO_4$, filtered and concentrated. The residue was purified by prep-TLC (PE:EtOAc=1:1) to give 8-methoxy-N-[(1R)-1-[3-nitro-5-(trifluoromethyl)phenyl]ethyl]-7-[(3S)-oxolan-3-yloxy]pyrazolo [1,5-a]quinazolin-5-amine (20 mg, 0.04 mmol, 86%) as a yellow solid. LCMS: m/z 518 $(M+H)^+$.

Step I. N-[(1R)-1-[3-amino-5-(trifluoromethyl)phenyl]ethyl]-8-methoxy-7-[(3S)-oxolan-3-yloxy]pyrazolo[1,5-a]quinazolin-5-amine To a stirred solution of 8-methoxy-N-[(1R)-1-[3-nitro-5-(trifluoromethyl)phenyl]ethyl]-7-[(3S)-oxolan-3-yloxy] pyrazolo[1,5-a]quinazolin-5-amine (20 mg, 0.04 mmol) in $CH_3CH_2OH$ (5 mL) was added Pd/C 10% (5 mg, 0.04 mmol) at rt. After stirred at rt using a $H_2$ balloon for 2 h, the mixture was filtered. The filtrate was concentrated. The residue was purified by prep-HPLC (C18, 40~90% MeCN in $H_2O$ with 0.1% HCOOH) to give N-[(1R)-1-[3-amino-5-(trifluoromethyl)phenyl]ethyl]-8-methoxy-7-[(3S)-oxolan-3-yloxy]pyrazolo[1,5-a]quinazolin-5-amine (3 mg, 0.006 mmol, 16%) as a white solid. LCMS: m/z 488 $(M+H)^+$. $^1H$ NMR (400 MHz, MeOD) δ 7.83 (s, 1H), 7.76 (d, J=1.5 Hz, 2H), 6.99 (d, J=6.1 Hz, 2H), 6.80 (s, 1H), 6.08 (d, J=2.2 Hz, 1H), 5.50 (d, J=7.1 Hz, 1H), 5.21 (t, J=4.7 Hz, 1H), 4.07-4.02 (m, 5H), 4.01-3.89 (m, 2H), 2.24 (ddd, J=8.9, 7.5, 4.7 Hz, 2H), 1.64 (d, J=7.0 Hz, 3H).

Example 56: Synthesis of 8-methoxy-7-(((S)-tetrahydrofuran-3-yl)oxy)-N—((R)-1-(3-(trifluoromethyl)phenyl)ethyl)imidazo[1,5-a]quinazolin-5-amine

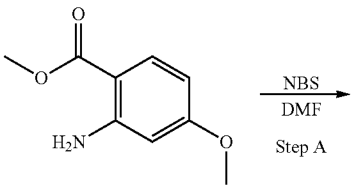

1

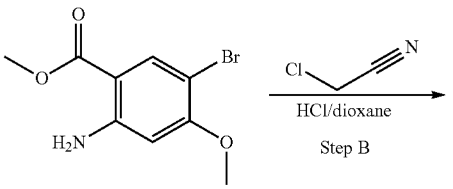

2

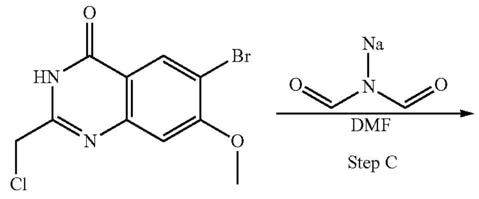

3

-continued

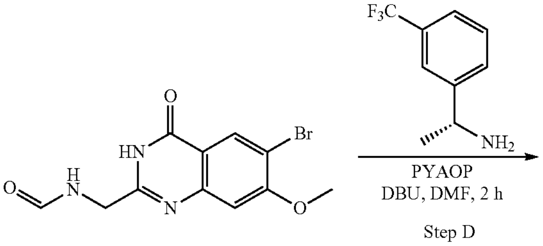

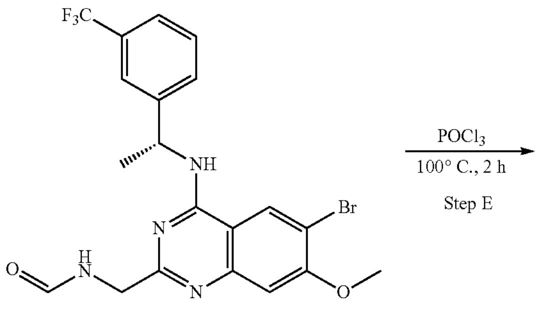

5

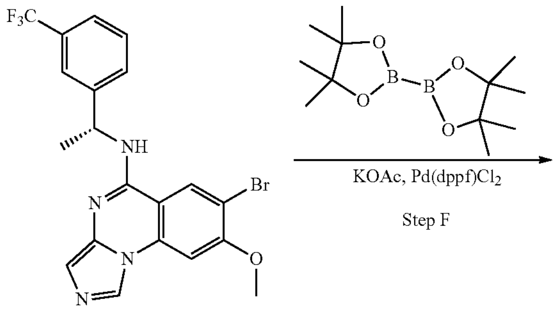

6

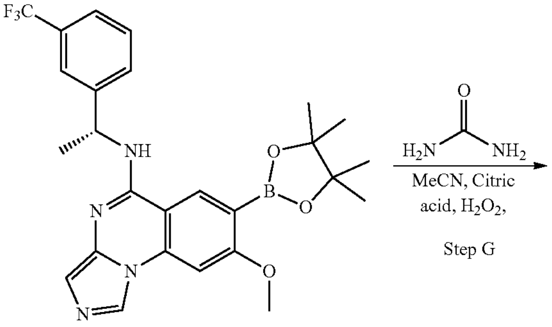

7

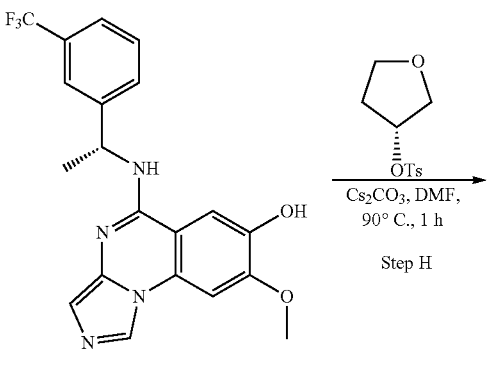

8

-continued

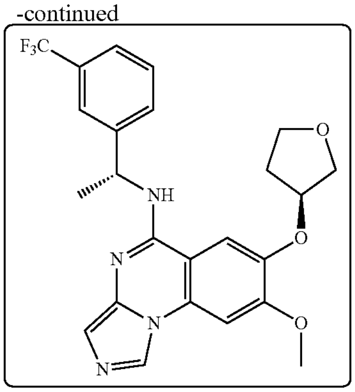

Example 56

Step A. methyl 2-amino-5-bromo-4-methoxybenzoate

To a stirred solution of methyl 2-amino-4-methoxybenzoate (3 g, 16.6 mmol) in DMF (20 mL) was added NBS (3.24 g, 18.2 mmol). The reaction mixture was stirred at room temperature for 2 h. The reaction mixture was poured into water and extracted with EtOAc, washed with brine. The organic layer was dried over $Na_2SO_4$ and concentrated in vacuum to give the residue and the residue was purified by column chromatography (silica gel, 40 g, 0-20% EtOAc in PE) to give methyl 2-amino-5-bromo-4-methoxybenzoate (4 g, 15.4 mmol, 92.9%) as a white solid. LCMS: m/z 260 $(M+H)^+$.

Step B. 6-bromo-2-(chloromethyl)-7-methoxyquinazolin-4(3H)-one

To a stirred solution of methyl 2-amino-5-bromo-4-methoxybenzoate (4 g, 15.4 mmol) in HCl/dioxane (30 mL) was added 2-chloroacetonitrile (1.95 mL, 30.7 mmol). The reaction mixture was filtered and the filter cake was washed with PE and water to give 6-bromo-2-(chloromethyl)-7-methoxy-3,4-dihydroquinazolin-4-one (4 g, 13.2 mmol, 85.7%) as a white solid. LCMS: m/z 303 $(M+H)^+$.

Step C. N-((6-bromo-7-methoxy-4-oxo-3,4-dihydroquinazolin-2-yl)methyl)formamide

To a stirred solution of 6-bromo-2-(chloromethyl)-7-methoxy-3,4-dihydroquinazolin-4-one (3 g, 9.89 mmol) in N,N-dimethylformamide (15 mL) was added N-formyl-N-sodioformamide (1.88 g, 19.7 mmol). The reaction mixture was filtered and the filter cake was washed with EtOAc and water to give N-[(6-bromo-7-methoxy-4-oxo-3,4-dihydroquinazolin-2-yl)methyl]formamide (1.5 g, 4.81 mmol, 48.6%) as a white solid. LCMS: m/z 312 $(M+H)^+$.

Step D. (R)—N-((6-bromo-7-methoxy-4-((1-(3-(trifluoromethyl)phenyl)ethyl)amino) quinazolin-2-yl)methyl)formamide To a stirred solution of N-[(6-bromo-7-methoxy-4-oxo-3,4-dihydroquinazolin-2-yl)methyl]formamide (200 mg, 0.641 mmol) in DMF (5 mL) was added PyAOP (400 mg, 0.77 mmol), (1R)-1-[3-(trifluoromethyl)phenyl]ethan-1-amine (121 mg, 0.64 mmol) and DBU (0.3 mL, 1.92 mmol). The reaction mixture was stirred at 25° C. for 2 h. The reaction mixture was poured into water, extracted with DCM, washed with brine, dried over $Na_2SO_4$ and concentrated in vacuum to give the residue and the residue was purified by column chromatography (silica gel, 40 g, 0~3% MeOH in DCM) to give N-[(6-bromo-7-methoxy-4-{[(1R)-1-[3-(trifluoromethyl)phenyl]ethyl]amino}quinazolin-2-yl)methyl]formamide (160 mg, 0.331 mmol, 51.7%) as a light yellow solid. LCMS: m/z 483 $(M+H)^+$.

Step E. (R)-7-bromo-8-methoxy-N-(1-(3-(trifluoromethyl)phenyl)ethyl)imidazo[1,5-a]quinazolin-5-amine To a stirred solution of N-[(6-bromo-7-methoxy-4-{[(1R)-1-[3-(trifluoromethyl) phenyl]ethyl]amino}quinazolin-2-yl)methyl]formamide (160 mg, 0.33 mmol) in toulene (3 mL) was added $POCl_3$ (1 mL). The reaction mixture was stirred at 100° C. for 1 h. The cooled reaction mixture was concentrated in vacuum to give the residue and the residue was purified by column chromatography (silica gel, 5 g, 0~4% MeOH in DCM) to give 7-bromo-8-methoxy-N-[(1R)-1-[3-(trifluoromethyl)phenyl]ethyl]imidazo[1,5-a]quinazolin-5-amine (100 mg, 0.21 mmol, 64.9%) as a light yellow solid. LCMS: m/z 465 $(M+H)^+$.

Step F. (R)-8-methoxy-7-(4,4,5,5-tetramethyl-1,3,2-dioxaborolan-2-yl)-N-(1-(3-(trifluoromethyl)phenyl)ethyl)imidazo[1,5-a]quinazolin-5-amine To a stirred solution of 7-bromo-8-methoxy-N-[(1R)-1-[3-(trifluoromethyl)phenyl]ethyl]imidazo[1,5-a]quinazolin-5-amine (100 mg, 0.21 mmol) in dioxane (5 mL) was added 4,4,5,5-tetramethyl-2-(tetramethyl-1,3,2-dioxaborolan-2-yl)-1,3,2-dioxaborolane (0.08 mL, 0.32 mmol), KOAc (42.19 mg, 0.43 mmol) and Pd(dppf)$Cl_2$ (31.4 mg, 0.04 mmol). The reaction mixture was stirred at 100° C. for 2 h. The reaction mixture was filtered and the filtrate was concentrated in vacuum to give the crude product 8-methoxy-7-(tetramethyl-1,3,2-dioxaborolan-2-yl)-N-[(1R)-1-[3-(trifluoromethyl)phenyl]ethyl]imidazo[1,5-a]quinazolin-5-amine (60 mg, 0.117 mmol, 54.5%) as a black solid. LCMS: m/z 513 $(M+H)^+$.

Step G. (R)-8-methoxy-5-((1-(3-(trifluoromethyl) phenyl)ethyl)amino)imidazo[1,5-a]quinazolin-7-ol To a stirred solution of 8-methoxy-7-(tetramethyl-1,3,2-dioxaborolan-2-yl)-N-[(1R)-1-[3-(trifluoromethyl)phenyl]ethyl]imidazo[1,5-a]quinazolin-5-amine (60 mg, 0.12 mmol) in MeCN (4 mL) was added urea hydrogen peroxide (22 mg, 0.23 mmol) and citric acid (100 mg, 0.52 mmol) in $H_2O$ (1 mL). The reaction mixture was stirred at 25° C. for 2 h. The reaction mixture was poured into water, extracted with EtOAc, washed with brine, dried over $Na_2SO_4$ and concentrated in vacuum to give the residue and the residue was purified by column chromatography (silica gel, 5 g, 0~4% MeOH in DCM) to give 8-methoxy-5-{[(1R)-1-[3-(trifluoromethyl)phenyl]ethyl]amino}imidazo[1,5-a]quinazolin-7-ol (30 mg, 0.07 mmol, 63.6%) as a light yellow solid. LCMS: m/z 403 $(M+H)^+$.

Step H. 8-methoxy-7-(((S)-tetrahydrofuran-3-yl) oxy)-N—((R)-1-(3-(trifluoromethyl)phenyl) ethyl) imidazo[1,5-a]quinazolin-5-amine To a stirred solution of 8-methoxy-5-{[(1R)-1-[3-(trifluoromethyl)phenyl]ethyl]amino}imidazo[1,5-a]quinazolin-7-ol (30 mg, 0.075 mmol) in DMF (2 mL) was added (3R)-oxolan-3-yl 4-methylbenzene-1-sulfonate (21.8 mg, 0.09 mmol) and $Cs_2CO_3$ (48.8 mg, 0.15 mmol). The reaction mixture was stirred at 90° C. for 1 h. The reaction mixture was poured into water, extracted with EtOAc, washed with brine and concentrated in vacuum to give the residue and the residue was purified by prep-TLC (2% MeOH in DCM) to give the crude product and the crude product was purified by prep-HPLC to give 8-methoxy-7-[(3S)-oxolan-3-yloxy]-N-[(1R)-1-[3-(trifluoromethyl)phenyl]ethyl]imidazo[1,5-a]quinazolin-5-amine (2 mg, 0.004 mmol, 5.68%) as a white solid. LCMS: m/z 473 $(M+H)^+$. $^1H$ NMR (400 MHz, MeOD) δ 9.60 (s, 1H), 7.94 (s, 1H), 7.83 (s, 1H), 7.75 (s, 2H), 7.53 (s, 2H), 7.24 (s, 1H), 5.61 (d, J=6.8 Hz, 1H), 5.30 (s, 2H), 4.07 (s, 3H), 3.99 (d, J=33.5 Hz, 3H), 2.41-2.15 (m, 2H), 1.70 (d, J=7.0 Hz, 3H).

Example 57: Synthesis of N—((R)-1-(3-amino-5-(trifluoromethyl)phenyl)ethyl)-8-methoxy-7-(((S)-tetrahydrofuran-3-yl)oxy)imidazo[1,5-a]quinazolin-5-amine. (The Title Compound was Synthesized from Compound 4 in Example 56.)

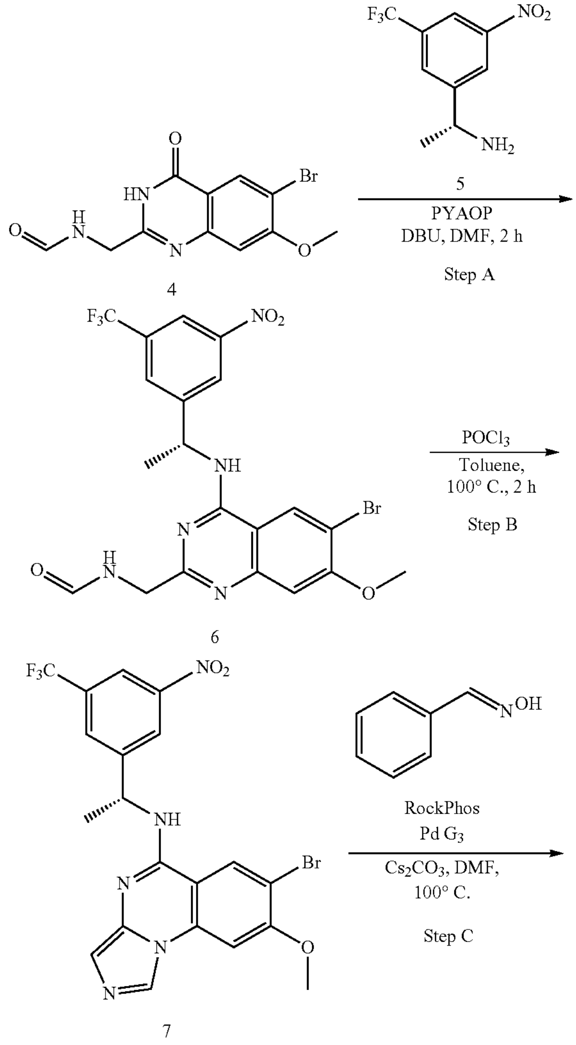

-continued

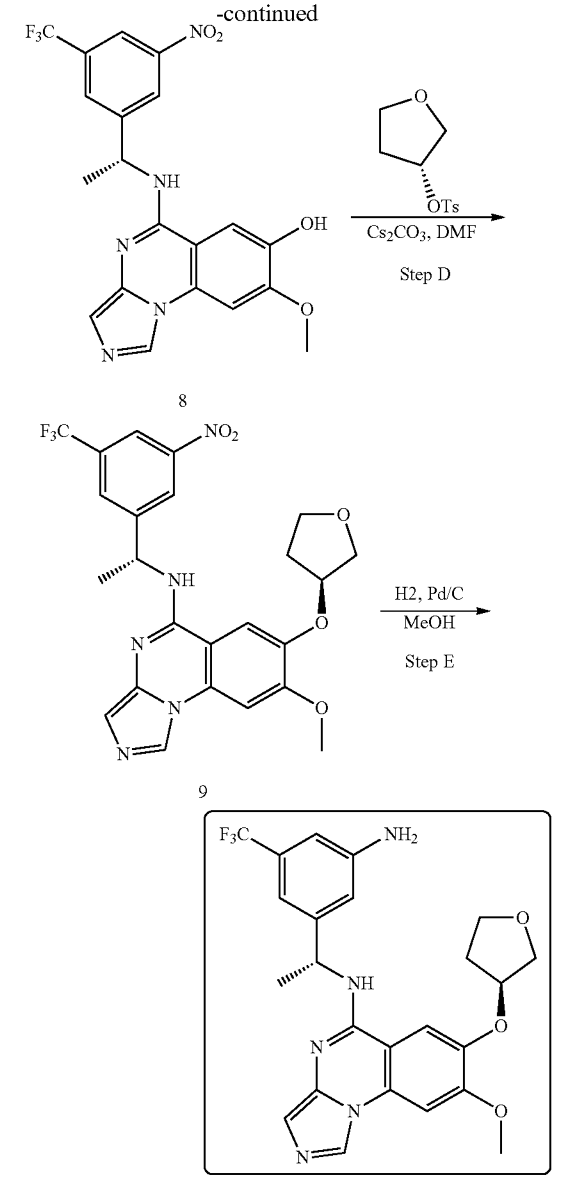

Example 57

Step A. (R)—N-((6-bromo-7-methoxy-4-((1-(3-nitro-5-(trifluoromethyl)phenyl)ethyl) amino)quinazolin-2-yl)methyl)formamide To a stirred solution of N-[(6-bromo-7-methoxy-4-oxo-3,4-dihydroquinazolin-2-yl)methyl]formamide (600 mg, 1.9 mmol)N-[(6-bromo-7-methoxy-4-oxo-3,4-dihydroquinazolin-2-yl)methyl]formamide (600 mg, 1.9 mmol) in DMF (5 mL) was added PyAOP (1002 mg, 1.9 mmol), (1R)-1-[3-nitro-5-(trifluoromethyl)phenyl]ethan-1-amine (450.1 mg, 1.9 mmol) and DBU (1.4 mL, 9.6 mmol). The reaction mixture was stirred at 25° C. for 2 h. The reaction mixture was poured into water, extracted with DCM, washed with brine, dried over $Na_2SO_4$ and concentrated in vacuum to give the residue and the residue was purified by column chromatography (silica gel, 40 g, 0~3% MeOH in DCM) to give N-[(6-bromo-7-methoxy-4-{[(1R)-1-[3-nitro-5-(trifluoromethyl)phenyl]ethyl]amino}quinazolin-2-yl)methyl]

formamide (600 mg, 1.13 mmol, 59.0%) as a light yellow solid. LCMS: m/z 528 $(M+H)^+$.

Step B. (R)-7-bromo-8-methoxy-N-(1-(3-nitro-5-(trifluoromethyl)phenyl)ethyl)imidazo[1,5-a]quinazolin-5-amine To a stirred solution of N-[(6-bromo-7-methoxy-4-{[(1R)-1-[3-nitro-5-(trifluoromethyl)phenyl]ethyl]amino}quinazolin-2-yl)methyl]formamide (600 mg, 1.1 mmol) in toluene (1 mL) was added $POCl_3$ (1 mL). The reaction mixture was stirred at 100° C. for 1 h. The reaction mixture was concentrated in vacuum to give the residue and the residue was purified by column chromatography (silica gel, 10 g, 0~2% MeOH in DCM) to give 7-bromo-8-methoxy-N-[(1R)-1-[3-nitro-5-(trifluoromethyl)phenyl]ethyl]imidazo[1,5-a]quinazolin-5-amine (200 mg, 0.392 mmol, 34.5%) as a light yellow solid. LCMS: m/z 509 $(M+H)^+$.

Step C. (R)-8-methoxy-5-((1-(3-nitro-5-(trifluoromethyl)phenyl)ethyl)amino)imidazo[1,5-a]quinazolin-7-ol To a stirred solution of 7-bromo-8-methoxy-N-[(1R)-1-[3-nitro-5-(trifluoromethyl)phenyl]ethyl]imidazo[1,5-a]quinazolin-5-amine (200 mg, 0.4 mmol) in DMF (2.0 mL) was added (E)-N-(phenylmethylidene)hydroxylamine (94.9 mg, 0.8 mmol), RockPhos Pd G3 (34.3 mg, 0.1 mmol) and $Cs_2CO_3$ (383 mg, 1.2 mmol). The reaction mixture was stirred at 100° C. for 2 h. The reaction mixture was concentrated in vacuum to give the residue and the residue was purified by column chromatography (silica gel, 10 g, 0~5% MeOH in DCM) to give 8-methoxy-5-{[(1R)-1-[3-nitro-5-(trifluoromethyl)phenyl]ethyl]amino}imidazo[1,5-a]quinazolin-7-ol (80 mg, 0.2 mmol, 45.6%) as a white solid. LCMS: m/z 448 $(M+H)^+$.

Step D. 8-methoxy-N—((R)-1-(3-nitro-5-(trifluoromethyl)phenyl)ethyl)-7-(((S)-tetrahydrofuran-3-yl)oxy)imidazo[1,5-a]quinazolin-5-amine To a stirred solution of 8-methoxy-5-{[(1R)-1-[3-nitro-5-(trifluoromethyl)phenyl]ethyl]amino}imidazo[1,5-a]quinazolin-7-ol (80 mg, 0.1 mmol) in DMF (5 mL) was added (3R)-oxolan-3-yl 4-methylbenzene-1-sulfonate (86.6 mg, 0.36 mmol) and $Cs_2CO_3$ (175 mg, 0.54 mmol). The reaction mixture was stirred at 90° C. for 2 h. The reaction mixture was poured into water, extracted with EtOAc. The organic layer was washed with brine, dried over $Na_2SO_4$ and concentrated. The residue was purified prep-TLC (80% EtOAc in PE) to give 8-methoxy-N-[(1R)-1-[3-nitro-5-(trifluoromethyl)phenyl]ethyl]-7-[(3S)-oxolan-3-yloxy]imidazo[1,5-a]quinazolin-5-amine (30 mg, 0.05 mmol, 32.4%) as a white solid. LCMS: m/z 518 $(M+H)^+$.

Step E. N—((R)-1-(3-amino-5-(trifluoromethyl)phenyl)ethyl)-8-methoxy-7-(((S)-tetrahydrofuran-3-yl)oxy)imidazo[1,5-a]quinazolin-5-amine To a stirred solution of 8-methoxy-N-[(1R)-1-[3-nitro-5-(trifluoromethyl)phenyl]ethyl]-7-[(3S)-oxolan-3-yloxy]imidazo[1,5-a]quinazolin-5-amine (30 mg, 0.06 mmol) in MeOH (5 mL) was added Pd/C 10% (0.1 mmol). The reaction mixture was stirred at room temperature for 2 h using a $H_2$ balloon. The reaction mixture was filtered and the filtrate was concentrated in vacuum to give the residue and the residue was purified prep-TLC (5% MeOH in DCM) and prep-HPLC to give N-[(1R)-1-[3-amino-5-(trifluoromethyl)phenyl]ethyl]-8-methoxy-7-[(3S)-oxolan-3-yloxy]imidazo[1,5-a]quinazolin-5-amine (1.0 mg, 0.002 mmol, 3.5%) as a white solid. $^1H$ NMR (400 MHz, MeOD) δ 8.52 (s, 1H), 7.82 (s, 1H), 7.66 (s, 1H), 6.98 (s, 1H), 6.81 (d, J=17.6 Hz, 1H), 5.44 (d, J=7.2 Hz, 1H), 4.02 (d, J=12.7 Hz, 5H), 4.00 (s, 1H), 3.92 (s, 1H), 2.20 (d, J=11.9 Hz, 2H), 1.62 (d, J=5.9 Hz, 2H). LCMS: m/z 488 $(M+H)^+$.

Example 58: Synthesis of 8-methoxy-7-(((S)-tetrahydrofuran-3-yl)oxy)-N—((R)-1-(3-(trifluoromethyl)phenyl)ethyl)imidazo[1,2-a]quinazolin-5-amine

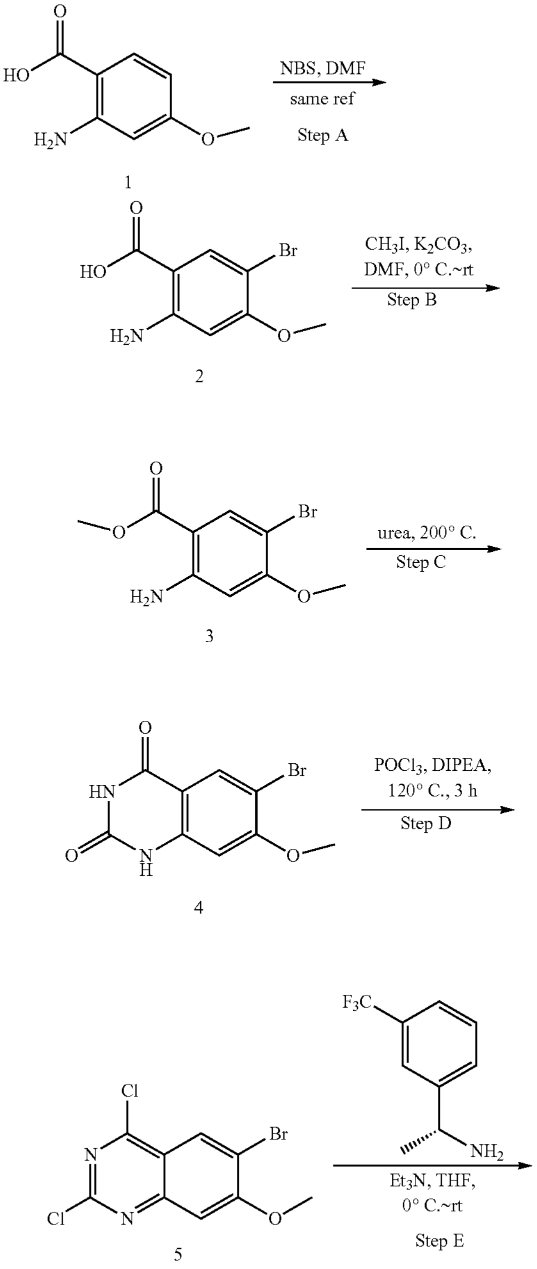

1
2
3
4
5

-continued

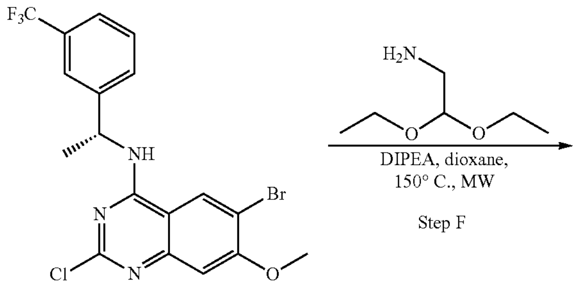

6

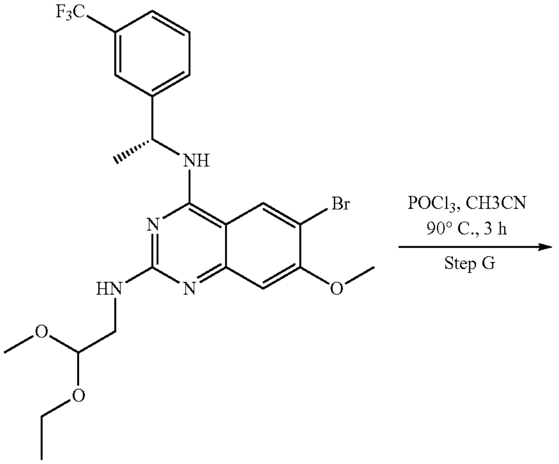

7

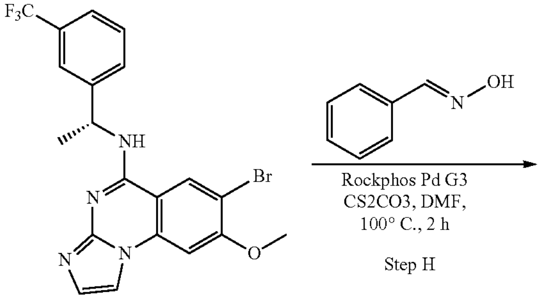

8

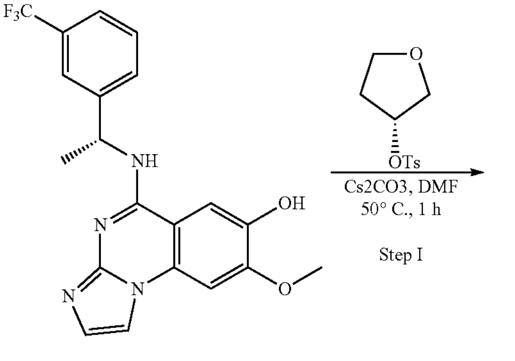

9

-continued

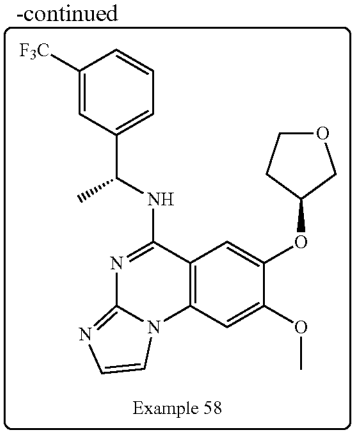

Example 58

Step B: methyl 2-amino-5-bromo-4-methoxybenzoate

To a stirred solution of 2-amino-5-bromo-4-methoxybenzoic acid (3.0 g, 12.2 mmol) and $K_2CO_3$ (2.2 g, 15.8 mmol) in DMF (40 mL) at 0° C. was added $CH_3I$ (1.8 g, 12.8 mmol) slowly. The reaction mixture was stirred at room temperature for 2 h. The reaction mixture was diluted with ice-water (50 mL), extracted with EtOAc (50 mL×3). The combined organic phase was washed by water and brine, dried over anhydrous $Na_2SO_4$, filtered and concentrated to give a crude product which was purified by column chromatography on silica gel (EtOAc in PE: 0~20%) to obtain methyl 2-amino-5-bromo-4-methoxybenzoate (2.6 g, 10.0 mmol, 82%) as a gray solid. LC/MS (ESI) m/z: 261 $(M+H)^+$.

Step C: 6-bromo-7-methoxyquinazoline-2,4(1H,3H)-dione

A stirring mixture of methyl 2-amino-5-bromo-4-methoxybenzoate (2.6 g, 10.0 mmol) and urea (12.1 g, 50.0 mmol) was heated at 200° C. for 2 h. The reaction mixture was cooled to room temperature and diluted with water (50 mL). The mixture stirred at 60° C. for 30 min. The precipitate was filtered and dried to obtain 6-bromo-7-methoxy-1,2,3,4-tetrahydroquinazoline-2,4-dione (2.0 g, 7.4 mmol, 73.8%) as a gray solid. LC/MS (ESI) m/z: 272 $(M+H)^+$.

Step D: 6-bromo-2,4-dichloro-7-methoxyquinazoline

To a stirred solution of 6-bromo-7-methoxy-1,2,3,4-tetrahydroquinazoline-2,4-dione (2.6 g, 9.6 mmol) in $POCl_3$ (40 mL) was added DIPEA (5 mL) slowly. The reaction mixture was stirred at 120° C. for 3 h under nitrogen atmosphere. The reaction mixture was cooled to room temperature and concentrated. The residue was diluted with ice-water (100 mL). The mixture was extracted with EtOAc (100 mL×3). The combined organic phase was washed by water and brine, dried over anhydrous $Na_2SO_4$, filtered and concentrated to give a crude product which was purified by column chromatography on silica gel (EtOAc in PE: 0·20%) to obtain 6-bromo-2,4-dichloro-7-methoxyquinazoline (1.8 g, 5.8 mmol, 60.9%) as a light yellow solid. LC/MS (ESI) m/z: 308 $(M+H)^+$.

Step E: (R)-6-bromo-2-chloro-7-methoxy-N-(1-(3-(trifluoromethyl)phenyl)ethyl)quinazolin-4-amine To a stirred solution of 6-bromo-2,4-dichloro-7-methoxyquinazoline (500 mg, 1.6 mmol) and TEA (493 mg, 4.8 mmol) in THE (10 mL) at 0° C. was added (1R)-1-[3-(trifluoromethyl)phenyl]ethan-1-amine (307 mg, 1.6 mmol) slowly. The reaction mixture was stirred at room temperature for 16 h. The reaction mixture was diluted with water (20 mL). The mixture was extracted with EtOAc (20 mL×3). The combined organic phase was washed by water and brine, dried over anhydrous $Na_2SO_4$, filtered and concentrated to give a crude product which was purified by column chromatography on silica gel (EtOAc in PE:0-30%) to obtain 6-bromo-2-chloro-7-methoxy-N-[(1R)-1-[3-(trifluoromethyl)phenyl]ethyl]quinazolin-4-amine (360 mg, 0.78 mmol, 48%) as an off-white solid. LC/MS (ESI) m/z: 461 $(M+H)^+$.

Step F: (R)-6-bromo-N2-(2,2-diethoxyethyl)-7-methoxy-N4-(1-(3-(trifluoromethyl)phenyl) ethyl) quinazoline-2,4-diamine To a stirred solution of 6-bromo-2-chloro-7-methoxy-N-[(1R)-1-[3-(trifluoromethyl) phenyl]ethyl]quinazolin-4-amine (360 mg, 0.78 mmol), DIPEA (151 mg, 1.17 mmol) in 1,4-dioxane (5 mL) was added 2,2-diethoxyethan-1-amine (125 mg, 0.94 mmol). The reaction mixture was stirred at 150° C. under microwave for 1 h. The cooled reaction mixture was diluted with water (20 mL), extracted with EtOAc (20 mL×3). The combined organic phase was washed by water and brine, dried over anhydrous $Na_2SO_4$, filtered and concentrated to give a crude product which was purified by column chromatography on silica gel (MeOH in DCM:0-12%) to obtain 6-bromo-N2-(2,2-diethoxyethyl)-7-methoxy-N4-[(1R)-1-[3-(trifluoromethyl)phenyl]ethyl]quinazoline-2,4-diamine (320 mg, 0.57 mmol, 73.4%) as a brown solid. LC/MS (ESI) m/z: 557 $(M+H)^+$.

Step G: (R)-7-bromo-8-methoxy-N-(1-(3-(trifluoromethyl)phenyl)ethyl)imidazo[1,2-a]quinazolin-5-amine A solution of 6-bromo-N2-(2,2-diethoxyethyl)-7-methoxy-N4-[(1R)-1-[3-(trifluoromethyl)phenyl]ethyl]quinazoline-2,4-diamine (320 mg, 0.57 mmol) in $CH_3CN$ (5 mL) and $POCl_3$ (5 mL) was stirred at 90° C. for 2 h. The reaction mixture was concentrated and diluted with ice-water (10 mL). The mixture was extracted with EtOAc (10 mL×3). The combined organic phase was washed by water and brine, dried over anhydrous $Na_2SO_4$, filtered and concentrated to give a crude product which was purified by column chromatography on silica gel (MeOH in DCM: 0~15%) to obtain 7-bromo-8-methoxy-N-[(1R)-1-[3-(trifluoromethyl)phenyl]ethyl]imidazo[1,2-a]quinazolin-5-amine (120 mg, 0.26 mmol, 44.9%) as a brown solid. LC/MS (ESI) m/z: 466 $(M+H)^+$.

Step H: (R)-8-methoxy-5-((1-(3-(trifluoromethyl) phenyl)ethyl)amino)imidazo[1,2-a]quinazolin-7-ol To a stirred solution of 7-bromo-8-methoxy-N-[(1R)-1-[3-(trifluoromethyl)phenyl]ethyl]imidazo[1,2-a]quinazolin-5-amine (60 mg, 0.13 mmol), (E)-Benzaldehyde oxime (23 mg, 0.19 mmol) and $Cs_2CO_3$ (84 mg, 0.26 mmol) in DMF (3 mL) was added Rock Phos Pd G3 (10 mg, 0.013 mmol). The reaction mixture was stirred at 100° C. for 2 h under nitrogen atmosphere. The reaction mixture was diluted with water (10 mL), the mixture was extracted with EtOAc (10 mL×3), the combined organic phase was washed by water and brine, the organic phase was dried over anhydrous $Na_2SO_4$, filtered and concentrated to give a crude product which was purified by column chromatography on silica gel (MeOH in DCM: 0~17%) to obtain 8-methoxy-5-{[(1R)-1-[3-(trifluoromethyl)phenyl]ethyl]amino}imidazo[1,2-a]quinazolin-7-ol (25 mg, 0.06 mmol, 48.2%) as a yellow solid. LC/MS (ESI) m/z: 403 $(M+H)^+$.

Step I: 8-methoxy-7-(((S)-tetrahydrofuran-3-yl) oxy)-N—((R)-1-(3-(trifluoromethyl)phenyl) ethyl) imidazo[1,2-a]quinazolin-5-amine To a stirred solution of 8-methoxy-5-{[(1R)-1-[3-(trifluoromethyl)phenyl]ethyl]amino}imidazo[1,2-a]quinazolin-7-ol (25 mg, 0.06 mmol), $Cs_2CO_3$ (30 mg, 0.09 mmol) in DMF (3 mL) was added (R)-tetrahydrofuran-3-yl 4-methylbenzenesulfonate (18 mg, 0.075 mmol). The reaction mixture was stirred at 50° C. for 1 h. The reaction mixture was diluted with water (5 mL), extracted with EtOAc (10 mL×3). The combined organic phase was washed by water and brine, dried over anhydrous $Na_2SO_4$, filtered and concentrated to give a crude product which was purified by prep-TLC (DCM:MeOH=15:1) to obtain 8-methoxy-7-[(3S)-oxolan-3-yloxy]-N-[(1R)-1-[3-(trifluoromethyl)phenyl]ethyl]imidazo [1,2-a]quinazolin-5-amine (16 mg, 0.034 mmol, 54.5%) as a white solid. LC/MS (ESI) m/z: 473 $(M+H)^+$. $^1H$ NMR (400 MHz, DMSO) δ 8.65 (s, 1H), 8.27 (s, 1H), 8.11 (s, 1H), 7.84 (s, 2H), 7.70 (s, 1H), 7.60 (s, 2H), 7.37 (s, 1H), 5.66 (s, 1H), 5.31 (s, 1H), 4.04-3.90 (m, 5H), 3.89-3.79 (m, 2H), 2.32 (d, J=7.6 Hz, 1H), 2.02 (d, J=7.5 Hz, 1H), 1.68 (d, J=6.2 Hz, 3H).

Example 59: (R)-5-((1-(3-(difluoromethyl)-2-fluorophenyl)ethyl)amino)-7-(tetrahydro-2H-pyran-4-yl) pyrazolo[1,5-a]pyrido[3,4-e]pyrimidin-8(7H)-one

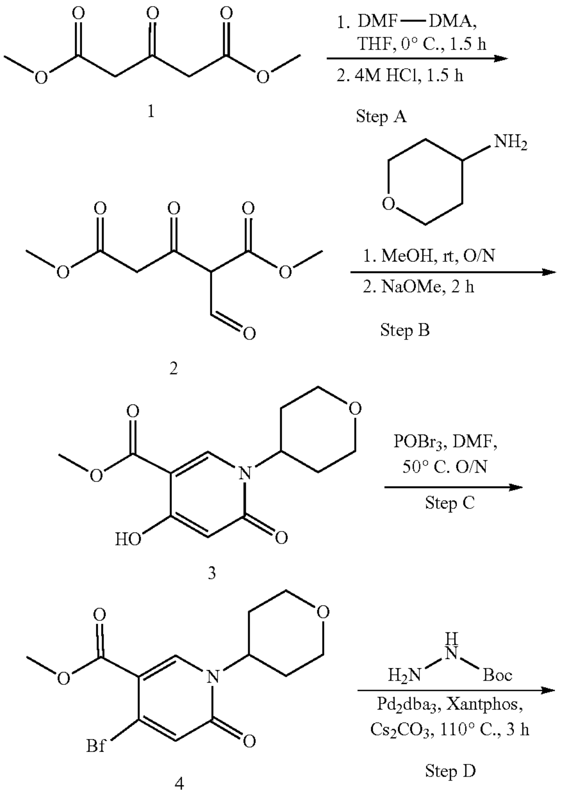

1
2
3
4

-continued

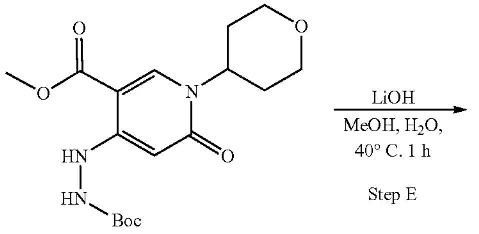

5

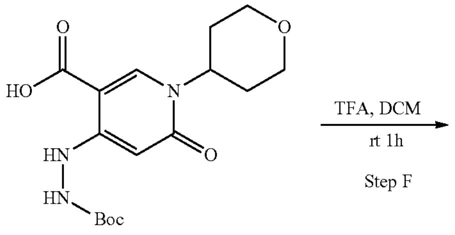

6

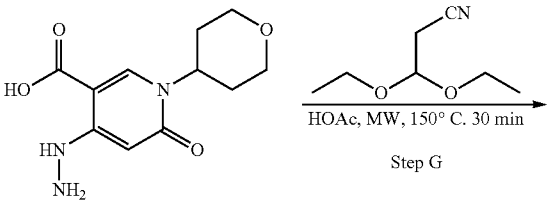

7

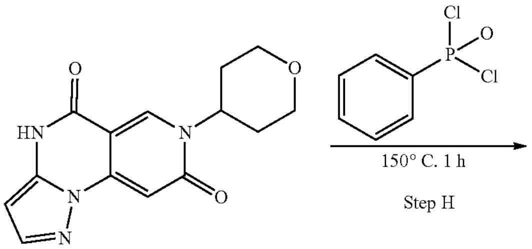

8

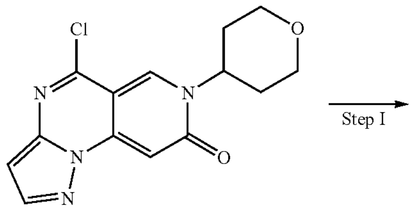

9

-continued

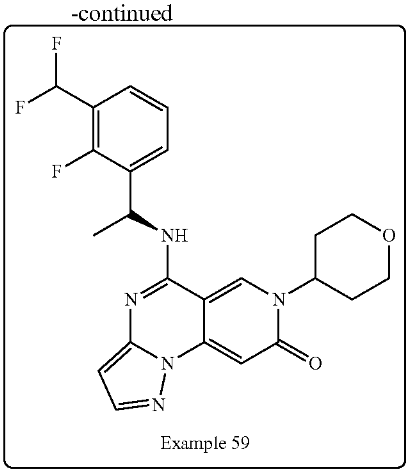

Example 59

Step A. dimethyl 2-formyl-3-oxopentanedioate

To a stirred solution of 1,5-dimethyl 3-oxopentanedioate (10 g, 57.4 mmol) in 2-Methyltetrahydrofuran (100 mL) at 0° C. was added DMF-DMA (6.8 g, 57.4 mmol). The reaction mixture was stirred at 0° C. for 1.5 h under nitrogen atmosphere before 4M HCl (28 mL, 13.1 mmol) was added. The result solution was allowed to warm to room temperature and stirred for 2 h. The reaction mixture was diluted with water (100 mL). The following mixture was extracted with EtOAc (10 mL*3). The combined organic phase was washed by water and brine, dried over anhydrous $Na_2SO_4$, filtered and concentrated to give the crude product which was purified by column chromatography on silica gel (PE: EtOAc=10:1 to 3:1) to obtain 1,5-dimethyl 2-formyl-3-oxopentanedioate (9.6 g, 47.5 mmol, yield 82.7%) as a colorless oil. LC/MS (ESI) m/z: 203.0 $(M+H)^+$ Step B: methyl 4-hydroxy-6-oxo-1-(tetrahydro-2H-pyran-4-yl)-1,6-dihydropyridine-3-carboxylate To a stirred solution of 1,5-dimethyl 2-formyl-3-oxopentanedioate (12.0 g, 59.3 mmol) in $CH_3OH$ (80 mL) at 0° C. was added oxan-4-amine (5.0 g, 49.4 mmol). The reaction mixture was stirred at room temperature for 16 h under nitrogen atmosphere before MeONa (40 mL, 59.3 mmol, 30% in $CH_3OH$) was added. The result solution was stirred at room temperature for 2 h. The reaction mixture was poured into ice-water (100 mL). $CH_3OH$ was removed by reduce power. The precipitate was filtered and dried to give a crude desire product. The filtrate was extracted with DCM (80 mL×3), the combined organic phase was washed by water and brine, the organic phase was dried over anhydrous $Na_2SO_4$, filtered and concentrated to give a crude product. The combined crude product was triturated with 100 mL PE:DCM=10:1 to give the desire product (11 g, 43.5 mmol, 73.3%) as an off-white solid. LC/MS (ESI) m/z: 253.9 $(M+H)^+$.

Step C: methyl 4-bromo-6-oxo-1-(tetrahydro-2H-pyran-4-yl)-1,6-dihydropyridine-3-carboxylate To a stirred solution of methyl 4-hydroxy-6-oxo-1-(tetrahydro-2H-pyran-4-yl)-1,6-dihydropyridine-3-carboxylate (8.0 g, 31.6 mmol) in DMF (50 mL) was added POBr3 (10.9 g, 37.9 mmol). The reaction mixture was stirred at 50° C. for 16 h under nitrogen atmosphere. The reaction mixture was poured into ice-water (100 mL), extracted with EtOAc (100 mL×3). The combined organic phase was washed by water and brine, the organic phase was dried over anhydrous $Na_2SO_4$, filtered and concentrated to give a crude product which was purified by column chromatography on silica gel (DCM:MeOH=100:1 to 30:1) to obtain methyl 4-bromo-6-oxo-1-(tetrahydro-2H-pyran-4-yl)-1,6-dihydropyridine-3-carboxylate (6.0 g, 19.0 mmol, yield 60%) as a light yellow solid. LC/MS (ESI) m/z: 317 $(M+H)^+$.

Step D: methyl 4-(2-(tert-butoxycarbonyl)hydrazinyl)-6-oxo-1-(tetrahydro-2H-pyran-4-yl)-1,6-dihydropyridine-3-carboxylate To a stirred solution of methyl 4-bromo-1-(oxan-4-yl)-6-oxo-1,6-dihydropyridine-3-carboxylate (6.0 g, 19.0 mmol), tert-butyl hydrazinecarboxylate (3.7 g, 28.5 mmol), Xantphos (1.0 g, 1.9 mmol) and $Cs_2CO_3$ (18.6 g, 56.9 mmol) in 1,4-dioxane (80 mL) at room temperature was added $Pd_2dba_3$ (915 mg, 1.0 mmol). The reaction mixture was stirred at 110° C. under nitrogen atmosphere for 3 h. The reaction mixture was filtered and concentrated to give a crude product which was purified by column chromatography on silica gel (DCM:MeOH=100:1 to 20:1) to obtain methyl 4-({[(tert-butoxy)carbonyl]amino}amino)-1-(oxan-4-yl)-6-oxo-1,6-dihydropyridine-3-carboxylate (5.1 g, 13.9 mmol, 73.1%) as a yellow solid. LC/MS (ESI) m/z: 367 $(M+H)^+$ Step E: 4-(2-(tert-butoxycarbonyl)hydrazinyl)-6-oxo-1-(tetrahydro-2H-pyran-4-yl)-1,6-dihydropyridine-3-carboxylic acid To a stirred solution of methyl 4-({[(tert-butoxy)carbonyl]amino}amino)-1-(oxan-4-yl)-6-oxo-1,6-dihydropyridine-3-carboxylate (5.1 g, 13.9 mmol) in $H_2O$ (20 mL) and $CH_3OH$ (20 mL) was added Lithium hydroxide (2.9 g, 69.4 mmol). The reaction mixture was stirred at 40° C. for 1.5 h. The reaction mixture was diluted with ice-water (30 mL). $CH_3OH$ was removed by reduce power. The mixture was adjust pH to 5-6 with 2N HCl, extracted with DCM (50 mL*3). The combined organic phase was washed by water and brine, dried over anhydrous $Na_2SO_4$, filtered and concentrated to give a crude product which was purified by column chromatography on silica gel (DCM:MeOH=50:1-5:1) to obtain 4-({[(tert-butoxy)carbonyl]amino}amino)-1-(oxan-4-yl)-6-oxo-1,6-dihydropyridine-3-carboxylic acid (3.3 g, 9.3 mmol, 67.3%) as a brown solid. LC/MS (ESI) m/z: 354 $(M+H)^+$.

Step F: 4-hydrazinyl-6-oxo-1-(tetrahydro-2H-pyran-4-yl)-1,6-dihydropyridine-3-carboxylic acid To a stirred solution of 4-({[(tert-butoxy)carbonyl]amino}amino)-1-(oxan-4-yl)-6-oxo-1,6-dihydropyridine-3-carboxylic acid (3.3 g, 9.3 mmol) in DCM (30 mL) was added $CF_3COOH$ (8 mL). The result solution was stirred at room temperature for 1 h. The reaction mixture was concentrated to give the desire product as a brown solid. 4-hydrazinyl-1-(oxan-4-yl)-6-oxo-1,6-dihydropyridine-3-carboxylic acid (1.8 g, 7.1 mmol, 76.1%). LC/MS (ESI) m/z: 254 $(M+H)^+$.

Step G: 7-(tetrahydro-2H-pyran-4-yl)pyrazolo[1,5-a]pyrido[3,4-e]pyrimidine-5,8(4H,7H)-dione To a stirred solution of 4-hydrazinyl-1-(oxan-4-yl)-6-oxo-1,6-dihydropyridine-3-carboxylic acid (1.8 g, 7.1 mmol) in HOAc (20 mL) at room temperature was added 3,3-diethoxypropanenitrile (1.0 g, 7.1 mmol). The reaction mixture was stirred at 150° C. under microwave for 30 min. The reaction mixture was concentrated to give a crude product which was purified by column chromatography on silica gel (DCM:MeOH=100:1 to 10:1) to obtain 11-(oxan-4-yl)-2,3,7,11-tetraazatricyclo[7.4.0.0^{2,6}]trideca-1(13),3,5,9-tetraene-8,12-dione (300 mg, 1.0 mmol, 14.7%) as a yellow solid. LC/MS (ESI) m/z: 287 $(M+H)^+$.

Step H: 5-chloro-7-(tetrahydro-2H-pyran-4-yl)pyrazolo[1,5-a]pyrido[3,4-e]pyrimidin-8(7H)-one A stirred solution of 11-(oxan-4-yl)-2,3,7,11-tetraazatricyclo[7.4.0.0^{2,6}]trideca-1(13),3,5,9-tetraene-8,12-dione (250 mg, 0.9 mmol) in phenylphosphonoyl dichloride (6 mL) was heated to 150° C. and stirred for 1 h under nitrogen atmosphere. The reaction mixture was cooled to room temperature and diluted with ice-water (5 mL). The mixture was extracted with EtOAc (5 mL×3), the combined organic phase was washed by sat. $NaHCO_3$and water and brine, dried over anhydrous $Na_2SO_4$, filtered and concentrated to give a crude product which was purified by column chromatography on silica gel (PE:EtOAc=10:1 to 3:1) to obtain 8-chloro-11-(oxan-4-yl)-2,3,7,11-tetraazatricyclo[7.4.0.0^{2,6}]trideca-1(13),3,5,7,9-pentaen-12-one (90 mg, 0.3 mmol, 33.8%) as a light yellow solid. LC/MS (ESI) m/z: 305 $(M+H)^+$.

Step I: (R)-5-((1-(3-(difluoromethyl)-2-fluorophenyl)ethyl)amino)-7-(tetrahydro-2H-pyran-4-yl)pyrazolo[1,5-a]pyrido[3,4-e]pyrimidin-8(7H)-one A solution of 8-chloro-11-(oxan-4-yl)-2,3,7,11-tetraazatricyclo[7.4.0.0^{2,6}]trideca-1(13),3,5,7,9-pentaen-12-one (30 mg, 0.1 mmol), DIPEA (37 mg, 0.3 mmol) and (1R)-1-[3-(difluoromethyl)-2-fluorophenyl]ethan-1-amine (37 mg, 0.2 mmol) in EtOH (3 mL) in a sealed tube stirred at 120° C. for 16 h, The reaction mixture was concentrated and the residue was diluted with water (5 mL), the mixture was extracted with EtOAc (5 mL×3), the combined organic phase was washed by water and brine, the organic phase was dried over anhydrous $Na_2SO_4$, filtered and concentrated to give the crude product which was purified by Pre-TLC (DCM:MeOH=20:1) to obtain 8-{[(1R)-1-[3-(difluoromethyl)-2-fluorophenyl]ethyl]amino}-11-(oxan-4-yl)-2,3,7,11-tetraazatricyclo[7.4.0.0^{2,6}]trideca-1(13),3,5,7,9-pentaen-12-one (7 mg, 0.015 mmol, yield: 15.6%) as a light yellow solid. LC/MS (ESI) m/z: 458.2 $(M+H)^+$. $^1H$ NMR (400 MHz, DMSO) δ 9.08 (s, 1H), 8.29 (d, J=7.1 Hz, 1H), 7.76 (d, J=1.9 Hz, 1H), 7.68 (t, J=7.2 Hz, 1H), 7.53 (t, J=6.9 Hz, 1H), 7.29 (dt, J=76.3, 35.7 Hz, 2H), 6.63 (s, 1H), 5.94 (d, J=1.9 Hz, 1H), 5.67 (t, J=7.1 Hz, 1H), 5.25-5.08 (m, 1H), 4.09 (dd, J=11.5, 3.9 Hz, 2H), 3.56 (t, J=11.1 Hz, 2H), 2.15 (td, J=12.1, 8.8 Hz, 2H), 1.82 (d, J=10.7 Hz, 2H), 1.60 (d, J=7.0 Hz, 3H).

The examples in the following Table 6 were prepared by using a method analogous to that used to prepare the examples as described herein.

TABLE 6

| Ex# | Structure & name | Analytical data | Method |
|---|---|---|---|
| Example 60 | 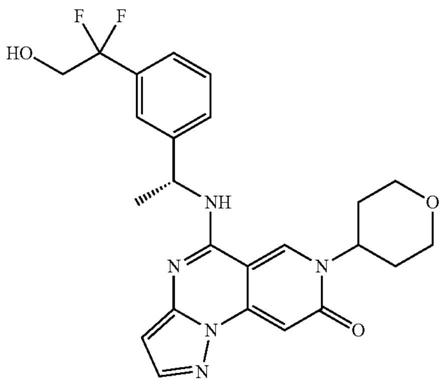 [SMILES: C[C@@H](Nc1nc2ccnn2c2cc(=O)n(C3CCOCC3)cc12)c1cccc(C(F)(F)CO)c1] (R)-5-((1-(3-(1,1-difluoro-2-hydroxyethyl)phenyl)ethyl)amino)-7-(tetrahydro-2H-pyran-4-yl)pyrazolo[1,5-a]pyrido[3,4-e]pyrimidin-8(7H)-one | LC/MS (ESI) m/z: 470.2 $(M + H)^+$. $^1H$ NMR (400 MHz, DMSO) δ 9.04 (s, 1H), 8.26 (d, J = 7.6 Hz, 1H), 7.77 (d, J = 1.9 Hz, 1H), 7.62-7.54 (m, 2H), 7.47 (t, J = 7.6 Hz, 1H), 7.40 (d, J = 7.8 Hz, 1H), 6.63 (s, 1H), 5.95 (d, J = 1.9 Hz, 1H), 5.62 (t, J = 6.3 Hz, 1H), 5.55 (t, J = 7.2 Hz, 1H), 5.24-5.11 (m, 1H), 4.07 (dd, J = 11.4, 3.9 Hz, 2H), 3.85 (td, J = 14.2, 6.3 Hz, 2H), 3.55 (t, J = 11.3 Hz, 2H), 2.19-2.05 (m, 2H), 1.81 (d, J = 11.0 Hz, 2H), 1.60 (d, J = 7.0 Hz, 3H). | Example 59 |
| Example 61 | 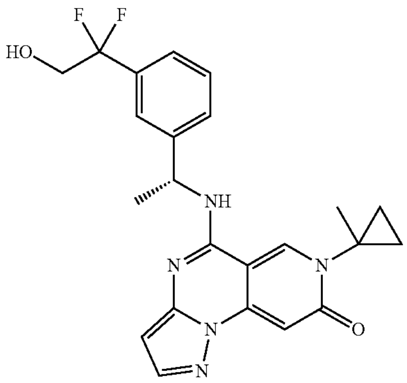 [SMILES: C[C@@H](Nc1nc2ccnn2c2cc(=O)n(C3(C)CC3)cc12)c1cccc(C(F)(F)CO)c1] (R)-5-((1-(3-(1,1-difluoro-2-hydroxyethyl)phenyl)ethyl)amino)-7-(1-methylcyclopropyl)pyrazolo[1,5-a]pyrido[3,4-e]pyrimidin-8(7H)-one | LC/MS (ESI) m/z: 440 $(M + H)^+$. $^1H$ NMR (400 MHz, DMSO) δ 9.17 (s, 1H), 8.21 (d, J = 7.6 Hz, 1H), 7.74 (d, J = 1.9 Hz, 1H), 7.62-7.54 (m, 2H), 7.45 (t, J = 7.7 Hz, 1H), 7.39 (d, J = 7.7 Hz, 1H), 6.53 (s, 1H), 5.93 (d, J = 1.9 Hz, 1H), 5.62 (t, J = 6.3 Hz, 1H), 5.51 (t, J = 7.1 Hz, 1H), 3.85 (td, J = 14.2, 6.3 Hz, 2H), 1.58 (d, J = 7.0 Hz, 3H), 1.52 (s, 3H), 1.14 (s, 2H), 1.03 (s, 2H). | Example 59 |
| Example 62 | 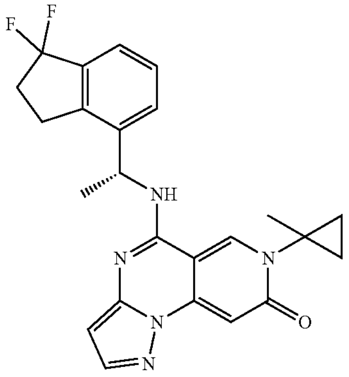 [SMILES: C[C@@H](Nc1nc2ccnn2c2cc(=O)n(C3(C)CC3)cc12)c1cccc2c1CCC2(F)F] (R)-5-((1-(1,1-difluoro-2,3-dihydro-1H-inden-4-yl)ethyl)amino)-7-(1-methylcyclopropyl)pyrazolo[1,5-a]pyrido[3,4-e]pyrimidin-8(7H)-one | LC/MS (ESI) m/z: 436 $(M + H)^+$. $^1H$ NMR (400 MHz, MeOD) δ 9.10 (s, 1H), 7.72 (d, J = 2.0 Hz, 1H), 7.59 (d, J = 6.9 Hz, 1H), 7.42-7.32 (m, 2H), 6.81 (s, 1H), 5.94 (d, J = 2.0 Hz, 1H), 5.51 (q, J = 7.0 Hz, 1H), 3.18-3.04 (m, 1H), 2.68-2.52 (m, 2H), 2.02 (d, J = 5.4 Hz, 1H), 1.63 (d, J = 7.0 Hz, 3H), 1.59 (s, 3H), 1.25-1.18 (m, 2H), 1.10 (q, J = 4.5 Hz, 2H). | Example 59 |

TABLE 6-continued

| Ex# | Structure & name | Analytical data | Method |
|---|---|---|---|
| Example 63 | 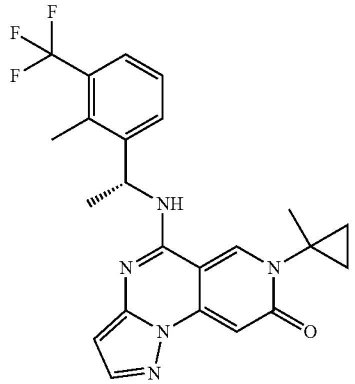 [SMILES: Cc1c([C@@H](C)Nc2nc3ccnn3c3cc(=O)n(C4(C)CC4)cc23)cccc1C(F)(F)F] (R)-5-((1-(2-methyl-3-(trifluoromethyl)phenyl)ethyl)amino)-7-(1-methylcyclopropyl)pyrazolo[1,5-a]pyrido[3,4-e]pyrimidin-8(7H)-one | LC-MS (ESI) m/z 442 $(M + H)^+$. $^1H$ NMR (400 MHz, MeOD) δ 9.11 (s, 1H), 7.72 (d, J = 2.0 Hz, 2H), 7.54 (d, J = 7.7 Hz, 1H), 7.32 (t, J = 7.9 Hz, 1H), 6.81 (s, 1H), 5.93 (d, J = 2.0 Hz, 1H), 5.69 (q, J = 6.9 Hz, 1H), 2.60 (s, 3H), 1.60 (d, J = 6.4 Hz, 6H), 1.23 (s, 2H), 1.10 (s, 2H). | Example 59 |
| Example 64 | 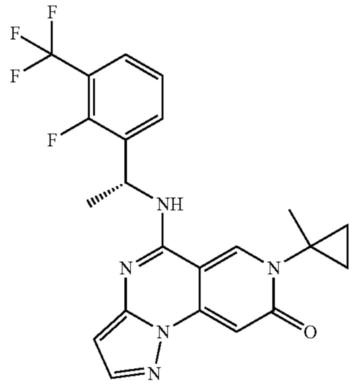 (R)-5-((1-(3-(1,1-difluoroethyl)-2-fluorophenyl)ethyl)amino)-7-(1-methylcyclopropyl)pyrazolo[1,5-a]pyrido[3,4-e]pyrimidin-8(7H)-one | LCMS: m/z 442 $(M + H)^+$. $^1H$ NMR (400 MHz, MeOD) δ 9.16 (s, 1H), 7.72 (d, J = 2.0 Hz, 1H), 7.56 (t, J = 6.9 Hz, 1H), 7.43 (t, J = 6.8 Hz, 1H), 7.19 (t, J = 7.8 Hz, 1H), 6.82 (s, 1H), 5.95 (d, J = 2.0 Hz, 1H), 5.68 (d, J = 7.0 Hz, 1H), 2.00 (dd, J = 18.9, 18.3 Hz, 3H), 1.65 (d, J = 7.0 Hz, 3H), 1.61 (s, 3H), 1.26 (d, J = 7.0 Hz, 2H), 1.12 (t, J = 6.1 Hz, 2H). | Example 59 |
| Example 65 | 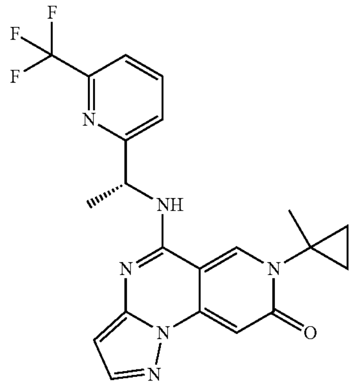 [SMILES: C[C@@H](Nc1nc2ccnn2c2cc(=O)n(C3(C)CC3)cc12)c1cccc(C(F)(F)F)n1] (R)-7-(1-methylcyclopropyl)-5-((1-(6-(trifluoromethyl)pyridin-2-yl)ethyl)amino)pyrazolo[1,5-a]pyrido[3,4-e]pyrimidin-8(7H)-one | LC-MS (ESI) m/z 429 $(M + H)^+$. $^1H$ NMR (400 MHz, MeOD) δ 9.15 (s, 1H), 7.94 (t, J = 7.8 Hz, 1H), 7.72 (d, J = 2.0 Hz, 1H), 7.70 (s, 1H), 7.64 (d, J = 7.7 Hz, 1H), 6.83 (s, 1H), 5.93 (d, J = 2.0 Hz, 1H), 5.53 (q, J = 7.1 Hz, 1H), 1.69 (d, J = 7.1 Hz, 3H), 1.61 (s, 3H), 1.25 (s, 2H), 1.12 (s, 2H). | Example 59 |

TABLE 6-continued

| Ex# | Structure & name | Analytical data | Method |
|---|---|---|---|
| Example 66 | 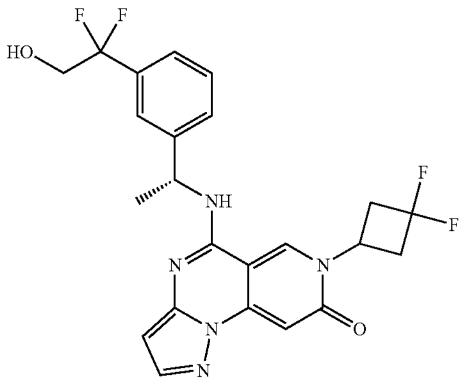 [SMILES: C[C@@H](Nc1nc2ccnn2c2cc(=O)n(C3CC(F)(F)C3)cc12)c1cccc(C(F)(F)CO)c1] (R)-5-((1-(3-(1,1-difluoro-2-hydroxyethyl)phenyl)ethyl)amino)-7-(3,3-difluorocyclobutyl)pyrazolo[1,5-a]pyrido[3,4-e]pyrimidin-8(7H)-one | LC/MS (ESI) m/z: 475 $(M + H)^+$. $^1$HNMR (400 MHz, $CD_3OD-d_4$) δ 8.84 (s, 1H), 7.73 (d, J = 2.0 Hz, 1H), 7.63 (s, 1H), 7.57 (d, J = 7.1 Hz, 1H), 7.40 (dd, J = 9.1, 7.6 Hz, 2H), 6.84 (s, 1H), 5.97 (d, J = 2.0 Hz, 1H), 5.53 (q, J = 7.0 Hz, 1H), 4.97-4.91 (m, 1H), 3.87 (t, J = 13.5 Hz, 2H), 3.27-3.14 (m, 4H), 1.66 (d, J = 7.0 Hz, 3H) | Example 59 |
| Example 67 | 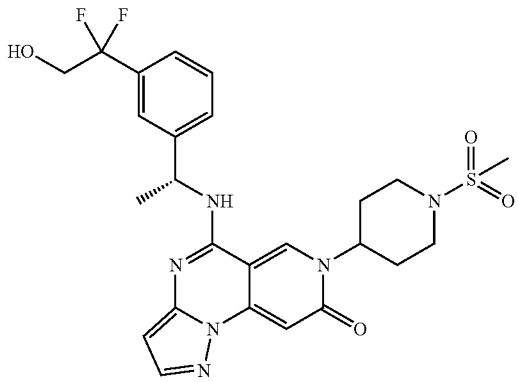 [SMILES: C[C@@H](Nc1nc2ccnn2c2cc(=O)n(C3CCN(S(C)(=O)=O)CC3)cc12)c1cccc(C(F)(F)CO)c1] (R)-5-((1-(3-(1,1-difluoro-2-hydroxyethyl)phenyl)ethyl)amino)-7-(1-(methylsulfonyl)piperidin-4-yl)pyrazolo[1,5-a]pyrido[3,4-e]pyrimidin-8(7H)-one | LCMS: m/z 547 $(M + H)^+$. $^1$H NMR (400 MHz, MeOD) δ 8.95 (s, 1H), 7.75 (d, J = 2.0 Hz, 1H), 7.62 (s, 1H), 7.56 (d, J = 7.2 Hz, 1H), 7.45-7.39 (m, 2H), 6.90 (s, 1H), 5.98 (d, J = 2.0 Hz, 1H), 5.53 (d, J = 6.9 Hz, 1H), 5.16 (s, 1H), 4.58 (s, 2H), 3.96 (d, J = 12.5 Hz, 2H), 3.87 (t, J = 13.5 Hz, 2H), 3.01 (t, J = 11.0 Hz, 2H), 2.91 (s, 3H), 2.16 (d, J = 4.1 Hz, 2H), 1.65 (d, J = 7.0 Hz, 3H). | Example 59 |
| Example 68 | 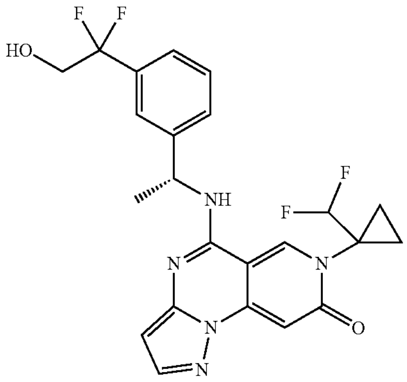 [SMILES: C[C@@H](Nc1nc2ccnn2c2cc(=O)n(C3(C(F)F)CC3)cc12)c1cccc(C(F)(F)CO)c1] (R)-5-((1-(3-(1,1-difluoro-2-hydroxyethyl)phenyl)ethyl)amino)-7-(1-(difluoromethyl)cyclopropyl)pyrazolo[1,5-a]pyrido[3,4-e]pyrimidin-8(7H)-one | LC/MS (ESI) m/z: 476 $(M + H)^+$. $^1$H NMR (400 MHz, DMSO) δ 9.11 (s, 1H), 8.31 (d, J = 7.6 Hz, 1H), 7.77 (d, J = 1.9 Hz, 1H), 7.59 (s, 1H), 7.56 (d, J = 7.6 Hz, 1H), 7.45 (t, J = 7.6 Hz, 1H), 7.39 (d, J = 7.7 Hz, 1H), 6.59 (s, 1H), 6.31 (t, J = 56.7 Hz, 1H), 5.94 (d, J = 1.9 Hz, 1H), 5.60 (t, J = 6.2 Hz, 1H), 5.56-5.49 (m, 1H), 3.89-3.80 (m, 2H), 1.58 (d, J = 7.0 Hz, 3H), 1.49 (s, 2H), 1.41 (s, 2H). | Example 59 |

TABLE 6-continued

| Ex# | Structure & name | Analytical data | Method |
|---|---|---|---|
| Example 69 | 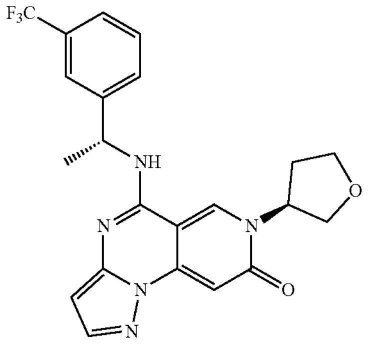 [SMILES: C[C@@H](Nc1nc2ccnn2c2cc(=O)n([C@H]3CCOC3)cc12)c1cccc(C(F)(F)F)c1] 7-((S)-tetrahydrofuran-3-yl)-5-(((R)-1-(3-(trifluoromethyl)phenyl)ethyl)amino)pyrazolo[1,5-a]pyrido[3,4-e]pyrimidin-8(7H)-one | LC/MS (ESI) m/z: 444 $(M + H)^+$. $^1$HNMR (400 MHz, MeOD-$d_4$) δ 8.75 (s, 1H), 7.82-7.64 (m, 3H), 7.53-7.51 (m, 2H), 6.88 (s, 1H), 5.96 (d, J = 2.0 Hz, 1H), 5.66 5.57 (m, 1H), 5.53 (q, J = 7.1 Hz,1H), 4.28-4.22 (m, 1H), 4.15-4.12 (m, 1H), 4.06-4.02 (m, 1H), 3.89 (dd, J = 15.8, 8.3 Hz, 1H), 2.67-2.53 (m, 1H), 2.32-2.18 (m, 1H), 1.66 (d, J = 7.1 Hz, 3H). | Example 59 |
| Example 70 | 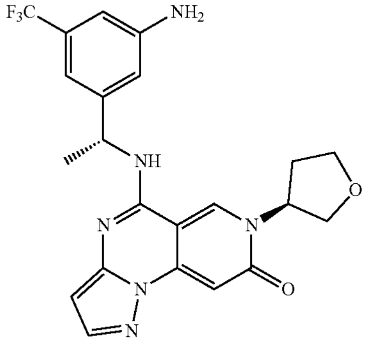 [SMILES: C[C@@H](Nc1nc2ccnn2c2cc(=O)n([C@H]3CCOC3)cc12)c1cc(N)cc(C(F)(F)F)c1] 5-(((R)-1-(3-amino-5-(trifluoromethyl)phenyl)ethyl)amino)-7-((S)-tetrahydrofuran-3-yl)pyrazolo[1,5-a]pyrido[3,4-e]pyrimidin-8(7H)-one | LC/MS (ESI) m/z: 459 $(M + H)^+$. $^1$HNMR (400 MHz, MeOD-$d_4$) δ 8.75 (s, 1H), 7.75 (d, J = 1.9 Hz, 1H), 6.97 (s, 2H), 6.89 (s, 1H), 6.80 (s, 1H), 5.99 (d, J = 1.9 Hz, 1H), 5.61 (dt, J = 8.3, 4.0 Hz, 1H), 5.43 (q, J = 7.0 Hz, 1H), 4.25 (td, J = 8.5, 5.3 Hz, 1H), 4.12 (dd, J = 10.4, 3.4 Hz, 1H), 4.04 (dd, J = 10.4, 6.4 Hz, 1H), 3.89 (dd, J = 15.9, 8.2 Hz, 1H), 2.70-2.55 (m, 1H), 2.30-2.20 (m, 1H), 1.61 (d, J = 7.0 Hz, 3H) | Example 59 |
| Example 71 | 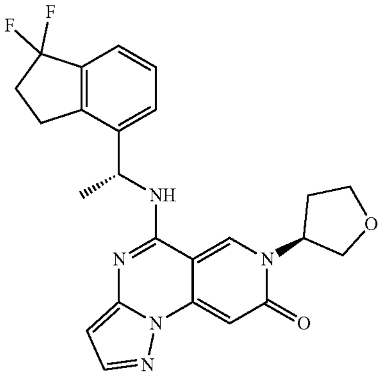 [SMILES: C[C@@H](Nc1nc2ccnn2c2cc(=O)n([C@H]3CCOC3)cc12)c1cccc2c1CCC2(F)F] 5-(((R)-1-(1,1-difluoro-2,3-dihydro-1H-inden-4-yl)ethyl)amino)-7-((S)-tetrahydrofuran-3-yl)pyrazolo[1,5-a]pyrido[3,4-e]pyrimidin-8(7H)-one | LC/MS (ESI) m/z: 452 $(M + H)^+$ $^1$HNMR (400 MHz, $CD_3OD$-$d_4$) δ 8.74 (d, J = 2.8 Hz, 1H), 7.73 (dd, J = 3.9, 2.0 Hz, 1H), 7.58 (d, J = 7.2 Hz, 1H), 7.36 (dq, J = 14.9, 7.6 Hz, 2H), 6.85 (d, J = 6.0 Hz, 1H), 5.94 (dd, J = 3.1, 2.0 Hz, 1H), 5.66-5.55 (m, 1H), 5.51 (q, J = 6.9 Hz, 1H), 4.58 (s, 1H), 4.30-4.20 (m, 1H), 4.15-4.05 (m, 1H), 4.06-3.99 (m, 1H), 3.88 (dd, J = 16.1, 7.9 Hz, 1H), 3.16-3.03 (m, 1H), 2.69 2.51 (m, 3H), 2.28-2.15 (m, 1H), 1.63 (d, J = 7.0 Hz, 3H) | Example 59 |

TABLE 6-continued

| Ex# | Structure & name | Analytical data | Method |
|---|---|---|---|
| Example 72 | 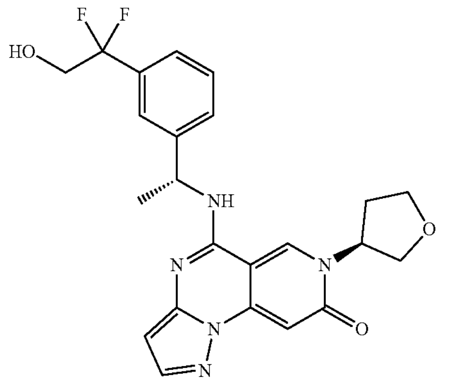 [SMILES: C[C@@H](Nc1nc2ccnn2c2cc(=O)n([C@H]3CCOC3)cc12)c1cccc(C(F)(F)CO)c1]<br>5-(((R)-1-(3-(1,1-difluoro-2-hydroxyethyl)phenyl)ethyl)amino)-7-((S)-tetrahydrofuran-3-yl)pyrazolo[1,5-a]pyrido[3,4-e]pyrimidin-8(7H)-one | LC/MS (ESI) m/z: 456 $(M + H)^+$. $^1$HNMR (400 MHz, MeOD-$d_4$) δ 8.67 (s, 1H), 7.65 (d, J = 2.0 Hz, 1H), 7.53 (s, 1H), 7.47 (d, J = 7.2 Hz, 1H), 7.37-7.26 (m, 2H), 6.79 (s, 1H), 5.89 (d, J = 2.0 Hz, 1H), 5.51 (dt, J = 7.9, 3.9 Hz, 1H), 5.43 (q, J = 7.0 Hz, 1H), 4.15 (td, J = 8.5, 5.3 Hz, 1H), 4.03 (dd, J = 10.4, 3.2 Hz, 1H), 3.95 (dd, J = 10.4, 6.4 Hz, 1H), 3.83-3.74 (m, 3H), 2.57-2.50 (m, 1H), 2.20-2.09 (m, 1H), 1.56 (d, J = 7.0 Hz, 3H). | Example 59 |
| Example 73 | 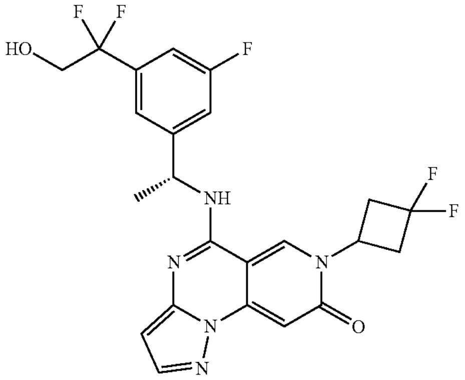 [SMILES: C[C@@H](Nc1nc2ccnn2c2cc(=O)n(C3CC(F)(F)C3)cc12)c1cc(F)cc(C(F)(F)CO)c1]<br>(R)-5-((1-(3-(1,1-difluoro-2-hydroxyethyl)-5-fluorophenyl)ethyl)amino)-7-(3,3-difluorocyclobutyl)pyrazolo[1,5-a]pyrido[3,4-e]pyrimidin-8(7H)-one | LC/MS (ESI) (m/z): 494 $(M + H)^+$. $^1$HNMR (400 MHz, $CD_3OD$-$d_4$) δ 8.87 (s, 1H), 7.75 (d, J = 2.0 Hz, 1H), 7.46 (s, 1H), 7.33 (d, J = 9.6 Hz, 1H), 7.14 (d, J = 9.0 Hz, 1H), 6.86 (s, 1H), 5.99 (d, J = 2.0 Hz, 1H), 5.50 (q, J = 6.9 Hz, 1H), 3.88 (t, J = 13.3 Hz, 2H), 3.28-3.15 (m, 4H), 1.65 (d, J = 7.1 Hz, 3H). | Example 59 |

Example 74: Synthesis of 8-{[(1R)-1-(5-{2-[(methylamino)methyl]phenyl}thiophen-2-yl)ethyl]amino}-11-(1-methylcyclopropyl)-2,3,7,11-tetraazatricyclo[7.4.0.0^{2,6}]trideca-1(13),3,5,7,9-pentaen-12-one. (The Title Compound was Synthesized from Intermediate in Example 61.)

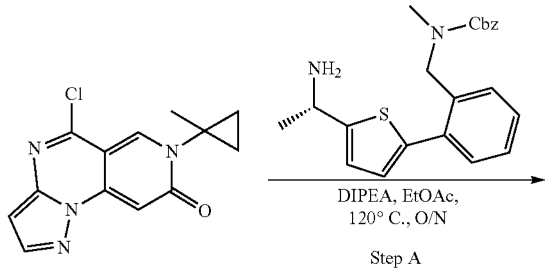

9

-continued

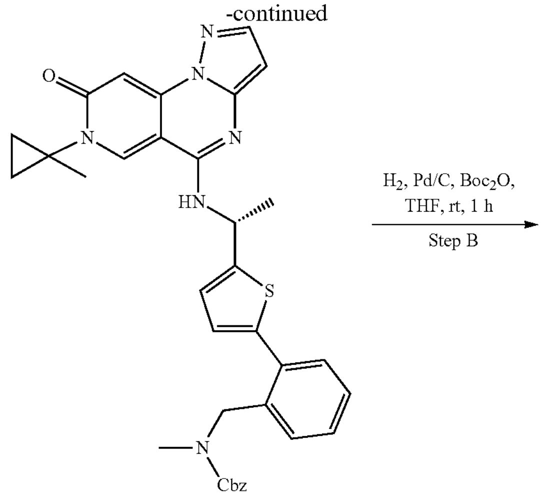

10

-continued

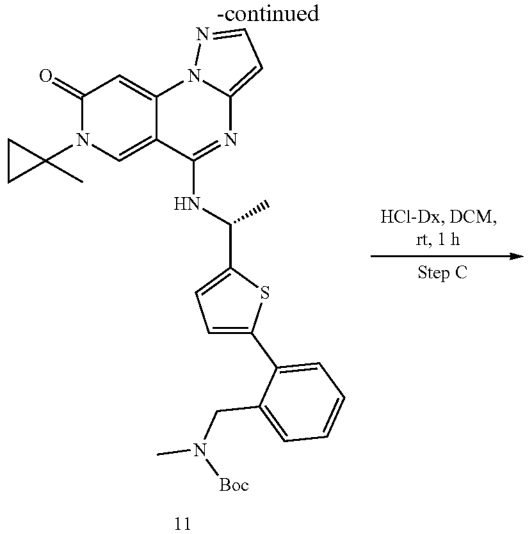

11

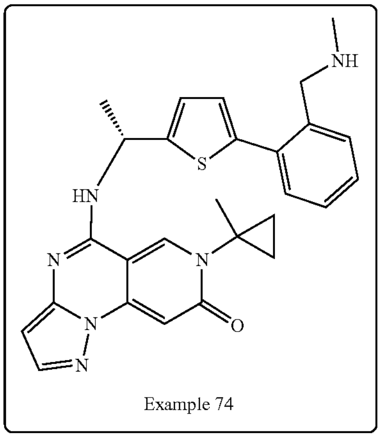 [SMILES: CNCc1ccccc1-c1ccc([C@@H](C)Nc2nc3ccnn3c3cc(=O)n(C4(C)CC4)cc23)s1]

Example 74

Step A. benzyl N-methyl-N-[(2-{5-[(1R)-1-{[11-(1-methylcyclopropyl)-12-oxo-2,3,7,11-tetraazatricyclo[7.4.0.0^{2,6}]trideca-1(13),3,5,7,9-pentaen-8-yl]amino}ethyl]thiophen-2-yl}phenyl)methyl]carbamate To a stirred solution of benzyl N-[(2-{5-[(1S)-1-aminoethyl]thiophen-2-yl}phenyl) methyl]-N-methylcarbamate (55 mg, 0.15 mmol) in EtOH (5 mL) was added 8-chloro-11-(1-methylcyclopropyl)-2,3,7,11-tetraazatricyclo[7.4.0.0^{2,6}]trideca-1(13),3,5,7,9-pentaen-12-one (20 mg, 0.07 mmol) and DIPEA (0.1 mL, 0.22 mmol) at rt. After stirred at 120° C. overnight, the mixture was poured into water (10 ml) and extracted with DCM (5 ml*2). The combined organic phase was washed with brine, dried over $Na_2SO_4$, filtered and concentrated. The residue was purified by chromatography (silica gel, 0-15%, MeOH in DCM) to give benzyl N-methyl-N-[(2-{5-[(1R)-1-{[11-(1-methylcyclopropyl)-12-oxo-2,3,7,11-tetraazatricyclo[7.4.0.0^{2,6}]trideca-1(13),3,5,7,9-pentaen-8-yl]amino}ethyl]thiophen-2-yl}phenyl)methyl]carbamate (35 mg, 0.06 mmol, 77%) as a yellow solid. LCMS: m/z 619 $(M+H)^+$.

Step B. tert-butyl N-methyl-N-[(2-{5-[(1R)-1-{[11-(1-methylcyclopropyl)-12-oxo-2,3,7,11-tetraazatricyclo[7.4.0.0^{2,6}]trideca-1(13),3,5,7,9-pentaen-8-yl]amino}ethyl]thiophen-2-yl}phenyl)methyl]carbamate To a stirred solution of benzyl N-methyl-N-[(2-{5-[(1R)-1-{[11-(1-methylcyclopropyl)-12-oxo-2,3,7,11-tetraazatricyclo[7.4.0.0^{2,6}]trideca-1(13),3,5,7,9-pentaen-8-yl]amino}ethyl]thiophen-2-yl}phenyl)methyl]carbamate (35 mg, 0.06 mmol) in THF (3 mL) was added 10% Pd—C (7 mg, 0.006 mmol) and $Boc_2O$ (0.1 mL, 0.6 mmol) at rt. After stirred at rt using a $H_2$ balloon for 1 h, the mixture was filtered. The filtrate was concentrated and purified by prep-TLC (DCM:MeOH=10:1) to give tert-butyl N-methyl-N-[(2-{5-[(1R)-1-{[11-(1-methylcyclopropyl)-12-oxo-2,3,7,11-tetraazatricyclo[7.4.0.0^{2,6}]trideca-1(13),3,5,7,9-pentaen-8-yl]amino}ethyl]thiophen-2-yl}phenyl)methyl]carbamate (20 mg, 0.03 mmol, 60%) as a yellow solid. LCMS: m/z 585 $(M+H)^+$.

Step C. 8-{[(1R)-1-(5-{2-[(methylamino)methyl]phenyl}thiophen-2-yl)ethyl]amino}-11-(1-methylcyclopropyl)-2,3,7,11-tetraazatricyclo[7.4.0.0^{2,6}]trideca-1(13),3,5,7,9-pentaen-12-one To a stirred mixture of tert-butyl N-methyl-N-[(2-{5-[(1R)-1-{[11-(1-methylcyclopropyl)-12-oxo-2,3,7,11-tetraazatricyclo[7.4.0.0^{2,6}]trideca-1(13),3,5,7,9-pentaen-8-yl]amino}ethyl]thiophen-2-yl}phenyl)methyl]carbamate (20 mg, 0.034 mmol) in DCM (1 mL) was added HCl-Dx (1 mL, 4 mol/L) at rt. After stirred at rt for 1 h, the mixture was concentrated. The residue was purified by prep-TLC (DCM:MeOH=8:1) and then prep-HPLC (C18, 40~90% MeCN in $H_2O$ with 0.1% HCOOH) to give 8-{[(1R)-1-(5-{2-[(methylamino)methyl]phenyl}thiophen-2-yl)ethyl]amino}-11-(1-methylcyclopropyl)-2,3,7,11-tetraazatricyclo[7.4.0.0^{2,6}]trideca-1(13),3,5,7,9-pentaen-12-one (8 mg, 0.02 mmol, 48%) as a yellow solid. LCMS: m/z 485 $(M+H)^+$. $^1H$ NMR (400 MHz, MeOD) δ 9.07 (s, 1H), 8.51 (s, 1H), 7.77 (d, J=1.9 Hz, 1H), 7.53 (dd, J=7.5, 2.0 Hz, 1H), 7.47-7.45 (m, 2H), 7.15 (d, J=3.3 Hz, 1H), 6.98 (d, J=3.6 Hz, 1H), 6.84 (s, 1H), 6.05 (d, J=1.9 Hz, 1H), 5.82 (d, J=6.9 Hz, 1H), 4.26 (s, 2H), 2.56 (s, 3H), 1.79 (d, J=7.0 Hz, 3H), 1.59 (s, 3H), 1.21 (d, J=5.4 Hz, 2H), 1.10 (d, J=2.7 Hz, 2H).

Example 75: 11-(1-acetylpiperidin-4-yl)-8-{[(1R)-1-[3-(1,1-difluoro-2-hydroxyethyl)phenyl]ethyl]amino}-2,3,7,11-tetraazatricyclo[7.4.0.0^{2,6}]trideca-1(13),3,5,7,9-pentaen-12-one

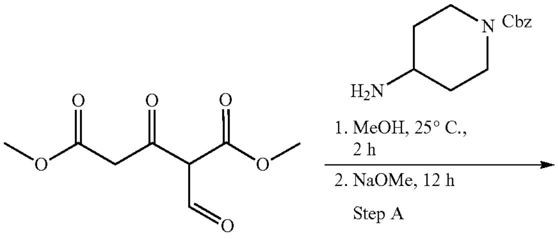

1

-continued

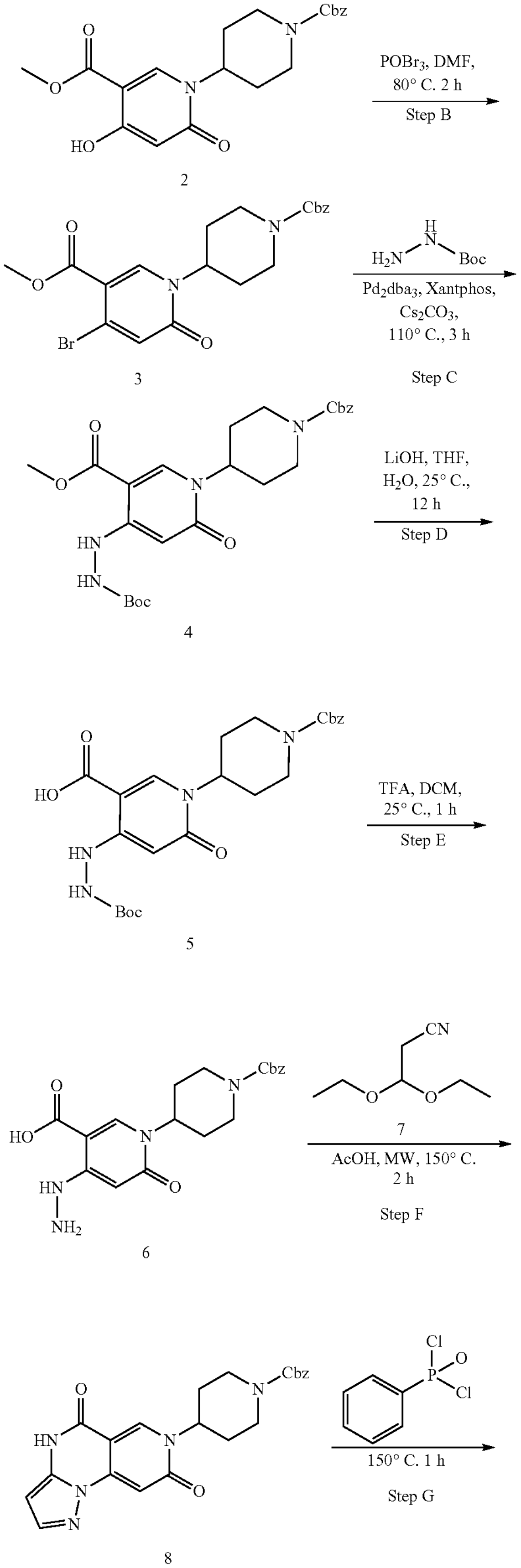

-continued

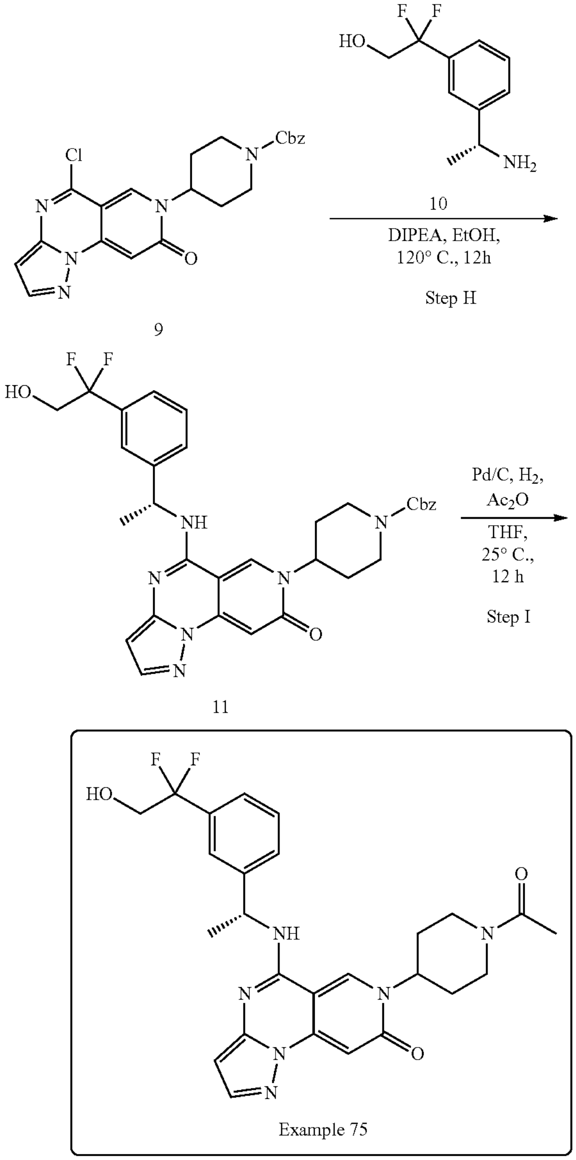

Step A. methyl 1-{1-[(benzyloxy)carbonyl]piperidin-4-yl}-4-hydroxy-6-oxo-1,6-dihydropyridine-3-carboxylate To a stirred solution of 1,5-dimethyl 2-formyl-3-oxopentanedioate (2.5 g, 12.3 mmol) in $CH_3OH$ (20 mL) at 25° C. was added benzyl 4-aminopiperidine-1-carboxylate (2.90 g, 12.4 mmol). The reaction mixture was stirred at 25° C. for 2 hrs under nitrogen atmosphere before MeONa (2.5 mL, 30% in $CH_3OH$) was added. The resulting solution was stirred at 25° C. for 12 hrs. The reaction mixture was adjusted to pH=5 with diluted hydrochloric acid (1 M) and extracted with DCM (40 mL×3). The combined organic phase was washed by water and brine. The organic phase was dried over anhydrous $Na_2SO_4$, filtered and concentrated to give a crude product. The residue was purified by chromatography on silica gel (DCM:MeOH=50: 1-20:1) to give desired product methyl 1-{1-[(benzyloxy)carbonyl]piperidin-4-yl}-4-hydroxy-6-oxo-1,6-dihydropyridine-3-carboxylate (1.8 g, 37%) as a yellow solid. LC/MS (ESI) m/z: 387 $(M+H)^+$.

Step B: methyl 1-{1-[(benzyloxy)carbonyl]piperidin-4-yl}-4-bromo-6-oxo-1,6-dihydropyridine-3-carboxylate To a stirred solution of methyl 1-{1-[(benzyloxy)carbonyl]piperidin-4-yl}-4-hydroxy-6-oxo-1,6-dihydropyridine-3-carboxylate (1.80 g, 4.65 mmol) in DMF (20 mL) was added POBr3 (1.60 g, 5.50 mmol). The reaction mixture was stirred at 80° C. for 2 hrs under nitrogen atmosphere. The reaction mixture was poured into ice-water (100 mL), extracted with EtOAc (100 mL*3). The combined organic phase was washed by water and brine, the organic phase was dried over anhydrous $Na_2SO_4$, filtered and concentrated to give a crude product, which was purified by column chromatography on silica gel (DCM:MeOH=100:1 to 30:1) to obtain methyl 1-{1-[(benzyloxy)carbonyl]piperidin-4-yl}-4-bromo-6-oxo-1,6-dihydropyridine-3-carboxylate (1.50 g, 71%) as a yellow solid. LC/MS (ESI) m/z: 449 $(M+H)^+$.

Step C: methyl 1-{1-[(benzyloxy)carbonyl]piperidin-4-yl}-4-({[(tert-butoxy)carbonyl]amino}amino)-6-oxo-1,6-dihydropyridine-3-carboxylate To a stirred mixture of methyl 1-{1-[(benzyloxy)carbonyl]piperidin-4-yl}-4-bromo-6-oxo-1,6-dihydropyridine-3-carboxylate (1.5 g, 3.33 mmol), (tert-butoxy)carbohydrazide (0.66 g, 5.00 mmol), XANT PHOS (0.19 g, 0.334 mmol) and $Cs_2CO_3$ (3.26 g, 10.0 mmol) in 1,4-dioxane (20 mL) at room temperature was added $Pd2(dba)_3$ (0.15 g, 0.167 mmol). The reaction mixture was stirred at 110° C. under nitrogen atmosphere for 3 hrs. The cooled reaction mixture was filtered and concentrated to give a crude product which was purified by column chromatography on silica gel (DCM:MeOH=100:1 to 20:1) to obtain methyl 1-{1-[(benzyloxy)carbonyl]piperidin-4-yl}-4-({[(tert-butoxy)carbonyl]amino}amino)-6-oxo-1,6-dihydropyridine-3-carboxylate (1 g, 59%) as a yellow solid. LC/MS (ESI) m/z: 501 $(M+H)^+$.

Step D: 1-{1-[(benzyloxy)carbonyl]piperidin-4-yl}-4-({[(tert-butoxy)carbonyl]amino}amino)-6-oxo-1,6-dihydropyridine-3-carboxylic acid To a stirred solution of methyl 1-{1-[(benzyloxy)carbonyl]piperidin-4-yl}-4-({[(tert-butoxy)carbonyl] amino}amino)-6-oxo-1,6-dihydropyridine-3-carboxylate (1 g, 1.99 mmol) in $H_2O$ (1 mL) and THE (10 mL) was added LiOH (170 mg, 3.99 mmol). The reaction mixture was stirred at 25° C. for 2 hrs. The reaction mixture was diluted with ice-water (30 mL). THE was removed by reduce power. The mixture was adjust pH to 5-6 with 2N HCl, extracted with DCM (50 mL*3). The combined organic phase was washed by water and brine, dried over anhydrous $Na_2SO_4$, filtered and concentrated to give a crude product which was purified by column chromatography on silica gel (DCM: MeOH=10: 1-5:1) to obtain 1-{1-[(benzyloxy)carbonyl]piperidin-4-yl}-4-({[(tert-butoxy)carbonyl]amino}amino)-6-oxo-1,6-dihydropyridine-3-carboxylic acid (500 mg, 51%) as a brown solid. LC/MS (ESI) m/z: 487 $(M+H)^+$.

Step E: 1-{1-[(benzyloxy)carbonyl]piperidin-4-yl}-4-hydrazinyl-6-oxo-1,6-dihydropyridine-3-carboxylic acid To a stirred solution of 1-{1-[(benzyloxy)carbonyl]piperidin-4-yl}-4-({[(tert-butoxy)carbonyl]amino}amino)-6-oxo-1,6-dihydropyridine-3-carboxylic acid (0.3 g, 0.617 mmol) in DCM (1 mL) was added $CF_3COOH$ (1 mL). The result solution was stirred at 25° C. for 2 hrs. The reaction mixture was concentrated to give the desired product 1-{1-[(benzyloxy)carbonyl]piperidin-4-yl}-4-hydrazinyl-6-oxo-1,6-dihydropyridine-3-carboxylic acid (200 mg, 83%) as a brown solid. LC/MS (ESI) m/z: 387 $(M+H)^+$.

Step F: benzyl 4-{8,12-dioxo-2,3,7,11-tetraazatricyclo[7.4.0.0^{2,6}]trideca-1(13),3,5,9-tetraen-11-yl}piperidine-1-carboxylate To a stirred solution of 1-{1-[(benzyloxy)carbonyl]piperidin-4-yl}-4-hydrazinyl-6-oxo-1,6-dihydropyridine-3-carboxylic acid (200 mg, 0.518 mmol) in AcOH (2 mL) at room temperature was added 3,3-diethoxypropanenitrile (0.388 mL, 2.58 mmol). The reaction mixture was stirred at 160° C. under microwave for 2 hrs. The reaction mixture was concentrated to give a crude product which was purified by column chromatography on silica gel (DCM:MeOH=100:1 to 20:1) to obtain benzyl 4-{8,12-dioxo-2,3,7,11-tetraazatricyclo[7.4.0.0^{2,6}]trideca-1(13),3,5,9-tetraen-11-yl}piperidine-1-carboxylate (60 mg, 27%) as a yellow solid. LC/MS (ESI) m/z: 420 $(M+H)^+$.

Step G: benzyl 4-{8-chloro-12-oxo-2,3,7,11-tetraazatricyclo[7.4.0.0^{2,6}]trideca-1(13),3,5,7,9-pentaen-11-yl}piperidine-1-carboxylate A stirred solution of benzyl 4-{8,12-dioxo-2,3,7,11-tetraazatricyclo [7.4.0.0^{2,6}]trideca-1(13),3,5,9-tetraen-11-yl}piperidine-1-carboxylate (20 mg, 0.048 mmol) in phenylphosphonoyl dichloride (0.5 mL) was heated to 150° C. and stirred for 1 h under nitrogen atmosphere. The reaction mixture was cooled to room temperature and diluted with ice-water (5 mL). The mixture was extracted with EtOAc (5 mL*3), the combined organic phase was washed by sat. $NaHCO_3$and water and brine, dried over anhydrous $Na_2SO_4$, filtered and concentrated to give a crude product which was purified by column chromatography on silica gel (DCM: MeOH=20:1) to obtain benzyl 4-{8-chloro-12-oxo-2,3,7,11-tetraazatricyclo[7.4.0.0^{2,6}]trideca-1(13),3,5,7,9-pentaen-11-yl}piperidine-1-carboxylate (10 mg, 47%) as a yellow solid. LC/MS (ESI) m/z: 438 $(M+H)^+$.

Step H: benzyl 4-(8-{[(1R)-1-[3-(1,1-difluoro-2-hydroxyethyl)phenyl]ethyl]amino}-12-oxo-2,3,7,11-tetraazatricyclo[7.4.0.0^{2,6}]trideca-1(13),3,5,7,9-pentaen-11-yl)piperidine-1-carboxylate A mixture of benzyl 4-{8-chloro-12-oxo-2,3,7,11-tetraazatricyclo[7.4.0.0^{2,6}]trideca-1(13),3,5,7,9-pentaen-11-yl}piperidine-1-carboxylate (20 mg, 0.046 mmol), 2-{3-[(1R)-1-aminoethyl]phenyl}-2,2-difluoroethan-1-ol (27 mg, 0.137 mmol) and EthyldiisopropylaMine (17 mg, 0.13 mmol) in EtOH (2 mL) in a sealed tube stirred at 120° C. for 12 hrs, The reaction mixture was concentrated and the residue was diluted with water (5 mL). The mixture was extracted with EtOAc (5 mL*3), the combined organic phase was washed by water and brine, the organic phase was dried over anhydrous $Na_2SO_4$, filtered and concentrated to give the crude product which was purified by prep-TLC (DCM:MeOH=20:1) to obtain benzyl 4-(8-{[(1R)-1-[3-(1,1-difluoro-2-hydroxyethyl)phenyl]ethyl]amino}-12-oxo-2,3,7,11-tetraazatricyclo [7.4.0.0^{2,6}]trideca-1(13),3,5,7,9-pentaen-11-yl)piperidine-1-carboxylate (8 mg, 29%) as a yellow solid. LC/MS (ESI) m/z: 603 $(M+H)^+$.

Step I: 11-(1-acetylpiperidin-4-yl)-8-{[(1R)-1-[3-(1,1-difluoro-2-hydroxyethyl)phenyl]ethyl]amino}-2,3,7,11-tetraazatricyclo[7.4.0.0^{2,6}]trideca-1(13),3,5,7,9-pentaen-12-one To a solution of benzyl 4-(8-{[(1R)-1-[3-(1,1-difluoro-2-hydroxyethyl)phenyl]ethyl]amino}-12-oxo-2,3,7,11-tetraazatricyclo[7.4.0.0^{2,6}]trideca-1(13),3,5,7,9-pentaen-11-yl)piperidine-1-carboxylate (8 mg, 0.013 mmol) in THE (1 mL) was added Pd/C 10% (1 mg), acetic anhydride (2 mg, 0.026 mmol). The reaction mixture was stirred at 25° C. under $H_2$ atmosphere for 12 hrs. The reaction mixture was filtered and concentrated to give a crude product which was purified by column chromatography on silica gel (DCM:MeOH=100:1 to 10:1) to obtain 11-(1-acetylpiperidin-4-yl)-8-{[(1R)-1-[3-(1,1-difluoro-2-hydroxyethyl)phenyl]ethyl]amino}-2,3,7,11-tetraazatricyclo[7.4.0.0^{2,6}]trideca-1(13),3,5,7,9-pentaen-12-one (3 mg, 0.006 mmol, 45.2%) as a yellow solid. LC/MS (ESI) m/z: 511 $(M+H)^+$ $^1H$ NMR (400 MHz, MeOD) δ 8.88 (s, 1H), 7.75 (d, J=1.9 Hz, 1H), 7.62 (s, 1H), 7.56 (d, J=7.3 Hz, 1H), 7.45-7.37 (m, 2H), 6.90 (s, 1H), 5.98 (d, J=1.9 Hz, 1H), 5.58-5.49 (m, 1H), 5.31-5.21 (m, 1H), 4.79-4.76 (m, 1H), 4.15 (d, J=12.4 Hz, 1H), 3.87 (t, J=13.4 Hz, 2H), 2.80 (d, J=14.0 Hz, 1H), 2.18 (d, J=2.5 Hz, 3H), 2.09-1.91 (m, 5H), 1.65 (d, J=7.1 Hz, 3H).

Example 76: Synthesis of (R)-5-((1-(3-(1,1-difluoro-2-hydroxyethyl)phenyl)ethyl)amino)-7-(1-methylpiperidin-4-yl)pyrazolo[1,5-a]pyrido[3,4-e]pyrimidin-8(7H)-one. (The Title Compound was Synthesized from Compound 11 in Example 75.)

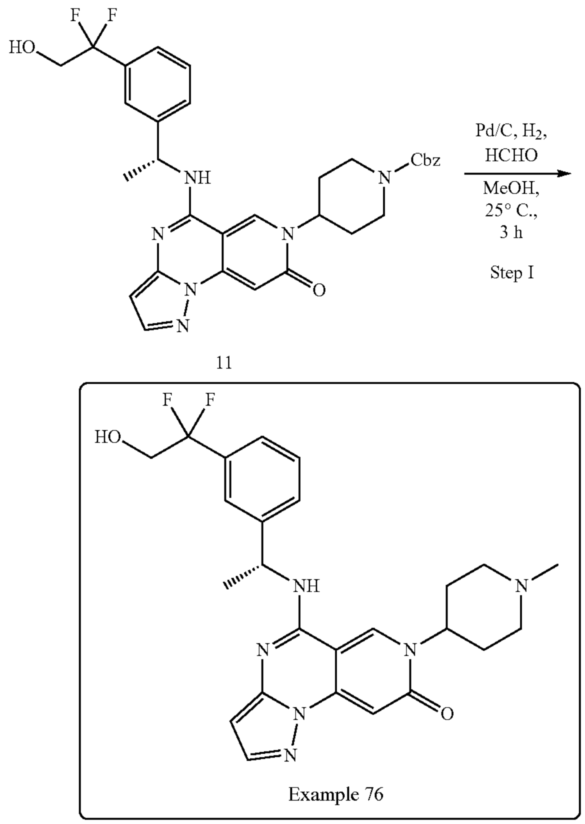

11

Example 76

Step I: (R)-5-((1-(3-(1,1-difluoro-2-hydroxyethyl)phenyl)ethyl)amino)-7-(1-methylpiperidin-4-yl)pyrazolo[1,5-a]pyrido[3,4-e]pyrimidin-8(7H)-one To a stirred solution of benzyl 4-(8-{[(1R)-1-[3-(1,1-difluoro-2-hydroxyethyl)phenyl]ethyl]amino}-12-oxo-2,3,7,11-tetraazatricyclo[7.4.0.0^{2,6}]trideca-1(13),3,5,7,9-pentaen-11-yl)piperidine-1-carboxylate (30 mg, 0.05 mmol) in MeOH (2 mL) at room temperature was added $(CH_2O)n$ (14.9 mg, 0.498 mmol) and Pd/C (0.001 mL, 0.005 mmol) slowly. The reaction mixture was stirred at room temperature for 3 h using a $H_2$ balloon. The reaction mixture was filtered and concentrated to give the crude product which was purified by prep-TLC (DCM:MeOH=10:1) to obtain (R)-5-((1-(3-(1,1-difluoro-2-hydroxyethyl)phenyl)ethyl)amino)-7-(1-methylpiperidin-4-yl)pyrazolo[1,5-a]pyrido[3,4-e]pyrimidin-8(7H)-one (3 mg, 0.006 mmol, 12.5%) as a green solid. LC/MS (ESI) m/z: 483 $(M+H)^+$. $^1H$ NMR (400 MHz, MeOD) δ 8.82 (s, 1H), 7.75 (d, J=2.0 Hz, 1H), 7.64 (s, 1H), 7.57 (d, J=6.8 Hz, 1H), 7.49-7.35 (m, 2H), 6.89 (s, 1H), 5.99 (d, J=2.0 Hz, 1H), 5.58-5.53 (m, 1H), 3.87 (t, J=13.5 Hz, 2H), 3.48 (s, 1H), 3.13-3.06 (m, 2H), 2.39 (s, 3H), 2.30 (t, J=11.6 Hz, 2H), 2.07 (dd, J=27.5, 19.4 Hz, 4H), 1.67 (d, J=7.1 Hz, 3H).

Example 77: Synthesis of 8-{[(1R)-1-[3-(1,1-difluoro-2-hydroxyethyl)phenyl]ethyl]amino}-11-(piperidin-4-yl)-2,3,7,11-tetraazatricyclo[7.4.0.0^{2,6}]trideca-1(13),3,5,7,9-pentaen-12-one. (The Title Compound was Synthesized from Compound 11 in Example 75.)

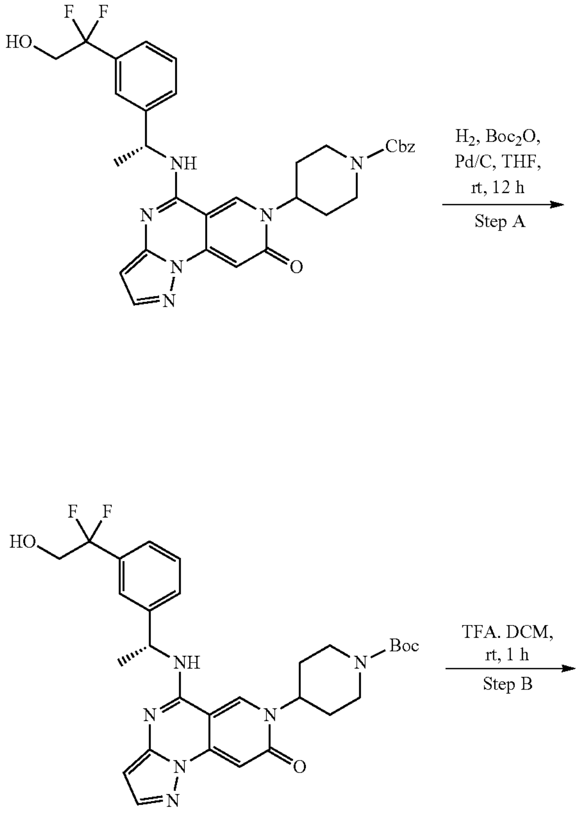

-continued

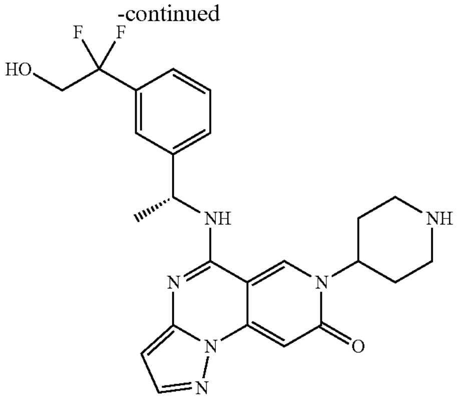

Example 77

Step A. tert-butyl 4-(8-{[(1R)-1-[3-(1,1-difluoro-2-hydroxyethyl)phenyl]ethyl]amino}-12-oxo-2,3,7,11-tetraazatricyclo[7.4.0.0^{2,6}]trideca-1(13),3,5,7,9-pentaen-11-yl)piperidine-1-carboxylate To a stirred solution of benzyl 4-(8-{[(1R)-1-[3-(1,1-difluoro-2-hydroxyethyl)phenyl]ethyl]amino}-12-oxo-2,3,7,11-tetraazatricyclo[7.4.0.0^{2,6}]trideca-1(13),3,5,7,9-pentaen-11-yl)piperidine-1-carboxylate (30 mg, 0.05 mmol) in THF (3 mL) at room temperature was added $(BOC)_2O$ (0.021 mL, 0.1 mmol) and Pd/C (0.005 mL, 0.050 mmol) slowly, the reaction mixture was stirred at room temperature for 12 h using a $H_2$ balloon. The reaction mixture was filtered and concentrated to give the crude product which was purified by prep-TLC (DCM:MeOH=20:1) to obtain tert-butyl 4-(8-{[(1R)-1-[3-(1,1-difluoro-2-hydroxyethyl)phenyl]ethyl]amino}-12-oxo-2,3,7,11-tetraazatricyclo[7.4.0.0^{2,6}]trideca-1(13),3,5,7,9-pentaen-11-yl)piperidine-1-carboxylate (18 mg, 0.032 mmol, 63.6%) as a green solid. LC/MS (ESI) m/z: 569 $(M+H)^+$.

Step B: 8-{[(1R)-1-[3-(1,1-difluoro-2-hydroxyethyl)phenyl]ethyl]amino}-11-(piperidin-4-yl)-2,3,7,11-tetraazatricyclo[7.4.0.0^{2,6}]trideca-1(13),3,5,7,9-pentaen-12-one To a stirred solution of tert-butyl 4-(8-{[(1R)-1-[3-(1,1-difluoro-2-hydroxyethyl)phenyl]ethyl]amino}-12-oxo-2,3,7,11-tetraazatricyclo[7.4.0.0^{2,6}]trideca-1(13),3,5,7,9-pentaen-11-yl)piperidine-1-carboxylate (18 mg, 0.032 mmol) in DCM (1 mL) at room temperature was added TFA (1 mL, 13.5 mmol) slowly, the reaction mixture was stirred at room temperature for 2 h under nitrogen atmosphere. The reaction mixture was concentrated to give the crude product which was purified by prep-TLC (DCM:MeOH=10:1) to obtain 8-{[(1R)-1-[3-(1,1-difluoro-2-hydroxyethyl)phenyl]ethyl]amino}-11-(piperidin-4-yl)-2,3,7,11-tetraazatricyclo[7.4.0.0^{2,6}]trideca-1(13),3,5,7,9-pentaen-12-one (2.8 mg, 0.006 mmol, 18.9%) as a green solid. LC/MS (ESI) m/z: 469 $(M+H)^+$. $^1H$ NMR (400 MHz, MeOD) δ 8.87 (s, 1H), 7.76 (d, J=1.9 Hz, 1H), 7.64 (s, 1H), 7.58 (d, J=6.8 Hz, 1H), 7.42 (d, J=7.3 Hz, 2H), 6.89 (s, 1H), 6.00 (d, J=1.9 Hz, 1H), 5.54 (d, J=6.7 Hz, 1H), 5.05 (s, 1H), 3.88 (t, J=13.4 Hz, 2H), 3.57 (d, J=12.3 Hz, 2H), 3.18 (dd, J=26.0, 11.4 Hz, 2H), 2.40 (d, J=11.9 Hz, 2H), 2.21 (d, J=12.5 Hz, 2H), 1.67 (d, J=7.1 Hz, 3H).

Example 78: (R)-5-((1-(3-(1,1-difluoro-2-hydroxyethyl)phenyl)ethyl)amino)-7-(3,3-difluorocyclobutyl)-3-fluoropyrazolo[1,5-a]pyrido[3,4-e]pyrimidin-8(7H)-one

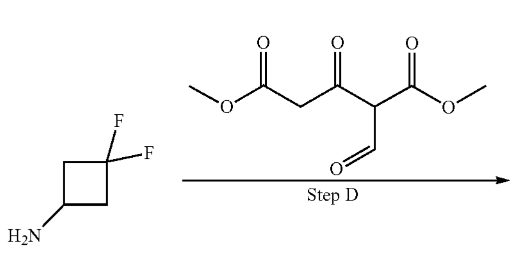

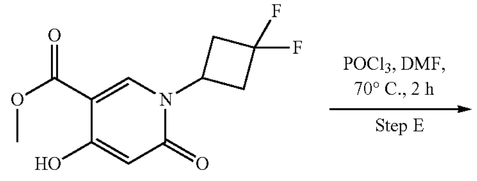

2

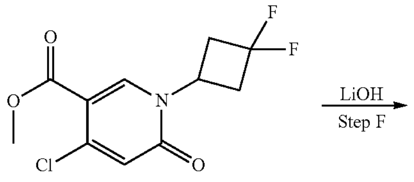

3

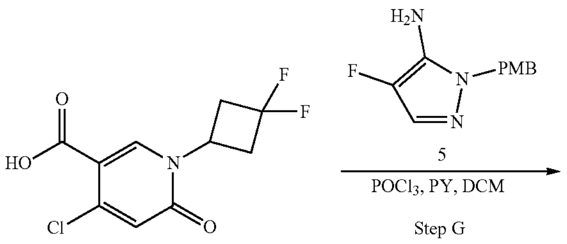

4

5

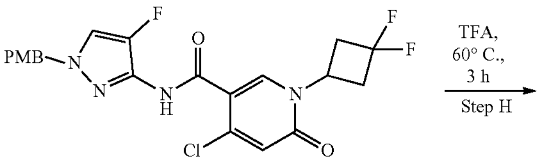

6

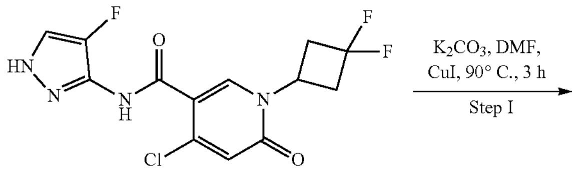

7

-continued

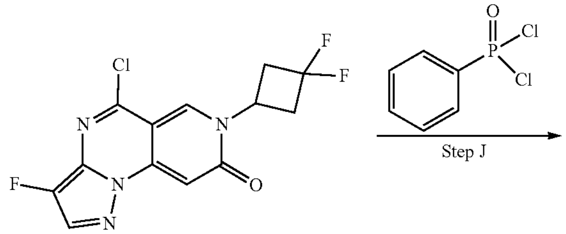

8

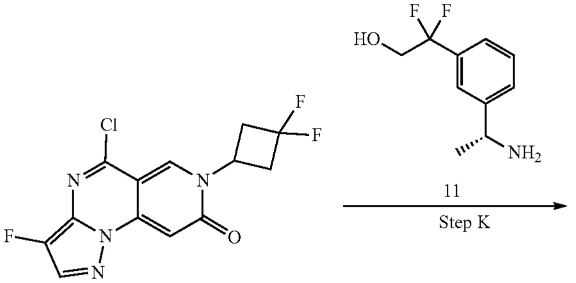

9

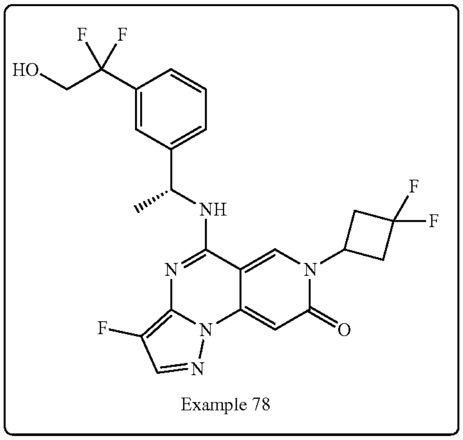

Example 78

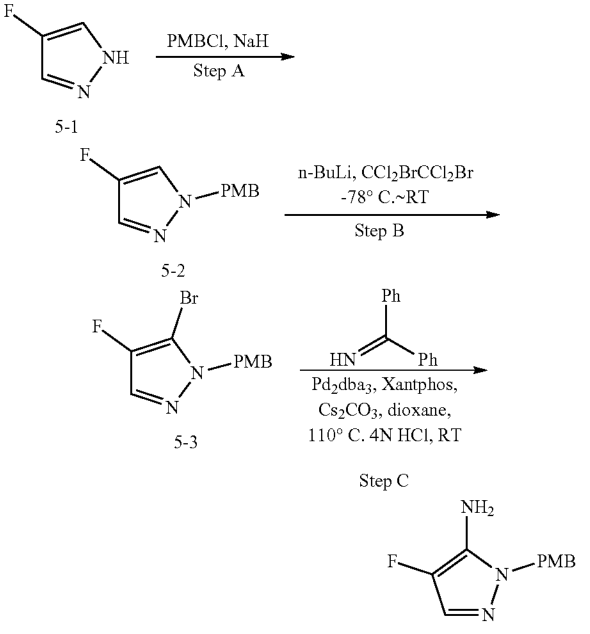

5-1

5-2

5-3

5

Step A: 4-fluoro-1-(4-methoxybenzyl)-1H-pyrazole

To a stirred solution of 4-fluoro-1H-pyrazole (1.0 g, 11.6 mmol) in anhydrous DMF (15 mL) at 0° C. was added NaH (600 mg, 15.1 mmol) by portions. The reaction mixture was stirred at 0° C. for 1 h under nitrogen atmosphere before 4-Methoxybenzylchloride (2.00 g, 12.8 mmol) was added. The resulting solution was stirred at room temperature for another 16 h. The reaction mixture was poured into ice-water (50 mL), extracted with EtOAc (50 mL×3). The combined organic phase was washed by water and brine, dried over anhydrous $Na_2SO_4$, filtered and concentrated to give a crude product which was purified by column chromatography on silica gel (PE:EtOAc=10:1 to 3:1) to obtain 4-fluoro-1-[(4-methoxyphenyl)methyl]-1H-pyrazole (2.2 g, 10.6 mmol, 91.8%) as a colorless oil. LC/MS (ESI) m/z: 207 $(M+H)^+$.

Step B: 3-bromo-4-fluoro-1-[(4-methoxyphenyl) methyl]-1H-pyrazole

To a stirred solution of 4-fluoro-1-[(4-methoxyphenyl) methyl]-1H-pyrazole (8.5 g, 41.2 mmol) in anhydrous THE (150 mL) at −78° C. was added n-Butyllithium (21.5 mL, 53.6 mmol) drop wise. The reaction mixture was stirred at −78° C. for 30 min under nitrogen atmosphere before a solution of 1,2-dibromo-1,1,2,2-tetrachloroethane (19 g, 58.2 mmol) in anhydrous THE (50 mL) was added drop wise. The result solution was allowed to warm to room temperature and stirred at room temperature for 2 h. The reaction mixture was quenched with saturated aqueous $NH_4Cl$ (100 mL) at 0° C. The mixture was extracted with EtOAc (100 mL×3). The combined organic phase was washed by water and brine, dried over anhydrous $Na_2SO_4$, filtered and concentrated to give a crude product which was purified by column chromatography on silica gel (PE:EtOAc=10:1 to 3:1) to obtain 3-bromo-4-fluoro-1-[(4-methoxyphenyl)methyl]-1H-pyrazole (10 g, 35 mmol, 85.1%) as a light yellow oil. LC/MS (ESI) m/z: 286 $(M+H)^+$.

Step C: 4-fluoro-1-[(4-methoxyphenyl)methyl]-1H-pyrazol-3-amine

To a stirred mixture of 3-bromo-4-fluoro-1-[(4-methoxyphenyl)methyl]-1H-pyrazole (10 g, 35 mmol), diphenylmethanimine (11.5 g, 52.6 mmol), $Cs_2CO_3$ (34.3 g, 105.2 mmol) and Xantphos (600 mg, 1 mmol) in anhydrous 1,4-dioxane (100 mL) was added Pd2(dba)$_3$ (960 mg, 1 mmol). The reaction mixture was stirred at 110° C. for 16 h under nitrogen atmosphere. The reaction mixture was diluted with water (100 mL), was extracted with EtOAc (100 mL×3). The combined organic phase was concentrated to give a brown solid. The above solid was dissolved in THE (100 mL) and cooled to 0° C., 4N HCl (100 mL) was added. The resulting solution was stirred at room temperature for 2 h. The mixture was extracted with EtOAc (80 mL), the organic phase was discarded. The water phase was adjusted pH to 8-9 with $NaHCO_3$, extracted with EtOAc (150 mL×3). The combined organic phase was washed by water and brine, dried over anhydrous $Na_2SO_4$, filtered and concentrated to give the crude product which was purified by column chromatography on silica gel (PE:EtOAc=10:1 to 1:1) to obtain 4-fluoro-1-[(4-methoxyphenyl)methyl]-1H-pyrazol-3-amine (4.4 g, 19.9 mmol, 56.7%) as a yellow oil. LC/MS (ESI) m/z: 222 $(M+H)^+$.

Step D: methyl 1-(3,3-difluorocyclobutyl)-4-hydroxy-6-oxo-1,6-dihydropyridine-3-carboxylate A stirred solution of 3,3-difluorocyclobutan-1-amine (5.0 g, 46.7 mmol) and 1,5-dimethyl 2-formyl-3-oxopentanedioate (10.4 g, 51.4 mmol) in MeOH (80 mL) was stirred at room temperature for 1 h under nitrogen atmosphere before sodium methanolate (18.7 mL, 30% in $CH_3OH$) was added. The result solution was stirred at room temperature for 16 h. The reaction mixture was diluted with ice-water (100 mL), adjusted pH to 5-6 with 1N HCl, extracted with DCM (100 mL×3). The combined organic phase was washed by water and brine, dried over anhydrous $Na_2SO_4$, filtered and concentrated to give a crude product which was purified by column chromatography on silica gel (PE:EtOAc=10:1 to 1:1) to obtain methyl 1-(3,3-difluorocyclobutyl)-4-hydroxy-6-oxo-1,6-dihydropyridine-3-carboxylate (3.0 g, 11.6 mmol, 24.8%) as a brown solid. LC/MS (ESI) m/z: 260 $(M+H)^+$.

Step E: methyl 1-(3,3-difluorocyclobutyl)-4-hydroxy-6-oxo-1,6-dihydropyridine-3-carboxylate To a stirred solution of methyl 1-(3,3-difluorocyclobutyl)-4-hydroxy-6-oxo-1,6-dihydropyridine-3-carboxylate (500 mg, 1.9 mmol) in DMF (10 mL) was added $POCl_3$ (0.9 mL, 9.6 mmol) slowly. The reaction mixture was stirred at 70° C. for 3 h under nitrogen atmosphere. The reaction mixture was diluted with ice-water (20 mL), extracted with EtOAc (30 mL×3). The combined organic phase was washed by water and brine, dried over anhydrous $Na_2SO_4$, filtered and concentrated to give a crude product which was purified by column chromatography on silica gel (PE:EtOAc=10:1 to 1:1) to obtain methyl 4-chloro-1-(3,3-difluorocyclobutyl)-6-oxo-1,6-dihydropyridine-3-carboxylate (370 mg, 1.3 mmol, 69.%) as an off-white solid. LC/MS (ESI) m/z: 278 $(M+H)^+$.

Step F: 4-chloro-1-(3,3-difluorocyclobutyl)-6-oxo-1,6-dihydropyridine-3-carboxylic acid To a stirred solution of methyl 4-chloro-1-(3,3-difluorocyclobutyl)-6-oxo-1,6-dihydropyridine-3-carboxylate (2.2 g, 7.9 mmol) in THE (20 mL) and $H_2O$ (20 mL) was added LiOH (1.6 g, 39.6 mmol), the reaction mixture was stirred at room temperature for 1 h. The reaction mixture was diluted with water (20 mL), extracted with EtOAc (50 mL). The organic phase was discarded. The aqueous phase was adjust pH to 5-6 with 2N HCl, extracted with EtOAc (50 mL×3). The combined organic phase was washed by water and brine, dried over anhydrous $Na_2SO_4$, filtered and concentrated to give a crude product 4-chloro-1-(3,3-difluorocyclobutyl)-6-oxo-1,6-dihydropyridine-3-carboxylic acid (1.6 g, 6.0 mmol, 76.6%) as a brown solid which was directly used for next step. LC/MS (ESI) m/z: 264 $(M+H)^+$.

Step G: 4-chloro-1-(3,3-difluorocyclobutyl)-N-{4-fluoro-1-[(4-methoxyphenyl)methyl]-1H-pyrazol-3-yl}-6-oxo-1,6-dihydropyridine-3-carboxamide To a stirred solution of 4-chloro-1-(3,3-difluorocyclobutyl)-6-oxo-1,6-dihydropyridine-3-carboxylic acid (2.0 g, 7.6 mmol) 4-fluoro-1-[(4-methoxyphenyl)methyl]-1H-pyrazol-3-amine (1.7 g, 7.6 mmol) and pyridine (3.00 g, 37.9 mmol) in DCM (30 mL) at 0° C. was added $POCl_3$ (2.3 g, 15 mmol) slowly. The reaction mixture was stirred at room temperature for 3 h under nitrogen atmosphere. The reaction mixture was poured into ice-water (50 mL), extracted with EtOAc (50 mL×3). The combined organic phase was washed by water and brine, dried over anhydrous $Na_2SO_4$, filtered and concentrated to give a crude product which was purified by column chromatography on silica gel (EtOAc in PE: 0-100%) to obtain 4-chloro-1-(3,3-difluorocyclobutyl)-N-{4-fluoro-1-[(4-methoxyphenyl)methyl]-1H-pyrazol-3-yl}-6-oxo-1,6-dihydropyridine-3-carboxamide (1.5 g, 3.2 mmol, 42%) as a yellow solid. LC/MS (ESI) m/z: 467 $(M+H)^+$.

Step H: 4-chloro-1-(3,3-difluorocyclobutyl)-N-(4-fluoro-1H-pyrazol-3-yl)-6-oxo-1,6-dihydropyridine-3-carboxamide A solution of 4-chloro-1-(3,3-difluorocyclobutyl)-N-{4-fluoro-1-[(4-methoxyphenyl) methyl]-1H-pyrazol-3-yl}-6-oxo-1,6-dihydropyridine-3-carboxamide (1.5 g, 3.2 mmol) in $CF_3COOH$ (8 mL) was stirred at 60° C. for 3 h under nitrogen atmosphere. The reaction mixture was concentrated and the residue was diluted with ice-water (20 mL), adjust pH to 7-8 with $NaHCO_3$. The following mixture was extracted with EtOAc (50 mL×3), washed by water and brine, dried over anhydrous $Na_2SO_4$, filtered and concentrated to give a crude product which was purified by column chromatography on silica gel (PE:EtOAc=10:1 to 1:1) to obtain 4-chloro-1-(3,3-difluorocyclobutyl)-N-(4-fluoro-1H-pyrazol-3-yl)-6-oxo-1,6-dihydropyridine-3-carboxamide (770 mg, 2.2 mmol, 69.1%) as a yellow solid. LC/MS (ESI) m/z: 347 $(M+H)^+$.

Step I: 11-(3,3-difluorocyclobutyl)-5-fluoro-2,3,7,11-tetraazatricyclo[7.4.0.0^{2,6}]trideca-1(13),3,5,9-tetraene-8,12-dione To a stirred mixture of 4-chloro-1-(3,3-difluorocyclobutyl)-N-(4-fluoro-1H-pyrazol-3-yl)-6-oxo-1,6-dihydropyridine-3-carboxamide (300 mg, 0.9 mmol), $K_2CO_3$ (358 mg, 2.6 mmol) in DMF (6 mL) was added CuI (32 mg, 0.17 mmol). The reaction mixture was stirred at 90° C. for 3 h under nitrogen atmosphere. The reaction mixture was diluted with ice-water (20 mL), adjusted pH to 5-6 with 1N HCl. The mixture was extracted with EtOAc (30 mL×3). The combined organic phase was washed by water and brine, dried over anhydrous $Na_2SO_4$, filtered and concentrated to give crude product which was purified by column chromatography on silica gel (DCM:MeOH=100:1 to 20:1) to obtain 11-(3,3-difluorocyclobutyl)-5-fluoro-2,3,7,11-tetraazatricyclo[7.4.0.0^{2,6}]trideca-1(13),3,5,9-tetraene-8,12-dione (200 mg, 0.6 mmol, 74.5%) as a yellow solid. LC/MS (ESI) m/z: 311 $(M+H)^+$.

Step J: 8-chloro-11-(3,3-difluorocyclobutyl)-5-fluoro-2,3,7,11-tetraazatricyclo [7.4.0.0^{2,6}]trideca-1(13),3,5,7,9-pentaen-12-one A solution of 11-(3,3-difluorocyclobutyl)-5-fluoro-2,3,7,11-tetraazatricyclo [7.4.0.0^{2,6}]trideca-1(13),3,5,9-tetraene-8,12-dione (200 mg, 0.6 mmol) in Phenylphosphonic dichloride (4 mL) was stirred at 150° C. for 30 min under nitrogen atmosphere. The reaction mixture was poured into ice-water (50 mL), adjusted Ph to 8~9 with saturated aqueous $NaHCO_3$. The mixture was extracted with EtOAc (50 mL×3), washed by water and brine, dried over anhydrous $Na_2SO_4$, filtered and concentrated to give a crude product which was purified by column chromatography on silica gel (DCM:MeOH=100:1 to 20:1) to obtain 8-chloro-11-(3,3-difluorocyclobutyl)-5-fluoro-2,3,7,11-tetraazatricyclo

[7.4.0.0^{2,6}]trideca-1(13),3,5,7,9-pentaen-12-one (80 mg, 0.2 mmol, 37.7%) as a brown solid. LC/MS (ESI) m/z: 329 $(M+H)^+$.

Step K: 8-{[(1R)-1-[3-(1,1-difluoro-2-hydroxyethyl) phenyl]ethyl]amino}-11-(3,3-difluorocyclobutyl)-5-fluoro-2,3,7,11-tetraazatricyclo[7.4.0.0^{2,6}]trideca-1(13),3,5,7,9-pentaen-12-one To a stirred solution of 8-chloro-11-(3,3-difluorocyclobutyl)-5-fluoro-2,3,7,11-tetraazatricyclo [7.4.0.0^{2,6}] trideca-1(13),3,5,7,9-pentaen-12-one (40 mg, 0.1 mmol) and 2-{3-[(1R)-1-aminoethyl]phenyl}-2,2-difluoroethan-1-ol (49 mg, 0.2 mmol) in EtOH (5 mL) was added N,N-Diisopropylethylamine (78 mg, 0.6 mmol) slowly, the reaction mixture was stirred at 120° C. for 16 h in a sealed tube. The reaction mixture was concentrated. the residue was diluted with water (10 mL), extracted with EtOAc (10 mL×3). The combined organic phase was washed by water and brine, the organic phase was dried over anhydrous $Na_2SO_4$, filtered and concentrated to give a crude product which was purified by prep-TLC (DCM:MeOH=15:1) to obtain 8-{[(1R)-1-[3-(1,1-difluoro-2-hydroxyethyl)phenyl] ethyl]amino}-11-(3,3-difluorocyclobutyl)-5-fluoro-2,3,7,11-tetraazatricyclo[7.4.0.0^{2,6}]trideca-1(13),3,5,7,9-pentaen-12-one (17 mg, 0.03 mmol, 28.3%) as a yellow solid. LC/MS (ESI) m/z: 494 $(M+H)^+$. $^1H$ NMR (400 MHz, DMSO) δ 8.85 (s, 1H), 8.34 (d, J=7.5 Hz, 1H), 7.96 (d, J=3.7 Hz, 1H), 7.65-7.54 (m, 2H), 7.47 (t, J=7.7 Hz, 1H), 7.41 (d, J=7.7 Hz, 1H), 6.61 (s, 1H), 5.63 (t, J=6.3 Hz, 1H), 5.56 (t, J=7.2 Hz, 1H), 4.83 (td, J=8.3, 2.9 Hz, 1H), 3.85 (td, J=14.3, 6.3 Hz, 2H), 3.26 (d, J=12.5 Hz, 2H), 3.19-3.10 (m, 2H), 1.61 (d, J=7.0 Hz, 3H).

Biological Assays

KRAS-WT (or G12C/G12D/G12V)/SOS1 Binding Assay

The KRAS-WT (or G12C/G12D/G12V)/SOS1 binding assay is designed to measure the potency with which compounds inhibit the protein protein interaction between KRAS-WT (or G12C/G12D/G12V) and SOS1 proteins using a HTRF (Homogeneous Time-resolved Fluorescence) methodology. Low IC50 values are indicative of high potency of the SOS1 inhibitor compounds in this assay setting.

The KRAS-WT (or G12C/G12D/G12V)/SOS1 binding assay is performed using an assay kit (Cisbio, Cat #63ADK000CB15PEG or 63ADK000CB16PEG/63ADK000CB17PEG/63ADK000CB18PEG) according to the procedure recommended by the manufacturer.

1) Thaw and prepare the working solution of Tag1-SOS1 protein and Tag2-KRAS-WT (or G12C/G12D/G12V) protein with final concentration of 10 μM GTP (Sigma, Cat #V900868).
2) Thaw and prepare the working solution of anti-Tag1-$Tb^{3+}$ anti-Tag2-XL665.
3) Dispense 2 μL of serially diluted compound, 4 μL of Tag1-SOS1 protein and 4 μL of Tag2-KRAS-WT (or G12C/G12D/G12V) protein with GTP into a ProxiPlate-384 Plus, white 384-shallow well microplate (PerkinElmer, Cat #6008280).
4) Incubate the plate for 15 minutes at room temperature.
5) Dispense 10 μL of pre-mixed anti-Tag1-$Tb^{3+}$ and anti-Tag2-XL665 into the plate.
6) Seal the plate and incubate for 2 hours at room temperature.
7) Remove the plate sealer and read on PHERAstar FS (BMG LABTECH, PHERAstar FS).
8) Calculate the ratio of the acceptor and donor emission signals for each individual well using the following equation.

$$\text{Ratio} = \frac{\text{Signal } 665 \text{ nm}}{\text{Signal } 620 \text{ nm}} \times 10^4$$

9) IC50 values are fitted and calculated by HTRF signal values and log of compound concentrations to nonlinear regression [Log (inhibitor) vs. Response—Variable Slope (four parameters)] using the GraphPad Prism 8.0.

TABLE 7

Activity Data in Kras: SOS1 Assay*

| Example No. | Wild Type | G12C | G12D |
|---|---|---|---|
| 1 | | A | A |
| 2 | | A | A |
| 3 | | B | |
| 4 | | A | |
| 5 | | A | |
| 6 | | A | |
| 7 | A | | A |
| 8 | A | | A |
| 9 | A | | A |
| 10 | A | | A |
| 11 | A | | A |
| 12 | A | | A |
| 13 | D | | D |
| 14 | A | | A |
| 15 | A | | A |
| 16 | A | | A |
| 17 | B | | B |
| 18 | A | | A |
| 19 | A | | A |
| 20 | A | | B |
| 21 | A | | A |
| 22 | A | | A |
| 23 | A | | A |
| 24 | A | | A |
| 25 | A | | A |
| 26 | D | | D |
| 27 | A | | A |
| 28 | A | | A |
| 29 | A | | A |
| 30 | A | | A |
| 31 | A | | A |
| 32 | B | | B |
| 33 | B | | B |
| 34 | B | | B |
| 35 | B | | B |
| 36 | A | | A |
| 37 | A | | A |
| 38 | A | | A |
| 39 | B | | B |
| 40 | A | | A |
| 41 | A | | A |
| 42 | A | | A |
| 43 | A | | A |
| 44 | A | | A |
| 45 | A | B | A |
| 46 | A | B | B |
| 47 | B | C | C |
| 48 | | B | |
| 49 | | B | |
| 50 | | B | |
| 51 | B | B | B |
| 52 | B | | B |
| 53 | B | | B |
| 54 | C | | C |
| 55 | B | | B |
| 56 | C | | C |
| 57 | B | | B |
| 58 | A | | A |
| 59 | | A | |
| 60 | A | A | A |

TABLE 7-continued

| Activity Data in Kras: SOS1 Assay* | | | |
|---|---|---|---|
| Example No. | Wild Type | G12C | G12D |
| 61 | A | | A |
| 62 | A | | A |
| 63 | A | | A |
| 64 | A | | A |
| 65 | C | | C |
| 66 | A | | A |
| 67 | A | | B |
| 68 | A | | A |
| 69 | B | | B |
| 70 | A | | A |
| 71 | A | | A |
| 72 | A | | A |
| 73 | A | | A |
| 74 | A | | A |
| 75 | A | | A |
| 76 | A | | A |
| 77 | A | | A |
| 78 | A | | A |

*A: <100 nM; B: 100~500 nM; C: 500~5□M; D: >5□M

We claim:

1. A compound of Formula (I),

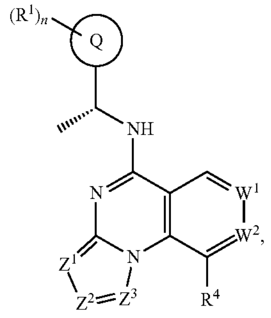

(I)

or a pharmaceutically acceptable salt thereof, and/or a tautomer thereof, and/or a stereoisomer thereof, wherein:

Q is phenyl;

$Z^1$ is $CR^5$;

$Z^2$ is $CR^6$;

$Z^3$ is N;

$W^1$ is $CR^2$ or $NR^2$;

$W^2$ is $CR^3$ when $W^1$ is $CR^2$, and $W^2$ is C (O) when $W^1$ is $NR^2$;

$R^1$ at each occurrence is independently hydrogen, halogen, $C_{1-6}$alkyl, halo$C_{1-6}$alkyl, $C_{1-6}$alkenyl, $C_{1-6}$alkynyl, —$NR^aR^b$, OH, $C_{1-6}$alkyl-OH, halo$C_{1-6}$alkyl-OH, $C_{1-6}$alkoxy, halo$C_{1-6}$alkoxy, CN, $C_{3-7}$cycloalkyl, $C_{3-7}$cycloalkyl-OH, $C_{3-7}$cycloalkoxy, —$S(O)_t$—$C_{1-6}$alkyl, —$S(O)_t$—$NR^aR^b$, phenyl, or 3-7-membered heterocyclyl, wherein the phenyl and 3-7-membered heterocyclyl are optionally substituted with 1-4 substituents independently selected from $C_{1-4}$alkyl, halo$C_{1-4}$alkyl, $C_{1-4}$alkoxy, halo$C_{1-4}$alkoxy, $C_{1-4}$alkyl-OH, halo$C_{1-4}$alkyl-OH, OH, halogen, CN, —$S(O)_t$—$C_{1-6}$alkyl, —$S(O)_t$—$NR^aR^b$, —$NR^aR^b$, or $C_{1-4}$alkyl-$NR^aR^b$; or two adjacent $R^1$ groups, together with the carbon atoms to which they are attached, form a 5-7-membered carbocyclic or heterocyclic ring optionally substituted with 1-3 substituents independently selected from $C_{1-4}$alkyl, halo$C_{1-4}$alkyl, $C_{1-4}$alkoxy, halo$C_{1-4}$alkoxy, $C_{1-4}$alkyl-OH, halo$C_{1-4}$alkyl-OH, OH, halogen, CN, —$NR^aR^b$, $C_{1-4}$alkyl-$NR^aR^b$, or oxo group (═O);

$R^2$ at each occurrence is independently hydrogen, halogen, CN, —$OR^a$, —$NR^aR^b$, $C_{1-6}$alkyl, halo$C_{1-6}$alkyl, $C_{2-6}$alkenyl, $C_{2-6}$alkynyl, $C_{3-7}$cycloalkyl, 3-7-membered heterocyclyl, phenyl, or 5-6-membered heteroaryl, wherein each of the $C_{1-6}$alkyl, halo$C_{1-6}$alkyl, $C_{2-6}$alkenyl, $C_{2-6}$alkynyl, $C_{3-7}$cycloalkyl, 3-7-membered heterocyclyl, phenyl, and 5-6-membered heteroaryl is optionally substituted with 1-5 $R^8$;

$R^3$ at each occurrence is independently hydrogen, halogen, $C_{1-6}$alkyl, halo$C_{1-6}$alkyl, $C_{1-6}$alkoxy, halo$C_{1-6}$ alkoxy, $C_{1-6}$alkyl-OH, CN, $C_{3-7}$cycloalkyl, $C_{3-7}$cycloalkyl-OH, $C_{3-7}$cycloalkoxy, $NH_2$, $NHC_{1-4}$alkyl, —$N(C_{1-4}$alkyl) 2, or 3-7-membered cyclic amine;

$R^4$ at each occurrence is independently hydrogen, halogen, $C_{1-6}$alkyl, halo$C_{1-6}$alkyl, $C_{1-6}$alkoxy, halo$C_{1-6}$alkoxy, CN, $NH_2$, $C_{3-7}$cycloalkyl or $C_{3-7}$cycloalkoxy;

$R^5$ at each occurrence is independently hydrogen, $C_{1-4}$alkyl, or halo$C_{1-4}$alkyl;

$R^6$ at each occurrence is independently hydrogen or $C_{1-4}$alkyl;

$R^8$ at each occurrence is independently hydrogen, halogen, $C_{1-4}$alkyl, halo$C_{1-4}$alkyl, $C_{1-4}$alkoxy, $C_{2-4}$alkenyl, $C_{2-4}$alkynyl, $C_{3-7}$cycloalkyl, $C_{3-7}$cycloalkoxy, 3-7-membered heterocyclyl, phenyl, 5-6-membered heteroaryl, —$OR^a$, —$SR^a$, $S(O)_tR^a$, —$S(O)_t$—$NR^aR^b$, —OC(O)—$R^a$, —$NR^aR^b$, —C(O)$R^a$, C(O)$OR^a$, —OC (O)$NR^aR^b{}_2$, —C(O) $NR^aR^b$, —N($R^a$)C(O)$OR^a$, —N($R^a$)C(O)$R^a$, —N($R^a$)C(O)$NR^aR^b$, N($R^a$)C(N$R^a$) $NR^aR^b$, —N($R^a$)$S(O)_t NR^aR^b$, —P(═O)($R^a$)($R^b$), —O—P(═O)($OR^a$)($OR^b$), or oxo group (═O);

$R^a$ and $R^b$ at each occurrence are independently hydrogen, $C_{1-6}$alkyl, halo$C_{1-6}$alkyl, $C_{1-6}$alkyl-OH, $C_{1-6}$alkoxy, $C_{3-7}$cycloalkyl, 3-7-membered heterocyclyl, $C_{1-6}$alkyl-$NH_2$, $C_{1-6}$alkyl-$NHC_{1-4}$alkyl, $C_{1-6}$alkyl-$N(C_{1-4}alkyl)_2$, or $C_{1-6}$alkyl-(3-7-membered cyclic amine); or $R^a$ and $R^b$, together with the nitrogen atom to which they are attached, form a saturated or unsaturated heterocyclic ring containing from three to seven ring atoms, which ring may optionally contain an additional one or two heteroatoms independently selected from the group consisting of nitrogen, oxygen and sulfur and which ring may be optionally substituted by from one to three substituents independently selected from the group consisting of $C_{1-4}$alkyl, phenyl and benzyl;

n at each occurrence is independently 1, 2 or 3, and t at each occurrence is independently 1 or 2.

2. The compound of claim 1, having the structure of Formula (IA):

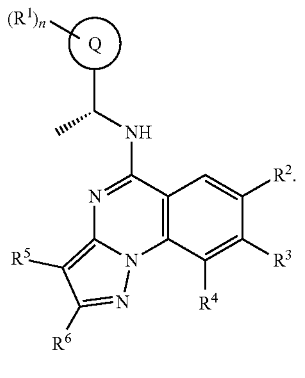

(IA)

3. The compound of claim 1, having the structure of Formula (IB):

(IB)

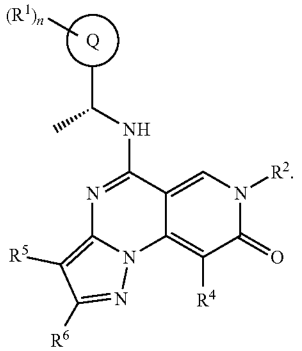

4. The compound of claim 1, wherein $R^1$ at each occurrence is independently hydrogen, halogen, $C_{1-6}$alkyl, halo$C_{1-6}$alkyl, —$NR^aR^b$, OH, $C_{1-6}$alkyl-OH, halo$C_{1-6}$alkyl-OH, $C_{1-6}$alkoxy, halo$C_{1-6}$alkoxy, CN, $C_{3-7}$cycloalkyl, $C_{3-7}$cycloalkyl-OH, $C_{3-7}$cycloalkoxy or —$S(O)_t$—$C_{1-6}$alkyl.

5. The compound of claim 1, wherein $R^1$ at each occurrence is independently phenyl or 3-7-membered heterocyclyl, wherein the phenyl and 3-7-membered heterocyclyl are optionally substituted with 1-4 substituents independently selected from $C_{1-4}$alkyl, halo$C_{1-4}$alkyl, $C_{1-4}$alkoxy, halo$C_{1-4}$alkoxy, $C_{1-4}$alkyl-OH, halo$C_{1-4}$alkyl-OH, OH, halogen, CN, —$S(O)_t$—$C_{1-6}$alkyl, —$S(O)_t$—$NR^aR^b$, —$NR^aR^b$ and $C_{1-4}$alkyl-$NR^aR^b$.

6. The compound of claim 1, wherein two adjacent $R^1$ groups at each occurrence, together with the carbon atoms to which they are attached, form a 5-7-membered carbocyclic or heterocyclic ring optionally substituted with 1-3 substituents independently selected from $C_{1-4}$alkyl, halo$C_{1-4}$alkyl, $C_{1-4}$alkoxy, halo$C_{1-4}$alkoxy, $C_{1-4}$alkyl-OH, halo$C_{1-4}$alkyl-OH, OH, halogen, CN, —$NR^aR^b$, $C_{1-4}$alkyl-$NR^aR^b$, and oxo group (═O).

7. The compound of claim 1, wherein two adjacent $R^1$ groups at each occurrence, together with the carbon atoms to which they are attached, form a 5-6-membered carbocyclic ring optionally substituted with 1-3 substituents independently selected from $C_{1-4}$alkyl, halo$C_{1-4}$alkyl, $C_{1-4}$alkoxy, halo$C_{1-4}$alkoxy, $C_{1-4}$alkyl-OH, halo$C_{1-4}$alkyl-OH, OH, halogen, CN, —$NR^aR^b$, $C_{1-4}$alkyl-$NR^aR^b$ and oxo group (═O).

8. The compound of claim 1, wherein two adjacent $R^1$ groups at each occurrence, together with the carbon atoms to which they are attached, form a 5-6-membered heterocyclic ring optionally substituted with 1-3 substituents independently selected from $C_{1-4}$alkyl, halo$C_{1-4}$alkyl, $C_{1-4}$alkoxy, halo$C_{1-4}$alkoxy, $C_{1-4}$alkyl-OH, halo$C_{1-4}$alkyl-OH, OH, halogen, CN, —$NR^aR^b$, $C_{1-4}$alkyl-$NR^aR^b$ and oxo group (═O).

9. The compound of claim 1, wherein Q together with its substituents $(R^1)_n$,

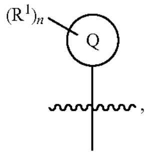

at each occurrence independently has the structure of

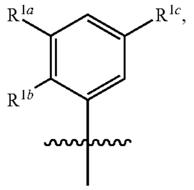

wherein:

$R^{1a}$ at each occurrence is independently hydrogen, halogen, $C_{1-6}$alkyl, halo$C_{1-6}$alkyl, $C_{1-6}$alkenyl, $C_{1-6}$alkynyl, OH, $C_{1-6}$alkyl-OH, halo$C_{1-6}$alkyl-OH, $C_{1-6}$alkoxy, halo$C_{1-6}$alkoxy, CN, $C_{3-7}$cycloalkyl, $C_{3-7}$cycloalkyl-OH, $C_{3-7}$cycloalkoxy, —$S(O)_t$—$C_{1-6}$alkyl, —$S(O)_t$—$NR^aR^b$, or 3-7-membered heterocyclyl, wherein the 3-7-membered heterocyclyl are optionally substituted with 1-4 substituents independently selected from $C_{1-4}$alkyl, halo$C_{1-4}$alkyl, $C_{1-4}$alkoxy, halo$C_{1-4}$alkoxy, $C_{1-4}$alkyl-OH, halo$C_{1-4}$alkyl-OH, OH, halogen, CN, —$S(O)_t$—$C_{1-6}$alkyl, —S(O)—$NR^aR^b$, —$NR^aR^b$, and $C_{1-4}$alkyl-$NR^aR^b$;

$R^{1b}$ at each occurrence is independently hydrogen, halogen, $C_{1-4}$alkyl or $C_{3-6}$cycloalkyl;

or $R^{1a}$ and $R^{1b}$, at each occurrence, together with the carbon atoms to which they are attached, form a 5-7-membered carbocyclic or heterocyclic ring optionally substituted with 1-3 substituents independently selected from $C_{1-4}$alkyl, halo$C_{1-4}$alkyl, $C_{1-4}$alkoxy, halo$C_{1-4}$alkoxy, $C_{1-4}$alkyl-OH, halo$C_{1-4}$alkyl-OH, OH, halogen, CN, —$NR^aR^b$, $C_{1-4}$alkyl-$NR^aR^b$, and oxo group (═O); and $R^{1c}$ at each occurrence is independently hydrogen, halogen, $NH_2$, or $C_{1-4}$alkyl.

10. The compound of claim 9, having the structure of Formula (IAa), (IAa)

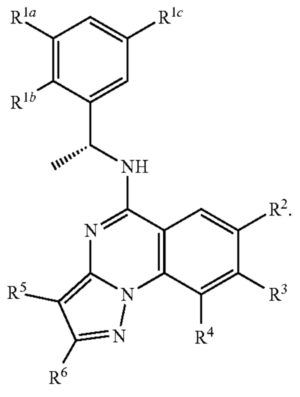

11. The compound of claim 9, having the structure of Formula (IBa), (IBa)

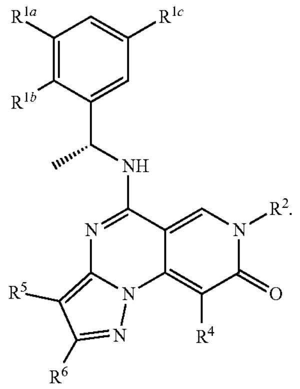

12. The compound of claim 9, wherein $R^{1a}$ at each occurrence is independently hydrogen, halogen, $C_{1-6}$alkyl, halo$C_{1-6}$alkyl, $C_{1-6}$alkenyl, $C_{1-6}$alkynyl, OH, $C_{1-6}$alkyl-OH, halo$C_{1-6}$alkyl-OH, $C_{1-6}$alkoxy, halo$C_{1-6}$alkoxy, CN, $C_{3-7}$cycloalkyl, $C_{3-7}$cycloalkyl-OH, $C_{3-7}$cycloalkoxy, —$S(O)_t$—$C_{1-6}$alkyl, or —$S(O)_t$—$NR^aR^b$.

13. The compound of claim 9, wherein $R^{1a}$ at each occurrence is independently 3-7-membered heterocyclyl optionally substituted with 1-4 substituents independently selected from $C_{1-4}$alkyl, halo$C_{1-4}$alkyl, $C_{1-4}$alkoxy, halo$C_{1-4}$ alkoxy, $C_{1-4}$alkyl-OH, halo$C_{1-4}$alkyl-OH, OH, halogen, CN, —$S(O)_t$—$C_{1-6}$alkyl, —S(O) t-$NR^aR^b$, —$NR^aR^b$, and $C_{1-4}$alkyl-$NR^aR^b$.

14. The compound of claim 9, wherein $R^{1a}$ at each occurrence is independently $CHF_2$, $CH_2F$, $CF_3$, $CF_2CH_3$ or $CF_2CH_2OH$.

15. The compound of claim 9, wherein $R^{1a}$ and $R^{1b}$, at each occurrence, together with the carbon atoms to which they are attached, form a 5- or 6-membered carbocyclic ring optionally substituted with 1-3 halogens.

16. The compound of claim 9, wherein $R^{1a}$ and $R^{1b}$, at each occurrence, together with the carbon atoms to which they are attached, form a carbocyclic ring having the structure of

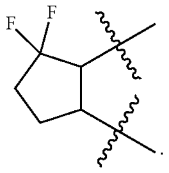

17. The compound of claim 9, wherein $R^{1b}$ at each occurrence is hydrogen.

18. The compound of claim 9, wherein $R^{1b}$ at each occurrence is independently halogen.

19. The compound of claim 9, wherein $R^{1b}$ at each occurrence is independently $C_{1-4}$alkyl.

20. The compound of claim 9, wherein $R^{1b}$ at each occurrence is independently F or methyl.

21. The compound of claim 9, wherein $R^{1c}$ at each occurrence is hydrogen.

22. The compound of claim 9, wherein $R^{1c}$ at each occurrence is independently halogen.

23. The compound of claim 9, wherein $R^{1c}$ at each occurrence is $NH_2$.

24. The compound of claim 9, wherein $R^{1c}$ at each occurrence is independently $C_{1-4}$alkyl.

25. The compound of claim 1, wherein $R^2$ at each occurrence is independently hydrogen, halogen, CN, —$OR^a$, —$NR^aR^b$, $C_{1-6}$alkyl, or halo$C_{1-6}$alkyl, wherein each of the $C_{1-6}$alkyl and halo$C_{1-6}$alkyl is optionally substituted with 1-5 $R^8$.

26. The compound of claim 1, wherein $R^2$ at each occurrence is independently $C_{3-7}$cycloalkyl optionally substituted with 1-5 $R^8$.

27. The compound of claim 1, wherein $R^2$ at each occurrence is independently 3-7-membered heterocyclyl optionally substituted with 1-5 $R^8$.

28. The compound of claim 1, wherein $R^2$ at each occurrence is independently phenyl optionally substituted with 1-5 $R^8$.

29. The compound of claim 1, wherein $R^2$ at each occurrence is independently 5-membered heteroaryl optionally substituted with 1-5 $R^8$.

30. The compound of claim 1, wherein $R^2$ at each occurrence is independently 6-membered heteroaryl optionally substituted with 1-5 $R^8$.

31. The compound of claim 1, wherein $R^3$ at each occurrence is independently hydrogen, halogen, $C_{1-6}$alkyl, halo$C_{1-6}$alkyl, or CN.

32. The compound of claim 1, wherein $R^3$ at each occurrence is independently $C_{1-6}$alkoxy, halo$C_{1-6}$alkoxy, or $C_{1-6}$alkyl-OH.

33. The compound of claim 1, wherein $R^3$ at each occurrence is independently $C_{3-7}$cycloalkyl or $C_{3-7}$cycloalkyl-OH.

34. The compound of claim 1, wherein $R^3$ at each occurrence is independently —$NH_2$, —$NHC_{1-4}$alkyl, —$N(C_{1-4}alkyl)_2$, or 3-7-membered cyclic amine.

35. The compound of claim 1, wherein $R^4$ at each occurrence is hydrogen.

36. The compound of claim 1, wherein $R^4$ at each occurrence is independently halogen or $C_{1-6}$alkyl.

37. The compound of claim 1, wherein $R^5$ at each occurrence is independently hydrogen or $C_{1-4}$alkyl.

38. The compound of claim 1, wherein $R^5$ at each occurrence is hydrogen.

39. The compound of claim 1, wherein $R^5$ at each occurrence is methyl.

40. The compound of claim 1, wherein $R^6$ at each occurrence is hydrogen.

41. The compound of claim 1, wherein Re at each occurrence is methyl.

42. The compound of claim 1, wherein $R^8$ at each occurrence is independently hydrogen, halogen, $C_{1-4}$alkyl, halo$C_{1-4}$alkyl, or $C_{1-4}$alkoxy.

43. The compound of claim 1, wherein $R^8$ at each occurrence is independently $C_{3-7}$cycloalkyl or 3-7-membered heterocyclyl.

44. The compound of claim 1, wherein $R^8$ at each occurrence is independently phenyl or 5-6-membered heteroaryl.

45. The compound of claim 1, wherein $R^8$ at each occurrence is independently —$OR^a$, —$SR^a$, —$S(O)_tR^a$, —S(O)—$NR^aR^b$, —OC(O)—$R^a$, —$NR^aR^b$, C(O)$R^a$, —C(O)$OR^a$, —OC(O)$NR^aR^b$, —C(O)$NR^aR^b$, —N($R^a$)C(O)$OR^a$, —N($R^a$)C(O)$R^a$, —N($R^a$)C(O)$NR^aR^b$, —N($R^a$)C($NR^a$)$NR^aR^b$, —N($R^a$)$S(O)_tNR^aR^b$, —P(═O)($R^a$)($R^b$), —O—P(═O)($OR^a$)($OR^b$), or oxo group (═O).

46. The compound of claim 1, wherein $R^8$ at each occurrence is oxo group (═O).

47. The compound of claim 1, wherein $R^8$ at each occurrence is independently —$NR^aR^b$.

48. The compound of claim 47, wherein said —$NR^aR^b$ at each occurrence is independently $NH_2$, —$NHC_{1-4}$alkyl, —N($C_{1-4}$alkyl) 2, or 3-7-membered cyclic amine.

49. The compound of claim 1, wherein $R^8$ at each occurrence is independently —$S(O)_t$—$C_{1-4}$alkyl.

50. The compound of claim 1, selected from:

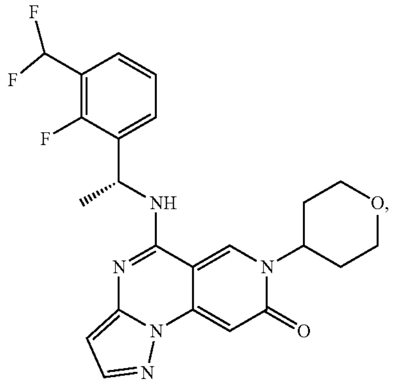

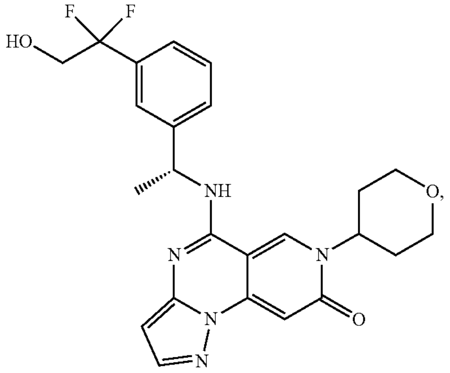

and

-continued

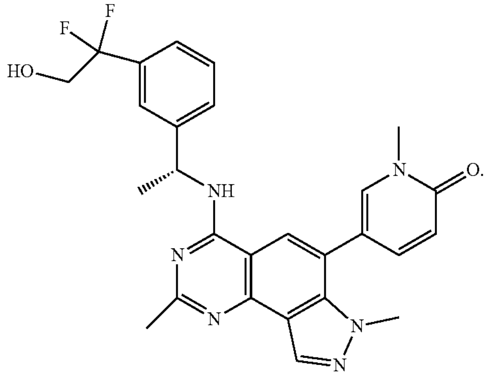

51. The compound of claim 1, selected from:

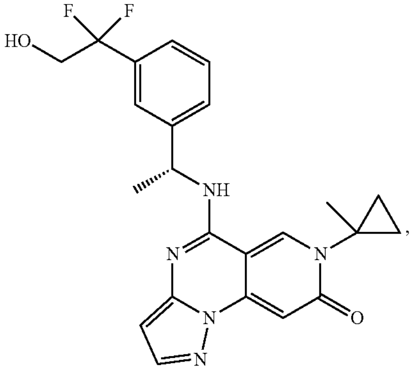

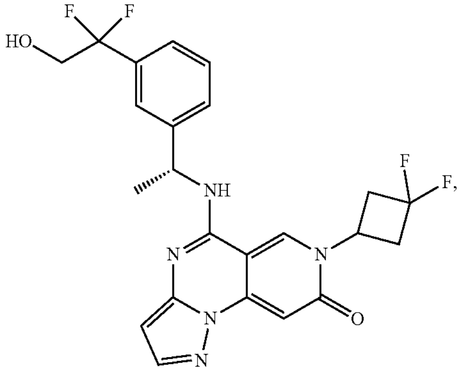

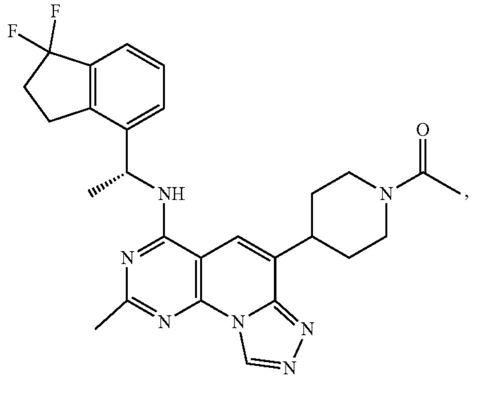

and

-continued

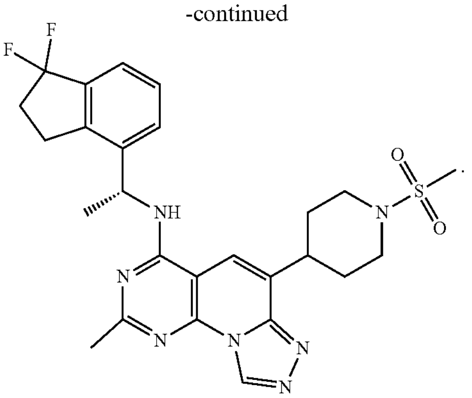

52. The compound of claim 1, selected from:

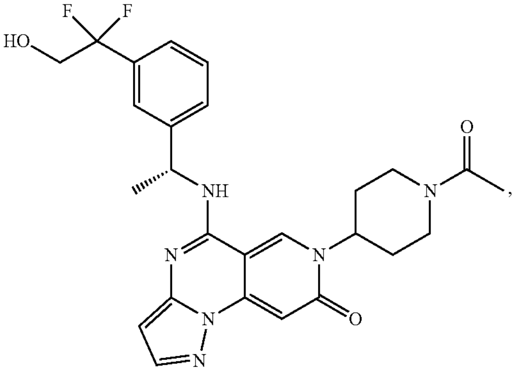

, and

-continued

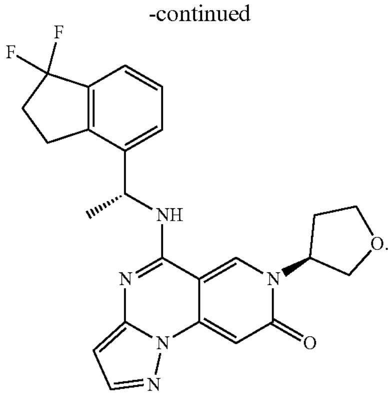

53. A pharmaceutical composition comprising the compound of claim 1, and a pharmaceutically acceptable carrier.

54. A method of inhibiting the protein-protein interaction between KRASWT and SOS1 protein in a subject in need thereof, comprising administering an effective amount of a compound of claim 1 to the subject, wherein diseases treatable by such inhibition are cancer.

55. The method of claim 54, wherein the cancer is breast cancer, leukemia, prostate cancer, ovarian cancer, pancreatic cancer, colon cancer, lung cancer, endometrial cancer, thyroid cancer, cholangiocarcinoma, multiple myeloma, melanoma, uterine cancer, head and neck squamous cell carcinoma, diffuse large B cell lymphoma, esophageal cancer, hepatocellular cancer, glioblastoma, renal cancer, sarcoma, bladder cancer, urothelial cancer, gastric cancer, or cervical cancer.

* * * * *